(12) United States Patent
Brown et al.

(10) Patent No.: US 8,088,791 B2
(45) Date of Patent: Jan. 3, 2012

(54) ANTIBACTERIAL AGENTS

(75) Inventors: David Ryall Brown, Yarnton (GB); Ian Collins, Yarnton (GB); Lloyd George Czaplewski, Yarnton (GB); David John Haydon, Yarnton (GB)

(73) Assignee: Biots Scientific Management Pty Ltd (AU)

( * ) Notice: Subject to any disclaimer, the term of this patent is extended or adjusted under 35 U.S.C. 154(b) by 623 days.

(21) Appl. No.: 12/293,608

(22) PCT Filed: Mar. 22, 2007

(86) PCT No.: PCT/GB2007/001012
§ 371 (c)(1),
(2), (4) Date: Sep. 19, 2008

(87) PCT Pub. No.: WO2007/107758
PCT Pub. Date: Sep. 27, 2007

(65) Prior Publication Data
US 2010/0173933 A1 Jul. 8, 2010

(30) Foreign Application Priority Data

Mar. 23, 2006 (GB) .................................. 0605881.2
Nov. 16, 2006 (GB) .................................. 0623070.0

(51) Int. Cl.
*A01N 43/42* (2006.01)
(52) U.S. Cl. ........ 514/301; 514/364; 514/367; 514/374; 546/114; 548/131; 548/179; 548/236
(58) Field of Classification Search ................... 514/301, 514/364, 367, 374; 546/111; 548/131, 179, 548/236
See application file for complete search history.

(56) References Cited

FOREIGN PATENT DOCUMENTS

| EP | 1 500 643 A1 | 1/2005 |
|----|---|---|
| WO | 00/66120 A | 11/2000 |
| WO | 2004/078748 A2 | 9/2004 |

OTHER PUBLICATIONS

"Tuberculostatics XXXVIII. Amides and N-alkylamides of 2-alkoxy-4-pyridine carboxylic acids", Hartl, Jiri et al., "Cesko-Slovensha Farmacie" (1986), 35(7), 322-4.
International Search Report, May 2007.

Primary Examiner — Brandon Fetterolf
Assistant Examiner — Jean Cornet
(74) Attorney, Agent, or Firm — Banner & Witcoff, Ltd.

(57) ABSTRACT

Compounds of formula (I) have antibacterial activity:

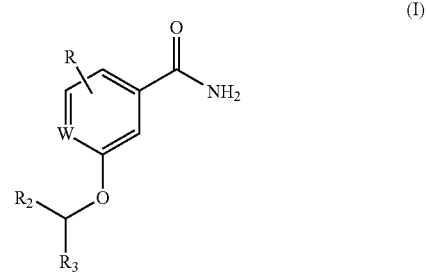

(I)

wherein R represents hydrogen or 1, 2 or 3 optional substituents; W is =C($R_1$)— or =N—; $R_1$ is hydrogen or an optional substituent and $R_2$ is hydrogen, methyl, or fluorine; or $R_1$ and $R_2$ taken together are —$CH_2$—, —$CH_2CH_2$—, —O—, or, in either orientation, —O—$CH_2$— or —$OCH_2CH_2$—; $R_3$ is a radical of formula -(Alk$^1$)$_m$-(Z)$_p$-(Alk$^2$)$_n$-Q wherein m, p and n are independently 0 or 1, provided that at least one of m, p and n is 1, Z is —O—, —S—, —S(O)—, —S($O_2$)—, —NH—, —N($CH_3$)—, —N($CH_2CH_3$)—, —C(=O)—, —O—(C=O)—, —C(=O)—O—, or an optionally substituted divalent monocyclic carbocyclic or heterocyclic radical having 3 to 6 ring atoms; or an optionally substituted divalent bicyclic heterocyclic radical having 5 to 10 ring atoms; Alk$^1$ and Alk$^2$ are optionally substituted $C_1$-$C_6$ alkylene, $C_2$-$C_6$ alkenylene, or $C_2$-$C_6$ alkynylene radicals, which may optionally terminate with or be interrupted by —O—, —S—, —S(O)—, —S($O_2$)—, —NH—, —N($CH_3$)—, or —N($CH_2CH_3$)—; and Q is hydrogen, halogen, nitrile, or hydroxyl or an optionally substituted monocyclic carbocyclic or heterocyclic radical having 3 to 6 ring atoms; or an optionally substituted bicyclic heterocyclic radical having 5 to 10 ring atoms.

1 Claim, No Drawings

ANTIBACTERIAL AGENTS

CROSS REFERENCE TO RELATED APPLICATIONS:

This application is a National Stage application of co-pending PCT application PCT/GB2007/001012 filed Mar. 22, 2007, which claims the benefit of Great Britian application number 0605881.2 filed Mar. 23, 2006 and Great Britian application number 0623070.0 filed Nov. 16, 2006. These applications are incorporated herein by reference in their entireties.

This invention relates to the use of a class of substituted benzamides and pyridylamides as antibacterial agents, to novel members of that class per se, and to pharmaceutical compositions comprising such compounds.

BACKGROUND TO THE INVENTION

Many classes of antibacterial agents are known, including the penicillins and cephalosporins, tetracyclines, sulfonamides, monobactams, fluoroquinolones and quinolones, aminoglycosides, glycopeptides, macrolides, polymyxins, lincosamides, trimethoprim and chloramphenicol. The fundamental mechanisms of action of these antibacterial classes vary.

Bacterial resistance to many known antibacterials is a growing problem. Accordingly there is a continuing need in the art for alternative antibacterial agents, especially those that have mechanisms of action fundamentally different from the known classes.

Amongst the Gram-positive pathogens, such as staphylococci, streptococci, mycobacteria and enterococci, resistant strains have evolved/arisen which make them particularly difficult to eradicate. Examples of such strains are methicillin resistant *Staphylococcus aureus* (MRSA), methicillin resistant coagulase negative staphylococci (MRCNS), penicillin resistant *Streptococcus pneumoniae* and multiply resistant *Enterococcus faecium*. In view of the rapid emergence of multidrug-resistant bacteria, the development of antibacterial agents with novel modes of action that are effective against the growing number of resistant bacteria, particularly the vancomycin resistant enterococci and beta-lactam antibiotic-resistant bacteria, such as methicillin-resistant *Staphylococcus aureus*, is of utmost importance.

Cell division has been of considerable interest to the pharmaceutical industry as a target because it comprises a group of well conserved target proteins that are all essential for the viability of a wide range of bacteria, and their activities are completely different from those of the proteins involved in cell division of mammalian cells. A number of compounds that act on components of the cell division machinery have been described (Ohashi, Y. et al. J. Bacteriol. 181, 1348-1351 (1999), Jennings, L. D. et al. Bioorg Med Chem 12, 5115-5131 (2004), Sutherland, A. G. et al. Org Biomol Chem 1, 4138-4140 (2003), Margalit, D. N. et al. Proc. Natl. Acad. Sci. USA 101, 11821-11826 (2004), Wang, J. et al. J. Biol. Chem. 278, 44424-44428 (2003), White, E. L. et al. J. Antimicrob. Chemother. 50, 111-114 (2002), Reynolds, R. C. et al. Bioorg Med Chem Lett 14, 3161-3164 (2004) and Stokes et al. J Biol. Chem. 280, 39709-39715 (2005)). So far, most effort has been directed at the FtsZ protein, since it has several biochemical activities that can be assayed in vitro. Unfortunately, most of the compounds described so far either have relatively low potency, undesirable pharmacological properties or unknown specificity.

BRIEF DESCRIPTION OF THE INVENTION

This invention is based on the finding that a class of substituted benzamides and pyridylamides has antibacterial activity as evidenced by inhibition of bacterial growth by members of that class. The compounds exhibit activity against strains of Gram-positive bacteria, such as staphylococci, clostridia, listeria and bacilli, for example *Staphylococcus aureus, Staphylococcus epidermidis, Staphylococcus haemolyticus* and *Staphylococcus saprophyticus, Bacillus subtilis, Bacillus anthracis* and *Bacillus cereus*. Whilst the invention is not limited by any particular hypothesis as to the mechanism of action of the compounds, it is presently believed that such activity is mediated by the compounds inhibiting cell division through binding to FtsZ.

DETAILED DESCRIPTION OF THE INVENTION

According to a broad aspect of the invention, there is provided the use of a compound which is a substituted benzamide or pyridylamide of formula (I) or a salt, hydrate, or solvate thereof, in the manufacture of a medicament for use in treating bacterial infection:

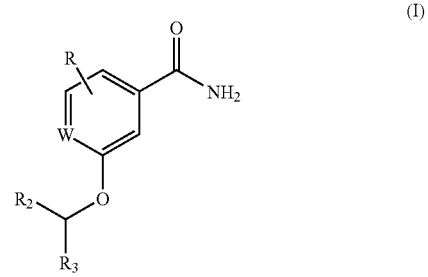

wherein
R represents hydrogen or 1, 2 or 3 optional substituents;
W is =C($R_1$)— or =N—;
$R_1$ is hydrogen or an optional substituent and $R_2$ is methyl, hydrogen or fluorine; or $R_1$ and
$R_2$ taken together are —$CH_2$—, —$CH_2CH_2$—, —O—, or, in either orientation, —O—$CH_2$—, —$OCH_2CH_2$—;
$R_3$ is a radical of formula -($Alk^1$)$_m$-(Z)$_p$-($Alk^2$)$_n$-Q wherein
m, p and n are independently 0 or 1, provided that at least one of m, p and n is 1,
Z is —O—, —S—, —S(O)—, —S($O_2$)—, —NH—, —N($CH_3$)—, —N($CH_2CH_3$)—, —C(=O)—, —O—, —(C=O)—, —C(=O)—O—, or an optionally substituted divalent monocyclic carbocyclic or heterocyclic radical having 3 to 6 ring atoms; or an optionally substituted divalent bicyclic heterocyclic radical having 5 to 10 ring atoms;
$Alk^1$ and $Alk^2$ are optionally substituted $C_1$-$C_6$ alkylene, $C_2$-$C_6$ alkenylene, or $C_2$-$C_6$ alkynylene radicals, which may optionally terminate with or be interrupted by —O—, —S—, —S(O)—, —S($O_2$)—, —NH—, —N($CH_3$)—, or —N($CH_2CH_3$)—; and
Q is hydrogen, halogen, nitrile (—CN), or hydroxyl or an optionally substituted monocyclic carbocyclic or heterocyclic radical having 3 to 7 ring atoms; or an optionally substituted bicyclic heterocyclic radical having 5 to 10 ring atoms.

In other broad aspects, the invention includes (i) a method of treating bacterial infection in a subject suffering such infection comprising administering to the subject an amount of a compound (I) as defined above, sufficient to inhibit bacterial growth;

(ii) a method of treating bacterial contamination of a substrate comprising applying to the site of such contamination an amount of a compound (I) as defined above, sufficient to inhibit bacterial growth;

(iii) a compound (I) as defined above for use in a method of treatment of the human body;

(iv) a compound (I) as defined above for use in treating bacterial infection;

Some members of the class of compounds defined by formula (I) above are believed novel in their own right, and the invention includes all such novel members of the class.

Thus the invention also includes novel compounds which are substituted benzamides or pyridylamides of formula (IC) and salts, hydrates or solvates thereof:

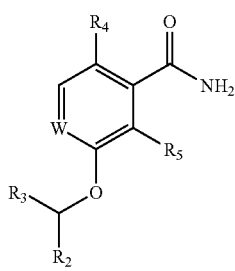
(IC)

wherein W is =C($R_1$)— or =N—; $R_1$ is hydrogen or an optional substituent and $R_2$ is hydrogen, methyl, or fluoro; or $R_1$ and $R_2$ taken together are —$CH_2$—, —$CH_2CH_2$—, —O— or, in either orientation, —O—$CH_2$— or —O$CH_2CH_2$—; $R_4$ and $R_5$ are independently fluoro or chloro, or one of $R_4$ and $R_5$ is hydrogen while the other is fluoro or chloro; and $R_3$ is a radical selected from those of the following formulae A-H, in which any vacant ring position is optionally substituted:

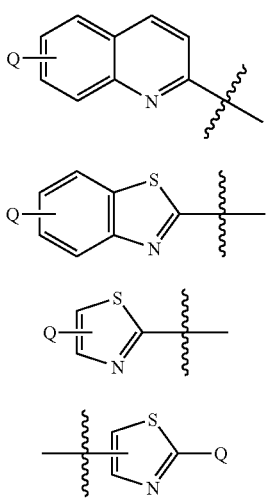

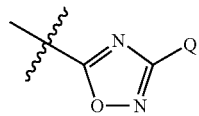
E

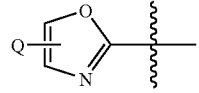
F

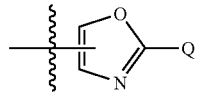
G

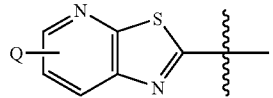
H wherein Q is hydrogen, halogen, nitrile, or hydroxyl; or an optionally substituted monocyclic carbocyclic or heterocyclic radical having 3 to 6 ring atoms; or an optionally substituted bicyclic heterocyclic radical having 5 to 10 ring atoms.

The invention also includes novel pyridylamide compounds of formula (ID) and salts, hydrates or solvates thereof:

(ID)

wherein $R_2$ is hydrogen, methyl, or fluoro; and $R_3$ is as defined in relation to formula (IC).

Terminology

As used herein, the term "($C_a$-$C_b$)alkyl" wherein a and b are integers refers to a straight or branched chain alkyl radical having from a to b carbon atoms. Thus when a is 1 and b is 6, for example, the term includes methyl, ethyl, n-propyl, isopropyl, n-butyl, isobutyl, sec-butyl, t-butyl, n-pentyl and n-hexyl.

As used herein the term "divalent ($C_a$-$C_b$)alkylene radical" wherein a and b are integers refers to a saturated hydrocarbon chain having from a to b carbon atoms and two unsatisfied valences. The term includes, for example, methylene, ethylene, n-propylene and n-butylene.

As used herein the term "($C_a$-$C_b$)alkenyl" wherein a and b are integers refers to a straight or branched chain alkenyl moiety having from a to b carbon atoms having at least one double bond of either E or Z stereochemistry where applicable. The term includes, for example, vinyl, allyl, 1- and 2-butenyl and 2-methyl-2-propenyl.

As used herein the term "divalent ($C_a$-$C_b$)alkenylene radical" means a hydrocarbon chain having from a to b carbon atoms, at least one double bond, and two unsatisfied valences. The term includes, for example, —CH=CH— (vinylene), —CH=CH—$CH_2$—, —$CH_2$—CH=CH—, —CH=CH—$CH_2$—$CH_2$—, —CH=CH—$CH_2$—$CH_2$—$CH_2$—, —CH═CH—CH═CH—, —CH═CH—CH═CH—CH₂—, —CH═CH—CH═CH—CH₂—CH₂—, —CH═CH—CH₂—CH═CH—, and —CH═CH—CH₂—CH₂—CH═CH—.

As used herein the term "C$_a$-C$_b$ alkynyl" wherein a and b are integers refers to straight chain or branched chain hydrocarbon groups having from a to b carbon atoms and having in addition at least one triple bond. This term would include for example, ethynyl, 1-propynyl, 1- and 2-butynyl, 2-methyl-2-propynyl, 2-pentynyl, 3-pentynyl, 4-pentynyl, 2-hexynyl, 3-hexynyl, 4-hexynyl and 5-hexynyl.

As used herein the term "divalent (C$_a$-C$_b$)alkynylene radical" wherein a and b are integers refers to a divalent hydrocarbon chain having from a to b carbon atoms, and at least one triple bond. The term includes, for example, —C≡C—, —C≡C—CH₂—, and —CH₂—C≡CH—.

As used herein the term "cycloalkyl" refers to a monocyclic or bridged monocyclic saturated carbocyclic radical having from 3-8 carbon atoms and includes, for example, cyclopropyl, cyclobutyl, cyclopentyl, cyclohexyl, cycloheptyl, cyclooctyl and bicyclo[2.2.1]hept-1-yl.

As used herein the unqualified term "aryl" refers to a mono- or bi-cyclic carbocyclic aromatic radical. Illustrative of such radicals are phenyl and naphthyl.

As used herein the unqualified term "heteroaryl" refers to a mono-, or bi-cyclic aromatic radical containing one or more heteroatoms selected from S, N and O, and includes radicals having two such monocyclic rings, or one such monocyclic ring and one monocyclic aryl ring, which are fused or directly linked by a covalent bond. Illustrative of such radicals are thienyl, benzthienyl, furyl, benzfuryl, pyrrolyl, imidazolyl, benzimidazolyl, thiazolyl, benzthiazolyl, thiazolopyridinyl, isothiazolyl, benzisothiazolyl, pyrazolyl, oxazolyl, benzoxazolyl, isoxazolyl, benzisoxazolyl, isothiazolyl, triazolyl, benztriazolyl, thiadiazolyl, oxadiazolyl, pyridinyl, pyridazinyl, pyrimidinyl, pyridazinyl, triazinyl, indolyl and indazolyl.

As used herein the unqualified term "heterocyclyl" or "heterocyclic" includes "heteroaryl" as defined above, and in addition means a mono-, or bi-cyclic non-aromatic radical containing one or more heteroatoms selected from S, N and O. Illustrative of such radicals are pyrrolyl, furanyl, thienyl, piperidinyl, imidazolyl, oxazolyl, isoxazolyl, thiazolyl, thiadiazolyl, pyrazolyl, pyridinyl, pyrrolidinyl, pyrimidinyl, morpholinyl, piperazinyl, indolyl, morpholinyl, benzfuranyl, pyranyl, isoxazolyl, benzimidazolyl, methylenedioxyphenyl, ethylenedioxyphenyl, maleimido and succinimido groups.

Unless otherwise specified in the context in which it occurs, the term "substituted" as applied to any moiety herein means substituted with up to four compatible substituents, each of which independently may be, for example, (C$_1$-C$_6$) alkyl, (C$_2$-C$_6$)alkenyl, (C$_2$-C$_6$)alkynyl, (C$_1$-C$_6$)alkoxy, hydroxy, hydroxy(C$_1$-C$_6$)alkyl, mercapto, mercapto(C$_1$-C$_6$) alkyl, (C$_1$-C$_6$)alkylthio, halo (including fluoro, bromo and chloro), fully or partially fluorinated (C$_1$-C$_3$)alkyl, (C$_1$-C$_3$) alkoxy or (C$_1$-C$_3$)alkylthio such as trifluoromethyl, trifluoromethoxy, and trifluoromethylthio, nitro, nitrile (—CN), oxo (═O), phenyl, phenoxy, monocyclic heteroaryl or heteroaryloxy with 5 or 6 ring atoms, —COOR$^A$, —COR$^A$, —OCOR$^A$, —SO₂R$^A$, —CONR$^A$R$^B$, —SO₂NR$^A$R$^B$, —NR$^A$R$^B$, OCONR$^A$R$^B$, —NR$^B$COR$^A$, —NR$^B$COOR$^A$, —NR$^B$SO₂OR$^A$ or —NR$^A$CONR$^A$R$^B$ wherein R$^A$ and R$^B$ are independently hydrogen or a (C$_1$-C$_6$)alkyl group or, in the case where R$^A$ and R$^B$ are linked to the same N atom, R$^A$ and R$^B$ taken together with that nitrogen may form a cyclic amino ring. Where the substituent is phenyl, phenoxy or monocyclic heteroaryl or heteroaryloxy with 5 or 6 ring atoms, the phenyl or heteroaryl ring thereof may itself be substituted by any of the above substituents except phenyl phenoxy, heteroaryl or heteroaryloxy. An "optional substituent" or "substituent" may be one of the foregoing specified groups.

As used herein the term "salt" includes base addition, acid addition and quaternary salts. Compounds of the invention which are acidic can form salts, including pharmaceutically acceptable salts, with bases such as alkali metal hydroxides, e.g. sodium and potassium hydroxides; alkaline earth metal hydroxides e.g. calcium, barium and magnesium hydroxides; with organic bases e.g. N-methyl-D-glucamine, choline tris (hydroxymethyl)amino-methane, L-arginine, L-lysine, N-ethyl piperidine, dibenzylamine and the like. Those compounds (I) which are basic can form salts, including pharmaceutically acceptable salts with inorganic acids, e.g. with hydrohalic acids such as hydrochloric or hydrobromic acids, sulphuric acid, nitric acid or phosphoric acid and the like, and with organic acids e.g. with acetic, tartaric, succinic, fumaric, maleic, malic, salicylic, citric, methanesulphonic, p-toluenesulphonic, benzoic, benzenesulfonic, glutamic, lactic, and mandelic acids and the like.

For a review on suitable salts, see *Handbook of Pharmaceutical Salts: Properties, Selection, and Use* by Stahl and Wermuth (Wiley-VCH, Weinheim, Germany, 2002).

The term 'solvate' is used herein to describe a molecular complex comprising the compound of the invention and a stoichiometric amount of one or more pharmaceutically acceptable solvent molecules, for example, ethanol. The term 'hydrate' is employed when said solvent is water.

Compounds of the invention which contain one or more actual or potential chiral centres, because of the presence of asymmetric carbon atoms, can exist as a number of enantiomers or diastereoisomers with R or S stereochemistry at each chiral centre. The invention includes all such enantiomers and diastereoisomers and mixtures thereof.

ASPECTS OF THE INVENTION

A particular subclass of compounds for antibacterial use in accordance with the invention is concerned consists of those of formula (IA)

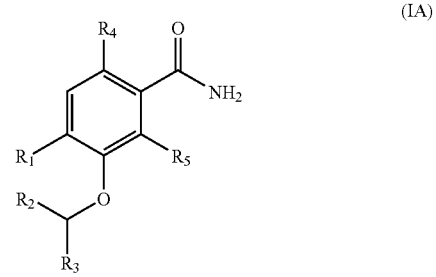

(IA)

wherein R$_4$ and R$_5$ are independently fluoro or chloro, or one of R$_4$ and R$_5$ is hydrogen while the other is fluoro or chloro, and R$_1$, R$_2$ and R$_3$ are as defined with reference to formula (I) above.

Another particular subclass of compounds for antibacterial use in accordance with the invention is concerned consists of those of formula (IB)

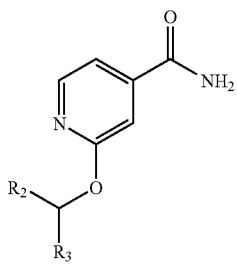
(IB)

wherein $R_2$ and $R_3$ are as defined with reference to formula (I) above.

In a narrow subclass of compounds for antibacterial use in accordance with the invention is concerned, including those of formula (IA) above, $R_1$ and $R_2$ are hydrogen; and in the compounds of formula (IB) above $R_2$ is hydrogen.

In the radical $R_3$, p may be 0, and m and/or n may be 1. Alternatively, p may be 1, and Z may be an optionally substituted carbocyclic or heteroaryl radical having 3 to 6 ring atoms or an optionally substituted bicyclic carbocyclic or heteroaryl radical having 5 to 10 ring atoms, which is linked to the -(Alk$^1$)$_m$- part of $R_3$ and to the -(Alk$^2$)$_n$-Q part of $R_3$ via ring carbon or nitrogen atoms. Examples of divalent radicals Z in this embodiment include those selected from the following, in either orientation:

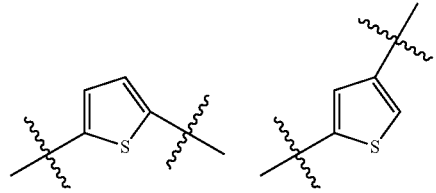

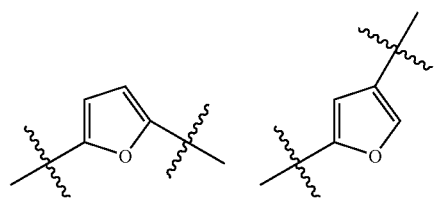

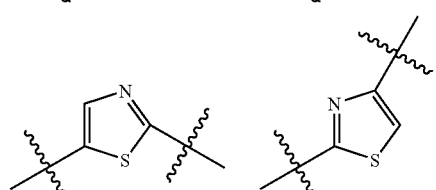

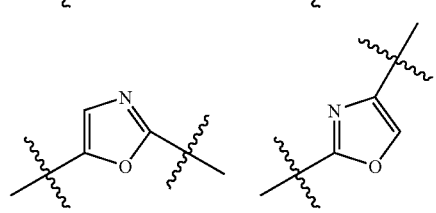

-continued

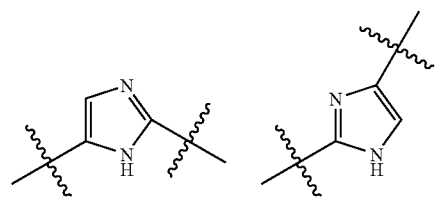

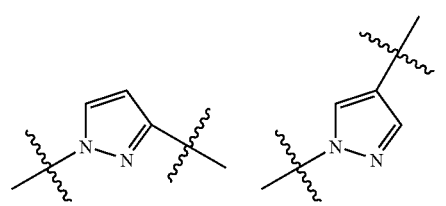

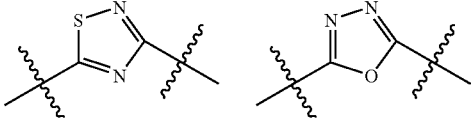

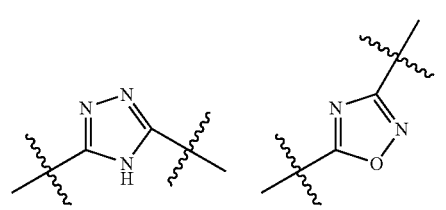

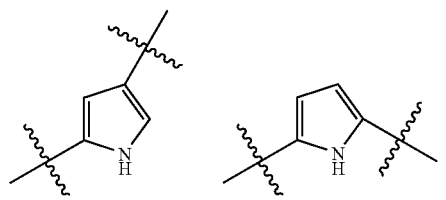

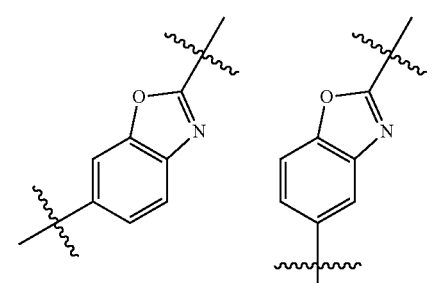

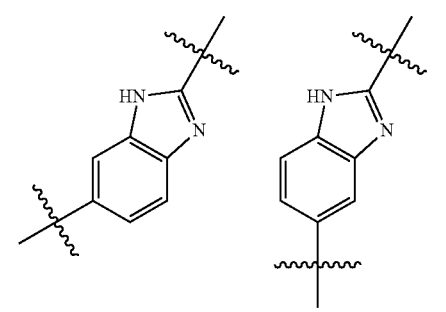

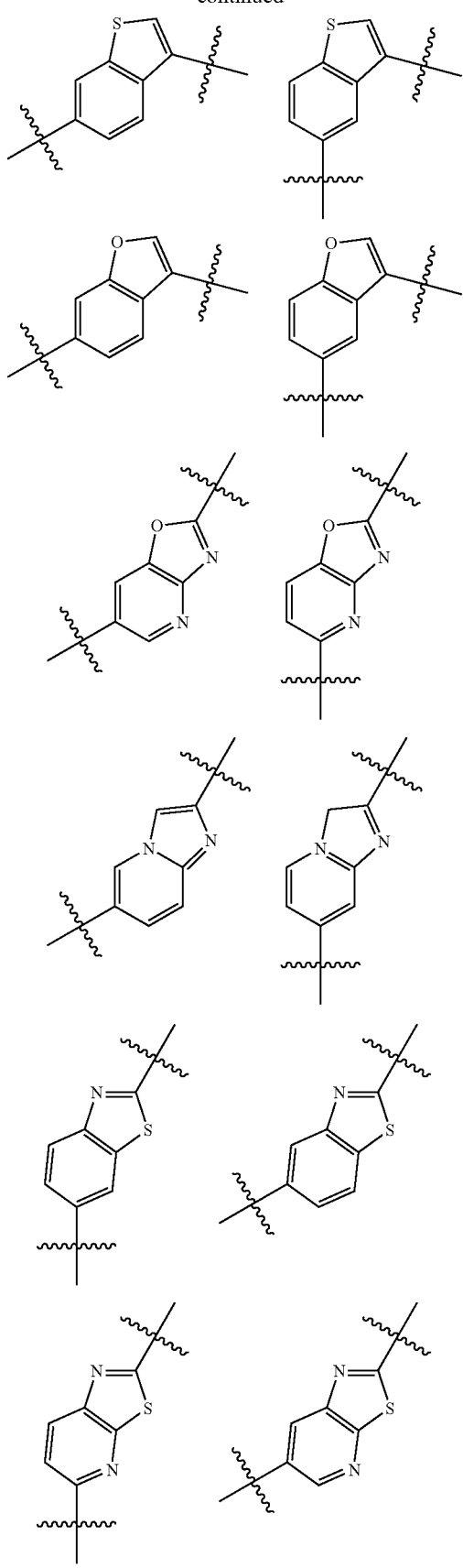

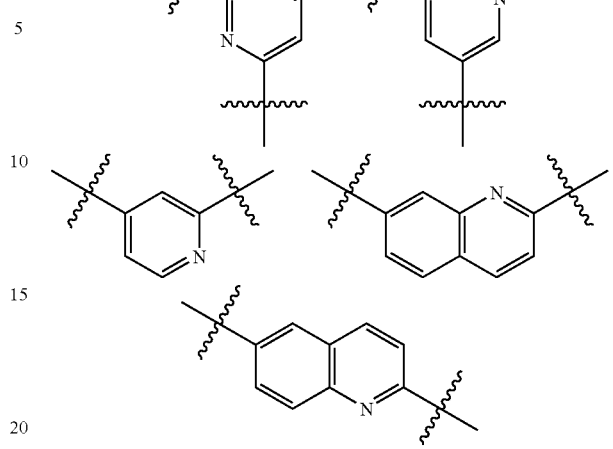

In another alternative embodiment p is 1, and Z is an optionally substituted monocyclic non-aromatic carbocyclic or heterocyclic radical having 3 to 6 ring atoms or an optionally substituted bicyclic non-aromatic carbocyclic or heterocyclic having 5 to 10 ring atoms, which is linked to the -(Alk$^1$)$_m$- part of R$_3$ and to the -(Alk$^2$)$_n$-Q part of R$_3$ via ring carbon or nitrogen atoms. Examples of Z radicals, which are optionally substituted, in this embodiment include those selected from the following, in either orientation:

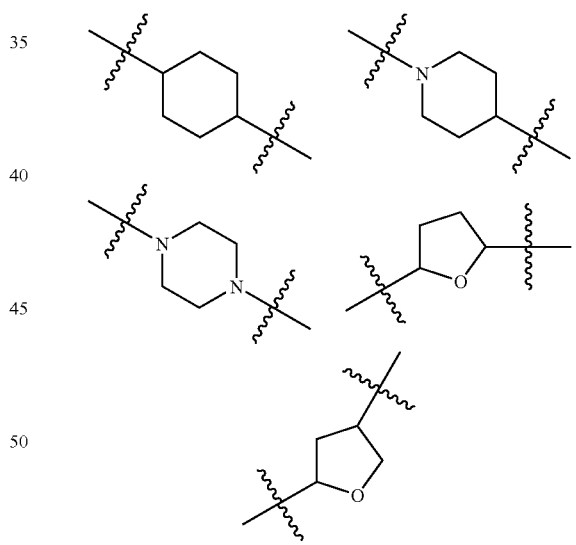

In the compounds with which the invention is concerned, and in any of the subclasses or embodiments of such compounds discussed above, Q may be hydrogen. However Q may also be a radical selected from any of the divalent Z radicals specifically identified above but with one of the unsatisfied valencies thereof satisfied with hydrogen or an optional substituent.

In the compounds with which the invention is concerned, and in any of the subclasses or embodiments of such compounds discussed above n and/or m may be 0.

In all compounds and classes of compounds with which the invention is concerned, it is typical that the radical R$_3$, when fully extended, does not exceed the length of an unbranched saturated hydrocarbon chain of 14 carbon atoms, ie does not exceed about 16 Angstroms. For example, that length may be equivalent to that of an unbranched saturated hydrocarbon chain of from 6 to 12, or 9 to 12 carbon atoms, ie from about 6 to about 14, and from about 10 to about 14 Angstroms respectively.

In the compounds with which the invention is concerned, $Alk^1$ and $Alk^2$, when present, may be, for example, optionally substituted straight chain $C_1$-$C_6$ alkylene, $C_2$-$C_6$ alkenylene, or $C_2$-$C_6$ alkynylene radicals, each of which may optionally terminate with or be interrupted by —O—, —S—, —S(O)—, —S(O$_2$)—, —NH—, —N(CH$_3$)—, or —N(CH$_2$CH$_3$)—, —C(=O)—, —O—(C=O)—, —C(=O)—O—.

Any optional substituents R and any optional substituents present in $Alk^1$, $Alk^2$, Z and Q may be selected from, for example, methyl, —OCH$_3$, —CF$_3$, —OCF$_3$, ethyl, cyclopropyl, oxo, hydroxyl, —F, —Cl, —Br, cyano, acetyl, amino, methylamino, dimethylamino, acetylamino, carbamate, —CONH$_2$, nitro, —COOH and —CH$_2$OH.

Compounds of formula (IC) per se, and salts, hydrates or solvates thereof constitute a distinct aspect of the invention:

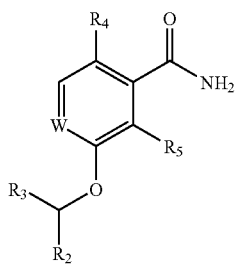

(IC)

wherein W is =C(R$_1$)— or =N—;

R$_1$ is hydrogen or an optional substituent and R$_2$ is hydrogen, methyl, or fluoro; or R$_1$ and R$_2$ taken together are —CH$_2$—, —CH$_2$CH$_2$—, —O—, or, in either orientation, —O—CH$_2$— or —OCH$_2$CH$_2$—;

R$_4$ and R$_5$ are independently fluoro or chloro, or one of R$_4$ and R$_5$ is hydrogen while the other is fluoro or chloro;

R$_3$ is a radical selected from those of the following formulae A-H, in which any vacant ring position is optionally substituted:

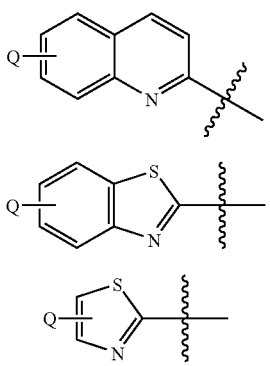

A

B

C

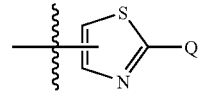

D

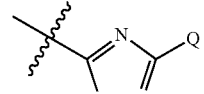

E

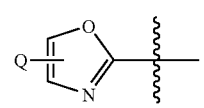

F

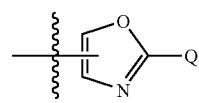

G

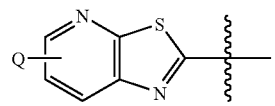

H wherein Q is as defined in relation to formula (I) above, and wherein any unsubstituted ring carbon is optionally substituted.

In compounds (IC) it is currently preferred that W be =CH— and R$_2$ be hydrogen.

In compounds (IC) Q in radical R$_3$ may be hydrogen or optionally substituted phenyl.

In a particular subset of compounds (IC), R$_3$ is optionally substituted quinolin-2-yl, benzothiazol-2-yl, thiazol-2-yl, thiazol-4-yl, thiazol-5-yl, oxadiazol-3-yl, oxadiazol-5-yl, oxazol-2-yl, oxazol-4-yl, oxazol-5-yl or thiazolopyridin-2-yl.

Optional substituents which may be present in R$_3$ in the compound per se aspect of the invention include methyl, —OCH$_3$, —CF$_3$, —OCF$_3$, ethyl, cyclopropyl, oxo, hydroxyl, —F, —Cl, —Br, cyano, acetyl, amino, methylamino, dimethylamino, acetylamino, carbamate, —CONH$_2$, nitro, —COOH and —CH$_2$OH.

Compounds of formula (ID) per se, and salts, hydrates or solvates thereof also constitute a distinct aspect of the invention:

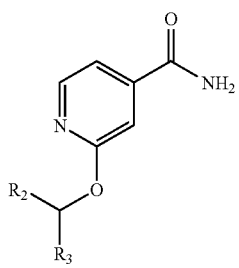

(ID)

wherein R$_2$ is hydrogen, methyl, or fluoro; and R$_3$ is as defined in relation to formula (IC).

Specific examples of compounds with which the invention is concerned include those of the Examples herein.

There are multiple synthetic strategies for the synthesis of the compounds (I) with which the present invention is concerned, but all rely on known chemistry, known to the synthetic organic chemist. Thus, compounds according to formula (I) can be synthesised according to procedures described in the standard literature and are well-known to the one skilled in the art. Typical literature sources are "*Advanced Organic Chemistry*", 4*th* Edition (Wiley), J March, "*Comprehensive Organic Transformation*", 2*nd* Edition (Wiley), R. C. Larock, "*Handbook of Heterocyclic Chemistry*", 2*nd* Edition (Pergamon), A. R. Katritzky), review articles such as found in "*Synthesis*", "*Acc. Chem. Res.*", "*Chem. Rev*", or primary literature sources identified by standard literature searches online or from secondary sources such as "*Chemical Abstracts*" or "*Beilstein*".

Compounds (I) may be prepared, for example, by introduction of the radical -(Alk$^1$)$_m$-(Z)$_p$-(Alk$^2$)$_n$-Q onto the hydroxyl group of a compound (II)

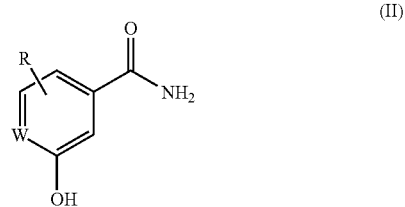

(II)

Further details of the synthetic approaches and schemes for the preparation of the intermediate (II) are given in the Examples herein.

As mentioned above, the compounds with which the invention are concerned are antibacterially active, since they inhibit bacterial growth. They are therefore of use in the treatment of bacterial infection in humans and non-human animals e.g. other mammals, birds and fish. The compounds include those which inhibit growth of Gram-positive organisms such as *Bacillus subtilis* and *Staphylococcus aureus* and some show activity against certain Gram-negative organisms also.

It will be understood that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy. As is required in the pharmaceutical art, safe and permitted doses will be determined by clinical trial, but daily dosages can vary within wide limits and will be adjusted to the individual requirements in each particular case. Typically, however, the dosage adopted for each route of administration when a compound is administered alone to adult humans is 0.0001 to 150 mg/kg body weight. Such a dosage may be given, for example, from 1 to 5 times daily. For intravenous injection a suitable daily dose is from 0.0001 to 150 mg/kg body weight. A daily dosage can be administered as a single dosage or according to a divided dose schedule.

The compounds with which the invention is concerned may be prepared for administration by any route consistent with their pharmacokinetic properties, such as oral, topical, or sterile parenteral solutions or suspensions. The orally administrable compositions may be in the form of tablets, capsules, powders, granules, lozenges, liquid or gel preparations. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

For topical application to the skin, the drug may be made up into a cream, lotion or ointment. Cream or ointment formulations which may be used for the drug are conventional formulations well known in the art, for example as described in standard textbooks of pharmaceutics such as the British Pharmacopoeia.

For topical application to the eye, the drug may be made up into a solution or suspension in a suitable sterile aqueous or non aqueous vehicle. Additives, for instance buffers such as sodium metabisulphite or disodium edeate; preservatives including bactericidal and fungicidal agents such as phenyl mercuric acetate or nitrate, benzalkonium chloride or chlorhexidine, and thickening agents such as hypromellose may also be included.

The active ingredient may also be administered parenterally in a sterile medium, either subcutaneously, or intravenously, or intramuscularly, or intrasternally, or by infusion techniques, in the form of sterile injectable aqueous or oleaginous suspensions. Depending on the vehicle and concentration used, the drug can either be suspended or dissolved in the vehicle. Advantageously, adjuvants such as a local anaesthetic, preservative and buffering agents can be dissolved in the vehicle.

Since the compounds with which the invention is concerned are antibacterially active and inhibit bacterial growth, they are also of use in treating bacterial contamination of a substrate, such as hospital instruments or work surfaces. In order to treat a contaminated substrate, the compounds may be applied to the site of such contamination in an amount sufficient to inhibit bacterial growth.

The following examples illustrate the synthesis of compounds with which the invention is concerned.

Analytical Method

The analytical methods used to characterise compounds included HPLC-MS and $^1$H NMR.

HPLC-MS Conditions—Method 1

| Mobile Phase: | A = Acetonitrile |  |  |
|---|---|---|---|
|  | B = 10 mM aqueous ammonium acetate |  |  |
|  | Time (mins) | % A | % B |
| Gradient: | 0.00 | 20 | 80 |
|  | 0.30 | 20 | 80 |
|  | 4.00 | 90 | 10 |
|  | 5.00 | 90 | 10 |
|  | 5.03 | 20 | 80 |
| Run Time: | 7 min |  |  |
| Flow Rate: | 1 ml/min |  |  |
| Injection vol: | variable dependant on sample concentration |  |  |
| Column temperature: | 40° C. |  |  |
| Column: | 50 × 4.6 mm Gemini C18; 5 µm |  |  |
| PDA Detector: | 220, 240, and 254 nm analysed |  |  |

HPLC-MS Conditions—Method 2

| Mobile Phase: | A = Acetonitrile<br>B = 10 mM aqueous ammonium acetate | | |
|---|---|---|---|
| | Time (mins) | % A | % B |
| Gradient: | 0.00 | 20 | 80 |
| | 0.30 | 20 | 80 |
| | 24.00 | 90 | 10 |
| | 28.00 | 90 | 10 |
| | 28.03 | 20 | 80 |
| Run Time: | 30 min | | |
| Flow Rate: | 1 ml/min | | |
| Injection vol: | variable dependant on sample concentration | | |
| Column temperature: | 40° C. | | |
| Column: | 50 × 4.6 mm Gemini C18; 5 μm | | |
| PDA Detector: | 220, 240, and 254 nm analysed | | |

HPLC-MS Conditions—Method 3

| Mobile Phase: | A = Acetonitrile + 0.1% Trifluoroacetic acid<br>B = Water + 0.1% Trifluoroacetic acid | | |
|---|---|---|---|
| | Time (mins) | % A | % B |
| Gradient: | 0.0 | 0 | 100 |
| | 1.8 | 95 | 5 |
| | 2.1 | 95 | 5 |
| | 2.3 | 0 | 100 |
| | 2.4 | 0 | 100 |
| Run time: | 2.4 min | | |
| Flow rate: | 1 ml/min | | |
| Injection vol: | 3 μl | | |
| Column temperature: | ambient (20° C.) | | |
| Column: | 50 × 2.0 mm Hypersil C18 BDS; 5 μm | | |
| UV Detector | Variable wavelength detector set at 215 nm | | |

HPLC-MS Conditions—Method 4

| Mobile Phase: | A = Acetonitrile + 0.1% Formic acid<br>B = Water + 0.1% Formic acid | | |
|---|---|---|---|
| | Time (mins) | % A | % B |
| Gradient: | 0.0 | 0 | 100 |
| | 2.5 | 100 | 0 |
| | 2.7 | 100 | 0 |
| | 2.71 | 0 | 100 |
| | 3.0 | 0 | 100 |
| Run time: | 3.5 min | | |
| Flow rate: | 1 ml/min | | |
| Injection vol: | 3 μl | | |
| Column temperature: | ambient (20° C.) | | |
| Column: | 50 × 2.1 mm Atlantis dC18; 5 μm | | |
| UV Detector | Variable wavelength detector set at 215 nm | | |

HPLC Analysis Conditions—Method 5

| Column | Purospher Star C-18 | | |
|---|---|---|---|
| Mobile Phase | ACN: 0.1% Formic acid (FA) | | |
| | Time % ACN | % FA | |
| Flow Mode | 0.00 | 10.0 | 90.0 |
| | 7.00 | 10.0 | 90.0 |
| | 15.00 | 90.0 | 10.0 |
| | 18.00 | 90.0 | 10.0 |
| | 25.00 | 10.0 | 90.0 |
| | 30.0 | 10.0 | 90.0 |
| Flow | 1.00 ml/min | | |
| UV Max | Variable | | |
| Column Temperature | 30° C. | | |
| Sample preparation | MeOH + DMSO + H₂O | | |
| Injection volume | Variable | | |

HPLC Analysis Conditions—Method 6

| Column | Discovery HSC-18 Column 250 × 4.6, 5.0 μm | | |
|---|---|---|---|
| Mobile Phase | A - Acetonitrile<br>B - 0.1% Formic acid | | |
| | Time | A | B |
| Flow Mode | 0.0 | 5.0 | 95.0 |
| | 4.0 | 5.0 | 95.0 |
| | 8.0 | 95.0 | 5.0 |
| | 16.0 | 950 | 5.0 |
| | 18.0 | 5 | 95.0 |
| | 20.0 | 5.0 | 95.0 |
| Flow | 1.00 ml/min | | |
| UV Max | 286.0 nm | | |
| Column Temperature | 45.0 deg. | | |
| Sample preparation | Acetonitrile:Water (50:50) | | |
| Injection volume | Variable | | |

HPLC Analysis Conditions—Method 7

| Column | Discovery HSC-18 Column 250 × 4.6, 5.0 μm | | |
|---|---|---|---|
| Mobile Phase | A - Acetonitrile<br>B - 0.1% Formic acid | | |
| | Time | A | B |
| Flow Mode | 0.0 | 5.0 | 95.0 |
| | 4.0 | 5.0 | 95.0 |
| | 8.0 | 95.0 | 5.0 |
| | 16.0 | 950 | 5.0 |
| | 18.0 | 5 | 95.0 |
| | 20.0 | 5.0 | 95.0 |
| Flow | 1.00 ml/min | | |
| UV Max | variable | | |
| Column Temperature | 45.0 deg. | | |
| Sample preparation | Methanol | | |
| Injection volume | Variable | | |

HPLC-MS Conditions—Method 8

| Mobile Phase: | A = Acetonitrile + 0.1% Formic acid<br>B = Water + 0.1% Formic acid | | |
|---|---|---|---|
| | Time (mins) | % A | % B |
| Gradient: | 0.0 | 10 | 90 |
| | 7.0 | 10 | 90 |
| | 15.0 | 90 | 10 |
| | 18.0 | 90 | 10 |
| | 25.0 | 10 | 90 |
| | 30.0 | 10 | 90 |
| Run time: | 30.0 min | | |
| Flow rate: | 1 ml/min | | |
| Column temperature: | Ambient (25° C.) | | |
| Column: | 250 × 4.6 mm Xbridge dC18; 5 μm | | |
| UV Detector | Variable wavelength detector set at 215 nm | | |

HPLC-MS Conditions—Method 9

| Mobile Phase: | A = Acetonitrile + 0.1% Formic acid<br>B = Water + 0.1% Formic acid |
|---|---|

-continued

| | Time (mins) | % A | % B |
|---|---|---|---|
| Gradient: | 0.0 | 10 | 90 |
| | 7.0 | 10 | 90 |
| | 15.0 | 90 | 10 |
| | 18.0 | 90 | 10 |
| | 25.0 | 10 | 90 |
| | 30.0 | 10 | 90 |
| Run time: | 30.0 min | | |
| Flow rate: | 1 ml/min | | |
| Column temperature: | ambient (25° C.) | | |
| Column: | 250 × 4.6 mm Purospher Star dC18; 5 μm | | |
| UV Detector | Variable wavelength detector set at 262 nm | | |

NMR $^1$H NMR spectra were consistent with the required structures.

Melting points were measured on a Stuart Scientific SMP10 apparatus and are uncorrected.

Yields given are not optimised.

EXPERIMENTAL PROCEDURES

Scheme 1:

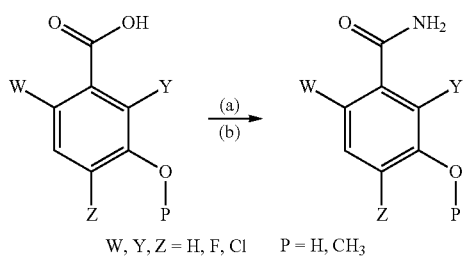

W, Y, Z = H, F, Cl    P = H, CH$_3$ (a) SOCl$_2$, toluene, reflux;
(b) aqueous NH$_3$.

General Procedure for the Conversion of a Carboxylic Acid to a Carboxylic Amide (Method A). 3-Hydroxybenzenecarboxamide.

3-Hydroxybenzoic acid (110.5 g, 0.8 mol, 1 equiv.) was suspended in toluene (500 ml) and thionyl chloride (88.0 ml, 1.2 mol, 1.5 equiv.) was added slowly, at room temperature. The solution was heated to reflux where it was maintained for 5 h. After this time, the reaction was cooled to room temperature and concentrated in vacuo. The residue was dissolved in tetrahydrofuran (300 ml) and cooled in an ice-methanol bath. Concentrated aqueous ammonia solution (~300 ml) was added slowly, dropwise and the reaction mixture was warmed slowly to room temperature where it was stirred for 16 h. The reaction mixture was concentrated in vacuo and the resulting solid was suspended in water and filtered. The collected solid was washed with additional water (×3) and then dried in vacuo to give 3-hydroxybenzamide as an off-white solid (79.9 g, 72.8%) mp 167-168° C. HPLC-MS (method 1): m/z 136 [M−H]$^-$. Rt=1.21 min. $^1$H NMR (d$_6$-DMSO) δ=9.53 (s, 1H), 7.78 (s, 1H), 7.30-7.15 (m, 4H), 6.88 (d, J=8 Hz, 1H).

General Procedure for the Alkylation of Phenols Using Alkyl Halides (Method B).

Scheme 2:

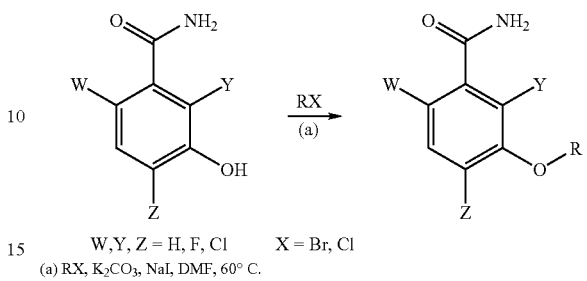

W, Y, Z = H, F, Cl    X = Br, Cl (a) RX, K$_2$CO$_3$, NaI, DMF, 60° C.

Example 1

3-Nonyloxy-benzenecarboxamide

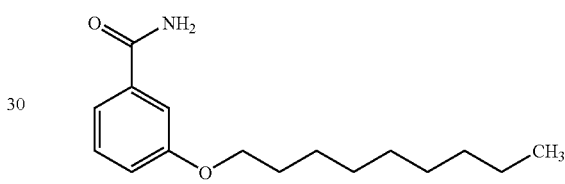

To a solution of 3-hydroxybenzenecarboxamide (200 mg, 1.46 mmol, 1 equiv.) in DMF (3 ml) was added K$_2$CO$_3$ (302 mg, 2.19 mmol, 1.5 equiv.) and NaI (43.5 mg, 0.29 mmol, 0.2 equiv). The suspension was stirred for 5 min before n-nonyl chloride (0.32 ml, 1.61 mmol, 1.1 equiv) was introduced. The resulting mixture was warmed to 60° C. where it was maintained for 16 h. After this time, the reaction was cooled to room temperature and partitioned between EtOAc and water. The organic phase was separated, washed with additional water (×2), dried (MgSO$_4$), filtered and concentrated in vacuo to reveal a colourless solid. In the case of 3-n-nonyloxybenzamide this colourless solid was stirred for 5 min with MeOH (~0.5 ml) [NB: 3-n-nonyloxybenzamide partially soluble in MeOH] and then filtered to reveal the desired compound as a colourless solid (116 mg, 30%). HPLC-MS (method 3): m/z 264 [M+H]$^+$, Rt=1.80 min. $^1$H NMR (d$_6$-DMSO) δ=7.95 (s, 1H), 7.44-7.31 (m, 4H), 7.06 (ddd, J=8 Hz, J=2 Hz, J=1 Hz, 1H), 3.99 (t, J=6.5 Hz, 2H), 1.72 (quintet, J=6.5 Hz, 2H), 1.42 (m, 2H), 1.34-1.26 (m, 10H), 0.86 (t, J=6.5 Hz, 3H).

NB 1: The final purification step was dependent on the nature of the R group. Other purification methods used in course of the library synthesis were:

1. Recrystallisation (e.g. neat MeOH, EtOAc/hexanes, CH$_3$CN).

2. Normal phase column chromatography (silica gel).

3. Preparative HPLC or preparative TLC.

NB 2: In the case of water soluble target compounds, the aqueous phase was concentrated in vacuo and then washed with MeOH. The methanolic fractions were concentrated in vacuo and the crude product purified by preparative HPLC.

Examples 2 to 44 (Table A)

Examples 2 to 44 were synthesised according to Method B, scheme 2

| Example | 2 | 3 | 4 | 5 |
|---|---|---|---|---|
| Structure | 3-propoxybenzamide | 3-isopropoxybenzamide | 3-(cyclopropylmethoxy)benzamide | 3-pentyloxybenzamide |
| HPLC-MS: method no., m/z, ion | 3, 180, [M + H]⁺ | 3, 180, [M + H]⁺ | 3, 192, [M + H]⁺ | 3, 208, [M + H]⁺ |
| Rt (min) | 1.10 | 1.05 | 1.11 | 1.78 |

| Example | 6 | 7 | 8 |
|---|---|---|---|
| Structure | 3-allyloxybenzamide | 3-butoxybenzamide | 3-hexyloxybenzamide |
| HPLC-MS: method no., m/z, ion | 3, 178, [M + H]⁺ | 3, 194, [M + H]⁺ | 3, 222, [M + H]⁺ |
| Rt (min) | 1.03 | 1.63 | 1.48 |

| Example | 9 | 10 | 11 |
|---|---|---|---|
| Structure | 3-(2-methoxyethoxy)benzamide | 3-(3-phenoxypropoxy)benzamide | 3-(2-methylallyloxy)benzamide |
| HPLC-MS: method no., m/z, ion | 3, 196, [M + H]⁺ | 3, 286, [M + H]⁺ | 3, 192, [M + H]⁺ |
| Rt (min) | 1.08 | 1.46 | 1.23 |

| Example | 12 | 13 | 14 |
|---|---|---|---|
| Structure | 3-(hept-6-enyloxy)benzamide | 3-(3-methylbutoxy)benzamide | 3-(4-methylpentyloxy)benzamide |
| HPLC-MS: method no., m/z, ion | 3, 248, [M + H]⁺ | 3, 208, [M + H]⁺ | 3, 222, [M + H]⁺ |
| Rt (min) | 1.59 | 1.38 | 1.48 |

-continued

| Example | 15 | 16 | 17 |
|---|---|---|---|
| Structure | 3-(hex-5-enyloxy)benzamide | 3-(2-propoxyethoxy)benzamide | 3-(hept-6-enyloxy)benzamide |
| HPLC-MS: method no., m/z, ion | 3, 220, [M + H]⁺ | 3, 224, [M + H]⁺ | 3, 234, [M + H]⁺ |
| Rt (min) | 1.40 | 1.16 | 1.51 |

| Example | 18 | 19 |
|---|---|---|
| Structure | 5-(3-carbamoylphenoxy)pentyl acetate | 3-(octyloxy)benzamide |
| HPLC-MS: method no., m/z, ion | 3, 266, [M + H]⁺ | 3, 250, [M + H]⁺ |
| Rt (min) | 1.20 | 1.67 |

| Example | 20 | 21 | 22 |
|---|---|---|---|
| Structure | 3-(4-phenylbutoxy)benzamide | 3-(5-phenylpentyloxy)benzamide | 3-(4-methylpentyloxy)benzamide |
| HPLC-MS: method no., m/z, ion | 3, 270, [M + H]⁺ | 3, 284, [M + H]⁺ | 3, 236, [M + H]⁺ |
| Rt (min) | 1.50 | 1.61 | 1.63 |

| Example | 23 | 24 | 25 |
|---|---|---|---|
| Structure | 3-(quinolin-2-ylmethoxy)benzamide | 3-(heptyloxy)benzamide | ethyl 4-(3-carbamoylphenoxy)butanoate |
| HPLC-MS: method no., m/z, ion | 3, 279, [M + H]⁺ | 3, 236, [M + H]⁺ | 3, 252, [M + H]⁺ |
| Rt (min) | 1.01 | 1.62 | 1.18 |

-continued

| Example | 26 | 27 | 28 |
|---|---|---|---|
| Structure | 3-(4-methoxy-4-oxobutoxy)benzamide | cyclohexyl 2-(3-carbamoylphenoxy)acetate | 3-(2-cycloheptylethoxy)benzamide |
| HPLC-MS: method no., m/z, ion | 3, 238, [M + H]+ | 3, 278, [M + H]+ | 3, 262, [M + H]+ |
| Rt (min) | 1.08 | 1.33 | 1.65 |

| Example | 29 | 30 | 31 |
|---|---|---|---|
| Structure | 3-((3-methylbenzyl)oxy)benzamide | 3-((E)-but-2-enyloxy)benzamide | 3-(hept-2-ynyloxy)benzamide |
| HPLC-MS: method no., m/z, ion | 3, 242, [M + H]+ | 3, 192, [M + H]+ | 3, 246, [M + H]+ |
| Rt (min) | 1.43 | 1.20 | 1.49 |

| Example | 32 | 33 | 34 |
|---|---|---|---|
| Structure | 3-(oct-4-ynyloxy)benzamide | ethyl 2-(3-carbamoylphenoxy)acetate | 3-(2-(4-fluorophenyl)ethoxy)benzamide |
| HPLC-MS: method no., m/z, ion | 3, 260, [M + H]+ | 3, 224, [M + H]+ | 3, 260, [M + H]+ |
| Rt (min) | 1.50 | 1.03 | 1.38 |

| Example | 35 |
|---|---|
| Structure | 3-(2-(4-methoxyphenyl)ethoxy)benzamide |
| HPLC-MS: method no., m/z, ion | 3, 272, [M + H]+ |
| Rt (min) | 1.35 |

-continued

| Example | 36 | 37 |
|---|---|---|
| Structure | 3-(6-phenylhexyloxy)benzamide | ethyl 6-(3-carbamoylphenoxy)hexanoate |
| Yield (%) | 70 | 70 |
| mp (° C.) | 100-101 | 98-99 |
| HPLC-MS: method no., m/z, ion | 1, 298, [M + H]$^+$ | 1, 280, [M + H]$^+$ |
| Rt (min) | 4.72 | 3.62 |

| Example | 38 | 39 |
|---|---|---|
| Structure | methyl 9-(3-carbamoylphenoxy)nonanoate | 3-(2-methylpentyloxy)benzamide |
| Yield (%) | 44 | 7 |
| mp (° C.) | 118-120 | 94-95 |
| HPLC-MS: method no., m/z, ion | 1, 322, [M + H]$^+$ | 1, 263, [M + H + CH$_3$CN]$^+$ |
| Rt (min) | 4.41 | 4.16 |

| Example | 40 | 41 | 42 |
|---|---|---|---|
| Structure | 3-(oct-3-enyloxy)benzamide | butyl 2-(3-carbamoylphenoxy)acetate | 3-(4-hydroxybutoxy)benzamide |
| Yield (%) | 46 | 56 | 16 |
| mp (° C.) | — | 135-137 | 107-109 |
| HPLC-MS: method no., m/z, ion | 1, 289, [M + H + CH$_3$CN]$^+$ | 1, 293, [M + H + CH$_3$CN]$^+$ | 1, 210, [M + H + CH$_3$CN]$^+$ |
| Rt (min) | 4.52 | 3.36 | 3.42 |

| Example | 43 | 44 |
|---|---|---|
| Structure | butyl 4-(3-carbamoylphenyl)butanoate | 3-(4-cyclohexylbutoxy)benzamide |
| Yield (%) | 40 | 54 |
| mp (° C.) | 70-72 | 109-111 |
| HPLC-MS: method no., m/z, ion | 1, 280, [M + H]$^+$ | 1, 317, [M + H + CH$_3$CN]$^+$ |
| Rt (min) | 3.76 | 5.11 |

Table of names of product compounds; Examples 2-44:

| Example | Compound name |
|---|---|
| 2 | 3-Propoxybenzenecarboxamide |
| 3 | 3-Isopropoxybenzenecarboxamide |
| 4 | 3-(Cyclopropylmethoxy)benzenecarboxamide |
| 5 | 3-(Pentyloxy)benzenecarboxamide |
| 6 | 3-(Allyloxy)benzenecarboxamide |
| 7 | 3-Butoxybenzenecarboxamide |
| 8 | 3-(Hexyloxy)benzenecarboxamide |
| 9 | 3-(2-Methoxyethoxy)benzenecarboxamide |
| 10 | 3-(4-Phenoxybutoxy)benzenecarboxamide |
| 11 | 3-[(2-Methyl-2-propenyl)oxy]benzenecarboxamide |
| 12 | 3-(7-Octenyloxy)benzenecarboxamide |
| 13 | 3-(Isopentyloxy)benzenecarboxamide |
| 14 | 3-[(4-Methylpentyl)oxy]benzenecarboxamide |
| 15 | 3-(5-Hexenyloxy)benzenecarboxamide |
| 16 | 3-(2-Propoxyethoxy)benzenecarboxamide |
| 17 | 3-(6-Heptenyloxy)benzenecarboxamide |
| 18 | 5-[3-(Aminocarbonyl)phenoxy]pentyl acetate |
| 19 | 3-(Octyloxy)benzenecarboxamide |
| 20 | 3-(4-Phenylbutoxy)benzenecarboxamide |
| 21 | 3-[(5-Phenylpentyl)oxy]benzenecarboxamide |
| 22 | 3-[(5-Methylhexyl)oxy]benzenecarboxamide |
| 23 | 3-(2-Quinolinylmethoxy)benzenecarboxamide |
| 24 | 3-(Heptyloxy)benzenecarboxamide |
| 25 | Ethyl 4-[3-(aminocarbonyl)phenoxy]butanoate |
| 26 | Methyl 4-[3-(aminocarbonyl)phenoxy]butanoate |
| 27 | Cyclohexyl 2-[3-(aminocarbonyl)phenoxy]acetate |
| 28 | 3-(2-Cycloheptylethoxy)benzenecarboxamide |
| 29 | 3-[(3-Methylbenzyl)oxy]benzenecarboxamide |
| 30 | 3-[2-Butenyloxy]benzenecarboxamide |
| 31 | 3-(2-Octynyloxy)benzenecarboxamide |
| 32 | 3-(4-Nonynyloxy)benzenecarboxamide |
| 33 | Ethyl 2-[3-(aminocarbonyl)phenoxy]acetate |
| 34 | 3-[(4-Fluorophenethyl)oxy]benzenecarboxamide |
| 35 | 3-[(4-Methoxyphenethyl)oxy]benzenecarboxamide |
| 36 | 3-[(6-Phenylhexyl)oxy]benzenecarboxamide |
| 37 | Ethyl 6-[3-(aminocarbonyl)phenoxy]hexanoate |
| 38 | Methyl 10-[3-(aminocarbonyl)phenoxy]decanoate |
| 39 | 3-[(2-Methylpentyl)oxy]benzenecarboxamide |
| 40 | 3-[(E)-3-Octenyloxy]benzenecarboxamide |
| 41 | Butyl 2-[3-(aminocarbonyl)phenoxy]acetate |
| 42 | 3-(4-Hydroxybutoxy)benzenecarboxamide |
| 43 | Butyl 4-[3-(aminocarbonyl)phenoxy]butanoate |
| 44 | 3-(4-Cyclohexylbutoxy)benzenecarboxamide |

General Procedure for the Alkylation of Phenols Using Alcohols Via Mitsunobu Reaction (Method C).

Scheme 3:

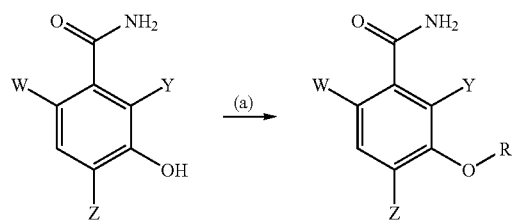

W, Y, Z = H, F, Cl
(a) ROH, PPh$_3$-PS, DIAD, Et$_3$N, THF, r.t.

Example 45

3-[(Z)-5-Decenyloxy]benzenecarboxamide

To a suspension of polymer-supported triphenyl phosphine (1.4 g, 3 mmol, based on a loading of 2.15 mmol/g [purchased from Argonaut], 1.5 equiv.) swollen in THF (20 ml) at room temperature was added diisopropylazodicarboxylate (0.47 ml, 2.4 mmol, 1.2 equiv.). The mixture was shaken for 5 min before 3-hydroxybenzamide (274 mg, 2 mmol, 1 equiv.), triethylamine (0.28 ml, 2 mmol, 1 equiv.) and cis-5-decenol (313 mg, 2 mmol, 1 equiv.) were added. The resulting suspension was shaken at room temperature for 16 h and then filtered. The resin was washed with additional THF (×3) and then the combined filtrate and washings were concentrated under reduced pressure, to give the crude product as a colourless semi-solid. It was purified by column chromatography on silica eluting with EtOAc/hexane (20%-40% gradient) to give the desired compound as a white solid (390 mg, 71%), mp 98-100° C. HPLC-MS (method 1): m/z 276 [M+H]$^+$, Rt=5.00 min. $^1$H NMR (CDCl$_3$) δ=7.35 (s, 1H), 7.32-7.28 (m, 2H), 7.08-7.02 (m, 1H), 6.18 (br, 2H), 5.41-5.32 (m, 2H), 3.98 (t, J=6.4 Hz, 2H), 2.12-2.05 (m, 2H), 2.05-1.98 (m, 2H), 1.79 (m, 2H), 1.51 (m, 2H), 1.34-1.28 (m, 4H), 0.88 (t, J=7.0 Hz, 3H).

NB 1: In some cases diethylazodicarboxylate (0.38 ml, 2.4 mmol, 1.2 equiv.) was used instead of diisopropylazodicarboxylate.

NB 2: In some cases unsupported triphenyl phosphine was used. In the case of phenols containing fluorine atoms, no product could be detected when using polymer-supported triphenyl phosphine and so the reactions were performed with triphenyl phosphine.

Examples 46-61 (Table B)

Examples 46 to 61 were synthesised according to Method C, scheme 3

| Example | 46 | 47 |
|---|---|---|
| Structure | 3-benzamide-O-(CH2)9-C≡CH | 3-benzamide-O-CH2-CH=CH-(CH2)5-CH3 (cis) |
| Yield (%) | 34 | 7.5 |
| mp (° C.) | 94-96 | 93-94 |
| HPLC-MS: method no., m/z, ion | 1, 288, [M + H]$^+$ | 1, 262, [M + H]$^+$ |
| Rt (min) | 4.73 | 4.78 |
| Example | 48 | 49 |
| Structure | 3-benzamide-O-(CH2)3-C≡C-(CH2)3-CH3 | 3-benzamide-O-CH2-CH=CH-(CH2)4-CH3 |
| Yield (%) | 56 | — |
| mp (° C.) | 133-134 | — |
| HPLC-MS: method no., m/z, ion | 1, 274, [M + H]$^+$ | 2, 262, [M + H]$^+$ |
| Rt (min) | 4.66 | 14.55 |
| Example | 50 | 51 |
| Structure | 3-benzamide-O-CH2-C≡C-(CH2)4-CH3 | 3-benzamide-O-(CH2)2-C≡C-(CH2)4-CH3 |
| Yield (%) | 10 | 14 |
| mp (° C.) | 88-90 | 133-135 |
| HPLC-MS: method no., m/z, ion | 1, 260, [M + H]$^+$ | 1, 260, [M + H]$^+$ |
| Rt (min) | 4.48 | 4.42 |
| Example | 52 | 53 |
| Structure | 3-benzamide-O-(CH2)3-CH=CH-CH2-CH3 | 3-benzamide-O-(CH2)2-O-(CH2)4-CH3 |

|  | 54 | 55 |
|---|---|---|
| Yield (%) | 44 | 60 |
| mp (° C.) | 101-102 | 86-87 |
| HPLC-MS: method no., m/z, ion | 1, 248, [M + H]⁺ | 1, 252, [M + H]⁺ |
| Rt (min) | 4.46 | 3.81 |

| Example | 54 | 55 |
|---|---|---|
| Structure | (3-(2-hexyloxyethoxy)benzamide) | (3-((3,7,11-trimethyldodeca-6,10-dien-1-yl)oxy)benzamide) |
| Yield (%) | 45 | — |
| mp (° C.) | 94-95 | — |
| HPLC-MS: method no., m/z, ion | 1, 266, [M + H]⁺ | 1, 330, [M + H]⁺ |
| Rt (min) | 4.14 | 5.64 |

| Example | 56 | 57 |
|---|---|---|
| Structure | (benzamide with octadienyloxy) | (benzamide with propyl-oxazole-CF3-tBu) |
| Yield (%) | 57 | 33 |
| mp (° C.) | 94-95 | 99-100 |
| HPLC-MS: method no., m/z, ion | 1, 260, [M + H]⁺ | 1, 371, [M + H]⁺ |
| Rt (min) | 4.47 | 4.50 |

| Example | 58 | 59 |
|---|---|---|
| Structure | (benzamide with nonenyloxy) | (benzamide with hexynyloxy) |
| Yield (%) | 56 | 13 |
| mp (° C.) | 103-104 | 135-136 |
| HPLC-MS: method no., m/z, ion | 1, 276, [M + H]⁺ | 1, 246, [M + H]⁺ |
| Rt (min) | 5.08 | 4.08 |

| Example | 60 | 61 |
|---|---|---|
| Structure | | |

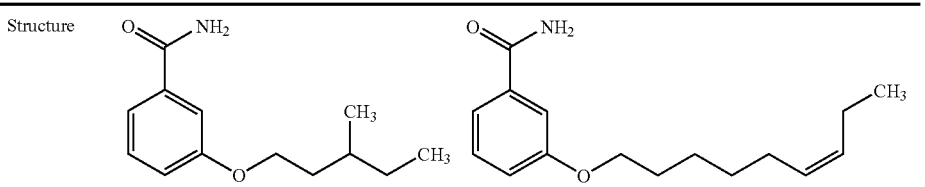

-continued

| | | |
|---|---|---|
| Yield (%) | 57 | 64 |
| mp (° C.) | 106-108 | — |
| HPLC-MS: method no., m/z, ion | 1, 263, [M + H + CH₃CN]⁺ | 1, 303, [M + H + CH₃CN]⁺ |
| Rt (min) | 4.07 | 4.27 |

Table of names of product compounds; Examples 46-61:

| Example | Compound name |
|---|---|
| 46 | 3-(10-Undecynyloxy)benzenecarboxamide |
| 47 | 3-[(Z)-2-Nonenyloxy]benzenecarboxamide |
| 48 | 3-(5-Decynyloxy)benzenecarboxamide |
| 49 | 3-[(E)-2-Nonenyloxy]benzenecarboxamide |
| 50 | 3-(2-Nonynyloxy)benzenecarboxamide |
| 51 | 3-(3-Nonynyloxy)benzenecarboxamide |
| 52 | 3-[(Z)-5-Octenyloxy]benzenecarboxamide |
| 53 | 3-[2-(Pentyloxy)ethoxy]benzenecarboxamide |
| 54 | 3-[2-(Hexyloxy)ethoxy]benzenecarboxamide |
| 55 | 3-{[(5E)-2,6,10-Trimethyl-5,9-undecadienyl]oxy}benzenecarboxamide |
| 56 | 3-[(2E,6Z)-2,6-Nonadienyloxy]benzenecarboxamide |
| 57 | 3-{3-[2-(tert-Butyl)-5-(trifluoromethyl)-1,3-oxazol-4-yl]propoxy}benzenecarboxamide |
| 58 | 3-[(E)-5-Decenyloxy]benzenecarboxamide |
| 59 | 3-(3-Octynyloxy)benzenecarboxamide |
| 60 | 3-[(3-Methylpentyl)oxy]benzenecarboxamide |
| 61 | 3-[(Z)-6-Nonenyloxy]benzenecarboxamide |

Scheme 4:

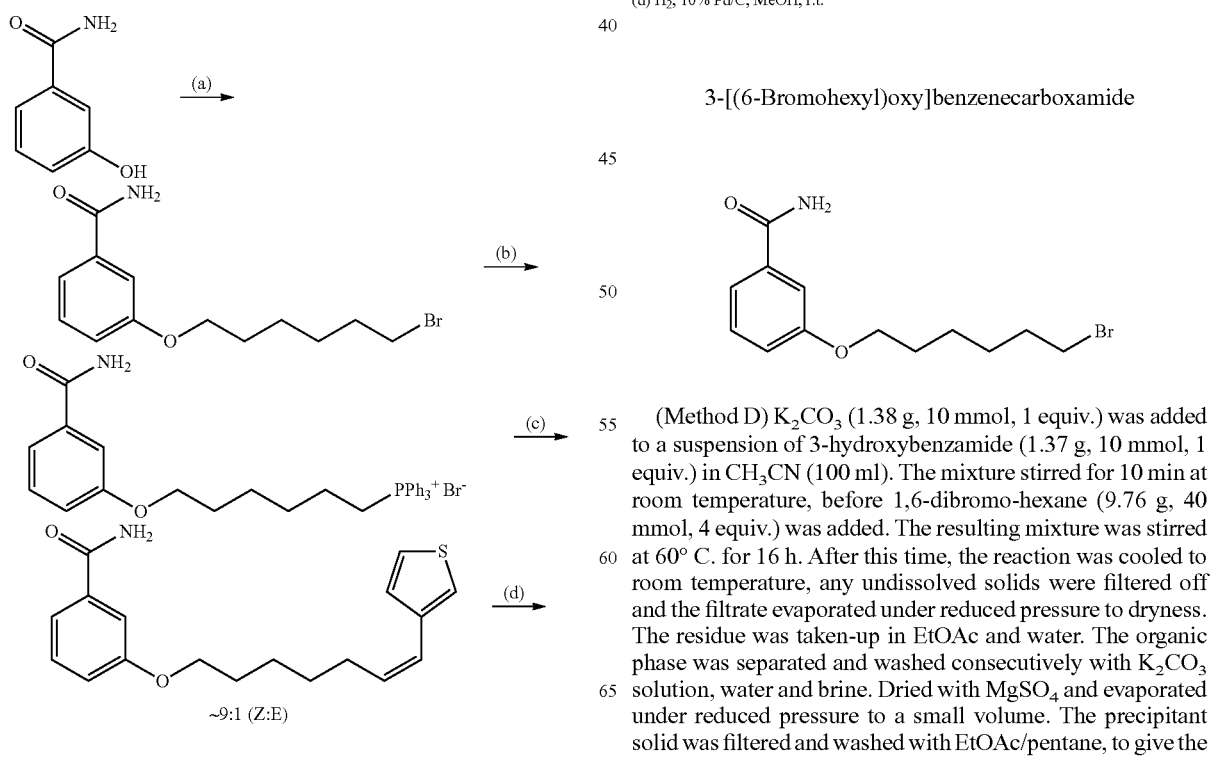

(a) Br(CH₂)₆Br, K₂CO₃, CH₃CN, 60° C.;
(b) PPh₃, CH₃CN, reflux;
(c) (i) KHMDS, toluene, 0° C.; (ii) RCHO, -78° C. to r.t.;
(d) H₂, 10% Pd/C, MeOH, r.t.

3-[(6-Bromohexyl)oxy]benzenecarboxamide

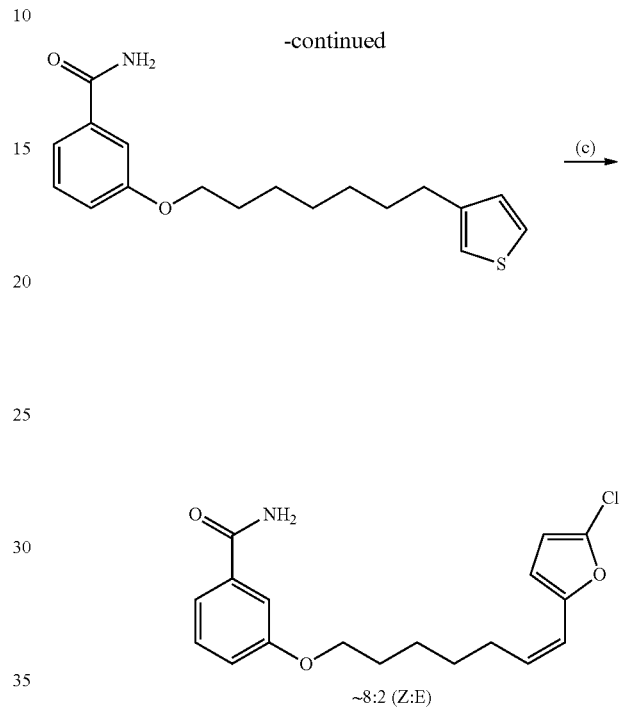

(Method D) K₂CO₃ (1.38 g, 10 mmol, 1 equiv.) was added to a suspension of 3-hydroxybenzamide (1.37 g, 10 mmol, 1 equiv.) in CH₃CN (100 ml). The mixture stirred for 10 min at room temperature, before 1,6-dibromo-hexane (9.76 g, 40 mmol, 4 equiv.) was added. The resulting mixture was stirred at 60° C. for 16 h. After this time, the reaction was cooled to room temperature, any undissolved solids were filtered off and the filtrate evaporated under reduced pressure to dryness. The residue was taken-up in EtOAc and water. The organic phase was separated and washed consecutively with K₂CO₃ solution, water and brine. Dried with MgSO₄ and evaporated under reduced pressure to a small volume. The precipitant solid was filtered and washed with EtOAc/pentane, to give the desired compound as a white solid (2.0 g, 67%), mp 115-117° C. HPLC-MS (method 1): m/z 300 [M]⁺, 302 [M+2H]⁺, Rt=4.08 min.

6-[3-(Aminocarbonyl)phenoxy]hexyl(triphenyl) phosphonium bromide

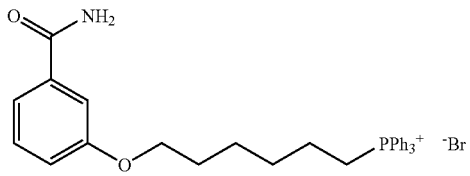

A mixture of 3-[(6-bromohexyl)oxy]benzenecarboxamide (2.10 g, 7 mmol, 1 equiv.) and triphenylphosphine (1.93 g, 7.35 mmol, 1.05 equiv.) in CH₃CN (30 ml) was heated under reflux for 72 h. The solvent was evaporated under reduced pressure and the residue was triturated with dry Et₂O until it solidified. The solid was filtered and dried in vacuo to give the desired compound as a white solid (4.0 g, 100%). HPLC-MS (method 1): m/z 482 [M–Br]⁺, Rt=3.65 min.

Example 62

3-{[(Z)-7-(3-Thienyl)-6-heptenyl]oxy}benzenecarboxamide

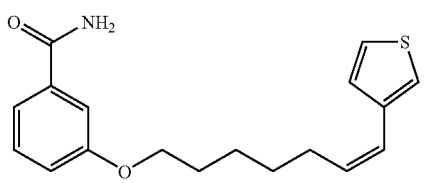

(Method E) To a stirred suspension of 6-[3-(aminocarbonyl)phenoxy]hexyl(triphenyl)phosphonium bromide (2.0 g, 3.55 mmol, 1.2 equiv.) in anhydrous toluene (28 ml) was added a solution of potassium bis(trimethylsilyl)amide (0.5M; 7.1 ml, 3.55 mmol, 1.2 equiv.) in toluene, slowly, dropwise over a period of 15 min at 0° C., under N₂. The dark orange solution was stirred for another 20 min at 0° C. and cooled to −78° C., when thiophene-3-carboxaldehyde was instantly added, and the temperature was left to rise—from −78° C. to r.t. The light yellow mixture was stirred at r.t. for 16 h. The reaction mixture was quenched with saturated aqueous NH₄Cl (20 ml) and the solvent was evaporated under reduced pressure. The residue was taken-up in CH₂Cl₂ and H₂O, the organic phase was separated, washed with brine and dried (Na₂SO₄). The solved was evaporated under reduced pressure and the residue was purified by column chromatography on silica eluting with EtOAc/hexane (10%-50% gradient) to give the desired compound as an off-white solid (300 mg, 35%), mp 71-73° C. By ¹H NMR analysis it consisted of a mixture of Z:E (90:10). HPLC-MS (method 1): m/z 316 [M+H]⁺, Rt=4.62 min.

Example 63

3-{[7-(3-Thienyl)heptyl]oxy}benzenecarboxamide

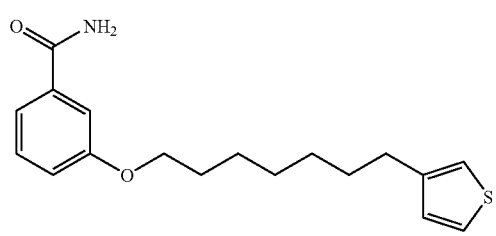

To a solution of example 62 3-{[(Z)-7-(3-Thienyl)-6-heptenyl]oxy}benzene carboxamide (260 mg, 0.82 mmol) in MeOH (8 ml), 10% Pd/C (30 mg) was added. The mixture was stirred under H₂ at r.t for 3 days. The catalyst was removed by filtration through a pad of Celite and the solvent was evaporated under reduced pressure, to a small volume. The precipitant solid was filtered and rinsed with Et₂O/pentane to give the desired compound as a white solid (130 mg, 48%), mp 97-100° C. HPLC-MS (method 1): m/z 318 [M+H]⁺, Rt=4.87 min.

Example 64

3-{[(Z)-7-(5-Chloro-2-furyl)-6-heptenyl]oxy}benzenecarboxamide

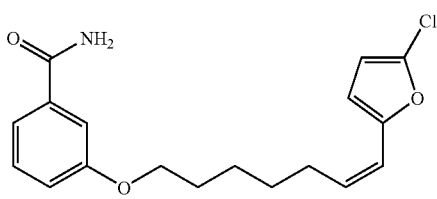

Synthesised from 6-[3-(aminocarbonyl)phenoxy]hexyl(triphenyl)phosphonium bromide according to Method E. Yield 72%, mp 53-56° C. By ¹H NMR analysis it consisted of a mixture of Z:E (81:19). HPLC-MS (method 1): m/z 334 [M+H]⁺, Rt=4.80 min.

Scheme 5:

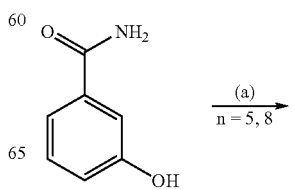

-continued

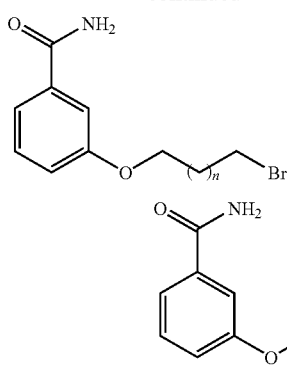

(a) Br(CH$_2$)$_n$Br (n = 5, 8) K$_2$CO$_3$, CH$_3$CN, 60° C.;
(b) Lithium acetylide ethylenediamine complex
[LiC≡CH(H$_2$NCH$_2$CH$_2$NH$_2$)], DMSO, r.t.

3-[(7-Bromoheptyl)oxy]benzenecarboxamide

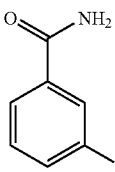

Synthesised according to Method D. HPLC-MS (method 1): m/z 314 [M]$^+$, 316 [M+2H]$^+$, Rt=4.37 min.

Example 65

3-(8-Nonynyloxy)benzenecarboxamide

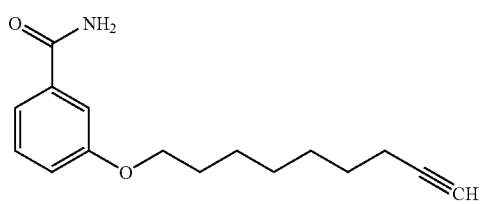

(Method F) Lithium acetylide ethylenediamine complex (305 mg, 3.3 mmol, 1.1 equiv.) was placed in a three-neck flask, degassed, flushed with N$_2$ and suspended in DMSO (2 ml). To the stirred suspension a solution of 3-[(7-bromoheptyl)oxy]benzenecarboxamide (943 mg, 3 mmol, 1 equiv.) in DMSO (2 ml), was added, slowly, dropwise, at r.t., under N$_2$. The reaction mixture was stirred at r.t. for 16 h. After that time it was diluted with 1N HCl solution and extracted with EtOAc (×3). The combined organic extracts were washed with brine, dried (Na$_2$SO$_4$) and evaporated to dryness under reduced pressure. The crude product was purified by column chromatography on silica eluting with EtOAc/hexane 20%, to give the desired compound as a white solid (100 mg, 13%), mp 82-83° C. HPLC-MS (method 1): m/z 260 [M+H]$^+$, Rt=4.26 min.

3-[(7-Bromodecyl)oxy]benzenecarboxamide

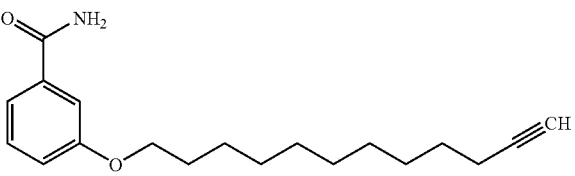

Synthesised according to Method D. Yield 32%, mp 114-116° C., HPLC-MS (method 1): m/z 356 [M]$^+$, 358 [M+2H]$^+$, Rt=5.15 min.

Example 66

3-(11-Dodecynyloxy)benzenecarboxamide

Synthesised from 3-[(7-bromodecyl)oxy]benzenecarboxamide according to Method F; mp 106-108° C., HPLC-MS (method 1): m/z 302 [M+H]$^+$, Rt=5.02 min.

Scheme 6:

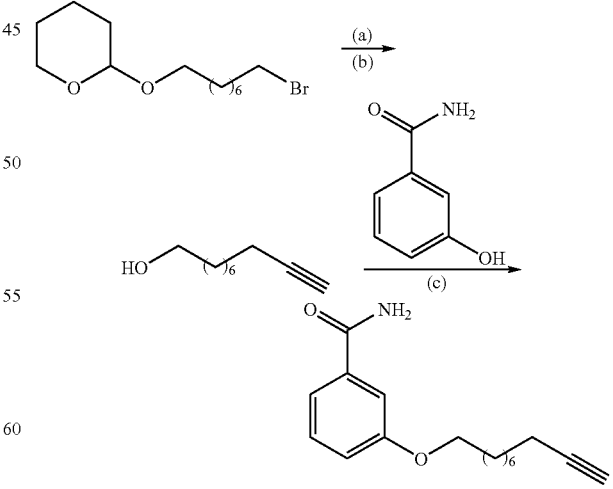

(a) Lithium acetylide ethylenediamine complex
[LiC≡CH(H$_2$NCH$_2$CH$_2$NH$_2$)], DMSO, r.t.;
(b) p-toluenesulfonic acid, EtOH, reflux;
(c) 3-hydroxybenzenecarboxamide, PPh$_3$-PS, DIAD, Et$_3$N, THF, r.t.

10-Undecyn-1-ol

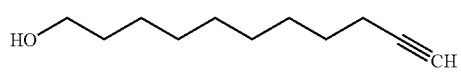

(Method G) A solution of commercially available 2-[(8-bromooctyl)oxy]tetrahydro-2H-pyran (1.0 g, 3.4 mmol, 1 equiv.) in DMSO (5 ml), was added, slowly, dropwise, at r.t., under $N_2$, to a stirred suspension of lithium acetylide ethylenediamine complex (350 mg, 3.8 mmol, 1.1 equiv.) in DMSO (5 ml). The reaction mixture was stirred at r.t. for 18 h and diluted with n-pentane (50 ml). The organic phase was washed with 1N HCl solution (2×20 ml) and water (2×20 ml), dried ($Na_2SO_4$) and evaporated to dryness under reduced pressure. The residue (colourless liquid, 570 mg, yield 70%) was dissolved in 95% EtOH (20 ml) together with p-toluenesulfonic acid (150 mg) and the mixture was heated under reflux for 2.5 h. After being cooled, the solvent was evaporated under reduced pressure. The residue was purified by column chromatography on silica eluting with EtOAc/hexane (10%-30% gradient), to give the desired compound as a colourless oil (240 mg, overall yield 48%).

Example 67

3-(9-Decynyloxy)benzenecarboxamide

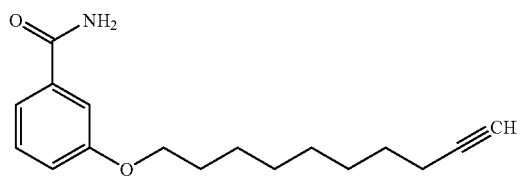

Synthesised from 3-hydroxybenzenecarboxamide and 10-undecyn-1-ol according to Method C, scheme 3; mp 111-112° C., HPLC-MS (method 1): m/z 274 $[M+H]^+$, Rt=4.61 min.

Scheme 7:

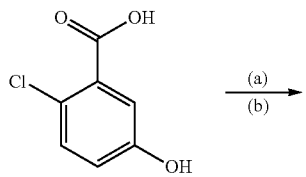

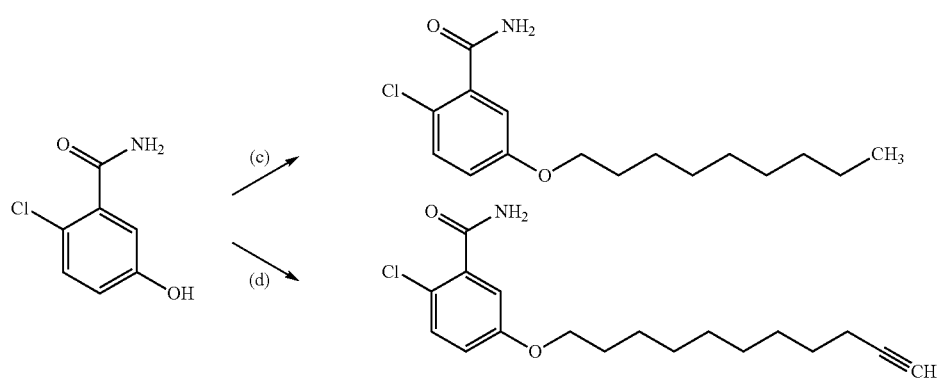

(a) $SOCl_2$, toluene, reflux;
(b) aqueous $NH_3$;
(c) n-Non-Br, $K_2CO_3$, NaI, DMF, 60° C.;
(d) 10-undecynol, $PPh_3$-PS, DIAD, $Et_3N$, THF, r.t.

2-Chloro-5-hydroxybenzenecarboxamide

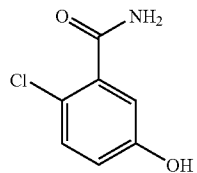

Synthesised from commercially available 2-chloro-5-hydroxybenzenecarboxylic acid, according to Method A, scheme 1. Yield 28%, mp 159-161° C., HPLC-MS (method 1): m/z 170 [M−H]⁻, Rt=1.48 min.

Example 68

2-Chloro-5-(nonyloxy)benzenecarboxamide

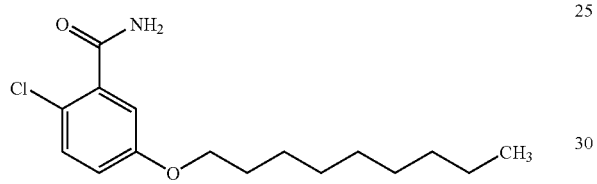

Synthesised from 2-chloro-5-hydroxybenzenecarboxamide according to Method B, scheme 2. Yield 80%, HPLC-MS (method 1): m/z 339 [M+H+CH$_3$CN]⁺, Rt=5.29 min.

Example 69

2-Chloro-5-(10-undecynyloxy)benzenecarboxamide

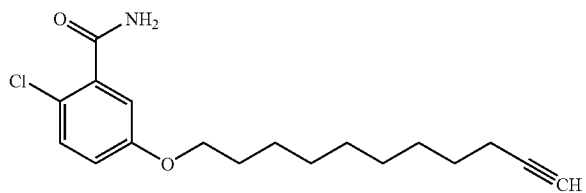

Synthesised from 2-chloro-5-hydroxybenzenecarboxamide according to Method C, scheme 3. Yield 13%, HPLC-MS (method 1): m/z 322 [M+H]⁺, Rt=4.94 min.

Scheme 8:

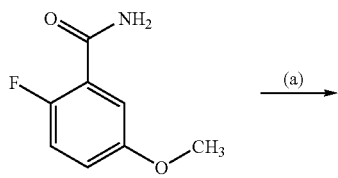

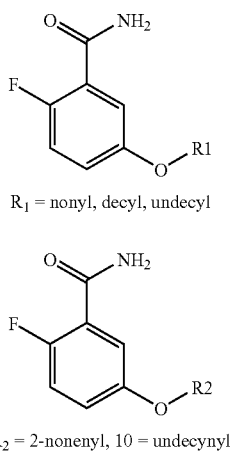

(a) BBr$_3$, CH$_2$Cl$_2$, r.t.;
(b) R$_1$-Br, K$_2$CO$_3$, NaI, DMF, 60° C.;
(c) R$_2$-OH, PPh$_3$-PS, DIAD, Et$_3$N, THF, r.t.

2-Fluoro-5-hydroxybenzenecarboxamide

(Method H) Boron tribromide solution (1.0 M in CH$_2$Cl$_2$, 23.6 ml, 23.6 mmol, 2 equiv.) was added slowly, dropwise to stirred solution of 2-fluoro-5-methoxybenzenecarboxamide (2.0 g, 11.8 mmol, 1 equiv.) in CH$_2$Cl$_2$ (60 ml), at r.t., under N$_2$. The reaction mixture was stirred at r.t. for 48 h. The solvent was removed under reduced pressure, the residue was dissolved in water (120 ml) and extracted with EtOAc (4×100 ml). The combined organic extracts were washed with water (2×100 ml), dried (Na$_2$SO$_4$) and filtered through a pad of silica gel. The filtrate was evaporated to dryness under reduced pressure, to give the desired compound as a grey solid (1.50 g, 82%).

Examples 70-75 (Table C)

Examples 70-72 were synthesised from 2-fluoro-5-hydroxybenzenecarboxamide according to Method B, scheme 2 and Examples 73-75 were synthesised from 2-fluoro-5-hydroxybenzenecarboxamide according to Method C, scheme 3.

| Example | 70 | 71 |
|---|---|---|
| Structure | 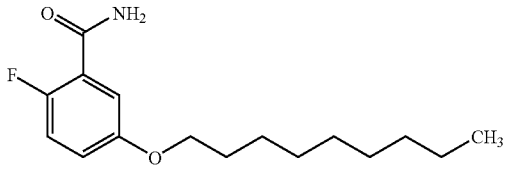 | 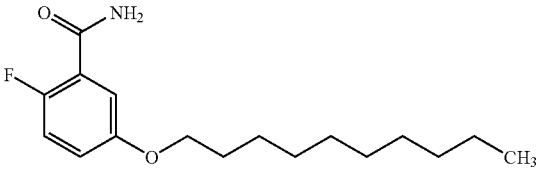 |
| Yield (%) | — | 40 |
| mp (° C.) | — | 78-80 |
| HPLC-MS: method no., m/z, ion | 4, 282, [M + H]$^+$ | 1, 337, [M + H + CH$_3$CN]$^+$ |
| Rt (min) | 2.42 | 5.69 |
| Example | 72 | 73 |
| Structure | 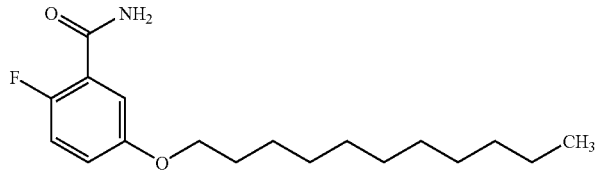 | 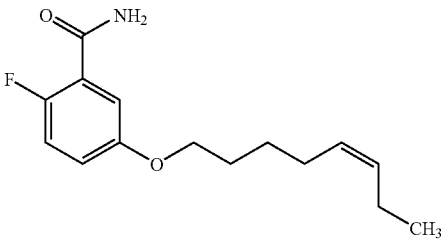 |
| Yield (%) | 42 | 8.5 |
| mp (° C.) | 82-83 | 69-71 |
| HPLC-MS: method no., m/z, ion | 1, 351, [M + H + CH$_3$CN]$^+$ | 1, 307, [M + H + CH$_3$CN]$^+$ |
| Rt (min) | 6.03 | 4.71 |
| Example | 74 | 75 |
| Structure | 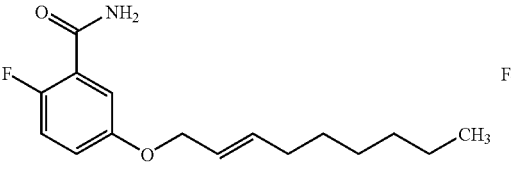 | 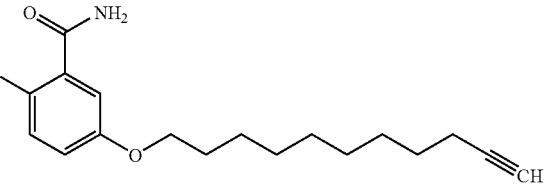 |
| Yield (%) | — | 8 |
| mp (° C.) | 75-76 | 72-74 |
| HPLC-MS: method no., m/z, ion | 1, 280, [M + H]$^+$ | 1, 306, [M + H]$^+$ |
| Rt (min) | 5.05 | 4.96 |

Table of names of product compounds; Examples 70-75:

| Example | Compound name |
|---------|---------------|
| 70 | 2-Fluoro-5-(nonyloxy)benzenecarboxamide |
| 71 | 2-Fluoro-5-(decyloxy)benzenecarboxamide |
| 72 | 2-Fluoro-5-(undecyloxy)benzenecarboxamide |
| 73 | 2-Fluoro-5-[(Z)-5-octenyloxy]benzenecarboxamide |
| 74 | 2-Fluoro-5-[(E)-2-nonenyloxy]benzenecarboxamide |
| 75 | 2-Fluoro-5-(10-undecynyloxy)benzenecarboxamide |

Scheme 9:

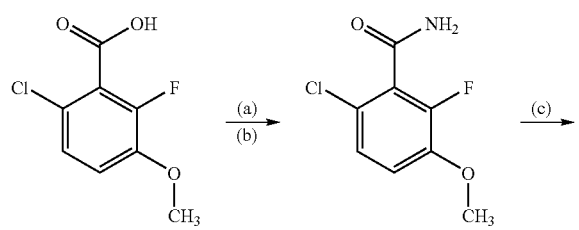

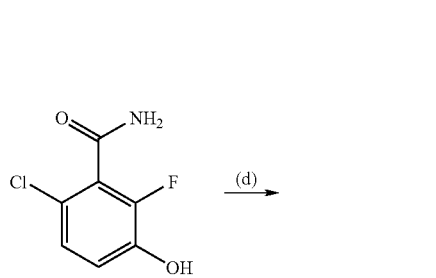

(a) SOCl$_2$, toluene, reflux, ; (b) aqueous NH$_3$; (c) BBr$_3$, CH$_2$Cl$_2$, r.t.; (d) n-Non-Br, K$_2$CO$_3$, NaI, DMF, 60° C.

6-Chloro-2-fluoro-3-methoxybenzenecarboxamide

Synthesised from commercially available 6-chloro-2-fluoro-3-methoxybenzenecarboxylic acid according to Method A, scheme 1. Yield 85%, mp 154-156° C., HPLC-MS (method 1): m/z 245 [M+H+CH$_3$CN]$^+$, Rt=2.37 min.

6-Chloro-2-fluoro-3-hydroxybenzenecarboxamide

Synthesised from 6-chloro-2-fluoro-3-methoxybenzenecarboxamide according to Method H. Yield 90%.

Example 76

6-Chloro-2-fluoro-3-(nonyloxy)benzenecarboxamide

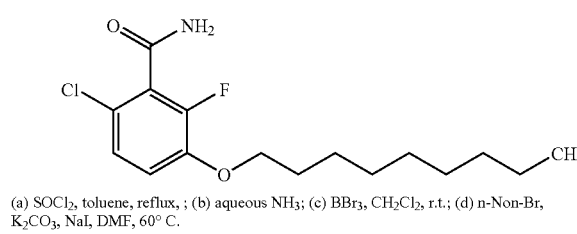

Synthesised from 6-chloro-2-fluoro-3-hydroxybenzenecarboxamide according to Method B, scheme 2. Yield 73%, mp 75-77° C., HPLC-MS (method 1): m/z 316 [M+H]$^+$, Rt=5.27 min.

Scheme 10:

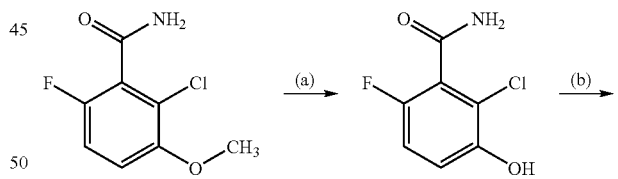

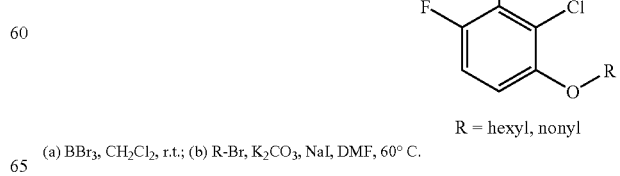

R = hexyl, nonyl (a) BBr$_3$, CH$_2$Cl$_2$, r.t.; (b) R-Br, K$_2$CO$_3$, NaI, DMF, 60° C.

2-Chloro-6-fluoro-3-hydroxybenzenecarboxamide

Synthesised from commercially available 2-chloro-6-fluoro-3-methoxybenzenecarboxamide, according to Method H. Yield 78%.

Example 77

2-Chloro-6-fluoro-3-(hexyloxy)benzenecarboxamide

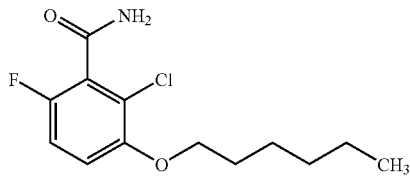

Synthesised from 2-chloro-6-fluoro-3-hydroxybenzenecarboxamide according to Method B, scheme 2. Yield 30%, mp 66-68° C., HPLC-MS (method 1): m/z 274 [M+H]$^+$, Rt=2.78 min.

Example 78

2-Chloro-6-fluoro-3-(nonyloxy)benzenecarboxamide

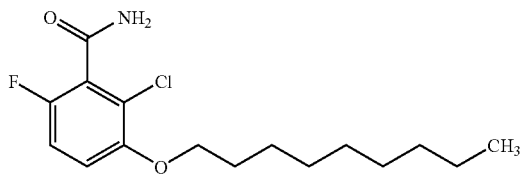

Synthesised from 2-chloro-6-fluoro-3-hydroxybenzenecarboxamide according to Method B, scheme 2. Yield 15%, mp 64-66° C., HPLC-MS (method 1): m/z 316 [M+H]$^+$, Rt=5.13 min.

Scheme 11:

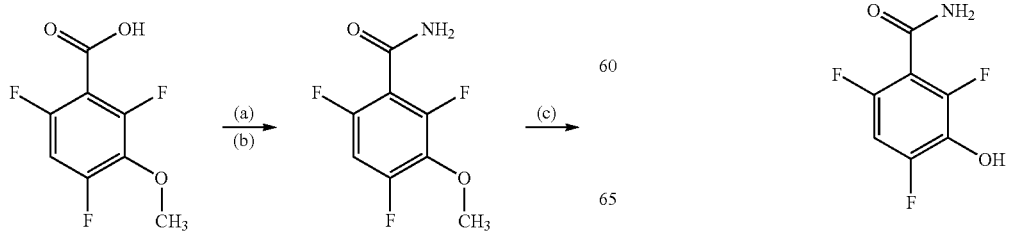

-continued

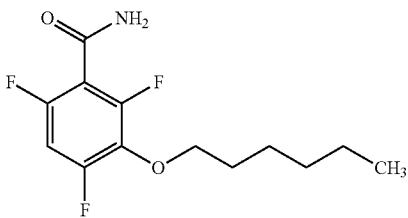

(a) SOCl$_2$, toluene, reflux;
(b) aqueous NH3;
(c) BBr3, CH$_2$Cl$_2$, r.t.;
(d) n-Hex-Br, K$_2$CO$_3$, NaI, DMF, 60° C.

2,4,6-Trifluoro-3-methoxybenzenecarboxamide

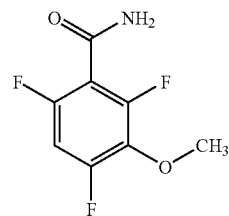

Synthesised from commercially available 2,4,6-trifluoro-3-methoxybenzenecarboxylic acid, according to Method A, scheme 1. Yield 85%, mp 102° C., HPLC-MS (method 1): m/z 206 [M+H]$^+$, Rt=2.40 min.

2,4,6-Trifluoro-3-hydroxybenzenecarboxamide

Synthesised from 2,4,6-trifluoro-3-methoxybenzenecarboxamide according to Method H. Yield 100%, HPLC-MS (method 1): m/z 190 [M−H]⁻, Rt=1.07 min.

Example 79

2,4,6-Trifluoro-3-(hexyloxy)benzenecarboxamide

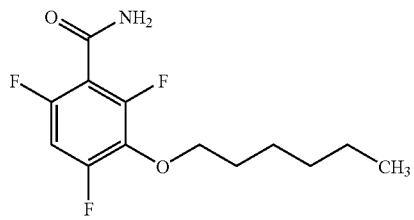

Synthesised from 2,4,6-trifluoro-3-hydroxybenzenecarboxamide according to Method B, scheme 2. Yield 54%, mp 89-90° C., HPLC-MS: m/z 276 [M+H]⁺, Rt=4.36 min.

Scheme 12:

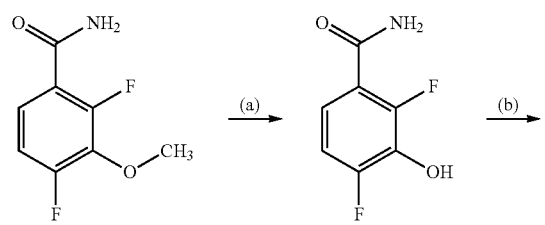

(a) BBr₃, CH₂Cl₂, r.t.;
(b) n-Hex-Br, K₂CO₃, NaI, DMF, 60° C.

2,4-Difluoro-3-hydroxybenzenecarboxamide

Synthesised from commercially available 2,4-difluoro-3-methoxybenzenecarboxamide according to Method H. Yield 98%, HPLC-MS (method 1): m/z 172 [M−H]⁻, Rt=1.03 min.

Example 80

2,4-Difluoro-3-(hexyloxy)benzenecarboxamide

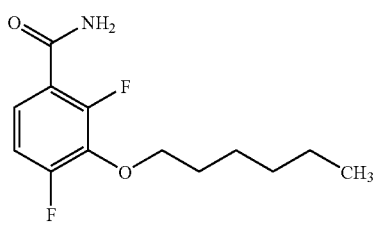

Synthesised from 2,4-difluoro-3-hydroxybenzenecarboxamide according to Method B, scheme 2. Yield 51%, mp 86-87° C.

Scheme 13:

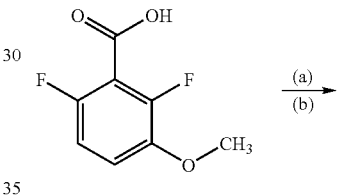

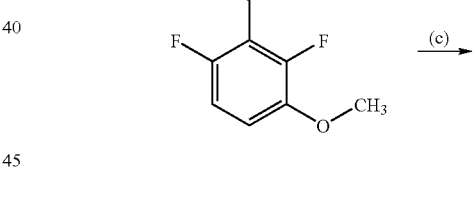

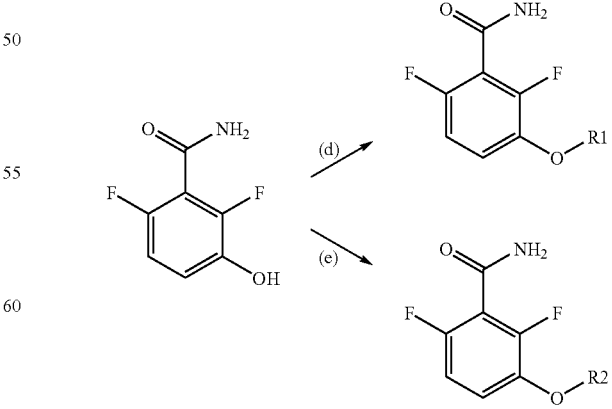

(a) SOCl₂, toluene, reflux; (b) aqueous NH₃; (c) BBr₃, CH₂Cl₂, r.t.; (d) R₁-Br, K₂CO₃, NaI, DMF, 60° C.; (e) R₂-OH, PPh₃-PS, DIAD, Et₃N, THF, r.t.

51

2,6-Difluoro-3-methoxybenzenecarboxamide

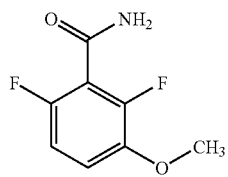

Synthesised from commercially available 2,6-difluoro-3-methoxybenzenecarboxylic acid according to Method A, scheme 1. Yield 84%, mp 167-169° C., HPLC-MS (method 1): m/z 188 [M+H]$^+$, Rt=2.00 min.

52

2,6-Difluoro-3-hydroxybenzenecarboxamide

Synthesised from 2,6-difluoro-3-methoxybenzenecarboxamide according to Method H. Yield 78%. HPLC-MS (method 1): m/z 172 [M−H]$^-$, Rt=1.25 min

Examples 81-87 (Table D)

Examples 81-83 were synthesised from 2,6-difluoro-3-hydroxybenzenecarboxamide according to Method B, scheme 2. Examples 84-88 were synthesised from 2,6-difluoro-3-hydroxybenzenecarboxamide according to Method C, scheme 3.

| Example | 81 | 82 |
|---|---|---|
| Structure | (structure) | (structure) |
| Yield (%) | 38 | 71 |
| mp (° C.) | 93-95 | 76-78 |
| HPLC-MS: method no., m/z, ion | 1, 258, [M + H]$^+$ | 1, 300, [M + H]$^+$ |
| Rt (min) | 4.38 | 5.16 |

| Example | 83 | 84 |
|---|---|---|
| Structure | (structure) | (structure) |
| Yield (%) | 37 | 29 |
| mp (° C.) | 99-101 | 67-69 |
| HPLC-MS: method no., m/z, ion | 1, 288, M + H]$^+$ | 1, 298, M + H]$^+$ |
| Rt (min) | 3.72 | 4.91 |

| Example | 85 | 86 |
|---|---|---|
| Structure | (structure) | (structure) |

-continued

| | | |
|---|---|---|
| Yield (%) | 6.5 | 16 |
| mp (° C.) | 62-64 | 57-59 |
| HPLC-MS: method no., m/z, ion | 1, 302, M + H]+ | 1, 288, [M + H]+ |
| Rt (min) | 4.18 | 4.65 |
| Example | 87 | 88 |
| Structure | (see image) | (see image) |
| Yield (%) | 16 | 21 |
| mp (° C.) | <40 | 87-89 |
| HPLC-MS: method no., m/z, ion | 1,312, [M + H]+ | 1, 324, [M + H]+ |
| Rt (min) | 4.94 | 4.67 |

Table of names of product compounds; Examples 81-88:

| Example | Compound name |
|---|---|
| 81 | 2,6-Difluoro-3-(hexyloxy)benzenecarboxamide |
| 82 | 2,6-Difluoro-3-(nonyloxy)benzenecarboxamide |
| 83 | Butyl 2-[3-(aminocarbonyl)-2,4-difluorophenoxy]acetate |
| 84 | 2,6-Difluoro-3-[(E)-2-nonenyloxy]benzenecarboxamide |
| 85 | 2,6-Difluoro-3-[2-(hexyloxy)ethoxy]benzenecarboxamide |
| 86 | 2,6-Difluoro-3-[(Z)-6-nonenyloxy]benzenecarboxamide |
| 87 | 2,6-Difluoro-3-[(Z)-5-decenyloxy]benzenecarboxamide |
| 88 | 2,6-Difluoro-3-(10-undecynyloxy)benzenecarboxamide |

Scheme 14:

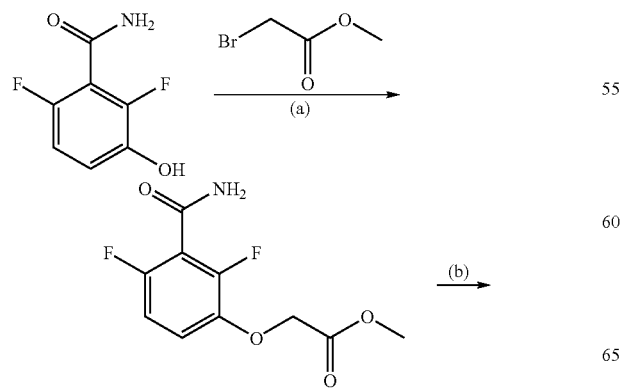

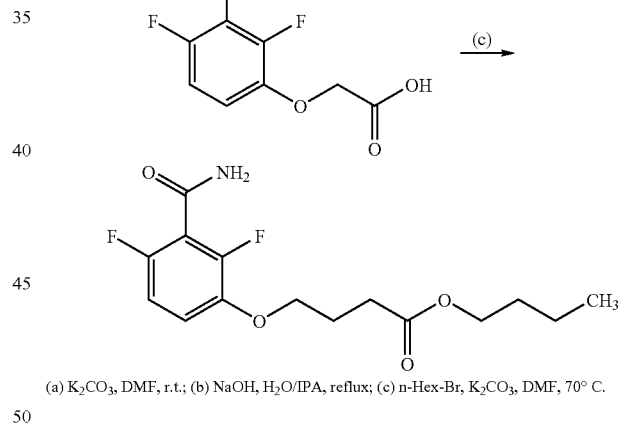

(a) $K_2CO_3$, DMF, r.t.; (b) NaOH, $H_2O$/IPA, reflux; (c) n-Hex-Br, $K_2CO_3$, DMF, 70° C.

Methyl 2-[3-(aminocarbonyl)-2,4-difluorophenoxy]acetate

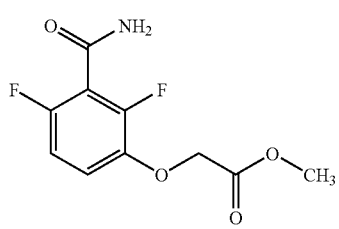

A mixture of 2,6-difluoro-3-hydroxybenzenecarboxamide (1.2 g, 7 mmol, 1 equiv.), K$_2$CO$_3$ (2.87 g, 21 mmol, 3 equiv.) and methyl bromoacetate (0.69 ml, 7.35 mmol, 1.05 equiv.) in DMF (30 ml) was stirred at r.t. for 18 h. The mixture was diluted with water and extracted with EtOAc (4×80 ml). The combined organic extracts were dried (MgSO$_4$) and evaporated to dryness under reduced pressure. The product was used crude on the next step. HPLC-MS (method 1): m/z 246 [M+H]$^+$, Rt=2.08 min.

2-[3-(Aminocarbonyl)-2,4-difluorophenoxy]acetic acid

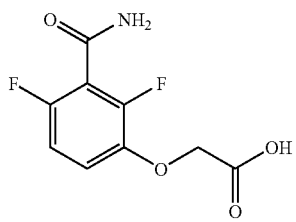

Methyl 2-[3-(aminocarbonyl)-2,4-difluorophenoxy]acetate (7 mmol, 1 equiv.) was added to a solution of NaOH (1 g, 25 mmol, 3.6 equiv.) in water (20 ml) and isopropyl alcohol (5 ml). The mixture was stirred under reflux for 1.5 h, diluted with water (40 ml) and extracted with CH$_2$Cl$_2$ (40 ml). The aqueous phase was acidified to pH 1 with conc. HCl solution. The precipitant solid was filtered and dried in vacuo to give the desired compound (130 mg, 8%), mp 152-153° C. HPLC-MS (method 1): m/z 312 [M−H+2CH$_3$CN]$^−$, Rt=0.91 min.

Example 89

Hexyl 2-[3-(aminocarbonyl)-2,4-difluorophenoxy]acetate

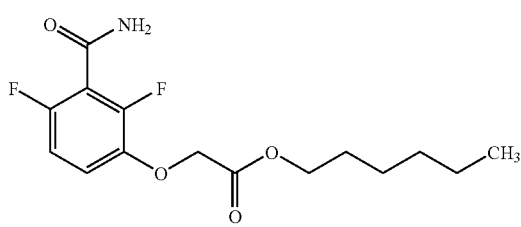

n-Bromohexane (0.077 ml, 0.55 mmol, 1.05 equiv.) was added to a suspension of 2-[3-(aminocarbonyl)-2,4-difluorophenoxy]acetic acid (120 mg, 0.52 mmol, 1 equiv.) and K$_2$CO$_3$ (215 mg, 1.56 mmol, 3 equiv.) in DMF (3 ml) and the mixture was stirred at 70° C. for 1.5 h. After cooling at r.t., the mixture was poured into water (25 ml) and the precipitant solid was filtered and washed with water (2×20 ml). After drying, the crude solid was triturated by stirring in hexane (10 ml), filtered and washed with hexane (3×10 ml), to give the desired compound as a white solid (99 mg, 60%), mp 108° C. HPLC-MS: m/z 316 [M+H]$^+$, Rt=4.09 min.

Scheme 15:

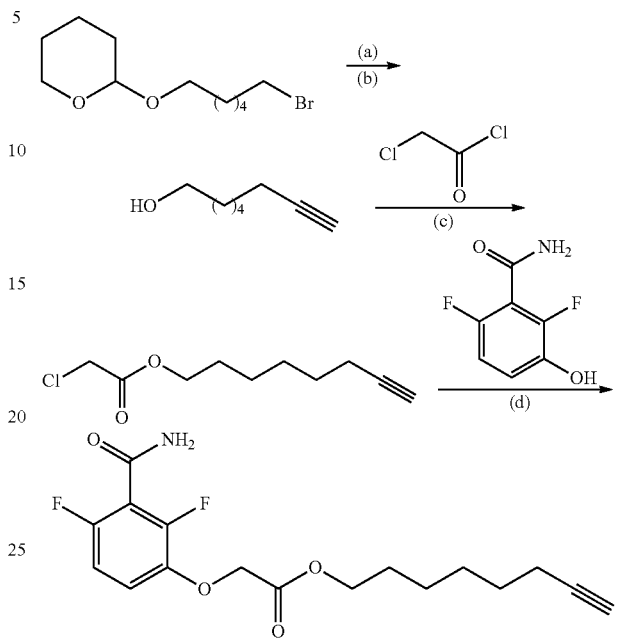

(a) Lithium acetylide ethylenediamine complex

[LiC≡CH(H$_2$NCH$_2$CH$_2$NH$_2$)], DMSO, r.t.; (b) p-toluenesulfonic acid, EtOH, reflux; (c) ClCH$_2$COCl, CH$_2$Cl$_2$, r.t; (d) K$_2$CO$_3$, NaI, DMF, 60° C.

7-Octyn-1-ol

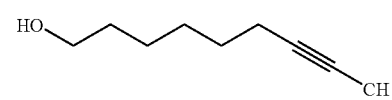

Synthesised from commercially available 2-[(8-bromohexyl)oxy]tetrahydro-2H-pyran according to Method G. Overall yield 55%, colourless oil.

7-Octynyl 2-chloroacetate

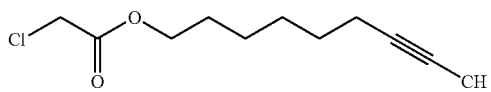

Chloroacetyl chloride (0.16 ml, 2.0 mmol, 1 equiv.) was added to a stirred solution of 7-Octyn-1-ol (300 mg, 2.4 mmol, 1.2 equiv.) in CH$_2$Cl$_2$ (6 m-) at −5° C. The reaction mixture was allowed to warm-up to r.t., were it was stirred for 4 h. The solvent was removed under reduced pressure and the residue was purified by column chromatography on silica eluting with EtOAc/hexane (10%) to give the desired compound as a pale yellow liquid (450 mg, 100%).

Example 90

7-Octynyl 2-[3-(aminocarbonyl)-2,4-difluorophenoxy]acetate

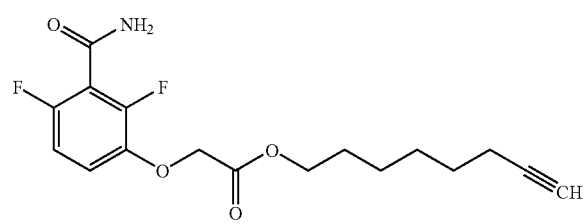

Synthesised from 2,6-difluoro-3-hydroxybenzenecarboxamide according to Method B, scheme 2. Yield 13%, mp 130-132° C., HPLC-MS (method 1): m/z 340 [M+H]$^+$, Rt=3.93 min.

Scheme 16:

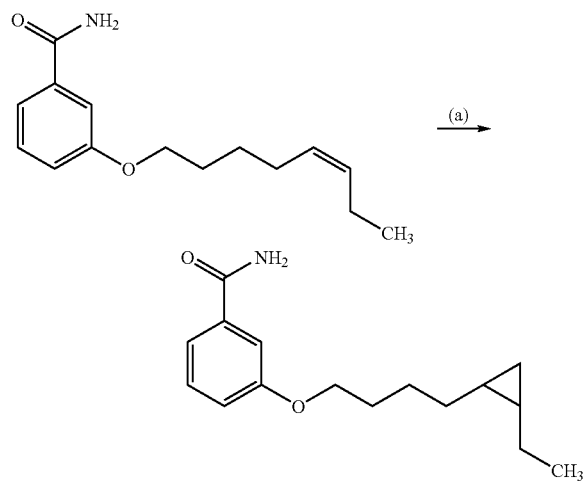

(a) ZnEt$_2$, CH$_2$I$_2$, toluene, r.t.

Example 91

3-[4-(2-Ethylcyclopropyl)butoxy]benzenecarboxamide

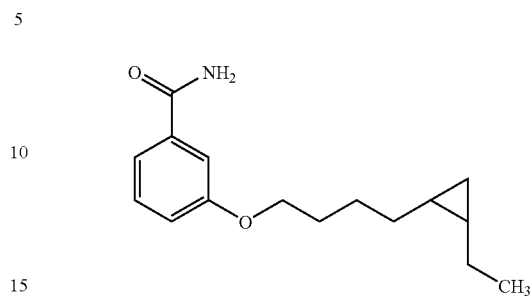

A solution of diethyl zinc (1.1 M in toluene, 1.84 ml, 2.02 mmol, 1 equiv.) was added to a solution of example 52 (500 mg, 2.02 mmol, 1 equiv.) in dry toluene (1 ml), at r.t., under N$_2$. Diiodomethane (0.244 ml, 3.03 mmol, 1.5 equiv.) was added slowly, dropwise and the reaction mixture was stirred at r.t. for 5 days. The mixture was diluted with water (40 ml) and extracted with CH$_2$Cl$_2$ (4×40 ml). The combined organic extracts were dried (MgSO$_4$) and the solvents were removed under reduced pressure. By HPLC-MS, the crude residue consisted of starting material (80%) and desired product (20%). The reaction was repeated in the same way, in toluene (15 ml) using diethyl zinc (1.1 M in toluene, 6.1 ml, 6.6 mmol, 3.3 equiv.) and diiodomethane (0.244 ml, 3.03 mmol, 1.5 equiv.). The reaction mixture was stirred at 50° C. for 5 days, diluted with water (80 ml) and extracted with CH$_2$Cl$_2$ (4×50 ml). The combined organic extracts were dried (MgSO$_4$) and the solvents were removed under reduced pressure. The residue was triturated by stirring in pentane (15 ml) and the precipitant solid was filtered and rinsed with pentane to give 196 mg of a white compound, mp 104-105° C. By HPLC-MS it consisted of starting material (65%) and the desired product (35%). HPLC-MS (method 1): m/z 303 [M+H+CH$_3$CN]$^+$, Rt=4.83 min.

Scheme 17:

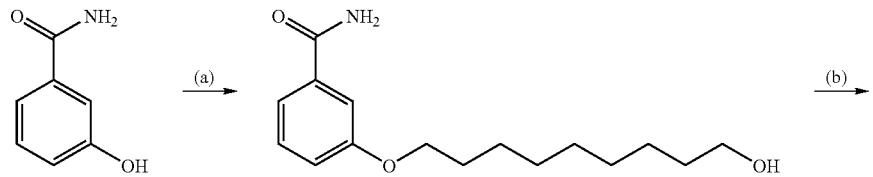

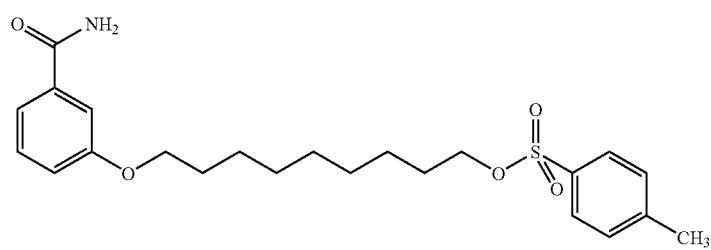

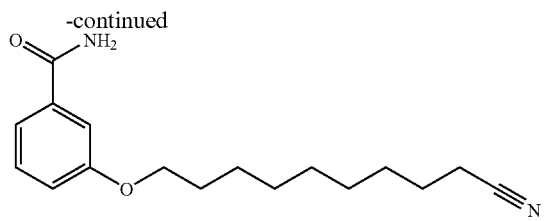

(a) Br(CH₂)₉OH, K₂CO₃, NaI, DMF, 60° C.;
(b) toluenesulfonyl chloride, Et₃N, CH₂Cl₂, r.t.;
(c) NaCN, H₂O/EtOH, 75° C.

3-[(9-Hydroxynonyl)oxy]benzenecarboxamide

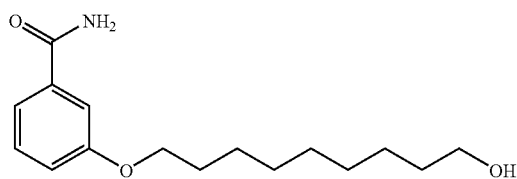

Synthesised according to Method B, scheme 2. Yield 75%, mp 118-120° C., HPLC-MS (method 1): m/z 280 [M+H]⁺, Rt=3.50 min.

Example 92

9-[3-(Aminocarbonyl)phenoxy]nonyl 4-methylbenzenesulfonate

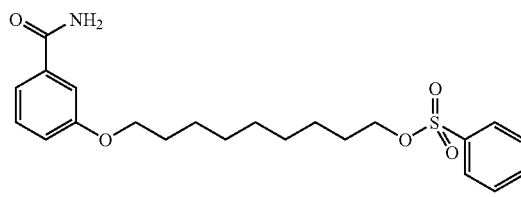

Toluenesulfonyl chloride (410 mg, 2.15 mmol, 1.5 equiv.) and triethylamine (0.40 ml, 2.88 mmol, 2 equiv.) were added to a solution of 3-[(9-hydroxynonyl)oxy]benzenecarboxamide (400 mg, 1.43 mmol, 1 equiv.) in CH₂Cl₂ (4 ml) and the reaction mixture was stirred at r.t. for 6 days. Saturated NaHCO₃ solution (40 ml) was added and the mixture was extracted with CH₂Cl₂ (3×30 ml). The combined organic extracts were dried (MgSO₄) and the solvent was evaporated under reduced pressure. The residue was purified by column chromatography on silica eluting with CH₃OH/CH₂Cl₂ (2%), to give the desired compound as white solid (428 mg, 69%), mp 78-80° C. HPLC-MS (method 1): m/z 434 [M+H]⁺, Rt=4.90 min.

Example 93

3-[(9-Cyanononyl)oxy]benzenecarboxamide

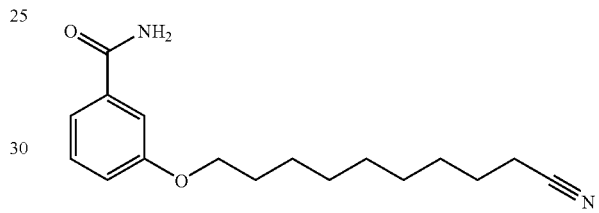

Sodium cyanide (60 mg, 1.22 mmol, 1.3 equiv.) was added to a solution of 9-[3-(aminocarbonyl)phenoxy]nonyl 4-methylbenzenesulfonate (407 mg, 0.94 mmol, 1 equiv.) in water (10 ml) and 95% EtOH (8 ml), and the reaction mixture was stirred at 75° C. for 2 days. After cooling at r.t., the mixture was diluted with water (10 ml) and extracted with CH₂Cl₂ (3×10 ml). The combined organic extracts were dried (MgSO₄) and the solvent was removed under reduced pressure. The crude residue was purified by column chromatography on silica eluting with EtOAc/hexane (50%), to give the desired compound as white solid (57 mg, 21%), mp 96-97° C. HPLC-MS (method 1): m/z 289 [M+H]⁺, Rt=4.16 min.

Scheme 18:

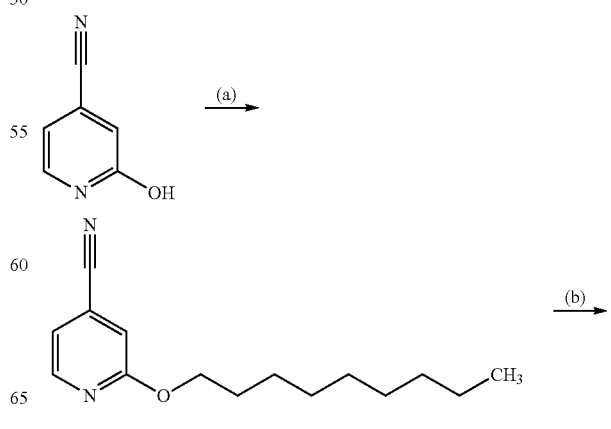

-continued

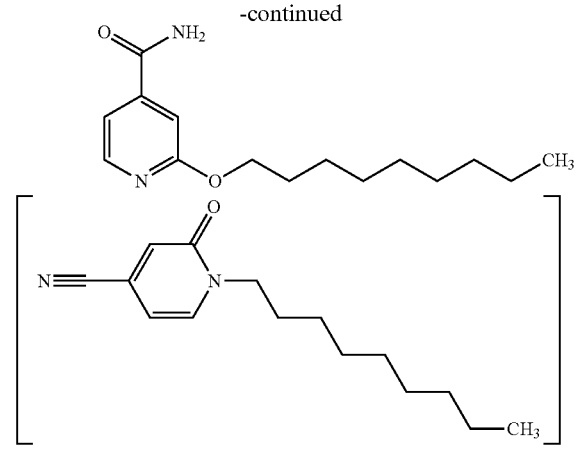

(a) n-Non-Br, K₂CO₃, NaI, DMF, 60° C.;
(b) LiOH, NaOCH₃, MeOH, reflux.

2-(Nonyloxy)isonicotinonitrile

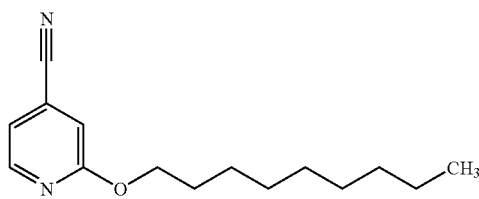

Synthesised from commercially available 2-hydroxyisonicotinonitrile according to Method B. Yield 30%, semi-solid, HPLC-MS (method 2): m/z 288 [M+H+CH$_3$CN]$^+$, Rt=21.46 min. The reaction gave also as by-product 1-nonyl-2-oxo-1,2-dihydro-4-pyridinecarbonitrile, yield 39%, mp 46-48° C., HPLC-MS (method 1): m/z 288 [M+H+CH$_3$CN]$^+$, Rt=4.94 min.

Example 94

2-(Nonyloxy)isonicotinamide

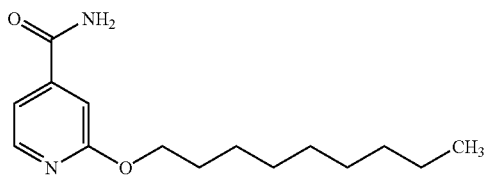

A solution of 2-(nonyloxy)isonicotinonitrile (250 mg, 1.0 mmol, 1 equiv.) and sodium methoxide (10 mg, 0.1 mmol, 0.1 equiv.) in dry CH$_3$OH (10 ml) was stirred at r.t. for 2.5 h. A solution of lithium hydroxide (24 mg, 1.0 mmol, 1 equiv.) in water (1 ml) was added and the reaction mixture was heated under reflux for 3.5 h. After cooling at r.t., the mixture was poured into water (40 ml). The precipitant solid was filtered and dried in vacuo at 50° C., to give the desired compound as a white solid (60 mg, 23%), mp 108-110° C. HPLC-MS (method 1): m/z 265 [M+H]$^+$, Rt=5.08 min.

Scheme 19:

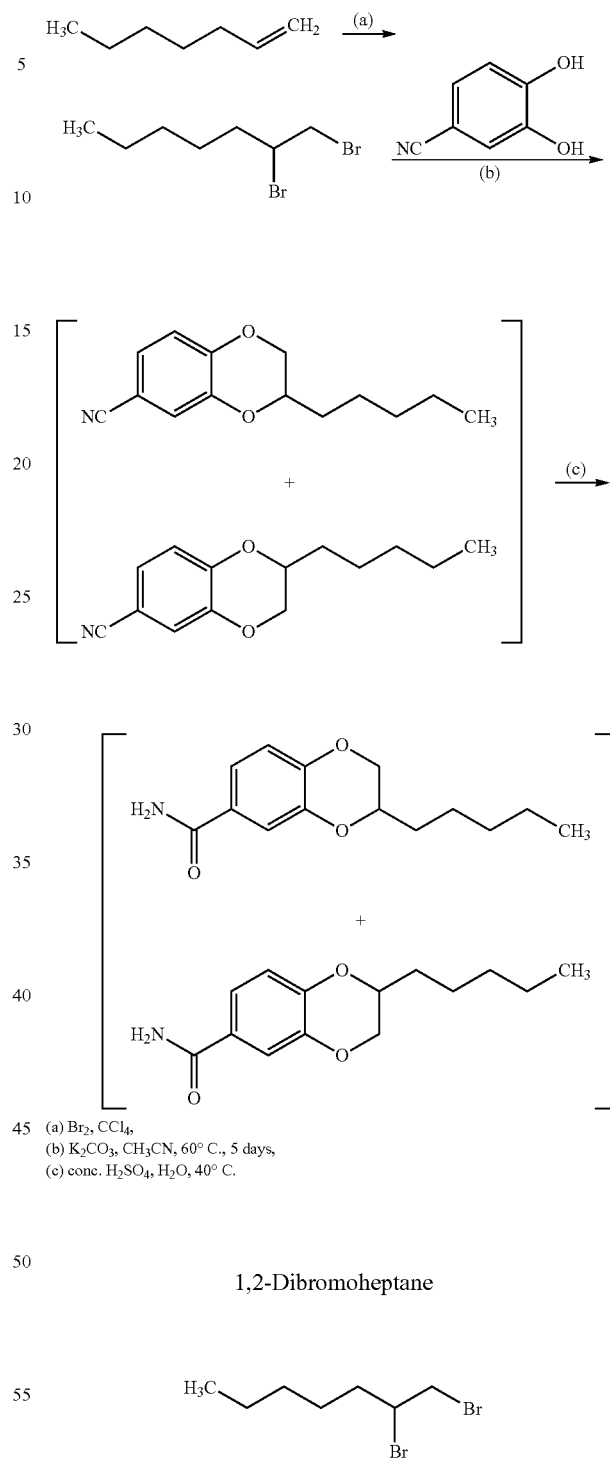

(a) Br₂, CCl₄,
(b) K₂CO₃, CH₃CN, 60° C., 5 days,
(c) conc. H₂SO₄, H₂O, 40° C.

1,2-Dibromoheptane

Bromine (1.9 ml, 37.28 mmol, 1.05 equiv.) was added slowly, dropwise, to a solution of 1-heptene (5 ml, 35.5 mmol, 1 equiv.) in CCl₄ (7 ml) cooled at −10° C., under N₂. The reaction mixture was stirred at r.t. for 16 h. The solvent was removed by evaporation under reduced pressure. The residue was partitioned between CH₂Cl₂ (200 ml) and 10% aqueous sodium metabisulfate solution (200 ml). The organic phase was separated, washed with brine and dried (Na₂SO₄). It was evaporated under reduced pressure to dryness, to give the desired compound as a colourless oil (8.94 g, 98%).

3-Pentyl-2,3-dihydro-1,4-benzodioxine-6-carbonitrile and 2-pentyl-2,3-dihydro-1,4-benzodioxine-6-carbonitrile

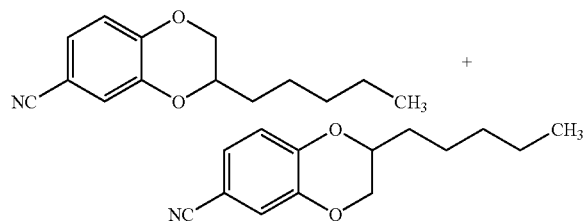

1,2-Dibromoheptane (5.11 g, 19.8 mmol, 1.1 equiv.) was added to a mixture of di-hydroxy benzonitrile (2.43 g, 18 mmol, 1 equiv.) and $K_2CO_3$ (12.4 g, 90 mmol, 5 equiv.) in $CH_3CN$ (100 ml). The reaction mixture was heated under reflux for 4 days. After cooling to r.t., the solvent was removed under reduced pressure; the residue was diluted with water (200 ml) and extracted with EtOAc (3×150 ml). The combined organic phases were washed with brine, dried ($Na_2SO_4$) and evaporated under reduced pressure to dryness. The residue was purified by column chromatography on silica eluting with EtOAc/hexane (5%-10% gradient) to give the desired compound as a colourless oil (390 mg, 9%); mixture of two regio-isomers. HPLC-MS (method 1): m/z 230 [M−H]⁻, Rt=5.28 min.

Example 95

3-Pentyl-2,3-dihydro-1,4-benzodioxine-6-carboxamide and 2-pentyl-2,3-dihydro-1,4-benzodioxine-6-carboxamide A mixture of regio-isomers 3-pentyl-2,3-dihydro-1,4-benzodioxine-6-carbonitrile and 2-pentyl-2,3-dihydro-1,4-benzodioxine-6-carbonitrile (50 mg, 0.22 mmol) was stirred vigorously in conc. $H_2SO_4$ (0.5 ml) and warmed to 40° C. Water (82 mg) was added dropwise and the mixture was stirred for 45 min at 40° C. The mixture was cooled at −5° C., and ice (25 ml) was added quickly, with vigorous stirring. The mixture stirred at r.t. for two more hours. The precipitant solid was filtered, washed with water and dried in vacuo, at 40° C. It was purified on preparative TLC plate (Analtech, 2 mm, 20×20) eluting with methyl-tert-butyl-ether, to give the desired compound as a white solid (50 mg, 93%), HPLC-MS (method 1): m/z 291 [M+H+$CH_3CN$]⁺, Rt=4.14 min.

Examples 96-99, 101-116, 117, 119, 122, 124, 128-134, 137-139, 142, 144-154, 156-159 and 161-163 (Table E)

The compounds of Examples 96-99, 101-116, 117, 119, 122, 124, 128-134, 137-139, 142, 144-154, 156-159 and 161-163 were synthesized according to the following general procedure: To a solution of reactant (A) in anhydrous DMF (B), 2,6-difluoro-3-hydroxybenzamide (C) and potassium carbonate (D) were added. The reaction mixture was stirred at room temperature or 25° C. under nitrogen atmosphere. The reaction mixture was evaporated to dryness under reduced pressure and the residue was purified by column chromatography on silica (230-400µ) using ethyl acetate/hexane as the eluent to provide the product compound.

TABLE E

| Example | 96 | 97 |
|---|---|---|
| Product | 2,6-Difluoro-3-(5-methyl-quinolin-2-ylmethoxy)-benzamide | 2,6-Difluoro-3-(6-methyl-quinolin-2-ylmethoxy)-benzamide |
| Reaction scheme | | |

TABLE E-continued

| | | |
|---|---|---|
| Reactant (A) | 2-Bromomethyl-5-methyl-quinoline | 2-Bromomethyl-6-methyl-quinoline |
| Quantities of A; B; C; D | 0.5 g, .0021 mol; 3 ml; 0.366 g, .0021 mol; 0.99 g, .0072 mol | 0.05 g, .0002 mol; 1 ml; 0.036 g, .002 mol; 0.1 g, .0007 mol |
| Stir temp/time | 25° C./124 h | 25° C./124 h |
| Ethyl acetate/hexane ratio | 35:65 | 20:80 |
| Yield | 0.3 g, 43%, off white solid | 0.039 g, 56%, white solid |
| $^1$H NMR (DMSO, 400 MHz, unless otherwise specified) | 2.51 (s, 3H), 5.42 (s, 2H), 7.06 (dt, 1H, J = 9.2 Hz (o-coupling), J = 1.6 Hz (m-coupling), 7.31 (dt, 1H, J = 9.2 Hz (o-coupling), J = 5.2 Hz), 7.63 (d, 2H, J = 8.4 Hz (o-coupling), 7.76 (s, 1H), 7.87 (s, 1H) 7.91 (d, 1H, J = 8.8 Hz (o-coupling), 8.16 (s, 1H), 8.34 (d, 1H, J = 8.8 Hz (o-coupling) | 2.51 (s, 3H), 5.42 (s, 2H), 7.06 (dt, 1H, J = 9.2 Hz (o-coupling), J = 1.6 Hz (m-coupling), 7.31 (dt, 1H, J = 9.2 Hz (o-coupling), J = 5.2 Hz), 7.63 (d, 2H, J = 8.4 Hz (o-coupling), 7.76 (s, 1H), 7.87 (s, 1H) 7.91 (d, 1H, J = 8.8 Hz (o-coupling), 8.16 (s, 1H), 8.34 (d, 1H, J = 8.8 Hz (o-coupling) |
| MS-ES+ | 329.05 | 329.05 |
| HPLC method no., Rt (min) | 5, 12.63 | 5, 9.59 |

| Example | 98 | 99 |
|---|---|---|
| Product | 2,6-Difluoro-3-(7-methoxy-quinolin-2-ylmethoxy)-benzamide | 3-[4-(2-Chloro-phenyl)-thiazol-2-ylmethoxy]-2,6-difluoro-benzamide |
| Reaction scheme | | |
| Reactant (A) | 2-Bromomethyl-7-methoxy-quinoline | 2-Bromomethyl-4-(2-chloro-phenyl)-thiazole |
| Quantities of A; B; C; D | 0.01 g, .00039 mol; 2 ml; 0.068 g, .00039 mol; 0.188 g, .0013 mol | 0.35 g, .0012 mol; 15 ml; 0.21 g, .0012 mol; 0.585 g, .0042 mol |
| Stir temp/time | 25° C./124 h | 25° C./124 h |
| Ethyl acetate/hexane ratio | 20:80 | 20:80 |
| Yield | 0.012 g, 9%, off white solid | 0.80 g, 17%, yellow brown solid |
| $^1$H NMR (DMSO, 400 MHz, unless otherwise specified) | 3.92 (s, 3H), 5.41 (s, 2H), 7.06 (m, 1H, J = 9.2 Hz (o-coupling) J = 1.2 Hz (m-coupling), 7.25-7.32 (m, 2H), 7.39 (1H, J = 2.0 Hz (m-coupling), 7.51 (d, 1H, J = 8.4 Hz (o-coupling), 7.88 (d, 1H, J = 4.8 Hz), 7.91 (broad s, 1H), 8.16 (s, 1H), 8.33 (d, 1H, J = 8.4 Hz (o-coupling) | 5.59 (s, 2H), 7.13 (dt, 1H, J = 8.8 Hz (o-coupling), J = 2.0 Hz (m-coupling), 7.39-7.48 (m, 3H), 7.57-7.59 (m, 1H), 7.85-7.86 (m, 1H), 7.89 (broad s, 1H), 8.17 (broad s, 2H) |
| MS-ES+ | 345.06 | 381.03 |
| HPLC method no., Rt (min) | 5, 8.73 | 5, 9.99 |

| Example | 101 | 102 |
|---|---|---|
| Product | 2,6-Difluoro-3-(3-fluoro-benzyloxy)-benzamide | 3-(Biphenyl-3-ylmethoxy)-2,6-difluoro-benzamide |
| Reaction scheme | | 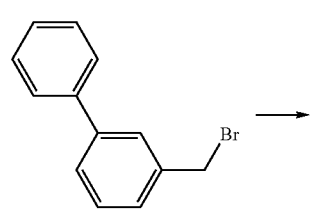 |

TABLE E-continued

| | | |
|---|---|---|
| | 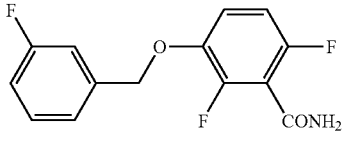 | 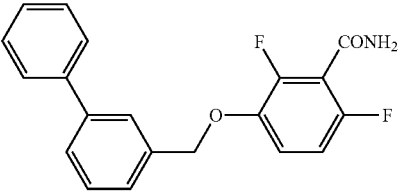 |
| Reactant (A) | 1-Bromomethyl-3-fluoro-benzene | 3-Bromomethyl-biphenyl |
| Quantities of A; B; C; D | 0.188 g, .001 mol; 2 ml; 0.173 g, .001 mol; 0.485 g, .0035 mol | 0.25 g, .001 mol; 2 ml; 0.173 g, .001 mol; 0.5 g, .0035 mol |
| Stir temp/time | 25° C., 24 h | 25° C., 24 h |
| Ethyl acetate/hexane ratio | 20:80 | 20:80 |
| Yield | 0.058 g, 18%, white solid | 0.15 g, 44%, white solid |
| $^1$H NMR (DMSO, 400 MHz, unless otherwise specified) | 5.21 (s, 2H), 7.07 (dt, 1H, J = 8.8 Hz (o-coupling), J = 1.6 Hz (m-coupling), 7.18 (dt, 1H, J = 8.8 Hz (o-coupling), J = 2.4 Hz (m-coupling)), 7.25-7.31 (m, 3H), 7.43-7.49 (m, 1H), 7.86 (broad s, 1H), 8.14 (broad s, 1H) | 5.26 (s, 2H), 7.07 (dt, 1H, J = 8.8 Hz (o-coupling), 7.31-7.36 (m, 1H), 7.39 (d, 1H, J = 7.2 Hz), 7.43-7.52 (m, 4H), 7.66 (t, 3H, J = 8.0 Hz (o-coupling), 7.74 (s, 1H), 7.85 (s, 1H), 8.13 (broad s, 1H) |
| MS-ES+ | 282.11 | 340.08 |
| HPLC method no., Rt (min) | 5, 9.41 | 5, 10.21 |

| Example | 103 | 104 |
|---|---|---|
| Product | 3-(7-Methylquinolin-2-ylmethoxy)-2,6-difluoro-benzamide | 2,6-Difluoro-3-(7-chloro-benzothiazol-2-ylmethoxy)-benzamide |
| Reaction scheme | 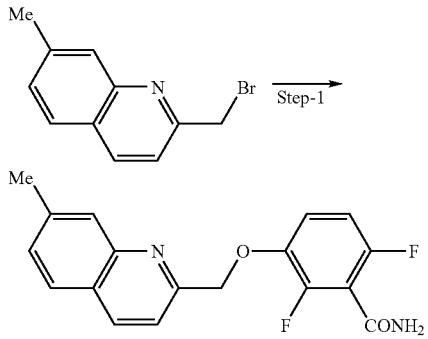 | 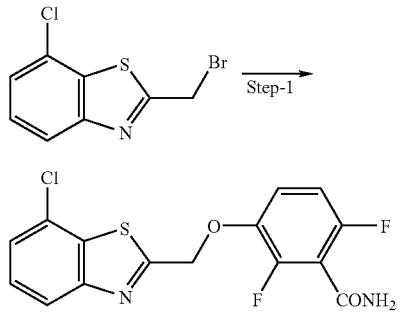 |
| Reactant (A) | 2-Bromomethyl-7-methyl-quinoline | 2-Bromomethyl-7-chloro-benzothiazole |
| Quantities of A; B; C; D | 0.5 g, .002 mol; 3 ml; 0.366 g, .002 mol; 0.99 g, .007 mol | 0.3 g, .001 mol; 3 ml; 0.198 g, .001 mol; 0.57 g, .004 mol |
| Stir temp/time | 25° C., 24 h | 25° C., 24 h |
| Ethyl acetate/hexane ratio | 35:65 | 30:70 |
| Yield | 0.3 g, 43%, off-white solid | 0.02 g, 5%, light yellow solid |
| $^1$H NMR (DMSO, 400 MHz, unless otherwise specified) | 2.53 (s, 3H), 5.42 (s, 2H), 7.05 (t, 1H, J = 8.8 Hz (o-coupling), 7.30 (dt, 1H, J = 9.2 Hz (o-coupling), J = 5.2 Hz), 7.47 (d, 1H, J = 8.4 Hz (o-coupling), 7.59 (d, 1H, J = 8.4 Hz (o-coupling), 7.80 (s, 1H), 7.89 (d, 2H, J = 8.8 Hz (o-coupling), 8.16 (s, 1H), 8.38 (d, 1H, J = 8.4 Hz (o-coupling) | 5.73 (s, 2H), 7.12 (dt, 1H, J = 8.8 Hz (o-coupling), J = 1.2 Hz (m-coupling), 7.41 (dt, 1H, J = 9.2 Hz (o-coupling) J = 5.2 Hz), 7.61 (dd, 2H, J = 7.6 Hz (o-coupling), 7.91 (broad s, 1H), 8.04 (dd, 1H, J = 7.2 Hz (o-coupling), J = 1.6 Hz (m-coupling), 8.19 (broad s, 1H) |
| MS-ES+ | 329.17 | 355.04 |
| HPLC method no., Rt (min) | 5, 11.00 | 5, 9.85 |

| Example | 105 | 106 |
|---|---|---|
| Product | 3-[4-(4-Methoxyphenyl)thiazol-2-ylmethoxy]-2,6-difluoro-benzamide | 3-[4-(4-Chloro-phenyl)-thiazol-2-ylmethoxy]2,6-difluoro-benzamide |
| Reaction scheme | 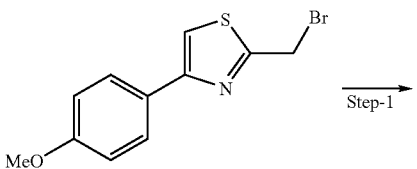 | 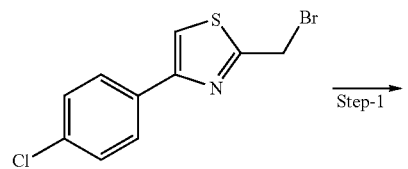 |

TABLE E-continued

| | | |
|---|---|---|
| |  |  |
| Reactant (A) | 2-Bromomethyl-4-(4-methoxy-phenyl)-thiazole | 2-Bromomethyl-4-(4-chloro-phenyl)-thiazole |
| Quantities of A; B; C; D | 0.085 g, .0003 mol; 2 ml; 0.052 g, .0003 mol; 0.142 g, .0010 mol | 0.45 g, .0015 mol; 5 ml; 0.273 g, .0015 mol; 0.747 g, .0055 mol |
| Stir temp/time | 25° C., 24 h | 25° C., 24 h |
| Ethyl acetate/hexane ratio | 40:60 | 40:60 |
| Yield | 0.048 g, 42%, white solid | 0.35 g, 58%, white solid |
| $^1$H NMR (DMSO, 400 MHz, unless otherwise specified) | 3.80 (s, 3H), 5.57 (s, 2H), 7.01 (d, 2H, J = 8.8 Hz), 7.12 (m, 1H), 7.41 (m, 1H), 7.88 (broad s, 2H), 7.90 (s, 1H), 8.02 (s, 1H), 8.17 (s, 1H) | 5.59 (s, 2H), 7.12 (dt, 1H, J = 8.8 Hz (o coupling), J = 2.0 Hz (m-coupling), 7.41 (dt, 1H, J = 9.2 Hz (o-coupling), J = 5.2 Hz), 7.52 (d, 2H, J = 8.4 (o-coupling), 7.89 (broad s, 1H), 7.99 (d, 1H, J = 8.8 Hz (o-coupling), 8.17 (broad s, 1H), 8.26 (s, 1H) |
| MS-ES+ | 377.04 | 381.03 |
| HPLC method no., Rt (min) | 5, 9.63 | 5, 10.23 |

| Example | 107 | 108 |
|---|---|---|
| Product | 2,6-Difluoro-3-(3-trifluoromethoxybenzyloxy)benzamide | 3-(3-Carbamoyl-2,4-difluoro-phenoxymethyl)-benzoic acid methyl ester |
| Reaction scheme | 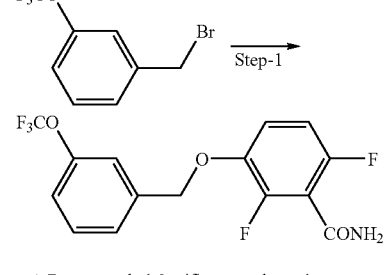 | 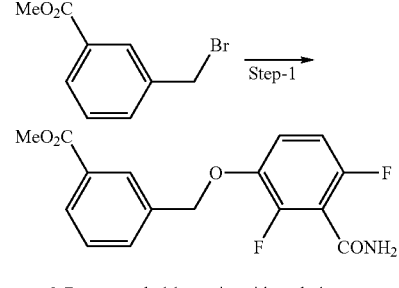 |
| Reactant (A) | 1-Bromomethyl-3-trifluoromethoxy-benzene | 3-Bromomethyl-benzoic acid methyl ester |
| Quantities of A; B; C; D | 0.243 g, .001 mol; 2 ml; 0.173 g, .001 mol; 0.485 g, .003 mol | 0.230 g, .001 mol; 2 ml; 0.173 g, .001 mol; 0.485 g, 003 mol |
| Stir temp/time | 25° C., 24 h | 25° C., 24 h |
| Ethyl acetate/hexane ratio | 20:80 | 20:80 |
| Yield | 0.058 g, 18.4%, white solid | 0.055 g, 18.4%, white solid |
| $^1$H NMR (DMSO, 400 MHz, unless otherwise specified) | 5.25 (s, 2H), 7.09 (dt, 1H, J = 8.8 Hz (o-coupling), J = 2.0 Hz (m-coupling), 7.29 (dt, 1H, J = 9.2 Hz (o-coupling), J = 5.2 Hz), 7.36 (d, 1H, J = 8.0 Hz), 7.48 (t, 2H, J = 8.8 Hz (o-coupling), 7.S6 (t, 1H, J = 8.0 Hz (o-coupling), 7.86 (broad s, 1H), 8.14 (s, 1H) | 3.87 (s, 3H), 5.28 (s, 2H), 7.08 (d, 1H, J = 9.2 Hz (o-coupling), 7.27-7.33 (m, 1H), 7.58 (t, 1H J = 7.6 Hz (o-coupling), 7.73 (d, 1H, J = 7.6 Hz (o-coupling), 7.86 (s, 1H), 7.94 (d, 1H, J = 8 0 Hz (o-coupling), 8.06 (s, 1H), 8.1S (s, 1H) |
| MS-ES+ | 348.11 | 322.13 |
| HPLC method no., Rt (min) | 5, 9.81 | 5, 9.29 |

| Example | 109 | 110 |
|---|---|---|
| Product | 3-(6-Methoxyquinolin-2-ylmethoxy)-2,6-difluoro-benzamide | 3-(6-Chloro-quinolin-2-ylmethoxy)-2,6-difluoro-benzamide |
| Reaction scheme | 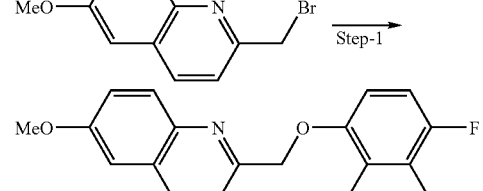 | 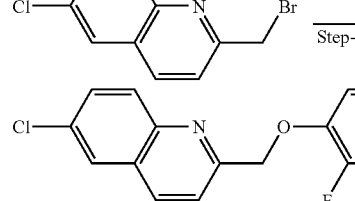 |

TABLE E-continued

| | | |
|---|---|---|
| Reactant (A) | 2-Bromomethyl-6-methoxy-quinoline | 2-Bromomethyl-6-chloro-quinoline |
| Quantities of A; B; C; D | 0.1 g, .0003 mol; 2 ml; 0.068 g, .0003 mol; 0.185 g, .00013 mol | 0.09 g, .00038 mol; 2 ml; 0.065 g, .00038 mol; 0.1 g, .0007 mol |
| Stir temp/time | 25° C., 24 h | 25° C., 24 h |
| Ethyl acetate/hexane ratio | 35:65 | 35:65 |
| Yield | 0.045 g, 33%, yellow solid | 0.02 g, 16%, white solid |
| $^1$H NMR (DMSO, 400 MHz, unless otherwise specified) | 3.90 (s, 3H), 5.39 (s, 2H), 7.06 (m, 1H, J = 8.8 Hz (o-coupling), J = 1.6 Hz (m-coupling), 7.32 (dt, 1H, J = 9.2 Hz (o-coupling), J = 5.2 Hz), 7.39-7.44 (m, 2H), 7.61 (d, 1H, J = 8.4 Hz (o-coupling), 7.87 (s, 1H) 7.92 (d, 1H, J = 9.2 Hz (o-coupling), 8.16 (s, 1H), 8.33 (d, 1H, J = 8.4 Hz (o-coupling) | 5.45 (s, 2H), 7.06 (dt, 1H, J = 8.8 Hz (o-coupling) J = 1.6 Hz (m-coupling), 7.31 (dt, 1H, J = 9.2 Hz (o-coupling), J = 5.2 Hz), 7.73 (d, 1H, J = 8.4 Hz), 7.80 (dd, 1H, J = 2.4 Hz (m-coupling), J = 8.8 Hz (o-coupling), 7.87 (s, 1H), 8.03 (d, 1H, J = 9.2 Hz (o-coupling), 8.16 (2H, J = 2.4 Hz (m-coupling), 8.44 (d, 1H, J = 8.8 Hz (o-coupling) |
| MS-ES+ | 345.06 | 349.01 |
| HPLC method no., Rt (min) | 5, 9.28 | 5, 9.99 |

| | | |
|---|---|---|
| Example | 111 | 112 |
| Product | 3-(7-Chloro-quinolin-2-ylmethoxy)-2,6-difluoro-benzamide | 3-(8-Chloro-quinolin-2-ylmethoxy)-2,6-difluoro-benzamide |
| Reaction scheme | | |
| Reactant (A) | 2-Bromomethyl-7-chloro-quinoline | 2-Bromomethyl-8-chloro-quinoline |
| Quantities of A; B; C; D | 0.068 g, .00028 mol; 2 ml; .050 g, 00028 mol; 0.139 g, .001 mol | 0.1 g, .0004 mol; 2 ml; 0.0733 g, 0004 mol; 0.175 g, .0014 mol |
| Stir temp/time | 25° C., 24 h | 25° C., 24 h |
| Ethyl acetate/hexane ratio | 35:65 | 50:50 |
| Yield | 0.015 g, 94%, white solid | 0.038 g, 27%, white solid |
| $^1$H NMR (DMSO, 400 MHz, unless otherwise specified) | 5.45 (s, 2H), 7.06 (m, 1H, J = 9.2 Hz (o-coupling) J = 1.6 Hz (m-coupling), 7.31 (dt, 1H, J = 9.2 Hz (o-coupling), J = 5.2 Hz), 7.68 (dd, 1H, J = 2.0 (m-coupling), 8.8 Hz (o-coupling)), 7.69 (d, 1H, J = 8.4 Hz (o-coupling), 7.87 (broad s, 1H), 8.06-8.08 (m, 2H), 8.16 (broad s, 1H), 8.50 (d, 1H, J = 8.8 Hz (o-coupling) | 7.38 (dt, 1H, J = 9.2 Hz (o-coupling), J = 5.2 Hz), 7.61 (t, 1H, J = 8.0 Hz (o-coupling), 7.78 (d, 1H, J = 8.4 Hz (o-coupling), 7.87 (broad s, 1H), 7.98-8.03 (m, 2H), 8.16 (broad s, 1H), 8.55 (d, 1H, J = 8.8 Hz (o-coupling) |
| MS-ES+ | 349.00 | 349.01 |
| HPLC method no., Rt (min) | 5, 10.01 | 5, 9.98 |

| | | |
|---|---|---|
| Example | 113 | 114 |
| Product | 2,6-Difluoro-3-(naphthalen-2-ylmethoxy)-benzamide | 2,6-Difluoro-3-(5-phenyl-benzothiazol-2-ylmethoxy)-benzamide |
| Reaction scheme | | |

TABLE E-continued

| | | |
|---|---|---|
| | 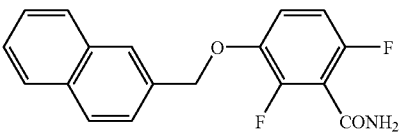 | 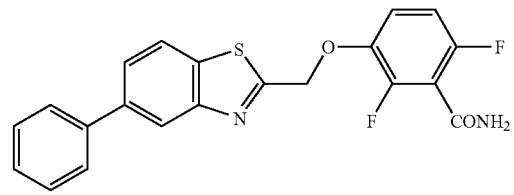 |
| Reactant (A) | 2-Bromomethyl-naphthalene | 2-Bromomethyl-5-phenyl-benzothiazole |
| Quantities of A; B; C; D | 0.5 g, .0022 mol; 5 ml; 0.391 g, .0022 mol; 1.06 g, .0076 mol | 0.23 g, .00075 mol; 5 ml; 0.13 g, .00075 mol; 0.36 g, .0026 mol |
| Stir temp/time | 25° C., 24 h | 25° C., 24 h |
| Ethyl acetate/hexane ratio | 35:65 | 30:70 |
| Yield | 0.35 g, 49%, off white solid | 0.012 g, 4%, light yellow solid |
| $^1$H NMR (DMSO, 400 MHz, unless otherwise specified) | 5.36 (s, 2H), 7.07 (dt, 1H, J = 9.2 Hz (o-coupling) J = 2.0 Hz (m-coupling), 7.34 (dt, 1H, J = 9.2 Hz (o-coupling), J = 5.2 Hz), 7.53-7.55 (m, 2H), 7.58 (dd, 1H, J = 8.4 Hz (o-coupling) J = 2.4 Hz (m- coupling), 7.86 (broad s, 1H,), 7.92-7.97 (m, 3H), 7.98 (broad s, 1H) 8.143 (broad s, 1H) | 5.73 (s, 2H), 7.11 (t, 1H, J = 9.2 Hz (o-coupling), 7.36-7.43 (m, 2H), 7.51 (t, 2H, J = 7.6 Hz (o-coupling), 7.78-7.81 (m, 3H), 7.90 (broad s, 1H), 8.16 (broad s, 1H), 8.29 (d, 1H, J = 8.4 Hz (o-coupling), 8.28-8.29 (d, 1H, J = 1.6 (m-coupling) |
| MS-ES+ | 314.06 | 397.11 |
| HPLC method no., Rt (min) | 5, 9.95 | 5, 10.28 |
| Example | 115 | 116 |
| Product | 2,6-Difluoro-3-(4-pyridin-2-yl-thiazol-2-ylmethoxy)-benzamide | 2,6-Difluoro-3-(3-methoxybenzyloxy)-benzamide |
| Reaction scheme | 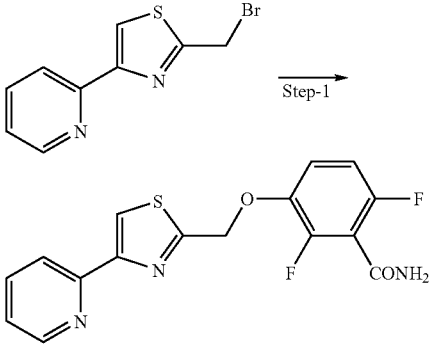 | 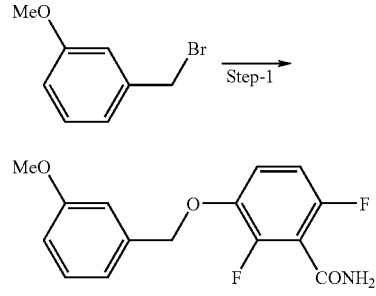 |
| Reactant (A) | 2-(2-Bromomethyl-thiazol-4-yl)-pyridine | 1-Bromomethyl-3-methoxy-benzene |
| Quantities of A; B; C; D | 0.23 g, .0009 mol; 3 ml; 0.156 g, .0009 mol; 0.424 g, .003 mol | 0.2 g, .001 mol; 2 ml; 0.173 g, .001 mol; 0.485 g, .0035 mol |
| Stir temp/time | 25° C., 24 h | 25° C., 24 h |
| Ethyl acetate/hexane ratio | 20:80 | 20:80 |
| Yield | 0.058 g, 18%, light yellow solid | 0.055 g, 18%, white solid |
| $^1$H NMR (DMSO, 400 MHz, unless otherwise specified) | 3.75 (s, 3H), 5.15 (s, 2H), 6.90 (d, 1H, J = 8.0 Hz (o-coupling), 7.00 (broad s, 1H), 7.05 (t, 2H, J = 8.8 Hz (a-coupling), 7.25-731 (m, 2H), 7.84 (broad s, 1H), 8.13 (broad s, 1H) | 3.75 (s, 3H), 5.15 (s, 2H), 6.90 (d, 1H, J = 8.0 Hz (o-coupling), 7.00 (broad s, 1H), 7.05 (t, 2H, J = 8.8 Hz (a-coupling), 7.25-731 (m, 2H), 7.84 (broad s, 1H), 8.13 (broad s, 1H) |
| MS-ES+ | 294.14 | 294.14 |
| HPLC method no., Rt (min) | 5, 8.29 | 5, 9.34 |
| Example | 117 | 119 |
| Product | 2,6-Difluoro-3-(5-nitro-benzothiazol-2-ylmethoxy)-benzamide | 2,6-Difluoro-3-(5-methoxy-benzothiazol-2-ylmethoxy)-benzamide |
| Reaction scheme | 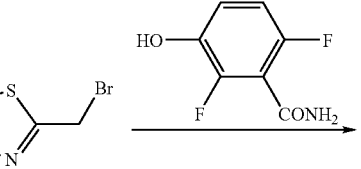 | 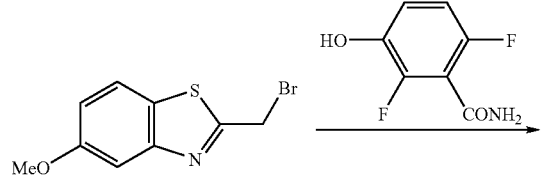 |

TABLE E-continued

| | | |
|---|---|---|
| | 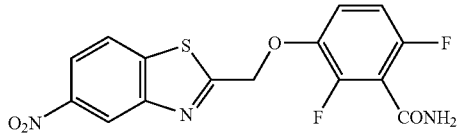 | 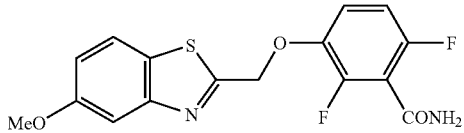 |
| Reactant (A) | 2-bromomethyl-5-nitro-benzothiazole | 2-bromomethyl-5-methoxy-benzothiazole |
| Quantities of A; B; C; D | 0.05 g, 0.183 mmol; 2 ml; 0.031 g, 0.183 mmol; 0.088 g, 0.64 mmol | 0.045 g, 0.174 mmol; 5 ml; 0.030 g, 0.174 mmol; 0.082 g, 0.609 mmol |
| Stir temp/time | 25° C., 24 h | RT, overnight |
| Ethyl acetate/hexane ratio | 35:65 | 35:65 |
| Yield | 0.040 g, 67%, yellow solid | 0.020 g, 33%, yellow solid |
| $^1$H NMR (DMSO, 400 MHz, unless otherwise specified) | δ 5.77 (s, 3H), 5.42 (s, 2H), 7.12 (t, 1H, J = 8.8 Hz (o-coupling), 7.42 (dt, 1H, J = 9.2 Hz (o-coupling) 7.90 (broad s, 1H), 8.18 (broad s, 1H), 8.32 (d, 1H, J = 8.8 Hz (o-coupling), 8.46 (d, 1H, J = 9.2 Hz (o-coupling), 8.83 (s, 1H) | δ 3.84 (broad s, 3H), 5.66 (s, 2H), 7.08-7.12 (m, 2H), 7.38 (dt, 1H, J = 8.4 Hz (o-coupling), 7.55-7.56 (m, 1H), 7.88 (broad s, 1H,) 7.99 (d, 3H J = 9.2 Hz (o-coupling), 8.17 (broad s, 1H) |
| MS-ES+ | 366.06 | 351.10 |
| HPLC method no., Rt (min) | 5, 15.63 | 5, 15.69 |

| Example | 122 | 124 |
|---|---|---|
| Product | 2,6-Difluoro-3-(4-phenethyl-thiazol-2-ylmethoxy)-benzamide | 3-[1-(5-Chloro-benzothiazol-2-yl)-ethoxy]-2,6-difluoro-benzamide |
| Reaction scheme | 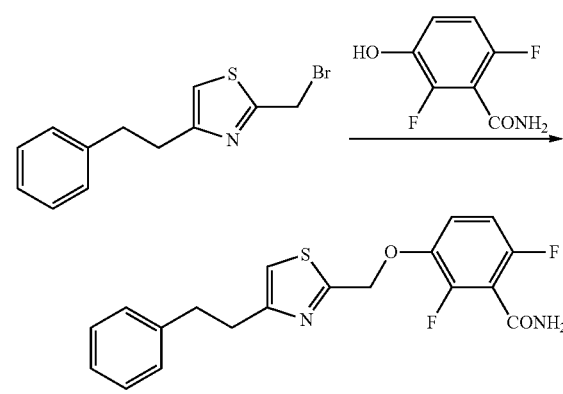 | 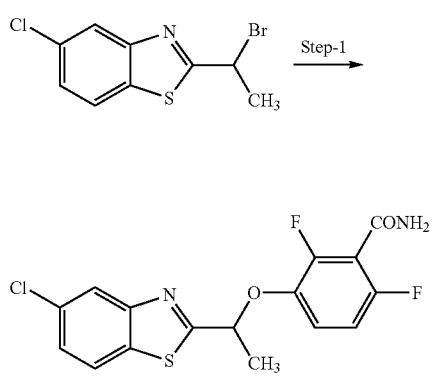 |
| Reactant (A) | 2-bromomethyl-4-phenethyl-thiazole | 2-(1-bromo-ethyl)-5-chloro-benzothiazole |
| Quantities of A; B; C; D | 0.200 g, 0.7 mmol; 5 ml; 0.125 g, 0.7 mmol; 0.300 g, 2.4 mmol | 0.3 g, 0.1 mmol; 2 ml; 0.188 g, 0.1 mol; 0.5 g, 0.3 mol |
| Stir temp/time | RT, overnight | 25° C., 2 h |
| Ethyl acetate/hexane ratio | 35:65 | 35:65 |
| Yield | 0.108 g, 41%, white solid | 0.1 g, 25%, yellow solid |
| $^1$H NMR (DMSO, 400 MHz, unless otherwise specified) | δ 2.98 (tt, 4H, J = 4.8 Hz), 5.48 (s, 2H), 7.08-7.15 (m, 1H), 7.17-7.28 (m, 4H), 7.33-7.38 (m, 2H), 7.87 (broad s, 1H), 8.16 (broad s, 1H) | δ 1.76 (d, 3H, J = 6.4 Hz), 6.01 (q, 1H, J = 6.4 Hz (o-coupling), 7.06 (dt, 1H, J = 8.8 Hz (o coupling), 7.34 (dt, 1H, J = 9.2 Hz (o-coupling, 5.2 Hz)), 7.52 (dd, 1H, J = 7.2 Hz (o-coupling), 7.89 (broad s, 1H), 8.11 (s, 1H), 8.17 (d, 2H, J = 8.4 Hz (o-coupling) |
| MS-ES+ | 375.14 | 369.06 |
| HPLC method no., Rt (min) | 5, 15.84 | 5, 10.5 |

| Example | 128 | 129 |
|---|---|---|
| Product | 2,6-Difluoro-3-(2-fluoro-3-methyl-benzyloxy)-benzamide | — |

TABLE E-continued

| Reaction scheme | 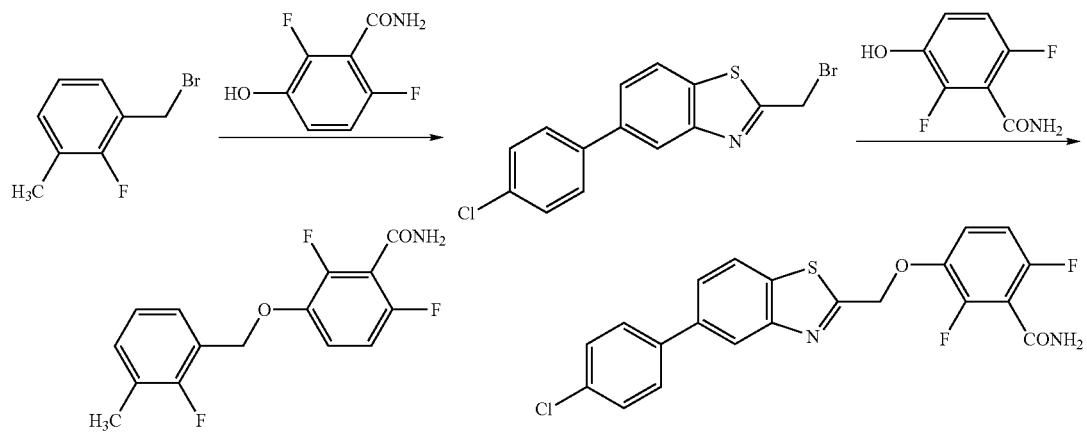 | 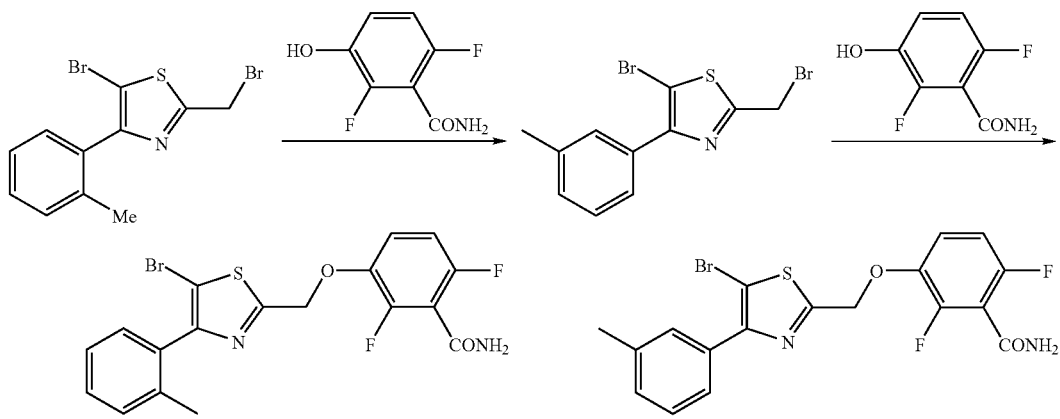 |
|---|---|---|
| Reactant (A) | 1-bromomethyl-2-fluoro-3-methyl-benzene | 2-bromomethyl-5-(4-chloro-phenyl)-benzothiazole |
| Quantities of A; B; C; D | 0.19 g, 1.0 mmol; 2 ml; 0.173 g, 1.0 mmol; 0.483 g, 3.5 mmol | 0.050 g, 0.147 mmol; 5 ml; 0.025 g, 0.147 mmol; 0.075 g, 0.517 mmol |
| Stir temp/time | RT, overnight | 25° C., overnight |
| Ethyl acetate/hexane ratio | 35:65 | 35:65 |
| Yield | 0.112 g, 38%, white solid | 0.020 g, 54%, white solid |
| $^1$H NMR (DMSO, 400 MHz, unless otherwise specified) | δ 2.26 (s, 3H), 5.18 (s, 2H), 7.06-7.14 (m, 2H), 7.29-7.37 (m, 3H) 7.85 (broad s, 1H), 8.14 (broad s, 1H) | δ 5.72 (s, 2H), 7.11 (dt, 1H, J = 8.0 Hz (o-coupling) & 8.4 Hz) 7.39 (m, 1H), 7.55 (d, 2H J = 8.4 Hz (o-coupling), 7.78-7.83 (m, 3H), 7.89 (broad s, 1H), 8.18 (broad s, 1H), 8.23 (d, 2H, J = 8.0 Hz (o-coupling), 8.30 (s, 1H) |
| MS-ES+ | 296.13 | 431.095 |
| HPLC method no., Rt (min) | 5, 11.02 | 5, 11.02 |

| Example | 130 | 131 |
|---|---|---|
| Product | — | — |
| Reaction scheme | | |
| Reactant (A) | 5-bromo-2-bromomethyl-4-o-tolyl-thiazole | 5-bromo-2-bromomethyl-4-m-tolyl-thiazole |
| Quantities of A; B; C; D | 0.5 g, 1.8 mmol; 10 ml; 0.313 g, 1.8 mmol; 0.884 g, 6.5 mmol | 0.70 g, 2.61 mmol; 10 ml; 0.450 g, 2.61 mmol; 1.2 g, 9.14 mmol |
| Stir temp/time | 25° C., overnight | 25° C., overnight |
| Ethyl acetate/hexane ratio | 35:65 | 35:65 |
| Yield | 0.281 g, 44%, off white solid | 0.371 g, 40%, yellow solid |

TABLE E-continued

| | | |
|---|---|---|
| ¹H NMR (DMSO, 400 MHz, unless otherwise specified) | δ 5.53 (s, 2H), 7.11 (dt, 1H, J = 8.8 Hz (o-coupling), 7.38 (m, 5H), 7.89 (broad s, 1H), 8.16 (broad s, 1H) | ¹H NMR (MeOH, 400 MHz); δ 2.70 (s, 3H), 5.23 (s, 2H), 6.93 (dt, 1H, J = 8.8 Hz (o-coupling) & 2.0 Hz (m-coupling), 7.23 (dt, 1H, J = 4.8 Hz), 7.48 (d, 1H, J = 8.0 Hz (o-coupling), 7.49 (s, 1H), 7.80-7.82 (m, 1H), 7.93 (broad s, 1H) |
| MS-ES+ | 439.09 | 439 & 441.08 |
| HPLC method no., Rt (min) | 5, 10.56 | 5, 10.53 |

| Example | 132 | 133 |
|---|---|---|
| Product | 2,6-Difluoro-3-(2-phenyl-oxazol-4-ylmethoxy)-benzamide | 2,6-Difluoro-3-(2-thiophen-2-yl-oxazol-4-ylmethoxy)-benzamide |
| Reaction scheme | | |
| Reactant (A) | 4-bromomethyl-2-phenyl-oxazole | 4-bromomethyl-2-thiophen-2-yl-oxazole |
| Quantities of A; B; C; D | 0.238 g, 1.0 mmol; 2 ml; 0.173 g, 1.0 mmol; 0.483 g, 3.5 mmol | 0.218 g, 1.0 mmol; 2 ml; 0.173 g, 1.0 mmol; 0.483 g, 3.5 mmol |
| Stir temp/time | 25° C., 24 h | RT, overnight |
| Ethyl acetate/hexane ratio | 35:65 | 35:65 |
| Yield | 0.099 g, 30%, white solid | 0.020 g, 33%, off white solid |
| ¹H NMR (DMSO, 400 MHz, unless otherwise specified) | δ 5.15 (s, 2H), 7.12 (dt, 1H, J = 8.8 Hz (o-coupling), 7.42 (dt, 1H, J = 9.2 Hz J = 5.2 Hz, (m-coupling), 7.55 (t, 3H, J = 3.2 Hz), 7.85 (broad s, 1H), 7.98-8.00 (m, 2H), 8.13 (broad s, 1H), 8.33 (s, 1H) | δ 5.11 (s, 2H), 7.09 (dt, 1H, J = 8.8 Hz (o-coupling), 7.23 (t, J = 4.8 Hz), 7.39 (dt, 1H, J = 5.2 Hz), 7.73 (d, 1H, J = 5.2 Hz), 7.82 (d, 1H, J = 5.2 Hz), 7.85 (broad s, 1H), 8.13 (broad s, 1H), 8.27 (s, 1H) |
| MS-ES+ | 331.1 | 337.1 |
| HPLC method no., Rt (min) | 5, 9.43 | 5, 9.21 |

| Example | 134 | 137 |
|---|---|---|
| Product | 2,6-Difluoro-3-(5-thiophen-2-yl-[1,2,4]oxadiazol-3-ylmethoxy)-benzamide | 3-(4-Benzyl-thiazol-2-ylmethoxy)-2,6-difluoro benzamide |
| Reaction scheme | | |
| Reactant (A) | 3-bromomethyl-5-thiophen-2-yl-[1,2,4]oxadiazole | 4-benzyl-2-bromomethyl-thiazole |

TABLE E-continued

| | | |
|---|---|---|
| Quantities of A; B; C; D | 0.245 g, 1.0 mmol; 2 ml; 0.173 g, 1.0 mmol; 0.483 g, 3.5 mmol | 0.268 g, 1 mmol; 2 ml; 0.173 g, 1 mmol; 0.483 g, 3.5 mmol |
| Stir temp/time | RT, overnight | 25° C., 24 h |
| Ethyl acetate/hexane ratio | 35:65 | 40:60 |
| Yield | 0.020 g, 6%, off white solid | 0.126 g, 35%, white solid |
| $^1$H NMR (DMSO, 400 MHz, unless otherwise specified) | δ 5.43 (s, 2H), 5.15 (s, 2H), 7.12 (dt, 1H, J = 9.2 Hz (o-coupling & 1.6 Hz (m-coupling), 7.34-7.41 (m, 2H), 7.87 (broad s, 1H), 8.06 (d, 1H, J = 4.0), 8.12 (d, 1H, J = 4.8 Hz), 8.16 (broad s, 1H) | 64.06 (s, 2H), 5.45 (s, 2H), 7.07 (dt, 1H, J = 7.6 Hz (o-coupling), 7.18 (t, 1H, J = 6.8 Hz), 7.23-7.36 (m, 5H), 7.37 (s, 1H), 7.86 (broad s, 1H), 8.14 (broad s, 1H) |
| MS-ES+ | 338.09 | 361.05 |
| HPLC method no., Rt (min) | 5, 9.2 | 5, 15.45 |

| Example | 138 | 139 |
|---|---|---|
| Product | 3-(5-Cyclopropyl-[1,3,4]thiadiazol-2-ylmethoxy)-2,6-difluoro-benzamide | 3-(6-Chloro-thiazolo[5,4-b]pyridin-2-ylmethoxy)-2,6-difluoro-benzamide |
| Reaction scheme | | |
| Reactant (A) | 2-bromomethyl-5-cyclopropyl-[1,3,4]thiadiazole | 2-bromomethyl-6-chloro-thiazolo[5,4-b]pyridine |
| Quantities of A; B; C; D | 0.21 9 g, 1 mmol; 2 ml; 0.173 g, 1 mmol; 0.483 g, 3.5 mmol | 0.1g, 0.38 mmol; 5 ml; 0.066 g, 0.38 mmol; 0.184 g, 1.336 mmol |
| Stir temp/time | RT, overnight | RT, overnight |
| Ethyl acetate/hexane ratio | 30:70 | 35:65 |
| Yield | 0.118 g, 38%, pink solid | 0.030 g, 22%, yellow solid |
| $^1$H NMR (DMSO, 400 MHz, unless otherwise specified) | δ 1.01-1.05 (m, 2H), 1.19-1.24 (m, 2H), 2.51-2.58 (m, 1H), 5.59 (s, 2H), 7.11 (dt, 1H, J = 9.2 Hz (o-coupling), 7.37 (dt, 1H, J = 9.2 Hz, (a-coupling), J = 1.2 Hz (m-coupling), 7.87 (broad s, 1H), 8.15 (broad s, 1H) | δ 5.72 (s, 2H), 7.12 (dt, 1H, J = 8.8 Hz (o-coupling), 7.37-7.43 (m, 1H), 7.90 (broad s, 1H), 8.18 (broad s, 1H), 8.68 (d, 1H, J = 2.0 Hz, (m-coupling), 8.73 (d, 1H, J = 2.0 Hz, (m-coupling) |
| MS-ES+ | 312.11 | 356.05 |
| HPLC method no., Rt (min) | 5, 8.79 | 5, 15.84 |

| Example | 142 | 144 |
|---|---|---|
| Product | 2,6-Difluoro-3-(5-m-tolyl-benzothiazol-2-ylmethoxy)-benzamide | 2,6-Difluoro-3-(2-pyrazol-1-yl-ethoxy)benzamide |
| Reaction scheme | | |

TABLE E-continued

| Reactant (A) | 2-bromomethyl-5-m-tolyl-benzothiazole | 1-(2-bromo-ethyl)-1H-pyrazole |
|---|---|---|
| Quantities of A; B; C; D | 0.160 g, 0.5 mmol; 5 ml; 0.087 g, 0.5 mmol; 0.240 g, 1.76 mmol | 0.175 g, 1 mmol; 2 ml; 0.173 g 1 mmol; 0.483 g 3.5 mmol |
| Stir temp/time | RT, overnight | 25° C., 24 h |
| Ethyl acetate/hexane ratio | 35:65 | 35:65 |
| Yield | 0.026 g, 10%, white solid | 0.112 g, 42%, yellow solid |
| $^1$H NMR (DMSO, 400 MHz, unless otherwise specified) | δ 2.82 (s, 3H), 5.28 (s, 2H), 7.08 (dt, 1H, J = 8.8 Hz (o-coupling, J = 1.2 Hz, (m-coupling), 7.34-7.35 (m, 1H), 7.47 (d, 1H, J = 7.2 Hz (o-coupling), 7.53 (t, 1H, J = 8.0 Hz (o-coupling), 7.71 (dd, 1H, J = 8.0 Hz (o-coupling) J = 1.2 Hz, (m-coupling), 7.7S (d, 1H, J = 8.0 Hz (o-coupling), 7.8S (broad s, 2H), 8.13 (d, 2H, J = 8.4 Hz), 8.18 (d, 1H, J = 1.2 Hz (m-coupling) | δ 4.39 (d, 2H, J 4.8 Hz), 4.50 (d, 2H, J = 4.8 Hz), 6.24 (m, 1H), 7.03 (dt, 1H, J = 1.6 Hz (m-coupling), 7.17 (dt, 1H), 7.46 (d, 1H, J = 2.0 Hz (m-coupling), 7.76 (d, 1H, J = 2.0 (m-coupling), 7.83 (broad s, 1H), 8.10 (broad s, 1H) |
| MS-ES+ | 411.17 | 268.13 |
| HPLC method no., Rt (min) | 5, 17.10 | 5, 13.38 |

| Example | 145 | 146 |
|---|---|---|
| Product | 3-[5-(3,5-Dimethyl-isoxazol-4-yl)-[1,2,4]oxadiazol-3-ylmethoxy]-2,6-difluoro-benzamide | 2,6-Difluoro-3-(8-methyl-quinolin-2-ylmethoxy)-benzamide |
| Reaction scheme | | |
| Reactant (A) | 5-(3,5-dimethyl-isoxazol-4-yl)-3-methyl-[1,2,4]oxadiazole | 2-Bromomethyl-8-methyl-quinoline |
| Quantities of A; B; C; D | 0,179 g, 1.0 mmol; 2 ml; 0.173 g, 1.0 mmol; 0.483 g, 3.5 mmol | 0.130 g, 0.550 mmol; 1.5 ml; 0.095 g, 0.550 mmol; 0.265 g, 1.92 mmol |
| Stir temp/time | 25° C., 24 h | RT, overnight |
| Ethyl acetate/hexane ratio | 40:60 | 35:65 |
| Yield | 0.098 g, 28%, white solid | 0.014 g, 8%, white solid |
| $^1$H NMR (DMSO, 400 MHz, unless otherwise specified) | δ 2.49 (s, 3H), 2.76 (s, 3H), 5.46 (s, 2H), 7.11 (dt, 1H, J = 8.8 Hz (o-coupling), 7.41 (dt, 1H, J = 9.2 Hz (o-coupling), & 5.2 Hz), 7.86 (broad s, 1H), 8.14 (broad s, 1H) | δ 2.71 (s, 3H), 5.46 (s, 2H), 7.06 (dt, 1H, J = 9.2 Hz (o-coupling, J = 1.6 Hz (m-coupling), 7.36 (dt, 1H, J = 9.2 Hz (o-coupling, J = 5.2 Hz), 7.51 (t, 1H, J = 7.6 Hz (o-coupling), 7.65 (t, 2H, J = 7.6 Hz (o-coupling), 7.82 (d, 1H, J = 8.0 Hz (o-coupling), 7.86 (broad s, 1H), 8.15 (broad s, 1H), 8.41 (d, 1H, J = 8.0 Hz (o-coupling) |
| MS-ES+ | 351.13 | 329.09 |
| HPLC method no., Rt (min) | 5, 8.57 | 5, 10.02 |

| Example | 147 | 148 |
|---|---|---|
| Product | 2,6-Difluoro-3-(4-fluoro-3-methyl-benzyloxy)-benzamide | 2,6-Difluoro-3-(5-methyl-benzothiazol-2-ylmethoxy)-benzamide |

TABLE E-continued

| Reaction scheme | 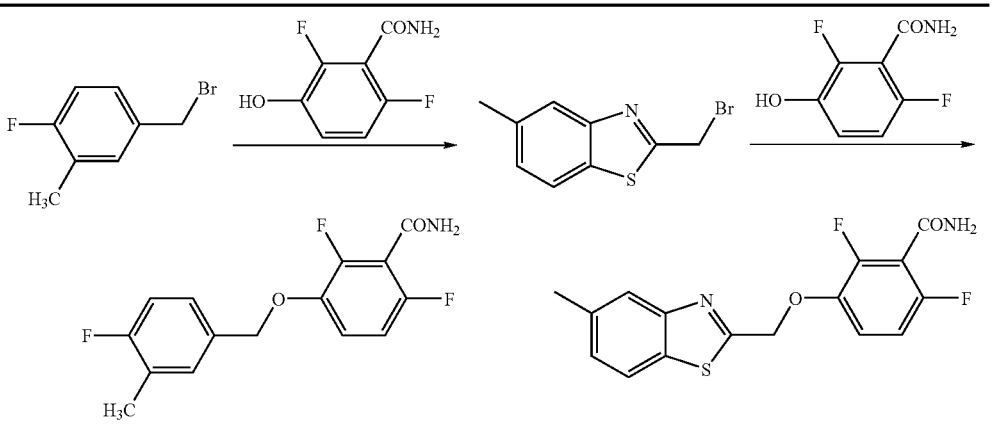 | 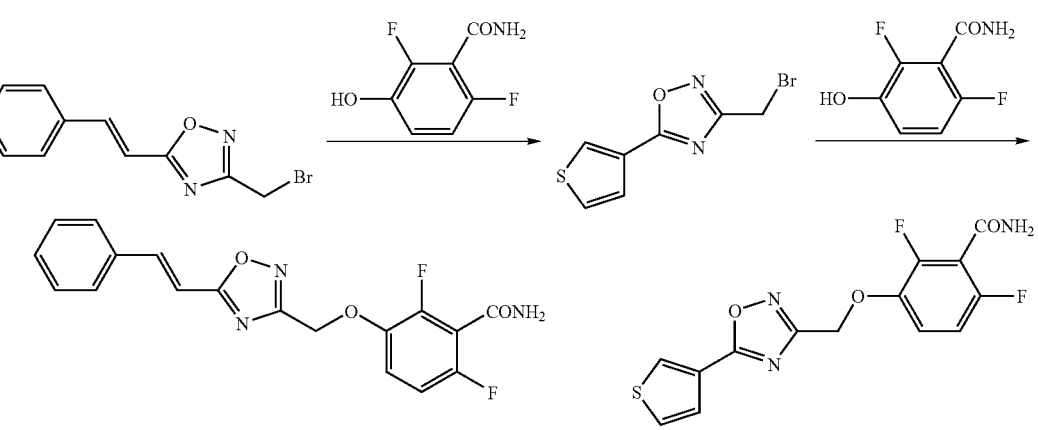 |
|---|---|---|
| Reactant (A) | 4-bromomethyl-1-fluoro-2-methyl-benzene | 2-bromomethyl-5-methyl-benzothiazole |
| Quantities of A; B; C; D | 0.203 g, 1 mmol; 2 ml; 0.173 g, 1 mmol; 0.483 g, 3.5 mmol | 0.06 g, 0.247 mmol; 2 ml; 0.0428 g, 0.247 mmol; 0.119 g, 0.866 mmol |
| Stir temp/time | RT, overnight | 25° C., 24 h |
| Ethyl acetate/hexane ratio | 30:70 | 35:65 |
| Yield | 0.0973 g, 33%, white solid | 0.023 g, 27%, yellow solid |
| $^1$H NMR (DMSO, 400 MHz, unless otherwise specified) | δ 2.24 (s, 3H), 5.10 (s, 2H), 7.06 (dt, 1H, J = 8.8 Hz (o-coupling), J = 1.6 Hz (m-coupling), 7.15 (t, 1H, J = 8.4 Hz (o-coupling), 7.26-7.31 (m, 2H), 7.36 (d, 1H, J = 7.6 Hz (o-coupling), 7.84 (broad s, 1H), 8.12 (broad s, 1H) | δ 2.46 (s, 3H), 5.67 (s, 2H), 7.10 (dt, J = 8.4 Hz (o-coupling), 7.30 (d, 1H, J = 8.0 Hz (o-coupling), 7.37 (dt, 1H, J = 5.2 Hz, J = 9.2 Hz), 7.83 (s, 1H), 7.88 (broad s, 1H), 8.00 (d, 1H, J = 8.4 Hz (o-coupling), 8.17 (broad s, 1H) |
| MS-ES+ | 296.11 | 335.09 |
| HPLC method no., Rt (min) | 5, 15.53 | 5, 15.29 |

| Example | 149 | 150 |
|---|---|---|
| Product | 2,6-Difluoro-3-(5-styryl-[1,2,4]oxadiazol-3-ylmethoxy)-benzamide | 2,6-Difluoro-3-(5-thiophen-3-yl-[1,2,4]oxadiazol-3-ylmethoxy)-benzamide |
| Reaction scheme | 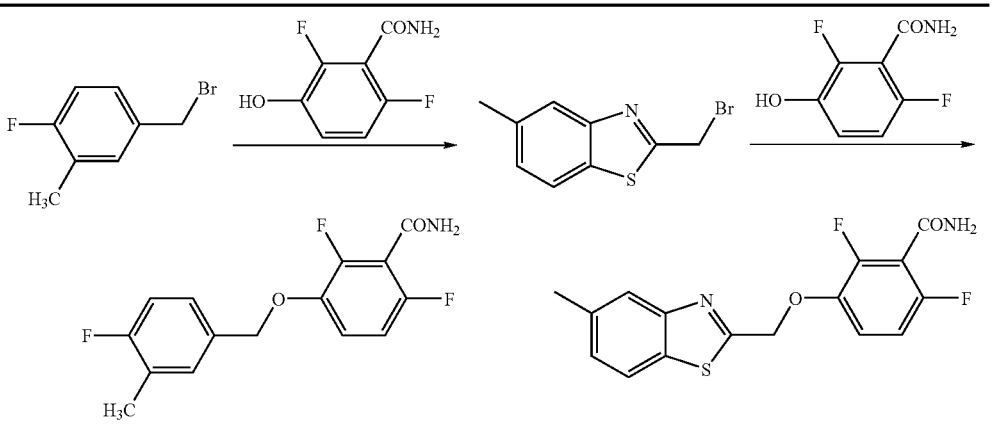 | 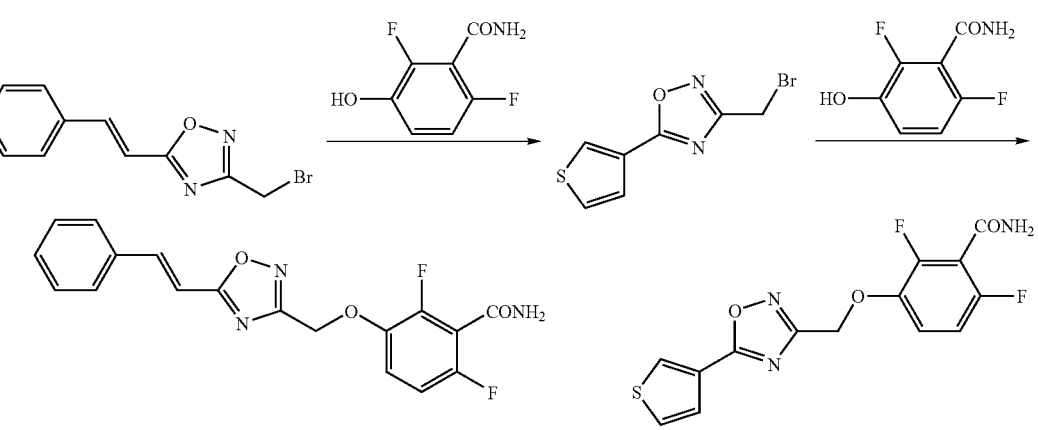 |
| Reactant (A) | 3-bromomethyl-5-styryl-[1,2,4]oxadiazole | 3-bromomethyl-5-thiophen-3-yl-[1,2,4]oxadiazole |
| Quantities of A; B; C; D | 0.265 g, 1.0 mmol; 2 ml; 0.173 g 1.0 mmol; 0.483 g 3.5 mmol | 0,245 g, 1.0 mmol; 2 ml; 0.173 g, 1.0 mmol; 0.483 g, 3.5 mmol |
| Stir temp/time | 25° C., 24 h | 25° C., 24 h |
| Ethyl acetate/hexane ratio | 40:60 | 30:70 |
| Yield | 0.089 g, 25%, white solid | 0.067 g, 20%, white solid |
| $^1$H NMR (DMSO, 400 MHz, unless otherwise specified) | δ 5.41 (s, 2H), 7.11 (dt, 1H, J = 8.4 Hz (o-coupling), 7.35-7.47 (m, 5H), 7.78- 7.93 (m, 4H), 8.16 (broad s, 1H) | δ 5.43 (s, 2H), 7.11 (dt, 1H, J = 8.8 Hz (o-coupling), 7.38 (dt, J = 5.2 Hz, J = 9.2 Hz), 7.70 (d, 1H, J = 5.2 Hz), 7.85-7.87 (m, 2H), 8.15 (broad s, 1H) 8.64 (t, 1H, J = 1.2) |
| MS-ES+ | 358.14 | 338.08 |

TABLE E-continued

| | | |
|---|---|---|
| HPLC method no., Rt (min) | 5, 9.2 | 5, 8.66 |
| Example | 151 | 152 |
| Product | 3-(5-Bromo-quinolin-2-ylmethoxy)-2,6-difluoro-benzamide | 2,6-Difluoro-3-(5-thiophen-2-yl-[1,3,4]oxadiazol-2-ylmethoxy)-benzamide |
| Reaction scheme | | |
| Reactant (A) | 5-bromo-2-bromomethyl-quinoline | 2-bromomethyl-5-thiophen-2-yl-[1,3,4]oxadiazole |
| Quantities of A; B; C; D | 0.300 g, 1.0 mmol; 1.5 ml; 0.173 g, 1.0 mmol; 0.483 g, 3.5 mmol | 0.245 g, 1.0 mmol; 2 ml; 0.173 g, 1.0 mmol; 0.483 g, 3.5 mmol |
| Stir temp/time | RT, overnight | RT, overnight |
| Ethyl acetate/hexane ratio | 35:65 | 30:70 |
| Yield | 0.086 g, 22%, white solid | 0.0842 g, 25%, off white solid |
| $^1$H NMR (DMSO, 400 MHz, unless otherwise specified) | δ 5.50 (s, 2H), 7.06 (dt, 1H, J = 8.4 Hz (o-coupling), 7.30-7.31 (m, 1H), 7.73 (t, 1H, J = 8.0 Hz), 7.83 (d, 1H, J = 8.8 Hz (o-coupling), 7.87 (broad s, 1H), 7.99 (d, 1H, J = 7.6 Hz (o-coupling), 8.06 (d, 1H, J = 8.8 Hz (o-coupling), 8.16 (broad s, 1H), 8.60 (d, 1H, J = 8.8 Hz (o-coupling) | δ 5.55 (s, 2H), 7.14 (dt, 1H, J = 9.2 Hz (o-coupling), 7.31 (dd, 1H, J = 4.8 Hz), 7.43 (dt, 1H, J = 9.2 Hz, J = 5.2 Hz), 7.86 (dd, 1H, J = 4.8 Hz), 7.88 (broad s, 1H), 7.99 (d, 1H, J = 5.2 Hz), 8.15 (broad s, 1H) |
| MS-ES+ | 393.01 | 338.1 |
| HPLC method no., Rt (min) | 5, 15.70 | 5, 8.95 |
| Example | 153 | 154 |
| Product | 2,6-Difluoro-3-(3-thiophen-2-yl-[1,2,4]oxadiazol-5-ylmethoxy)-benzamide | 3-(3-Benzyloxy-benzyloxy)-2,6-difluoro-benzamide |
| Reaction scheme | | |
| Reactant (A) | 5-bromomethyl-3-thiophen-2-yl-[1,2,4]oxadiazole | 3-benzyloxy-benzylbromide |
| Quantities of A; B; C; D | 0.245 g, 1.0 mmol; 2 ml; 0.1 73 g, 1.0 mmol; 0.483 g, 3.5 mmol | 0,276 g, 1.0 mmol; 2 ml; 0.1 73 g, 1.0 mmol; 0.483 g, 3.5 mmol |
| Stir temp/time | 25° C., 24 h | 25° C., 24 h |
| Ethyl acetate/hexane ratio | 50:50 | 45:55 |
| Yield | 0.045 g, 13%, yellow solid | 0.035 g, 10%, off white solid |
| $^1$H NMR (DMSO, 400 MHz, unless | δ 5.67 (s, 2H), 7.13 (dt, 1H, J = 8.8 Hz (o-coupling), J = 1.6 Hz (m-coupling), 7.28 (dd, 1H, | δ 5.10 (s, 2H), 5.15 (s, 2H), 6.98-7.09 (m, 4H), 7.22-7.28 (m, 3H), 7.39 (t, 2 H, J = 7.2, (o- |

TABLE E-continued

| | | |
|---|---|---|
| otherwise specified | J = 4.0 Hz (o-coupling), 7.38 (dt, 1H J = 9.2 Hz (o-coupling, 5.2 Hz), 7.83 (dd, 1H, J = 3.6 Hz (o-coupling), 7.91 (broad s, 1H), 7.92 (s, 1H), 8.18 (broad s, 1H) | coupling), 7.37 (d, 2H, J = 7.2 (o-coupling), 7.85 (broad s, 1H), 8.13 (broad s, 1H) |
| MS-ES+ | 338.13 | 370.17 |
| HPLC method no., Rt (min) | 5, 9.26 | 5, 10.18 |

| Example | 156 | 157 |
|---|---|---|
| Product | 3-(6-Chloro-thiazolo[5,4-c]pyridin-2-ylmethoxy)-2,6-difluoro-benzamide | 2,6-Difluoro-3-[5-(2-hydroxy-phenyl)-benzothiazol-2-ylmethoxy]-benzamide |
| Reaction scheme | | |
| Reactant (A) | 2-bromomethyl-6-chloro-thiazolo[5,4-c]pyridine | 2-(2-bromomethyl-benzothiazol-5-yl)-phenol |
| Quantities of A; B; C; D | 0.050 g, 0.189 mmol; 5 ml; 0.0328 g, 0.189 mmol; 0.0916 g, 0.663 mmol | 0.036 g, 0.1 mmol; 5 ml; 0.020 g, 0.11 mmol; 0.030 g, 0.385 mmol |
| Stir temp/time | 25° C., overnight | 25° C., overnight |
| Ethyl acetate/hexane ratio | 50:50 | 50:50 |
| Yield | 0.012 g, 18%, yellow solid | 0.005g, 10.0%, yellow solid |
| $^1$H NMR (DMSO, 400 MHz, unless otherwise specified) | δ 5.78 (s, 2H), 7.12 (dt, 1H, J = 8.8 Hz (o-coupling), 7.38-7.44 (m, 1H), 7.91 (broad s, 1H), 8.20 (broad s, 2H), 9.25 (s, 1H) | δ 5.71 (s, 2H), 6.91 (t, 1H, J = 5.6 Hz), 6.97 (d, 1H, J = 8.4 Hz (o-coupling), 7.11 (dt, 1H, J = 9.2 Hz (o-coupling), 7.20 (t, 1H, J = 7.6 Hz), 7.35 (d, 1H, J = 8.8 Hz (o-coupling), 7.39-7.43 (m, 1H), 7.64 (d, 1H, J = 8.8 Hz (o-coupling), 7.89 (broad s, 1H), 8.13 (d, 2H, J = 8.4 Hz), 8.18 (broad s, 1H) |
| MS-ES+ | 355.9 | 413.01 |
| HPLC method no., Rt (min) | 5, 15.25 | 5, 15.22 |

| Example | 158 | 159 |
|---|---|---|
| Product | 3-[5-Bromo-4-(4-methoxy-phenyl)-thiazol-2-ylmethoxy]-2,6-difluoro-benzamide | 3-[5-Bromo-4-(4-chloro-phenyl)-thiazol-2-ylmethoxy]-2,6-difluoro-benzamide |
| Reaction scheme | | | ns
TABLE E-continued

| | 91 | 92 |
|---|---|---|
| | 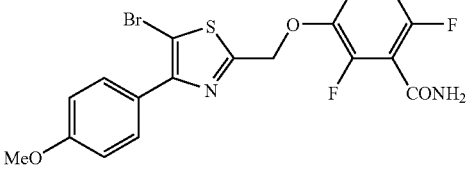 | 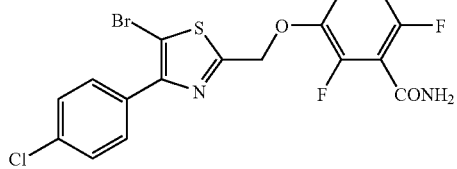 |
| Reactant (A) | 5-Bromo-2-bromomethyl-4-(4-methoxy-phenyl)-thiazole | 5-Bromo-2-bromomethyl-4-(4-chloro-phenyl)-thiazole |
| Quantities of A; B; C; D | 1.1 g, 3.0 mmol; 10 ml; 0.524 g, 3.0 mmol; 1.46 g, 10.2 mmol | 0.3511 g, 0.950 mmol; 10 ml; 0.203 g, 1.1 mmol; 0.570 g, 4.1 mmol |
| Stir temp/time | 25° C., overnight | 25° C., overnight |
| Ethyl acetate/hexane ratio | 35:65 | 35:65 |
| Yield | 0.140 g, 10%, off white solid | 0.280 g, 60%, yellow solid |
| | 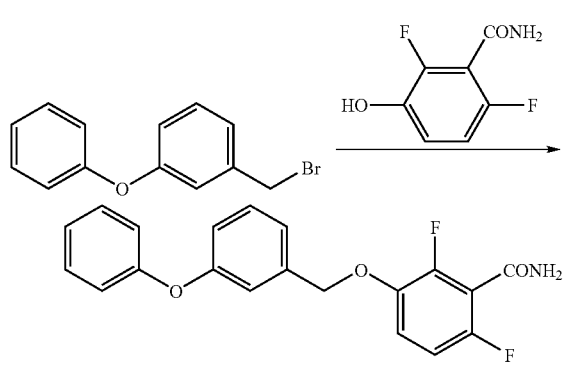 | |
| $^1$H NMR (DMSO, 400 MHz, unless otherwise specified) | δ 3.81 (s, 3H), 5.54 (s, 2H), 7.06 (d, 2H, J = 8.4 Hz (o-coupling), 7.12 (dt, 1H, J = 9.2 Hz (o-coupling), 7.40 (dt, 1H, J = 9.2 Hz (o-coupling), 7.84 (d, 2H, J = 8.8 Hz (o-coupling), 7.89 (broad s, 1H), 8.16 (broad s, 1H) | δ 5.55 (s, 2H), 7.13 (dt, 1H, J = 8.8 Hz (o-coupling), 7.40 (dt, 1H, J = 9.2 Hz (o-coupling), 7.59 (d, 2H, J = 8.4 Hz (o-coupling), 7.91 (d, 2H, J = 8.4 Hz (o-coupling), 7.89 (s, 1H), 8.16 (broad s, 1H) |
| MS-ES+ | 455.08 & 457.07 | 459.05, 461.05 |
| HPLC method no., Rt (min) | 5, 10.49 | 5, 11.26 |
| Example | 161 | 162 |
| Product | 2,6-Difluoro-3-(3-pyrrol-1-yl-benzyloxy)-benzamide | 2,6-Difluoro-3-(3-phenoxy-benzyloxy)-benzamide |
| Reaction scheme | 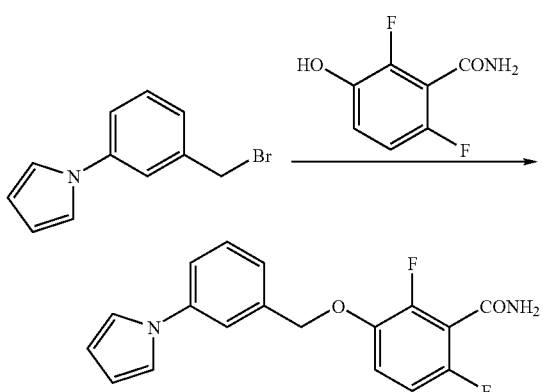 | |
| Reactant (A) | 1-(3-Bromomethyl-phenyl)-1H-pyrrole | 3-phenoxy benzyl bromide |
| Quantities of A; B; C; D | 0.235 g, 1.0 mmol; 5 ml; 0.173 g, 1.0 mmol; 0.483 g, 3.5 mmol | 0.263 g, 1.0 mmol; 5 ml; 0.1 73 g, 1.0 mmol; 0.483 g, 3.5 mmol |
| Stir temp/time | 25° C., overnight | 25° C., overnight |
| Ethyl acetate/hexane ratio | 35:65 | 35:65 |

TABLE E-continued

| Yield | 0.120 g, 35%, white solid | 0.105 g, 31%, white solid |
|---|---|---|
| $^1$H NMR (DMSO, 400 MHz, unless otherwise specified) | δ 5.23 (s, 2H), 6.28 (t, 2H, J = 2.0, Hz (m-coupling), 7.07 (dt, 1H), 7.30 (d, 2H, J = 8.0, (o-coupling), 7.37 (t, 2H, J = 2.0 Hz (m-coupling), 7.48 (t, 1H, J = 8.0 Hz (o-coupling), 7.56 (d, 1H, J = 9.2 Hz (o-coupling), 7.66 (s, 1H), 7.85 (broad s, 1H), 8.13 (broad s, 1H) | δ 5.17 (s, 2H), 6.96-7.05 (m, 3H), 7.07 (d, 2H, J = 8.0 Hz), 7.16 (t, 1H, J = 7.6 Hz (o-coupling), 7.20 (d, 1H, J = 7.6 Hz (o-coupling), 7.25 (dt, 1H, J = 9.2 Hz (o-coupling), J = 5.2 Hz), 7.38-7.43 (m, 3 H), 7.85 (broad s, 1H), 8.13 (broad s, 1H) |
| MS-ES+ | 329.08 | 356.09 |
| HPLC method no., Rt (min) | 5, 9.90 | 5, 10.29 |

| | Example | 163 |
|---|---|---|
| | Product | 2,6-Difluoro-3-(5-phenyl-isoxazol-3-ylmethoxy)-benzamide |
| | Reaction scheme | 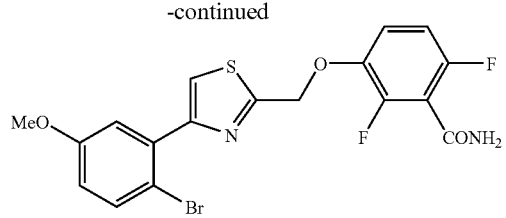 |
| | Reactant (A) | 4-Bromomethyl-2-thiophen-2-yl-thiazole |
| | Quantities of A; B; C; D | 0.260 g, 1 mmol; 5 ml; 0.173 g,1mmol; 0.483 g, 3.5 mmol |
| | Stir temp/time | 25° C., overnight |
| | Ethyl acetate/hexane ratio | 35:65 |
| | Yield | 0.105 g, 30%, white solid |
| | $^1$H NMR (DMSO, 400 MHz, unless otherwise specified) | δ 5.2S (s, 3H), 7.09 (t, 2H, J = 8.4 Hz (o-coupling), 7.16-7.18 (m, 1H), 7.38 (m, 1H), 7.68 (d, 1H, J = 3.6 Hz (o-coupling), 7.74 (d, 1H, J = 4.8 Hz (o-coupling), 7.8S (broad s, 1H), 8.13 (broad s, 1H) |
| | MS-ES+ | 353.08 |
| | HPLC method no., Rt (min) | 5, 9.02 |

Example 100

3-[4-(2-Bromo-5-methoxy-phenyl)-thiazol-2-yl-methoxy]-2,6-difluoro-benzamide

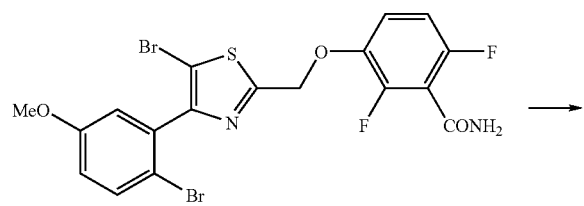

To a solution of 3-[5-Bromo-4-(2-bromo-5-methoxy-phenyl)-thiazol-2-ylmethoxy]-2,6-difluoro-benzamide (0.06 g, 0.0001 mol) in 6 ml of acetic acid was added zinc (0.06 g, 0.0001 mol). The reaction mixture was refluxed for 30 min. The reaction mixture was allowed to come at 25° C. The reaction mixture was filtered on celite bed; the product was precipitated by adding water to the filtrate. The white solid was filtered and dried (0.006 g, 12%). $^1$H NMR (DMSO, 400 MHz), 3.79 (s, 3H), 5.59 (s, 2H), 6.94 (dd, 1H, J=8.8 Hz (o-coupling), J=4.0 Hz), 7.09-7.15 (m, 1H), 7.27 (d, 1H, J-4.0 Hz), 7.40-7.43 (m, 1H), 7.63 (d, 1H, J=8.8 Hz (o-coupling), 7.89 (broad s, 1H), 8.11 (s, 1H), 8.18 (s, 1H); MS ES+ (455.08 & 457.08). HPLC (method 5) Rt=10.21 min.

Example 118

2,6-Difluoro-3-[4-(4-methoxy-phenyl)-5-propyl-thiazol-2-ylmethoxy]-benzamide

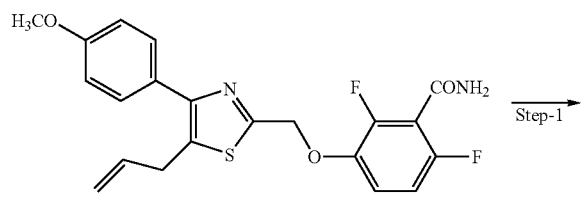

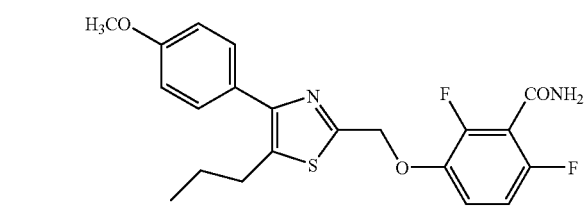

To a solution of 3-[5-allyl-4-(4-methoxy-phenyl)-thiazol-2-ylmethoxy]-2,6-difluoro-benzamide (0.1 g, 0.02 mmol) in 5 ml of anhydrous methanol was added dry 50 mg of dry Pd—C. The reaction mixture was stirred at 25° C. for 12 h under hydrogen atmosphere. The reaction mixture was filtered over the bed of celite. The filtrate was evaporated to dryness under reduced pressure and the residue was purified by column chromatography on silica (230-400μ) using ethyl acetate/hexane (50:50) as the eluent to provide the title compound as white solid (0.02 g, 2%). $^1$H NMR (DMSO-d$_6$, 400 MHz); δ 0.92 (t, 3H, J=7.2 Hz), 1.63-1.65 (m, 2H), 2.8 (t, 2H, J=7.6 Hz (o-coupling), 3.79 (s, 3H), 5.47 (s, 2H), 7.02 (d, 2H, J=8.8 Hz (o-coupling), 7.11 (m, 1H), 7.42 (m, 1H), 7.53 (d, 2H, J=8.8 Hz (o-coupling), 7.88 (s, 1H), 8.16 (s, 1H), 8.38 (d, 1H, J=8.4 Hz (o-coupling). MS ES+ (419.14), HPLC (method 5) Rt=16.58

Example 120

3-[5-Allyl-4-(4-methoxy-phenyl)-thiazol-2-yl-methoxy]-2,6-difluoro-benzamide

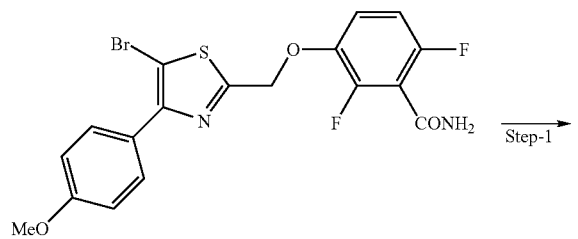

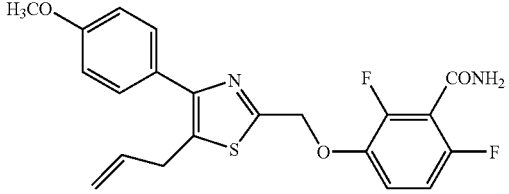

To a solution of 3-[5-bromo-4-(4-methoxy-phenyl)-thiazol-2-ylmethoxy]-2,6-difluoro-benzamide (0.1 g, 0.0002 mol) in 5 ml of anhydrous DMF was added Allyl tributyltin (0.072 g, 0.0002 mol) and degassed the reaction mixture for the 10 minutes. Then added tetraphenylphosphine Palladium (0) (0.025 g, 0.00002 mol). The reaction mixture was heated at 120° C. for 12 h under the nitrogen atmosphere. Then reaction mixture was cooled to rt. 100 ml of water was added into it and extracted the compound with ethyl acetate, The combined organic layers were dried over anhydrous Na$_2$SO$_4$, and evaporated to dryness under reduced pressure. The compound was purified by column chromatography on silica (230-400μ) using methanol/DCM (2:98) as the eluent to provide the title compound as brown solid (0.120 g, 60%). $^1$H NMR (DMSO-d$_6$, 400 MHz): δ 3.79 (s, 3H), 5.11-5.14 (m, 1H), 5.16 (s, 1H), 5.48 (s, 2H), 5.57 (s, 1H), 5.99-6.06 (m, 1H), 7.03 (d, 2H, J=8.4 Hz (o-coupling), 7.11 (dt, 1H, J=9.2 Hz (o-coupling), 7.36-7.42 (m, 1H), 7.56 (d, 2H, J=8.8 Hz (o-coupling), 7.88 (broad s, 1H), 8.16 (broad s, 1H). MS ES+ (417.06), HPLC (method 5) Rt=16.96 min.

Example 121

2,6-Difluoro-3-[4-(4-methoxy-phenyl)-5-pyridin-3-yl-thiazol-2-ylmethoxy]-benzamide

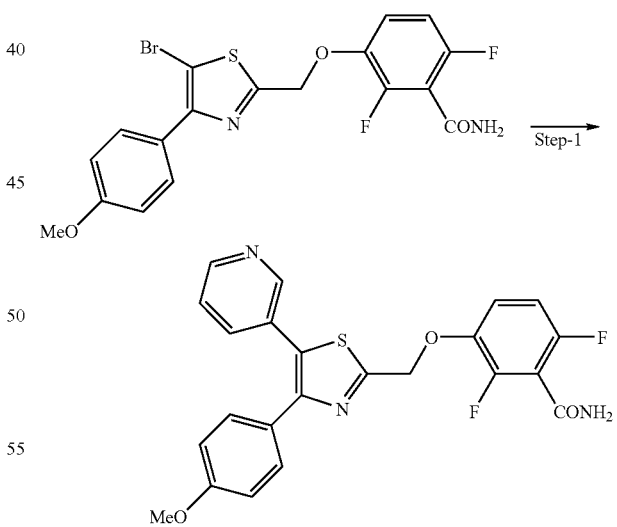

To a solution of 3-[5-bromo-4-(4-methoxy-phenyl)-thiazol-2-ylmethoxy]-2,6-difluoro-benzamide (0.1 g, 0.02 mmol) in DMF:H$_2$O (2:1), 3-pyridine boronic acid (0.054 g, 0.04 mmol), potassium phosphate (0.056 g, 0.025 mmol) was added. The reaction mixture was degassed for 10 min and then dichlorobis [(triphenylphosphine)-Palladium (II) (0.023 g, 0.003 mmol) was added and again degassed for 10 min. The reaction mixture was heated at 120° C. for 12 h under the nitrogen atmosphere. DMF was distilled off, after cooling to r.t., water was added into reaction mixture and extracted with ethyl acetate, The combined organic layers were dried over anhydrous $Na_2SO_4$, and evaporated to dryness under reduced pressure. The compound was purified by chromatography on silica (230-400μ) using ethyl acetate/hexane (50:50) as the eluent to provide the title compound as yellow solid (0.050 g, 50%). $^1$H NMR (DMSO-$d_6$, 400 MHz): δ 3.75 (s, 3H), 5.59 (s, 2H), 6.92 (d, 2H, J=8.8 Hz (o-coupling), 7.14 (dt, 1H, J=9.2 Hz (o-coupling), 7.36 (d, 2H, J=8.4 Hz (o-coupling), 7.45 (dt, 2H, J=9.2 Hz (o-coupling) J=5.2 Hz (o-coupling), 7.79 (m, 1H), 7.88 (broad s, 1H), 8.16 (broad s, 1H), 8.53 (d, 1H, J=2.0 Hz (m-coupling), 8.57 (d, 1H, J=4.8 Hz). MS ES+ (454.10), HPLC (method 5) Rt=15.26 min.

Example 123

3-(5-Bromo-benzothiazol-2-ylmethoxy)-2,6-difluoro-benzamide

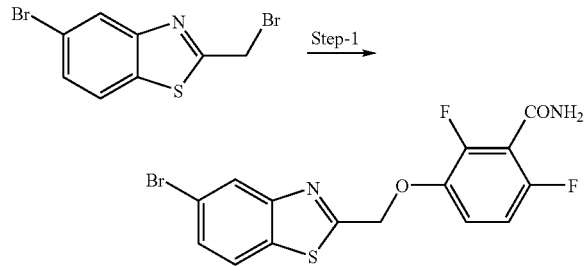

To a solution of 5-bromo-2-bromomethyl-benzothiazole (1.1 g, 0.358 mmol) in 5 ml of anhydrous DMF was added 2,6-difluoro-3-hydroxybenzamide (0.620 g, 0.22 mol) and potassium carbonate (1.73 g, 1.25 mmol). The reaction mixture was stirred at 25° C. for 24 h under nitrogen atmosphere. Water was added to the reaction mixture the compound was precipitated out, filtered and washed with diethylether to give the title compound as yellow solid (1.1 g, 76%). $^1$H NMR (DMSO-$d_6$, 400 MHz): δ 5.71 (s, 2H), 7.11 (dt, 1H J=8.8 Hz (o-coupling), 7.38-7.39 (m, 1H), 7.65 (d, 1H, J=8.8 Hz (o-coupling), 7.90 (broad s, 1H), 8.13 (d, 1H, J=8.8 Hz (o-coupling), 8.18 (s, 1H), 8.26 (broad s, 1H). MS ES+ (400.9), HPLC (method 5) Rt=16.57 min.

Example 125

2,6-Difluoro-3-[4-(4-methoxy-phenyl)-5-pyridin-2-yl-thiazol-2-ylmethoxy]-benzamide

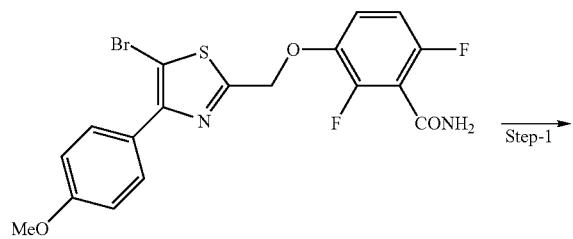

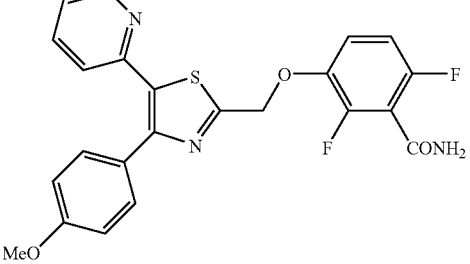

To a solution of 3-[5-bromo-4-(4-methoxy-phenyl)-thiazol-2-ylmethoxy]-2,6-difluoro-benzamide (0.1 g, 0.02 mmol) in 5 ml of anhydrous DMF 2-tributylstannyl pyridine (0.081 g, 0.02 mmol) was added and degassed for the 10 min. Tetrakis (triphenylphosphine) Palladium (0) (0.026 g, 0.002 mmol) was added to the reaction mixture and again degassed for 10 min. and then heated at 120° C. for 12 h under the nitrogen atmosphere. Then reaction mixture was cooled to r.t. water was added and extracted with ethyl acetate, The combined organic layers were dried over anhydrous $Na_2SO_4$, and evaporated to dryness under reduced pressure. The compound was purified by column chromatography on silica (230-400μ) using ethyl acetate (40:60) as the eluent to provide the title compound as white solid (0.120 g, 60%). $^1$H NMR (DMSO-$d_6$, 400 MHz): δ 3.80 (s, 3H), 5.55 (s, 2H), 6.99 (d, 2H, J=8.8 Hz (o-coupling), 7.12 (dt, 1H, J=8.8 Hz (o-coupling), 7.23 (d, 1H, J=8.0 Hz (o-coupling), 7.29-7.32 (m, 1H), 7.44 (d, 2H, J=8.8 Hz (o-coupling), 7.62 (m, 1H), 7.69 (dt, 1H, J=8.0 Hz (o-coupling), 7.88 (broad s, 1H), 8.17 (broad s, 1H), 8.60 (d, 1H, J=4.0 Hz), MS ES+ (454.18), HPLC (method 5) Rt=15.6 min.

Example 126

3-(5-Allyl-benzothiazol-2-ylmethoxy)-2,6-difluoro-benzamide

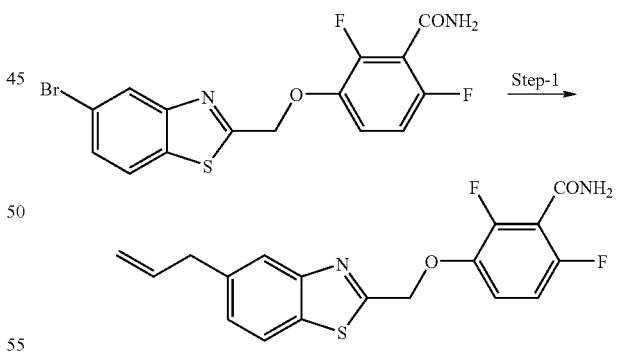

To a solution of 3-(5-bromo-benzothiazol-2-ylmethoxy)-2,6-difluoro-benzamide (0.1 g, 0.025 mol) in 5 ml of anhydrous DMF was added Allyl tributyltin (0.083 g, 0.025 mol) and degassed the reaction mixture for the 10 minutes. Tetrakis (triphenylphosphine) Palladium (0) (0.029 g, 0.0025 mol) was added and again degassed for 10 min. The reaction mixture was heated at 120° C. for 1 h under the nitrogen atmosphere, then cooled to r.t. Water was added to the reaction mixture and extracted with ethyl acetate, The combined organic layers were dried over anhydrous $Na_2SO_4$, and evaporated to dryness under reduced pressure. The compound was crystallized with ethyl acetate/hexane to give the title compound as brown solid (0.050 g, 55%). $^1$H NMR (DMSO-$d_6$, 400 MHz): δ 3.52 (d, 2H, J=6.4 Hz), 5.07-5.13 (m, 1H) 5.68 (s, 2H) 5.98-6.05 (m, 1H), 7.10 (dt, 1H, J=8.4 Hz (o-coupling), 7.31 (d, 1H, J=8.4 Hz (o-coupling), 7.38 (dt, 1H, J=9.2 Hz (o-coupling), J=5.2 Hz), 7.83 (s, 1H), 7.89 (broad s, 1H), 8.05 (d, 1H, J=8.4 Hz (o-coupling), 8.17 (broad s, 1H) MS ES+ (361.05), HPLC (method 5) Rt=16.74 min.

Example 127

2,6-Difluoro-3-[4-(4-methoxy-phenyl)-5-pyridin-4-yl-thiazol-2-ylmethoxy]-benzamide

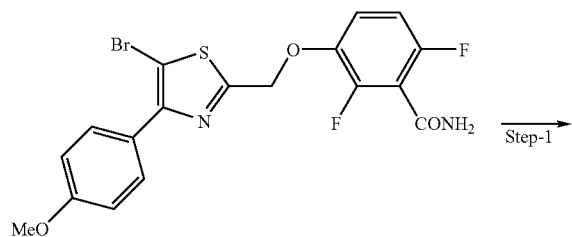

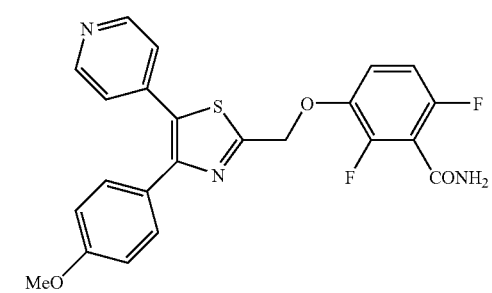

To a solution of 3-[5-bromo-4-(4-methoxy-phenyl)-thiazol-2-ylmethoxy]-2,6-difluoro-benzamide (0.2 g, 0.43 mmol) in 5 ml of anhydrous DMF:H$_2$O (2:1) 4-pyridine boronic acid (0.108 g, 0.87 mmol), potassium phosphate (0.112 g, 0.51 mmol) was added. Then degassed the reaction mixture for the 10 minutes, and added dichlorobis [(triphenylphosphine)-palladium (II) (0.046 g, 0.06 mmol) and again degassed for 10 min. The reaction mixture was heated at 120° C. for 12 h under the nitrogen atmosphere. DMF was distilled off, after cooling to r.t. water was added into reaction mixture and extracted with ethyl acetate, The combined organic layers were dried over anhydrous Na$_2$SO$_4$, and evaporated to dryness under reduced pressure. The compound was purified by chromatography on silica (230-400µ) using ethyl acetate/hexane (50:50) as the eluent to provide the title compound as white solid (0.045 g, 49%). $^1$H NMR (DMSO-$d_6$, 400 MHz): δ 3.80 (s, 3H), 5.59 (s, 2H), 6.94 (d, 2H, J=8.8 Hz (o-coupling), 7.14 (dt, 1H), 7.34 (d, 1H, J=6.0 Hz (o-coupling), 7.38 (d, 2H, J=8.8 Hz (o-coupling), 7.41-7.45 (m, 1H), 7.89 (broad s, 1H), 8.17 (s, 1H), 8.60 (dd, 1H) MS ES+ (454.12), HPLC (method 5) Rt=13.55 min.

Example 135

2,6-Difluoro-3-(5-propyl-benzothiazol-2-ylmethoxy)-benzamide

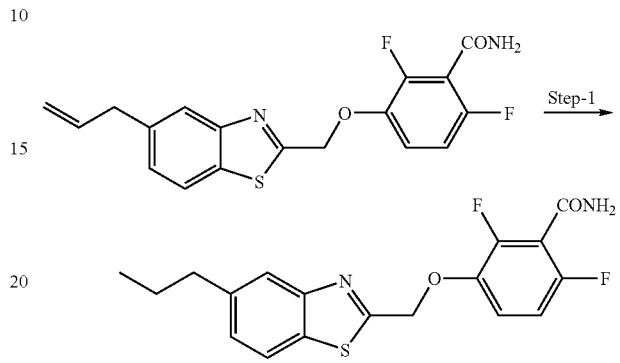

To a solution of 3-(5-allyl-benzothiazol-2-ylmethoxy)-2,6-difluoro-benzamide (0.1 g, 0.27 mmol) in 5 ml of anhydrous methanol was added to 20 mg of dry Pd—C. The reaction mixture was stirred at 25° C. for 12 h under hydrogen atmosphere. The reaction mixture was filtered over the celite bed. The filtrate was evaporated to dryness under reduced pressure and the compound was crystallized with ethyl acetate/hexane to give the title compound as light yellow solid (0.014 g, 14%). $^1$H NMR (DMSO-$d_6$, 400 MHz): δ 0.92 (t, 3H, J=7.2 Hz), 1.62-1.68 (m, 2H), 2.71, 2H, J=7.2 Hz), 5.67 (s, 2H), 7.12 (dt, 1H, J=8.8 Hz (o-coupling) J=1.6 Hz), 7.32 (d, 1H, J=8.4 (o-coupling), 7.38 (dt, 1H, J=9.2 Hz (o-coupling), J=5.2 Hz), 7.83 (s, 1H), 7.89 (broad s, 1H), 8.01 (d, 1H, J=8.4 Hz (o-coupling). 8.17 (broad s, 1H). MS ES+ (363.08), HPLC (method 5) Rt=17.64 min.

Example 136

2,6-Difluoro-3-[5-(3-hydroxy-phenyl)-benzothiazol-2-ylmethoxy]-benzamide

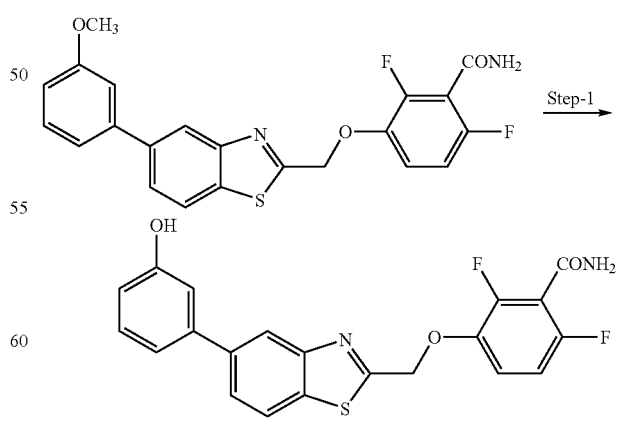

To a suspension of 2,6-difluoro-3-[5-(3-methoxy-phenyl)-benzothiazol-2-ylmethoxy]-benzamide (0.14 g, 0.3 mmol) in 15 ml of anhydrous DCM was added drop wise boron tribromide (0.493 g, 1.9 mmol) at −78° C. The reaction mixture was stirred at −78° C. for 3 h under nitrogen atmosphere. To the reaction mixture 5 ml of water was added at 0° C. The compound was extracted with ethyl acetate. The combined organic layers were dried over anhydrous $Na_2SO_4$, and evaporated to dryness under reduced pressure. The compound was purified by column chromatography on silica (230-400μ) using ethyl acetate (40:60) as the eluent to provide the title compound as yellow solid (0.020 g, 14%). $^1$H NMR (DMSO-$d_6$, 400 MHz): δ 5.71 (s, 2H), 6.80 (dd, 1H, J=9.6 Hz (o-coupling), 7.11 (dt, 1H, J=8.0 Hz (o-coupling), 7.17 (dt, 1H, J=8.0 Hz (o-coupling), 7.29 (t, 1H, J=8.0 Hz (o-coupling), 7.39-7.43 (m, 1H), 7.71 (dd, 1H, J=9.6 Hz) 7.89 (broad s, 1H), 8.18-8.22 (m, 2H). MS ES+ (413.01), HPLC (method 5) Rt=14.95 min Example 140

2,6-Difluoro-3-[5-(4-hydroxy-phenyl)-benzothiazol-2-ylmethoxy]-benzamide

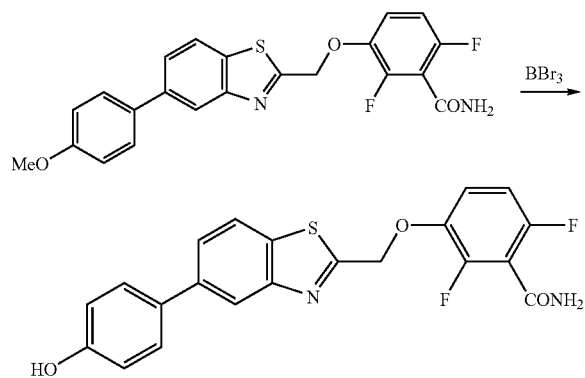

Compound 2,6-difluoro-3-[5-(4-methoxy-phenyl)-benzothiazol-2-ylmethoxy]-benzamide (0.095 g, 0.223 mmol) was dissolved in 5 ml of DCM and cooled to −70° C. To this, $BBr_3$ (0.1 ml 0.156 mmol) was added drop wise. After complete addition, reaction mixture was stirred at r.t. for 30 min. The reaction mixture was quenched with MeOH. Reaction mixture was concentrated and purified by column chromatography to obtain (0.0025 g, 3%) compound as white solid. $^1$H NMR (DMSO-$d_6$, 400 MHz); δ 5.70 (s, 2H), 6.88 (d, 1H, J=8.4 Hz (o-coupling), 7.10 (m, 1H), 7.41 (m, 2H), 7.60 (d, 2H, J=8.8 Hz, (o-coupling), 7.71 (d, 2H), 7.89 (broad s, 1H), 8.13-8.17 (m, 2H), 9.62 (broad s, 1 H); MS ES+ (413.0).

Example 141

3-[5-(2-Amino-phenyl)-benzothiazol-2-ylmethoxy]-2,6-difluoro-benzamide

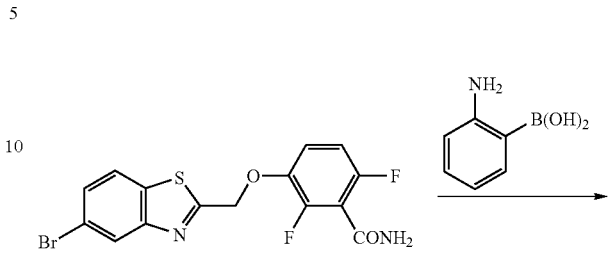

To the solution of compound 3-(5-bromo-benzothiazol-2-ylmethoxy)-2,6-difluoro-benzamide (0.3 g 0.755 mmol) in dry DMF:$H_2O$ (5 mL: 2.5 mL), phenylamine-2-boronic acid (0.260 g, 1.5 mmol), and $K_2CO_3$ (0.125 g, 0.9 mmol) was added under nitrogen atmosphere at room temperature. After that reaction mixture was degassed for half an hour. Dichlorobis [(triphenylphosphine)-palladium (II) was added to the reaction mixture (0.080 g, 0.113 mmol) and again degassed for half an hour and the reaction mixture was heated at 120° C. for 2 hrs under nitrogen atmosphere. DMF was distilled off, after cooling to r.t. water was added into reaction mixture and extracted with ethyl acetate, The combined organic layers were dried over anhydrous $Na_2SO_4$, and evaporated to dryness under reduced pressure. The compound was purified by chromatography on silica (230-400μ) using ethyl acetate/hexane (50:50 as the eluent to provide the title compound as yellow solid (0.025 g, 8%). $^1$H NMR (DMSO-$d_6$, 400 MHz); δ 4.86 (broad s, 2H), 5.71 (s, 2H), 6.66 (dt, 1H, J=8.4 Hz (o-coupling), 6.78 (d, 1 H, J=7.2 Hz (o-coupling), 7.04-7.13 (m, 3H), 7.37-7.44 (m, 1H), 7.51 (dd, 1H, J=8.4 Hz (o-coupling), J=1.6 Hz (m-coupling), 7.89 (broad s, 1H), 8.00 (broad s, 1H), 8.18 (d, 2H, J=4.0 Hz); MS ES+ (412.16), HPLC (method 5) Rt=15.33 min.

Example 143

2,6-Difluoro-3-[5-(3-methoxy-phenyl)-benzothiazol-2-ylmethoxy]-benzamide

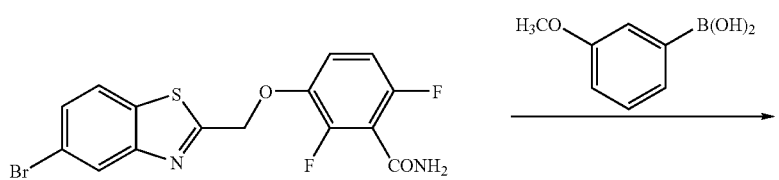

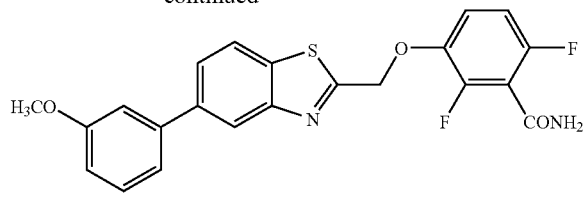

To the solution of compound 3-(5-bromo-benzothiazol-2-ylmethoxy)-2,6-difluoro-benzamide (0.300 g, 0.755 mmol) in dry DMF:H$_2$O (5 mL: 2.5 mL), added 3-methoxyphenyl boronic acid (0.228 g, 1.5 mmol), and K$_3$PO$_4$ (0.190 g, 0.9 mmol) under the inert condition at room temperature and degassed for half an hour. Then to the reaction mixture added dichlorobis [(triphenylphosphine)-palladium (II) (0.078 g, 0.075 mmol) and again degassed for half an hour. The reaction mixture was heated at 120° C. for 2 hrs under nitrogen atmosphere. DMF was distilled off, after cooling to r.t. water was added into reaction mixture and extracted with ethyl acetate, The combined organic layers were dried over anhydrous Na$_2$SO$_4$, and evaporated to dryness under reduced pressure. The compound was purified by chromatography on silica (230-400μ) using ethyl acetate/hexane (50:50 as the eluent to provide the title compound as white solid (0.140 g, 43%). $^1$H NMR (DMSO-d$_6$, 400 MHz); δ 3.85 (s, 3H), 5.72 (s, 2H), 6.97 (t, 1H, J=6.8 Hz (o-coupling), 7.11 (t, 1 H, J=8.8 Hz, (o-coupling), 7.30 (broad s, 1 H), 7.34 (d, 1H, J=8.8 Hz (o-coupling), 7.40 (dd, 2H, J=8.0 Hz (o-coupling), 7.79 (d, 1H, J=8.0 Hz (o-coupling), 7.90 (broad s, 1H), 8.18 (broad s, 1H), 8.21 (d, 1H, J=8.0 Hz); MS ES+ (427.14), HPLC (method 5) Rt=16.48 min.

Example 155

2,6-Difluoro-3-[4'-(4-methoxy-phenyl)-[2,5']bithiazolyl-2'-ylmethoxy]-benzamide

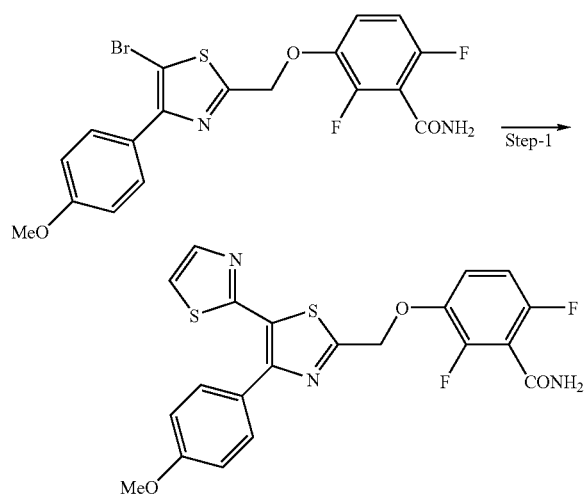

To a solution of 3-[5-bromo-4-(4-methoxy-phenyl)-thiazol-2-ylmethoxy]-2,6-difluoro-benzamide (0.1 g, 0.2 mmol) in 5 ml of anhydrous DMF was added 2-tributylstannyl thiazole (0.071 g, 0.2 mmol) and degassed the reaction mixture for the 10 minutes. Then added tetraphenylphosphine palladium (0) (0.026 g, 0.2 mmol). The reaction mixture was heated at 120° C. for 12 h under the nitrogen atmosphere. Then reaction mixture was cooled to rt. 100 ml of water was added into it and extracted the compound with ethyl acetate, The combined organic layers were dried over anhydrous Na$_2$SO$_4$, and evaporated to dryness under reduced pressure. The compound was purified by column chromatography on silica (230-400μ) using ethyl acetate (40:60) as the eluent to provide the title compound as yellow solid (0.003 g, 3%). $^1$H NMR (DMSO-d$_6$, 400 MHz): δ 3.82 (s, 3H), 5.57 (s, 2H), 7.06 (d, 1H, J=8.4 Hz (o-coupling), 7.13 (dt, 1H), 7.39-7.47 (m, 1H), 7.51 (d, 2H, J=8.4 Hz (o-coupling), 7.52-7.58 (m, 1H), 7.59-7.86 (m, 2H), 7.68 (d, 1 H, J=3.2 Hz), 7.84 (d, 1 H, J=3.2 Hz), 7.89 (broad s, 1H), 8.18 (broad s, 1H), 9.12 (s, 1H); MS ES+ (460.01), HPLC (method 5) Rt=15.64 min.

Example 160

2,6-Difluoro-3-[3-(5-methyl-2-phenyl-thiazol-4-yl)-propoxy]-benzamide

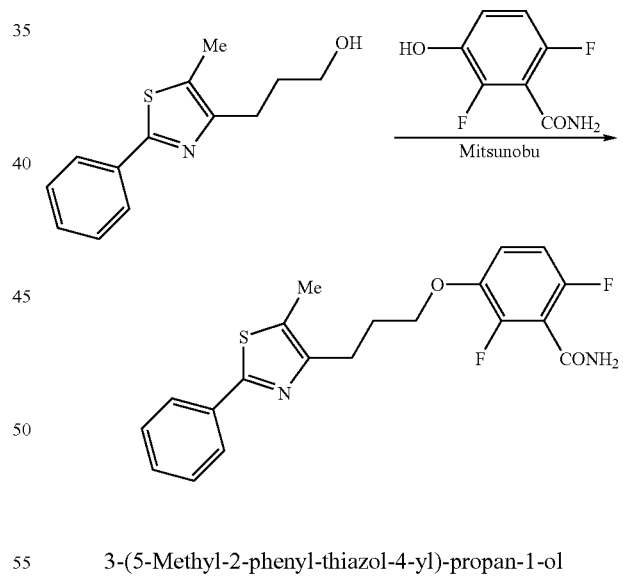

3-(5-Methyl-2-phenyl-thiazol-4-yl)-propan-1-ol

To a solution of 3-(5-methyl-2-phenyl-thiazol-4-yl)-propan-1-ol (0.219 g, 1.0 mmol) in 5 ml of anhydrous DMF, 2,6-difluoro-3-hydroxybenzamide (0.173 g, 1.0 mmol), PPh$_3$ (0.262 g, 1.0 mmol) and diisopropyl azodicarboxylate (0.202 g, 1.0 mmol) was added. The reaction mixture was stirred at 80° C. for overnight under nitrogen atmosphere. The reaction mixture was evaporated to dryness under reduced pressure and the residue was purified by column chromatography on silica (230-400μ) using ethyl acetate/hexane (35:65) as the eluent to provide the title compound as white solid (0.050 g, 13%). $^1$H NMR (DMSO-d$_6$, 400 MHz): δ 2.44 (broad s, 3H), 3.14 (t, 2H, J=6.4 Hz), 4.35 (t, 2H, J=6.4 Hz), 7.04 (dt, 1H, J=9.2 Hz (o-coupling), 7.22-7.28 (m, 1H), 7.43-7.49 (m, 3H), 7.83-7.86 (m, 3H), 8.10 (s, 1H); MS ES+ (375.15), HPLC (method 5) Rt=10.67 min.

Example 164

2,6-Difluoro-3-[4-(4-methoxy-phenyl)-[5,5']bithiazolyl-2-ylmethoxy]-benzamide

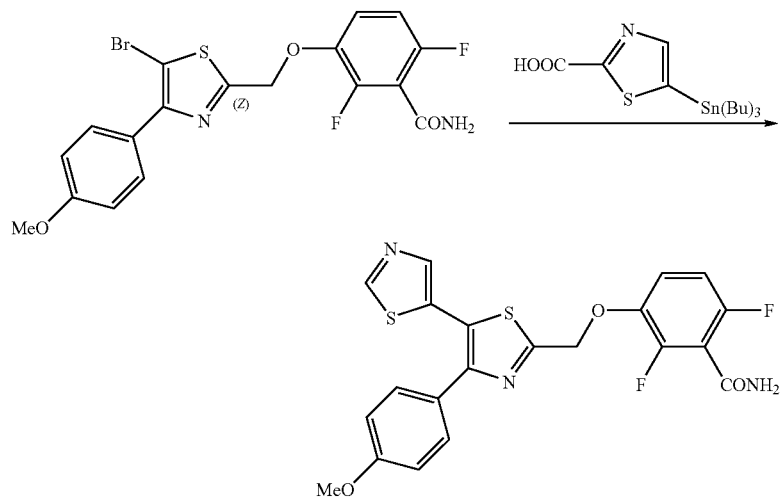

To a solution of 2,6-difluoro-3-[4-(4-methoxy-phenyl)-[5,5']bithiazolyl-2-ylmethoxy]-benzamide (0.100 g, 0.2 mmol) in 5 ml of anhydrous DMF, and 5-Tributylstannanyl-thiazole-2-carboxylic acid (0.091 g, 0.2 mmol) was added. The reaction mixture was stirred at 80° C. for overnight under nitrogen atmosphere. The reaction mixture was evaporated to dryness under reduced pressure and the residue was purified by column chromatography on silica (230-400µ) using ethyl acetate/hexane (35:65) as the eluent to provide the title compound as white solid (0.025 g, 25%). $^1$H NMR (DMSO-d$_6$, 400 MHz): δ 3.78 (s, 3H), 5.57 (s, 2H), 6.97 (d, 2H, J=8.8 Hz (o-coupling), 7.13 (t, 1H), 7.44 (d, J=8.8, (o-coupling, 3H), 7.89 (broad s, 1H), 8.05 (s, 1H), 8.17 (broad s, 1H), 9.12 (s, 1H); MS ES+ (459.94), HPLC (method 5) Rt=15.21 min.

Example 165

2-Fluoro-3-Hexoxy-benzamide

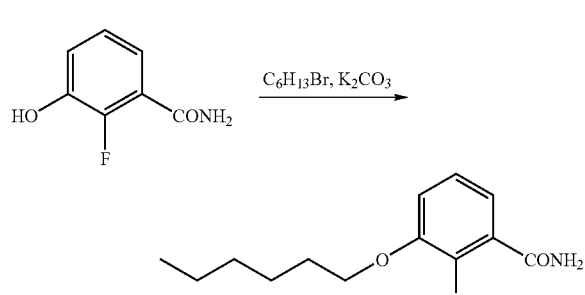

To the solution of 2-fluoro-3-Hydroxy-benzamide (0.12 g, 0.774 mmol) in 20 mL DMF 1-bromohexane (0.13 mL, 1.0 mmol), Potassium Carbonate (0.213, 1.4 mmol) was added. The reaction mixture was stirred at 90° C. for 4 h. DMF was distilled off and the reaction mixture was extracted with EtOAc. The obtained crude compound was purified by column chromatography on silica (230-400µ) using ethyl acetate/hexane (50:50) as the eluent to provide the title compound. (0.05 g, 28%). $^1$H NMR (DMSO-d$_6$, 400 MHz with D$_2$O): δ 0.82-0.99 (m, 3H), 1.10-1.33 (m, 6H), 1.67-1.71 (m, 2H), 3.99-4.15 (t, 2H, J=8.0 Hz), 7.08-7.24 (m, 2H). MS ES+ (214.33), HPLC (method 6) Rt=11.15 min.

Example 166

2-Hydroxy-3-Hexoxy-benzamide

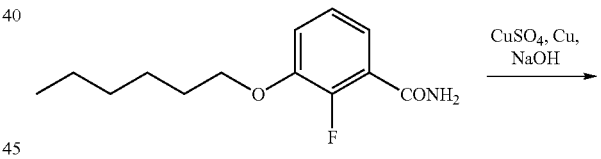

A mixture of 2-fluoro-3-Hexoxy-benzamide (0.30 g, 1.2 mmol), copper sulfate (0.10 g, 0.4 mol) copper (0.015 g, 0.2 mmol) and NaOH (2.5 ml) was stirred at 100° C. for 14 hrs. After completion of reaction the reaction mixture was acidified and extracted with EtOAc. The obtained crude compound was purified by column chromatography on silica (230-400µ) using ethyl acetate/hexane (50:50) as the eluent to provide the title compound as yellow (0.15 g, 50%). $^1$H NMR (DMSO-d$_6$, 400 MHz with D$_2$O): δ 3.9 (s, 3H), 7.11-7.18 (m, 2H), 7.53-7.58 (m, 1H). MS ES+ (229.0 M+2H adduct). HPLC (Method 7) Rt=11.16 min.

Example 167

Synthesis of 3-Fluoro-5-hexyloxy benzamide

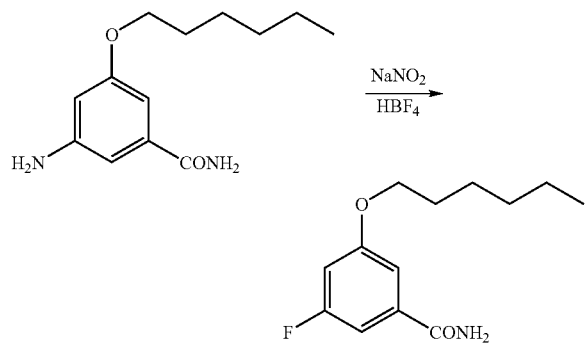

To a solution of 3-amino-5-hexyloxy benzamide (0.9 g, 3.8 mmol) in tetrafluoroboric acid (20 ml), a solution of sodium nitrite (0.315 mg, 4.6 mmol) in water (5 ml) was added at 0° C. and stirred for 1 hr. Later it was allowed to come to RT and stirred for 1 hr followed by heating at 60° C. for 2 hrs. It was then basify to pH=14 using saturated NaOH solution and extracted with dichloromethane (3×30 ml). The solvent was evaporated to yield crude product, which was purified by column chromatography using silica gel (230-400 mesh) and dichloromethane as an eluent (100 mg, 11%). $^1$H NMR (DMSO-d$_6$, 400 MHz with D$_2$O): δ 0.88 (t, J=7.2 Hz, 3H), 1.32 (m, 2H), 1.41 (m, 4H), 1.72 (m, 2H), 4.0 (t, J=7.2 Hz, 2H), 6.97 (m, 1H), 7.22 (m, 1H), 7.28 (m, 1H), 7.52 (br s, 1H), 8.03 (br s, 1H). MS ES+ (238.0, 239.0), HPLC (method 7) Rt=11.34 min.

Example 168

Synthesis of 3-(Pyrazol-1-ylmethoxy)-benzamide

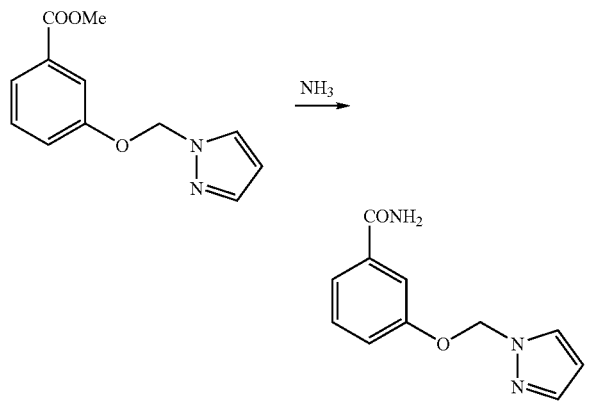

3-(Pyrazol-1-ylmethoxy)-benzoic acid methyl ester (250 mg, 1.1 eq.) was taken in a pressure vessel along with 5 ml of aq. ammonia, heated at 110° C. for 12 hr. reaction mass was then poured in water (25 ml), extracted with dichloromethane (25 ml×4). Organic layer was dried over sodium sulphate and concentrated to obtain crude solid. Product was purified by column chromatography using 80% EtOAc-DCM as an eluent over 230-400 mesh silica gel. Pure product was obtained as solid powder (50 mg, 19%). $^1$H NMR (DMSO-d$_6$, 400 MHz with D$_2$O): δ 6.12 (s, 2H), 6.33 (m, 1H), 7.25 (m, 1H), 7.37 (m, 1H), 7.41 (m, 1H), 7.51 (m, 1H), 7.56 (m, 2H), 7.95 (br s, 1H), 7.99 (m, 1H). MS ES+ (218.0, 235.0-Ammonium adduct), HPLC (method 7) Rt=9.08 min.

Example 169

3-[(2-Methylcyclopropyl)methoxy]benzenecarboxamide

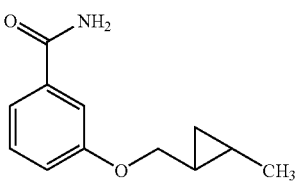

Synthesised according to Method C, scheme 3. Yield 27%, mp 119-121° C., HPLC-MS (method 1): m/z 206 [M+H]$^+$, Rt=3.47 min.

Example 170

3-[(5-Methyl-3-pyridinyl)methoxy]benzenecarboxamide

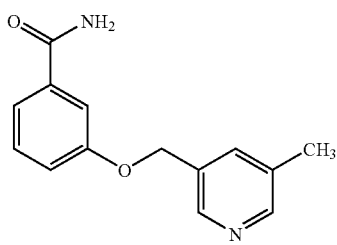

N-Bromosuccinimide (2.13 g, 12 mmol) and subsequently α,α'-azoisobutyronitrile (16 mg, 0.1 mmol) were added to a solution of 3,5-lutidine (1.14 ml, 10 mmol) in CCl$_4$ (40 ml). The reaction mixture was stirred at reflux for 2 hrs. After cooling, succinimide was removed by filtration and the filtrate was evaporated to smaller volume (10 ml). To this filtrate, a mixture of 3-hydroxybenzenecarboxamide (550 mg, 4 mmol) and K$_2$CO$_3$ (830 mg, 6 mmol) in DMF (5 ml) was added and the new reaction mixture was stirred at 60° C. for 24 h. After diluting with CH$_2$Cl$_2$ (100 ml), the solution was washed with Na$_2$CO$_3$ solution (40 ml) and water (40 ml), dried (Na$_2$SO$_4$) and evaporated to dryness, under reduced pressure. The brown oil residue was extracted by trituration with Et$_2$O (2×10 ml), and from the Et$_2$O extracts, the precipitant solid was filtered and washed with pentane, to give 70 mg (7.2% yield) of the desired product. Mp 152-154° C., HPLC-MS: m/z 243 [M+H]$^+$, Rt=2.28 min.

Example 171

3-[(3-Bromobenzyl)oxy]benzenecarboxamide

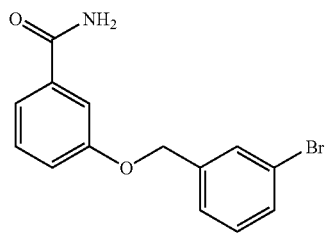

Synthesised according to Method B, scheme 2. Yield 54%, mp 129-131° C., HPLC-MS (method 1): m/z 347 [M+H+CH$_3$CN]$^+$, Rt=3.99 min.

Scheme 20:

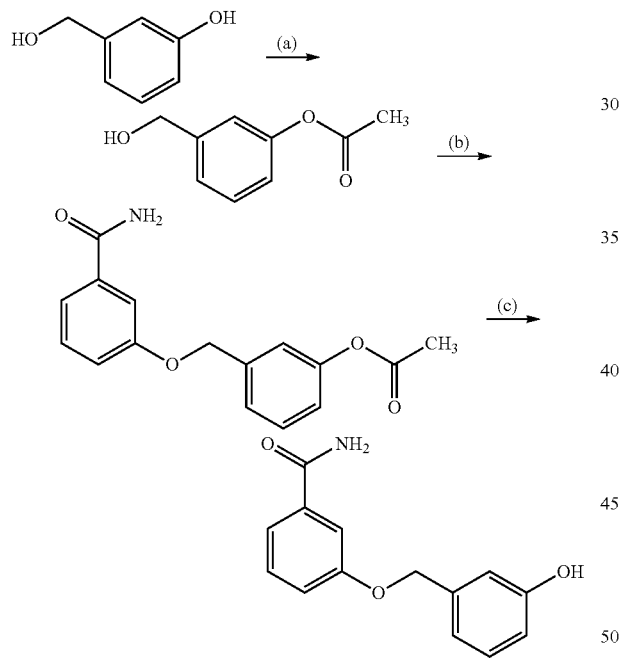

(a) KOH aq, (CH$_3$CO)$_2$O;
(b) 3-hydroxybenzenecarboxamide, PPh$_3$, DIAD, Et$_3$N, THF, r.t.;
(c) K$_2$CO$_3$, MeOH, H$_2$O.

3-(Hydroxymethyl)phenyl acetate

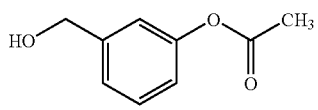

To a stirred solution of 3-hydroxybenzylalcohol (1.0 g, 8 mmol, 1 equiv.) in 6.4N KOH solution (1.86 ml, 12 mmol, 1.5 equiv.) at r.t., ice (4 g) was added followed by acetic anhydride (0.95 ml, 10 mmol, 1.25 equiv.). The reaction mixture was stirred at r.t. for 3 h. Water (50 ml) was added and the mixture was stirred for 30 min, before extracting with CH$_2$Cl$_2$ (2×50 ml). The combined organic extracts were washed with brine (50 ml), dried (Na$_2$SO$_4$) and evaporated to dryness, under reduced pressure. The clear oil residue was purified by column chromatography on silica, eluted with EtOAc/hexane (1:2), to give the desired product as a clear oil (714 mg, 54% yield). HPLC-MS (method 1): m/z 165 [M−H]$^-$. Rt=2.52 min.

Example 172

3-[3-(Aminocarbonyl)phenoxy]methylphenyl acetate

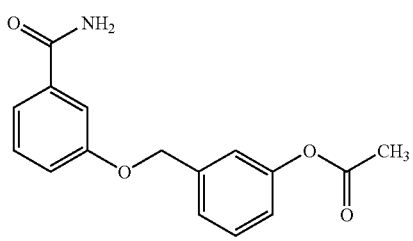

Synthesised according to Method C, scheme 3. Yield 32%, HPLC-MS (method 1): m/z 286 [M+H]$^+$. Rt=3.44 min.

Example 173

3-[(3-Hydroxybenzyl)oxy]benzenecarboxamide

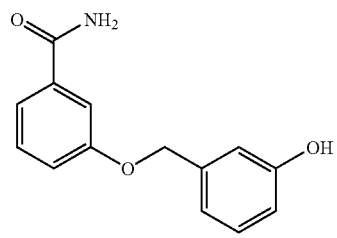

A solution of K$_2$CO$_3$ (500 mg, 3.62 mmol, 5.75 equiv.) in water (5 ml) was added to a solution of 3-[3-(aminocarbonyl)phenoxy]methylphenyl acetate (180 mg, 0.63 mmol, 1 equiv.) and the mixture was stirred at r.t., under N$_2$, for 3 h; The mixture was acidified with 10% HCl solution to pH 1, and was extracted with EtOAc (2×30 ml). The combined organic extracts were washed with water (30 ml), dried (Na$_2$SO$_4$) and evaporated to dryness under reduced pressure, to give a clear oil residue which, after trituration with Et$_2$O, solidified to a white solid (70 mg, 46% yield). Mp 122-123° C., HPLC-MS (method 1): m/z 244 [M+H]$^+$. Rt=2.92 min.

Scheme 21:

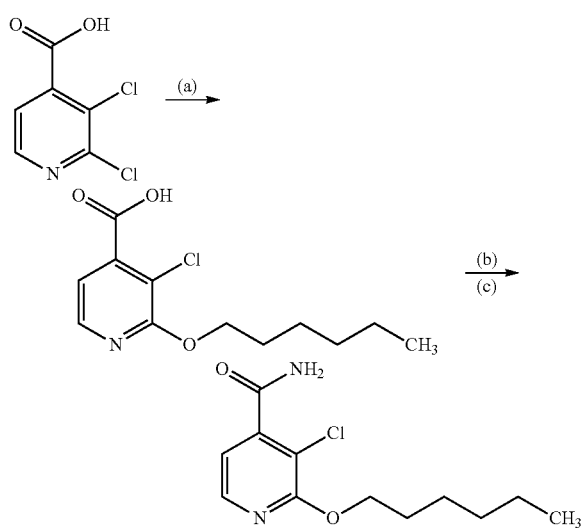

(a) Hexanol, 3 equ. NaH, 100-200° C.;
(b) SOCl₂, toluene, reflux;
(c) aqueous NH₃.

3-Chloro-2-(hexyloxy)isonicotinic acid

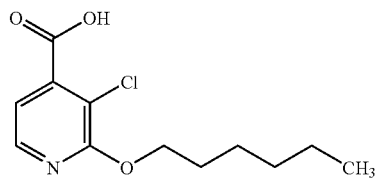

A solution of sodium hydride (60% in mineral oil, 600 mg, 15.0 mmol, 3 equiv.) in hexanol (10 ml) was stirred at r.t. for 2 h. 2,3-Dichloro-isonicotinic acid (960 mg, 5.0 mmol, 1 equiv.) was added and the reaction mixture was stirred at 100° C. for 16 h. The mixture was diluted with water (100 ml) and pentane (300 ml), and the two phases were separated. The aqueous phase was neutralised with 1N HCl solution to pH 6.0 and extracted with EtOAc (3×80 ml). The combined EtOAc extracts were dried (MgSO₄) and evaporated under reduced pressure to dryness. The residue was triturated with pentane, cooled at 0° C. and the precipitant solid was filtered, to give 410 mg of a white compound (yield 32%). By ¹H-NMR analysis, it consisted of about 80% of the desired product, which was used to the next step without further purification. HPLC-MS: m/z 256 [M−H]⁻, Rt=2.94 min.

Example 174

3-Chloro-2-(hexyloxy)isonicotinamide

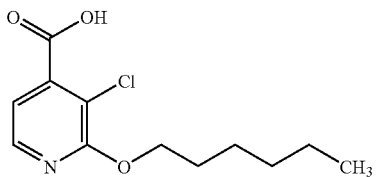

Synthesised from 3-chloro-2-(hexyloxy)isonicotinic acid according to Method A. Yield 85% (crude); purified further by preparative TLC, mp 75-77° C., HPLC-MS: m/z 298[M+H+CH₃CN]⁺, Rt=4.16 min.

2-fluoro-3-hydroxybenzenecarboxamide

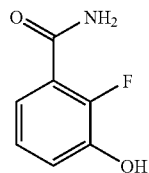

Synthesised from commercially available 2-fluoro-3-methoxybenzenecarboxamide according to Method H. Yield 82%, mp 196-197° C., HPLC-MS (method 1): m/z 154 [M−H]⁻, Rt=1.24 min.

Example 175-178 (Table F)

Examples 175-178 were synthesised from 2-fluoro-3-hydroxybenzenecarboxamide. Examples 175, 176 and 178 according to Method B, scheme 2 and Example 177 according to Method C, scheme 3.

| Example | 175 | 176 |
|---|---|---|
| Structure | ![structure 175] | ![structure 176] |
| Yield (%) | 62 | 70 |
| mp (° C.) | 76-77 | 91-92 |

-continued

| | | |
|---|---|---|
| HPLC-MS: method no., m/z, ion | 1, 282, [M + H]⁺ | 1, 270, [M + H]⁺ |
| Rt (min) | 5.13 | 3.48 |

| Example | 177 | 178 |
|---|---|---|
| Structure | 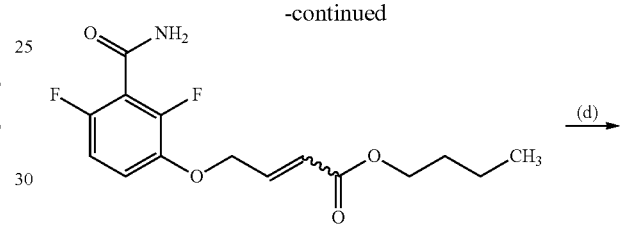 | |
| Yield (%) | 7 | 6 |
| mp (° C.) | 98-100 | 70-72 |
| HPLC-MS: method no., m/z, ion | 1, 306, [M + H]⁺ | 1, 246, [M + H]⁺ |
| Rt (min) | 4.78 | 3.52 |

Table of names of product compounds; Examples 175-178:

| Example | Compound name |
|---|---|
| 175 | 2-Fluoro-3-(nonyloxy)benzenecarboxamide |
| 176 | Butyl 2-[3-(aminocarbonyl)-2-fluorophenoxy]acetate |
| 177 | 2-Fluoro-3-(10-undecynyloxy)benzenecarboxamide |
| 178 | 2,6-Difluoro-3-(4-hydroxybutoxy)benzenecarboxamide |

Scheme 22:

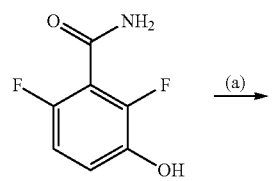

(a)

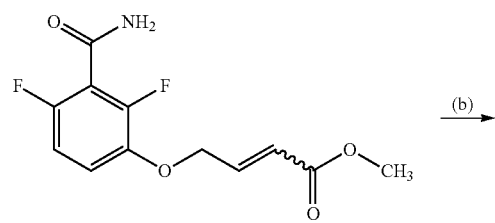

(b)

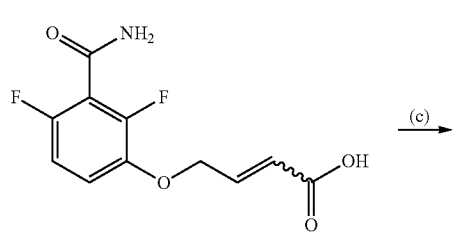

(c)

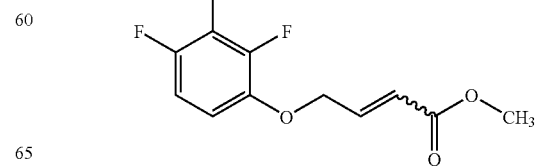

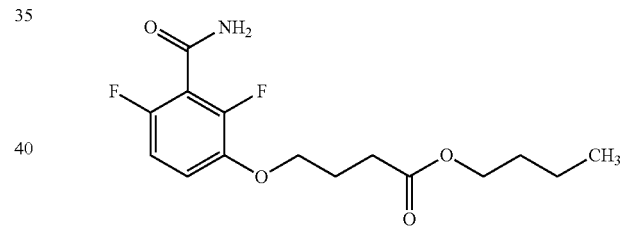

(d)

(a) Methyl 4-bromocrotonate, K₂CO₃, DMF, r.t.;
(b) NaOH, IPA/H₂O, reflux;
(c) n-BuBr, K₂CO₃, DMF, 50° C.;
(d) H₂, 5% Rh/C, BuOH, r.t.

Example 179

Methyl 4-[3-(aminocarbonyl)-2,4-difluorophenoxy]-2-butenoate

Synthesised from 2,6-difluoro-3-hydroxybenzenecarboxamide according to Method B, scheme 2. Yield 41%, mp 122-123° C., HPLC-MS (method 1): m/z 272 [M+H]$^+$, Rt=2.80 min.

4-[3-(aminocarbonyl)-2,4-difluorophenoxy]-2-butenoic acid

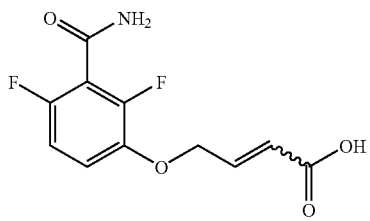

A solution of methyl 4-[3-(aminocarbonyl)-2,4-difluorophenoxy]-2-butenoate (1.25 g, 4.61 mmol, 1 equiv.) and NaOH (0.75 g, 18.44 mmol, 4 equiv.) in isopropanol (10 ml) and H$_2$O (20 ml) was heated under reflux for 1 h. After cooling to r.t., the mixture was acidified with conc. HCl to pH 1. The white precipitant solid was filtered and washed with Et$_2$O (50 ml), to give 568 mg, 48% yield, mp 187-188° C., HPLC-MS (method 1): m/z 258 [M+H]$^+$, Rt=0.98 min. By $^1$H-NMR analysis it was determined to be a mixture of isomeres in a ratio (3:2) E:Z.

The aqueous phase was extracted with Et$_2$O (2×50 ml) and the combined extracts were dried (Na$_2$SO$_4$) and evaporated to dryness under reduced pressure, to give a light orange solid, 418 mg, 35% yield, mp 127-128° C., HPLC-MS (method 1): m/z 258 [M+H]$^+$, Rt=0.99 min. By $^1$H-NMR analysis it was determined to be a mixture of isomeres in a ratio (3:40) E:Z.

Example 180

Butyl 4-[3-(aminocarbonyl)-2,4-difluorophenoxy]-2-butenoate

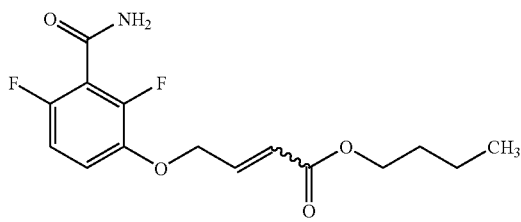

4-[3-(Aminocarbonyl)-2,4-difluorophenoxy]-2-butenoic acid, mixture of isomeres (3:2) E:Z, (526 mg, 2 mmol, 1 equiv.) was dissolved in dry DMF (5 ml). K$_2$CO$_3$ (850 mg, 6 mmol, 3 equiv.) and n-butylbromide (0.23 ml, 2.1 mmol, 1.05 equiv.) were added and the reaction mixture was heated for 70 h at 50° C. and for 1.5 h at r.t. After cooling at r.t., the mixture was diluted with H$_2$O (50 ml) and extracted with EtOAc (3×40 ml). The combined organic extracts were washed with H$_2$O (6×30 ml), dried (MgSO$_4$) and evaporated to dryness under reduced pressure. The oily residue was purified by column chromatography on silica, eluted with CH$_2$Cl$_2$ and MeOH/CH$_2$Cl$_2$ (1%), to give 364 mg, 57% yield, mp<40° C. HPLC-MS (method 1): m/z 314 [M+H]$^+$, Rt=3.88 min. By $^1$H-NMR analysis it was determined to be a mixture of isomeres in a ratio (5:7) E:Z. When the same reaction was performed on the acid (3:40) E:Z mixture of isomeres, the product obtained was determined to be a mixture of isomeres in a ratio (1:4) E:Z.

Example 181

Butyl 4-[3-(aminocarbonyl)-2,4-difluorophenoxy]butanoate

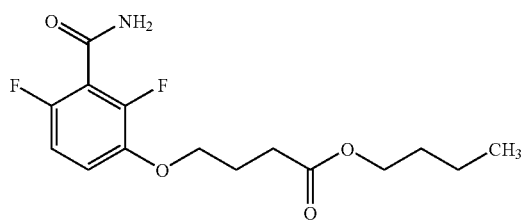

4-[3-(Aminocarbonyl)-2,4-difluorophenoxy]-2-butenoic acid (100 mg, 0.32 mmol) was stirred with 5% Rh/C (5 mg) in butanol (5 ml) under H$_2$, at r.t. for 21 h. The reaction mixture was filtered through a pad of celite and rinsed with CH$_2$Cl$_2$ (3×5 ml). The filtrate was evaporated to dryness, under reduced pressure, to give 88 mg of the desired product, yield 87%, mp 53-55° C. HPLC-MS (method 1): m/z 316 [M+H]$^+$, Rt=3.49 min.

Example 182-197 (Table G)

Examples 182-197 were synthesised from 2,6-difluoro-3-hydroxybenzenecarboxamide: Examples 182, 190, 192, 193 and 195 according to according to Method B, scheme 2 and Examples 183-189, 191, 194 and 196-197 according to Method C, scheme 3.

| Example | 182 | 183 | 184 |
|---|---|---|---|
| Structure | (difluorobenzamide phenoxy-CH$_2$-5-methylisoxazol-3-yl) | (difluorobenzamide phenoxy-CH$_2$-furan-2-yl) | (difluorobenzamide phenoxy-CH$_2$-furan-3-yl) |

-continued

| | | | |
|---|---|---|---|
| Yield (%) | 11 | 4 | 10 |
| mp (° C.) | 130-132 | 86-88 | — |
| HPLC-MS: method no., m/z, ion | 1, 269, [M + H]⁺ | 1, 254, [M + H]⁺ | 1, 254, [M + H]⁺ |
| Rt (min) | 2.84 | 3.15 | 3.11 |

| Example | 185 | 186 | 187 |
|---|---|---|---|
| Structure | (5-methylfuran-2-ylmethoxy benzamide, 2,6-difluoro) | (thiophen-2-ylmethoxy benzamide, 2,6-difluoro) | (4-methylthiophen-2-ylmethoxy benzamide, 2,6-difluoro) |
| Yield (%) | 7 | 30 | 9 |
| mp (° C.) | 92-93 | 155-156 | 111-112 |
| HPLC-MS: method no., m/z, ion | 1, 268, [M + H]⁺ | 1, 268, [M − H]⁺ | 1, 284, [M + H]⁺ |
| Rt (min) | 3.49 | 3.38 | 3.73 |

| Example | 188 | 189 | 190 |
|---|---|---|---|
| Structure | (thiophen-3-ylmethoxy benzamide) | (thiazol-5-ylmethoxy benzamide) | (2-methylthiazol-4-ylmethoxy benzamide) |
| Yield (%) | 17 | 8.4 | 13 |
| mp (° C.) | 161-162 | 130-132 | 194-196 |
| HPLC-MS: method no., m/z, ion | 1, 270, [M + H]⁺ | 1, 271, [M + H]⁺ | 1, 285, [M + H]⁺ |
| Rt (min) | 3.42 | 2.37 | 2.73 |

| Example | 191 | 192 | 193 |
|---|---|---|---|
| Structure | (thiazol-2-ylmethoxy benzamide) | (5-methylthiazol-2-ylmethoxy benzamide) | (4-methylthiazol-2-ylmethoxy benzamide) |
| Yield (%) | 8 | 46 | 49 |
| mp (° C.) | 175-177 | 172-174 | 172-173 |
| HPLC-MS: method no., m/z, ion | 1, 271, [M + H]⁺ | 1, 285, [M + H]⁺ | 1, 285, [M + H]⁺ |
| Rt (min) | 2.51 | 2.85 | 2.80 |

-continued

| Example | 194 | 195 |
|---|---|---|
| Structure | (2,6-difluoro-3-[(1-methyl-1H-imidazol-2-yl)methoxy]benzamide) | (2,6-difluoro-3-[(3-methylbenzyl)oxy]benzamide) |
| Yield (%) | 14 | 30 |
| mp (° C.) | 167-168 | 103-105 |
| HPLC-MS: method no., m/z, ion | 1, 268, [M + H]+ | 1, 278, [M + H]+ |
| Rt (min) | 1.86 | 3.89 |

| Example | 196 | 197 |
|---|---|---|
| Structure | (3-[(3-ethoxybenzyl)oxy]-2,6-difluorobenzamide) | (2,6-difluoro-3-[(6-methyl-2-pyridinyl)methoxy]benzamide) |
| Yield (%) | 3 | 57 |
| mp (° C.) | 137-138 | 201-202 |
| HPLC-MS: method no., m/z, ion | 1, 308, [M + H]+ | 1, 279, [M + H]+ |
| Rt (min) | 3.51 | 2.89 |

Table of names of product compounds; Examples 182-197:

| Example | Compound name |
|---|---|
| 182 | 2,6-Difluoro-3-[(5-methyl-3-isoxazolyl)methoxy]benzenecarboxamide |
| 183 | 2,6-Difluoro-3-(2-furylmethoxy)benzenecarboxamide |
| 184 | 2,6-Difluoro-3-(3-furylmethoxy)benzenecarboxamide |
| 185 | 2,6-Difluoro-3-[(5-methyl-2-furyl)methoxy]benzenecarboxamide |
| 186 | 2,6-Difluoro-3-(2-thienylmethoxy)benzenecarboxamide |
| 187 | 2,6-Difluoro-3-[(4-methyl-2-thienyl)methoxy]benzenecarboxamide |
| 188 | 2,6-Difluoro-3-(3-thienylmethoxy)benzenecarboxamide |
| 189 | 2,6-Difluoro-3-(1,3-thiazol-5-ylmethoxy)benzenecarboxamide |
| 190 | 2,6-Difluoro-3-[(2-methyl-1,3-thiazol-4-yl)methoxy]benzenecarboxamide |
| 191 | 2,6-Difluoro-3-(1,3-thiazol-2-ylmethoxy)benzenecarboxamide |
| 192 | 2,6-Difluoro-3-[(5-methyl-1,3-thiazol-2-yl)methoxy]benzenecarboxamide |
| 193 | 2,6-Difluoro-3-[(4-methyl-1,3-thiazol-2-yl)methoxy]benzenecarboxamide |
| 194 | 2,6-Difluoro-3-[(1-methyl-1H-imidazol-2-yl)methoxy]benzenecarboxamide |
| 195 | 2,6-Difluoro-3-[(3-methylbenzyl)oxy]benzenecarboxamide |
| 196 | 3-[(3-Ethoxybenzyl)oxy]-2,6-difluorobenzenecarboxamide |
| 197 | 2,6-Difluoro-3-[(6-methyl-2-pyridinyl)methoxy]benzenecarboxamide |

Scheme 23:

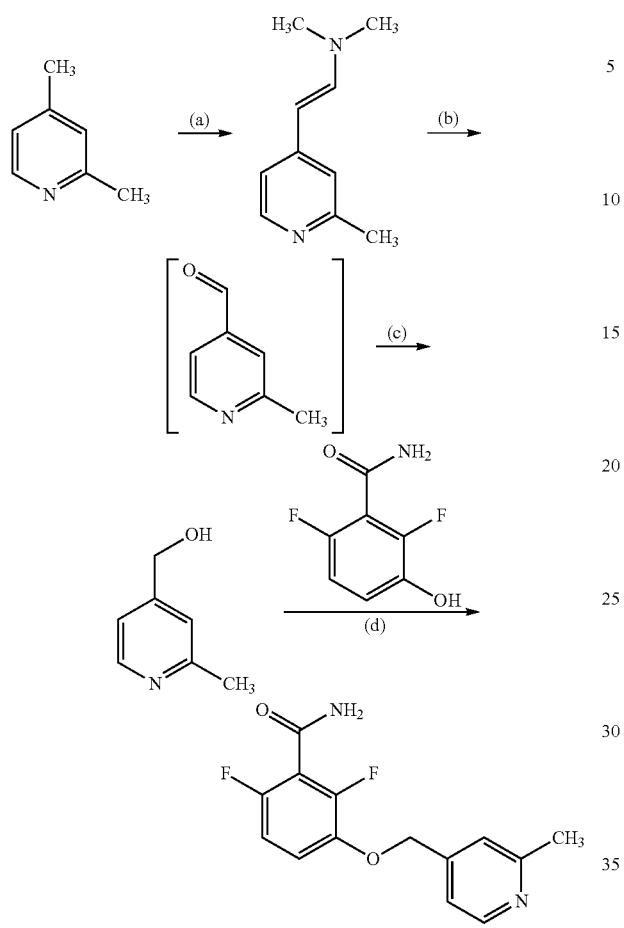

(a) n-BuLi, Et₂NH, THF;
(b) NaIO₄, MeOH;
(c) NaBH4, MeOH;
(d) PPh₃, DIAD, Et₃N, THF, r.t.

Example 198

2,6-Difluoro-3-[(2-methyl-4-pyridinyl)methoxy]benzenecarboxamide

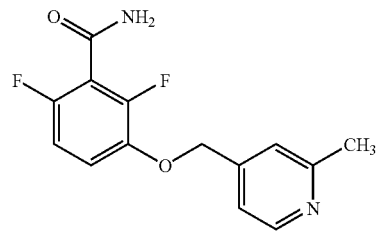

Synthesised from 2,6-difluoro-3-hydroxybenzenecarboxamide according to Method C, scheme 3. The required building block, 4-hydroxymethyl-2-methylpyridine, was synthesised according to the literature method, shown in Scheme 23 (Ragan, J. A., Jones, B. P., Meltz, C. N., Teixeira J. J. Jr.; Synthesis 2002, 483-486. Yield 34%, mp 185-186° C., HPLC-MS (method 1): m/z 279 [M+H]⁺, Rt=2.50 min.

Example 199

2,6-Difluoro-3-([1,3]oxazolo[4,5-b]pyridin-2-ylmethoxy)benzenecarboxamide

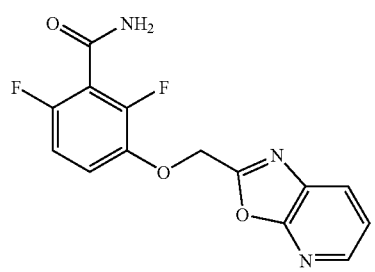

Synthesised from 2,6-difluoro-3-hydroxybenzenecarboxamide according to Method B, scheme 2. Yield 8%, mp 180-181° C., HPLC-MS (method 1): m/z 306 [M+H]⁺, Rt=2.30 min.

Example 200

2,6-Difluoro-3-(2-quinolinylmethoxy)benzenecarboxamide

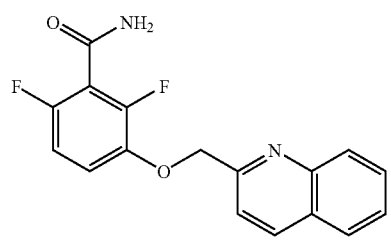

Synthesised from 2,6-difluoro-3-hydroxybenzenecarboxamide according to Method B, scheme 2. Yield 48%, mp 216-218° C., HPLC-MS (method 1): m/z 315 [M+H]⁺, Rt=3.43 min.

Example 201

3-(1-Benzothiophen-5-ylmethoxy)-2,6-difluorobenzenecarboxamide

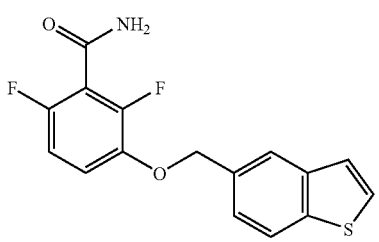

Synthesised from 2,6-difluoro-3-hydroxybenzenecarboxamide according to Method B, scheme 2. The required building block, 5-(chloromethyl)-1-benzothiophene, was synthesised by chlorination of commercially available 1-benzothiophen-5-ylmethanol with thionyl chloride. Yield 10%, mp 146-148° C., HPLC-MS (method 1): m/z 320 [M+H]$^+$, Rt=3.95 min.

Examples 202-207 (Table H)

Examples 202-207 were synthesised from 2,6-difluoro-3-hydroxybenzenecarboxamide according to Method C, scheme 3.

Table of names of product compounds; Examples 202-207:

| Example | Compound name |
|---|---|
| 202 | 3-(1-Benzothiophen-3-ylmethoxy)-2,6-difluorobenzenecarboxamide |
| 203 | 2,6-Difluoro-3-(imidazo[1,2-a]pyridin-2-ylmethoxy)benzenecarboxamide |

| Example | 202 | 203 |
|---|---|---|
| Structure | | |
| Yield % | 29 | 9 |
| mp (° C.) | 154-156 | — |
| HPLC-MS: method no., m/z, ion | 1, 320, [M + H]$^+$ | 1, 304, [M + H]$^+$ |
| Rt (min) | 3.97 | 2.52 |
| Example | 204 | 205 |
| Structure | | |
| Yield % | 13 | 23 |
| mp (° C.) | 84-86 | 149-150 |
| HPLC-MS: method no., m/z, ion | 1, 322, [M + H]$^+$ | 1, 334, [M + H]$^+$ |
| Rt (min) | 3.73 | 3.88 |
| Example | 206 | 207 |
| Structure | | |
| Yield % | 63 | 26 |
| mp (° C.) | 142-143 | 135-136 |
| HPLC-MS: method no., m/z, ion | 1, 320, [M + H]$^+$ | 1, 304, [M + H]$^+$ |
| Rt (min) | 4.02 | 3.82 |

-continued

| Example | Compound name |
|---|---|
| 204 | 3-(2,3-Dihydro-1,4-benzodioxin-2-ylmethoxy)-2,6-difluorobenzenecarboxamide |
| 205 | 2,6-Difluoro-3-[(5-methyl-1-benzothiophen-2-yl)methoxy]benzenecarboxamide |
| 206 | 3-(1-Benzothiophen-2-ylmethoxy)-2,6-difluorobenzenecarboxamide |
| 207 | 3-(1-Benzofuran-2-ylmethoxy)-2,6-difluorobenzenecarboxamide |

[5-(Trifluoromethyl)-1-benzothiophen-2-yl]methanol

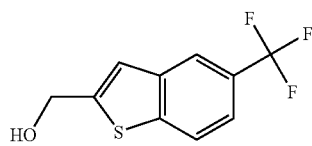

Pyridine (0.37 ml, 4.72 mmol, 1.5 equiv.) and subsequently cyanuric fluoride (0.53 ml, 6.3 mmol, 2 equiv.) were added to a stirred solution of commercially available 5-(trifluoromethyl)-1-benzothiophene-2-carboxylic acid (776 mg, 3.15 mmol, 1 equiv.) in $CH_2Cl_2$ (16 ml), kept under $N_2$, at −20 to −10° C. Precipitation of cyanuric acid occurred and increased gradually as the reaction proceeded. After the mixture was stirred at −20 to −10° C. for 2 h, ice-cold water was added along with 100 ml $CH_2Cl_2$. Undissolved solids were filtered off; from the filtrate, the organic phase was separated and the aqueous layer was extracted once more with $CH_2Cl_2$ (50 ml). The combined organic layers were washed with ice-cold water (50 ml), dried ($Na_2SO_4$) and concentrated under reduced pressure to a small volume (15 ml). $NaBH_4$ (240 mg, 6.3 mmol, 2 equiv.) was added in one portion, and MeOH (6.5 ml) was then added, dropwise, over 15 min at r.t. The reaction mixture was neutralised with 1N $H_2SO_4$, and the organic solvents were evaporated under reduced pressure. The residue was taken-up in EtOAc (80 ml) and water (40 ml); the organic layer was separated, and the aqueous layer was extracted with EtOAc (2×60 ml). The combined organic layers were washed with 1N $H_2SO_4$ and brine, dried ($Na_2SO_4$) and the solvent was evaporated under reduced pressure. The residue was purified by column chromatography on silica, using EtOAc/hexane (10-20% gradient) as eluent, to give 400 mg (54.6% yield) of the required product as a white solid. HPLC-MS (method 1) gave one peak with Rt=4.02 min, but no ionization.

Example 208

2,6-Difluoro-3-[5-(trifluoromethyl)-1-benzothiophen-2-yl]methoxybenzenecarboxamide

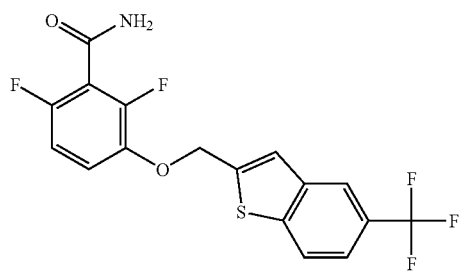

Synthesised from 2,6-difluoro-3-hydroxybenzenecarboxamide and [5-(trifluoromethyl)-1-benzothiophen-2-yl]methanol according to Method C, scheme 3. Yield 3%, mp 150-152° C., HPLC-MS (method 1): m/z 386 [M−H]−, Rt=4.39 min.

Examples 209-217 (Table I)

Examples 209-217 were synthesised from 2,6-difluoro-3-hydroxybenzenecarboxamide according to Method B, scheme 2.

| Example | 209 | 210 |
|---|---|---|
| Structure | (structure) | (structure) |
| Yield (%) | 37 | 62 |
| mp (° C.) | 138-139 | — |
| HPLC-MS: method no., m/z, ion | 1, 305, [M + H]+ | 1, 339, [M + H]+ |
| Rt (min) | 3.28 | 3.72 |

-continued
| Example | 211 | 212 |
|---|---|---|
| Structure | 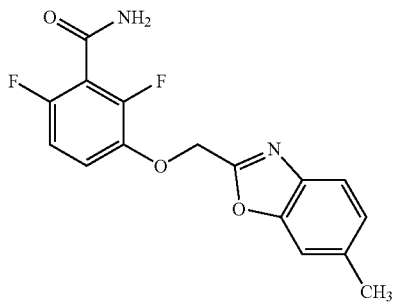 | 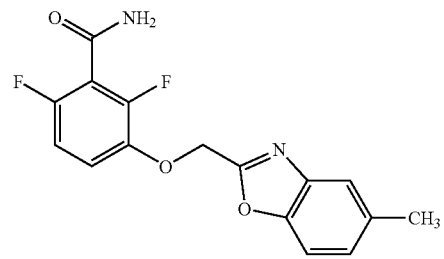 |
| Yield (%) | 16 | 32 |
| mp (° C.) | 172-173 | 150-151 |
| HPLC-MS: method no., m/z, ion | 1, 319, [M + H]+ | 1, 319, [M + H]+ |
| Rt (min) | 3.60 | 3.60 |
| Example | 213 | 214 |
|---|---|---|
| Structure | 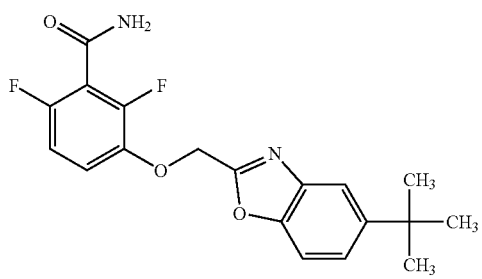 | 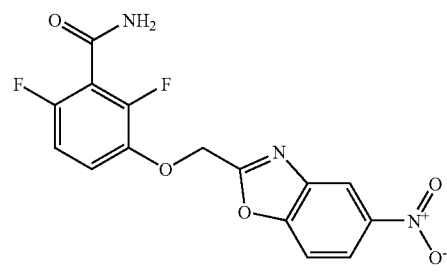 |
| Yield (%) | 50 | 14 |
| mp (° C.) | 160-161 | 153-155 |
| HPLC-MS: method no., m/z, ion | 1, 361, [M + H]+ | 1, 348, [M − H]− |
| Rt (min) | 4.29 | 3.32 |
| Example | 215 | 216 |
|---|---|---|
| Structure | 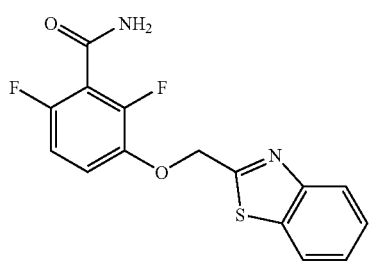 | 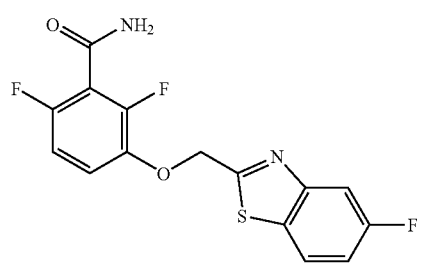 |
| Yield (%) | 15 | 25 |
| mp (° C.) | 185-186 | 195-197 |
| HPLC-MS: method no., m/z, ion | 1, 321, [M + H]+ | 1, 339, [M + H]+ |
| Rt (min) | 3.46 | 3.67 |

| Example | 217 |
|---|---|
| Structure | (structure shown) |
| Yield (%) | 60 |
| mp (° C.) | 223-224 |
| HPLC-MS: method no., m/z, ion | 1, 389, [M + H]$^+$ |
| Rt (min) | 4.15 |

Table of names of product compounds; Examples 209-217:

| Example | Compound name |
|---|---|
| 209 | 3-(1,3-Benzoxazol-2-ylmethoxy)-2,6-difluorobenzenecarboxamide |
| 210 | 3-[(5-Chloro-1,3-benzoxazol-2-yl)methoxy]-2,6-difluorobenzenecarboxamide |
| 211 | 2,6-Difluoro-3-[(6-methyl-1,3-benzoxazol-2-yl)methoxy]benzenecarboxamide |
| 212 | 2,6-Difluoro-3-[(5-methyl-1,3-benzoxazol-2-yl)methoxy]benzenecarboxamide |
| 213 | 3-[5-(tert-Butyl)-1,3-benzoxazol-2-yl]methoxy-2,6-difluorobenzenecarboxamide |
| 214 | 2,6-Difluoro-3-[(5-nitro-1,3-benzoxazol-2-yl)methoxy]benzenecarboxamide |
| 215 | 3-(1,3-Benzothiazol-2-ylmethoxy)-2,6-difluorobenzenecarboxamide |
| 216 | 2,6-Difluoro-3-[(5-fluoro-1,3-benzothiazol-2-yl)methoxy]benzenecarboxamide |
| 217 | 2,6-Difluoro-3-[5-(trifluoromethyl)-1,3-benzothiazol-2-yl]methoxybenzenecarboxamide |

5-Chloro-2-(chloromethyl)-1,3-benzothiazole

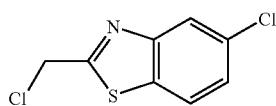

4-Chloro-2-amino-benzothiol (4.05 g, 25.4 mmol, 1 equiv.) and 2-chloro-1,1,1-trimethoxy ethane (5.0 ml, 37 mmol, 1.45 equiv.) were heated with stirring at 60° C. for 2 h. The reaction mixture was cooled at r.t. and triturated with diethyl ether (10 ml). The undissolved solid was filtered and rinsed with Et$_2$O and pentane, to give 1.54 g (28% yield) of the desired product. The mother liquors were evaporated to dryness, the orange solid residue was dissolved in Et$_2$O (50 ml) and washed consecutively with 1N HCl (25 ml), water (25 ml), 5% NaHCO$_3$ solution (25 ml) and brine (25 ml). The organic layer was dried (MgSO4) and evaporated to smaller volume, under reduced pressure. The precipitant solid was filtered and washed with Et$_2$O and pentane, to give a second fraction of the desired product 1.88 g (34% yield). Total yield 62%, mp 102-104° C., HPLC-MS (method 1): m/z 260 [M+H+CH$_3$CN]$^+$, Rt=4.52 min.

Examples 218-221 (Table J)

Examples 218-221 were synthesised from 2,6-difluoro-3-hydroxybenzenecarboxamide and 5-chloro-2-(chloromethyl)-1,3-benzothiazole according to Method B, scheme 2.

| Example | 218 | 219 |
|---|---|---|
| Structure | (structure shown) | (structure shown) |

| | | |
|---|---|---|
| Yield (%) | 81 | 67 |
| mp (° C.) | 235-236 | 204-205 |
| HPLC-MS: method no., m/z, ion | 1, 355, [M + H]+ | 1, 337, [M + H]+ |
| Rt (min) | 3.89 | 392 |
| Example | 220 | 221 |
| Structure | | |
| Yield (%) | 50 | 35 |
| mp (° C.) | 240-242 | 218-220 |
| HPLC-MS: method no., m/z, ion | 1, 371, [M + H]+ | 1, 371, [M + H]+ |
| Rt (min) | 4.02 | 3.98 |

Table of names of product compounds; Examples 218-221:

| Example | Compound name |
|---|---|
| 218 | 3-[(5-Chloro-1,3-benzothiazol-2-yl)methoxy]-2,6-difluorobenzenecarboxamide |
| 219 | 3-[(5-Chloro-1,3-benzothiazol-2-yl)methoxy]-2-fluorobenzenecarboxamide |
| 220 | 6-Chloro-3-[(5-chloro-1,3-benzothiazol-2-yl)methoxy]-2-fluorobenzenecarboxamide |
| 221 | 2-Chloro-3-[(5-chloro-1,3-benzothiazol-2-yl)methoxy]-6-fluorobenzenecarboxamide |

Scheme 24:

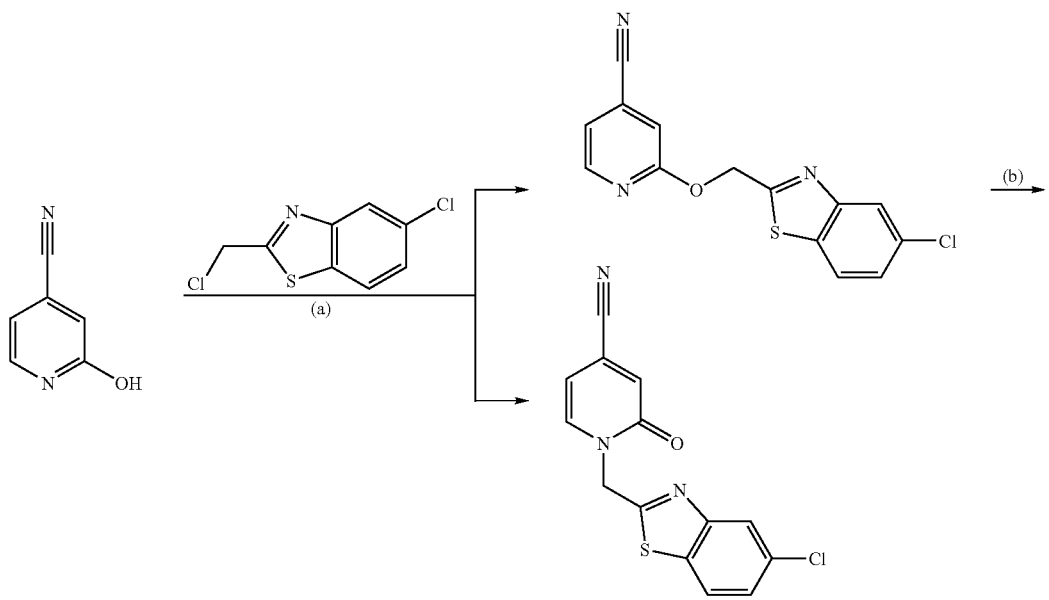

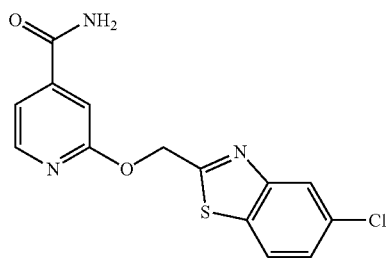

(a) K₂CO₃, NaI, DMF, 60° C.;
(b) conc. H₂SO₄, H₂O, 40° C.

2-[(5-Chloro-1,3-benzothiazol-2-yl)methoxy]isonicotinonitrile

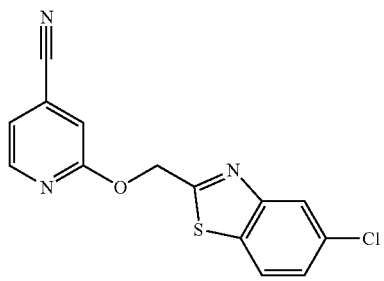

2-Hydroxy-4-cyano-pyridine (240 mg, 2 mmol, 1 equiv.) was dissolved in DMF (6 ml), K₂CO₃ (415 mg, 3 mmol, 1.5 equiv.) and NaI (60 mg, 0.4 mmol, 0.2 equiv.) were added and the mixture was stirred at r.t. for 10 min. 5-Chloro-2-(chloromethyl)-1,3-benzothiazole (436 mg, 2 mmol, 1 equiv.) was added and the reaction mixture was stirred at 60° C. for 3 h and at r.t. overnight. By addition of H₂O, brown solid precipitated, which was filtered, rinsed with H₂O, dried and recrystallised from CH₃CN. Yield 280 mg (46%), mp 224-227° C., HPLC-MS (method 1): m/z 302 [M+H]⁺, Rt=3.80 min. By ¹³C-NMR analysis it was identified to be the N-alkylated derivative (Scheme 24). The DMF-H₂O mother liquors were evaporated to dryness under reduced pressure and the residue was purified by column chromatography on silica, eluted with EtOAc/hexane (10%-100% gradient) to give 45 mg (7.5% yield) of a brown solid, HPLC-MS (method 1): m/z 302 [M+H]⁺, Rt=4.86 min. By ¹³C-NMR analysis, it was identified to be the desired O-alkylated derivative (Scheme 24).

Example 222

2-[(5-Chloro-1,3-benzothiazol-2-yl)methoxy]isonicotinamide

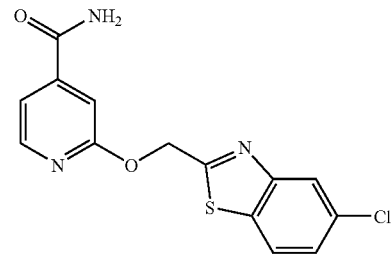

2-[(5-Chloro-1,3-benzothiazol-2-yl)methoxy]isonicotinonitrile (40 mg, 0.13 mmol) was dissolved in conc. H₂SO₄ (0.36 ml) and the solution was heated at 40° C., under vigorous stirring. Water (50 mg) was added dropwise and the mixture was stirred at 40° C. for 3 h. After cooling at −5° C., crushed ice (25 ml) was added quickly, with vigorous stirring, and the mixture was stirred at r.t. for two more hours. Ammonia solution was added (pH 10) and the precipitant solid was filtered, rinsed with H₂O and dried. The brown solid was purified by preparative TLC, eluted with EtOAc, to give 20 mg (47% yield), mp 220-222° C., HPLC-MS (method 1): m/z 320 [M+H]⁺, Rt=3.76 min.

Scheme 25:

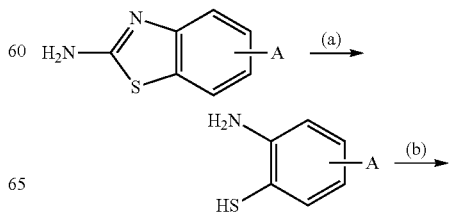

-continued

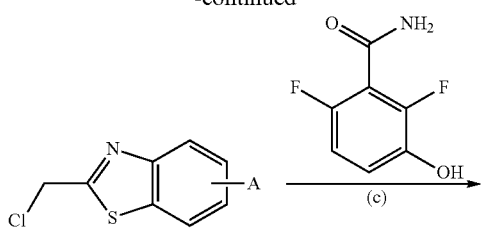

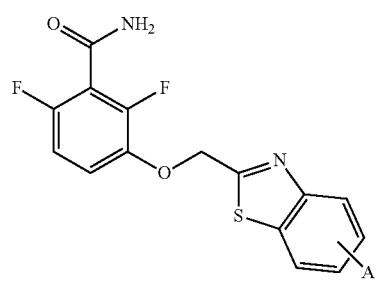

(a) KOH, 2-methoxy-ethanol:H₂O (1:1), reflux;
(b) ClCH₂C(OCH₃)₃;
(c) K₂CO₃, NaI, DMF, 60° C.

2-(Chloromethyl)-4-ethyl-1,3-benzothiazole

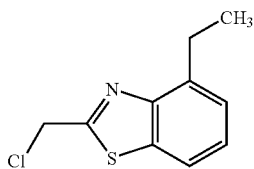

(Method J) A solution of 4-ethyl-1,3-benzothiazol-2-amine (1.0 g, 5.6 mmol, 1 equiv.) and KOH (7.4 g, 112.2 mmol, 20 equiv.) in 2-methoxy-ethanol (9 ml) and H₂O (9 ml), was stirred under N₂ and under reflux, for 20 h. After cooling at r.t., the mixture was poured into water (150 ml) and extracted with CH₂Cl₂ (2×40 ml). The aqueous phase was neutralised with conc. HCl and extracted again with CH₂Cl₂ (3×70 ml). The combined neutral extracts were washed with water (2×60 ml), dried (Na₂SO₄) and evaporated to dryness under reduced pressure. The yellow-green semi-solid residue (790 mg) was mixed with 2-chloro-1,1,1-trimethoxy ethane (1.62 g, 10.4 mmol) and the mixture was stirred, under N₂, at 60° C., for 4 h. Volatiles were removed by evaporation under reduced pressure and the brown liquid residue was purified by column chromatography on silica, eluted with CH₂Cl₂/hexane (10% and 50%), to give a yellow liquid (406 mg, 34% yield over two steps). HPLC-MS (method 1): m/z 212 [M+H]⁺, Rt=5.00 min Example 223

3-[(4-Ethyl-1,3-benzothiazol-2-yl)methoxy]-2,6-difluorobenzenecarboxamide

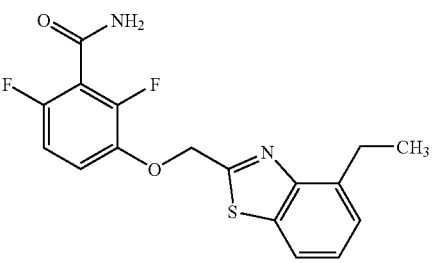

Synthesised from 2,6-difluoro-3-hydroxybenzenecarboxamide and 2-(chloromethyl)-4-ethyl-1,3-benzothiazole according to Method B, scheme 2. Yield 17%, mp 184-186° C., HPLC-MS (method 1): m/z 349 [M+H]⁺, Rt=4.16 min.

2-(Chloromethyl)-6-methoxy-1,3-benzothiazole

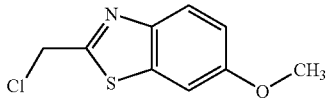

Synthesised from commercially available 6-methoxy-1,3-benzothiazol-2-amine according to Method J, scheme 25. It was used crude on the next step.

Example 224

2,6-Difluoro-3-[(6-methoxy-1,3-benzothiazol-2-yl)methoxy]benzenecarboxamide

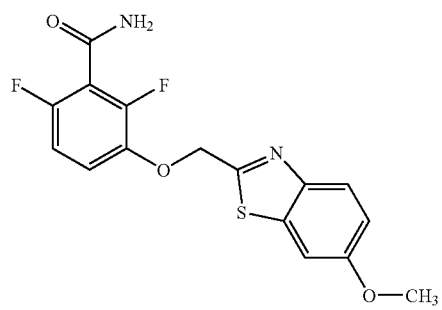

Synthesised from 2,6-difluoro-3-hydroxybenzenecarboxamide and 2-(chloromethyl)-6-methoxy-1,3-benzothiazole according to Method B, scheme 2. Yield 19%, mp 190-192° C., HPLC-MS (method 1): m/z 351 [M+H]⁺, Rt=3.50 min.

Scheme 26:

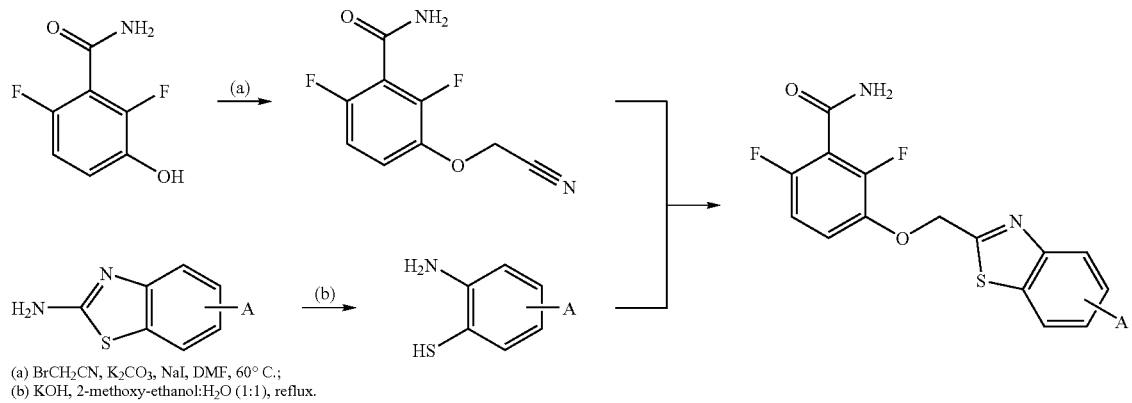

(a) BrCH₂CN, K₂CO₃, NaI, DMF, 60° C.;
(b) KOH, 2-methoxy-ethanol:H₂O (1:1), reflux.

Example 225

3-(Cyanomethoxy)-2,6-difluorobenzenecarboxamide

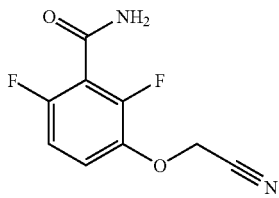

Synthesised from 2,6-difluoro-3-hydroxybenzenecarboxamide according to Method B, scheme 2. Yield 86%, mp 122-123° C., HPLC-MS (method 1): m/z 213 [M+H]⁺, Rt=1.97 min.

Example 226

3-[(4-Chloro-1,3-benzothiazol-2-yl)methoxy]-2,6-difluorobenzenecarboxamide

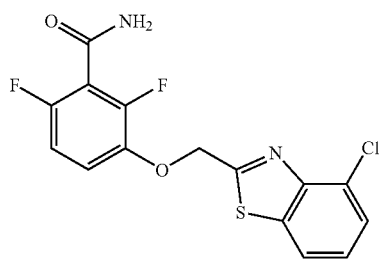

(Method K) A solution of KOH (15.15 g, 270 mmol, 20 equiv.) in H₂O (25 ml) was added to a solution of 4-chloro-1,3-benzothiazol-2-amine (2.5 g, 13.5 mmol, 1 equiv.) in 2-methoxy-ethanol (25 ml) and the reaction mixture was heated under reflux overnight. After cooling at r.t., the mixture was diluted with H₂O (200 ml), acidified with 5N HCl solution to pH 4 and extracted with CH₂Cl₂ (3×150 ml). The combined organic extracts were washed with brine (100 ml), dried (Na₂SO₄) and concentrated under reduced pressure to dryness, to give 1.5 g (70% yield). From this crude residue, 167 mg (assuming 1.05 mmol), were mixed with 3-(cyanomethoxy)-2,6-difluorobenzenecarboxamide (150 mg, 0.7 mmol) and the mixture was stirred at 120° C., in a pre-heated oil bath, under N₂, for 2 h. EtOH (2 ml) was added and the reaction mixture was heated for a further 2 h. After cooling at r.t., the solid was filtered, washed with EtOH and re-crystallised from EtOAc/pentane, to give the desired product as a pale yellow solid, 62 mg (25% yield on second step). HPLC-MS (method 1): m/z 355 [M+H]⁺, Rt=3.75 min.

Example 227

3-[(6-Chloro-1,3-benzothiazol-2-yl)methoxy]-2,6-difluorobenzenecarboxamide

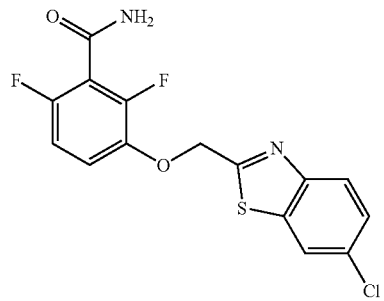

Synthesised from 6-chloro-1,3-benzothiazol-2-amine and 3-(cyanomethoxy)-2,6-difluorobenzene carboxamide, according to Method K, scheme 26. Yield 38% (second step), mp 190-191° C., HPLC-MS (method 1): m/z 355 [M+H]⁺, Rt=3.85 min.

Example 228

2,6-Difluoro-3-[(4-methyl-1,3-benzothiazol-2-yl)methoxy]benzenecarboxamide

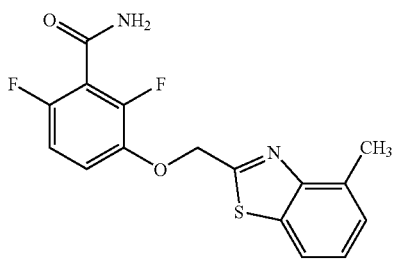

Synthesised from 4-methyl-1,3-benzothiazol-2-amine and 3-(cyanomethoxy)-2,6-difluorobenzene carboxamide, according to Method K, scheme 26. Yield 36% (second step), mp 201-202° C., HPLC-MS (method 1): m/z 335 [M+H]$^+$, Rt=3.79 min.

Example 229

2,6-Difluoro-3-[(6-methyl-1,3-benzothiazol-2-yl)methoxy]benzenecarboxamide

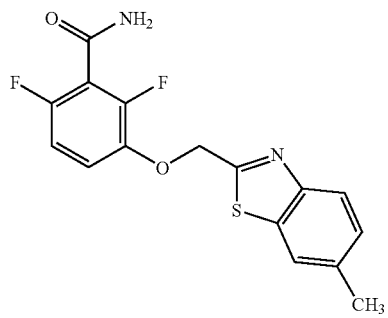

Synthesised from 6-methyl-1,3-benzothiazol-2-amine and 3-(cyanomethoxy)-2,6-difluorobenzene carboxamide, according to Method K, scheme 26. Yield 17% (second step), HPLC-MS (method 1): m/z 335 [M+H]$^+$, Rt=3.70 min.

Example 230

2,6-Difluoro-3-[6-(trifluoromethoxy)-1,3-benzothiazol-2-yl]methoxybenzenecarboxamide

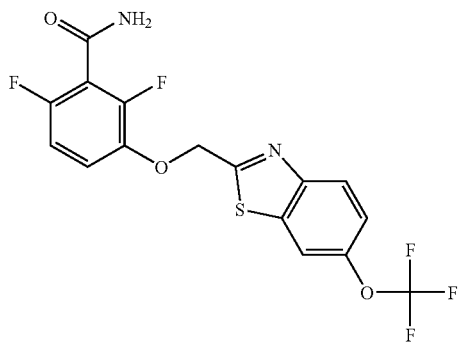

Synthesised from 6-(trifluoromethoxy)-1,3-benzothiazol-2-amine and 3-(cyanomethoxy)-2,6-difluorobenzenecarboxamide, according to Method K, scheme 26. Yield 34% (second step), mp 174-175° C., HPLC-MS (method 1): m/z 405 [M+H]$^+$, Rt=4.14 min.

6-Propyl-1,3-benzothiazol-2-amine

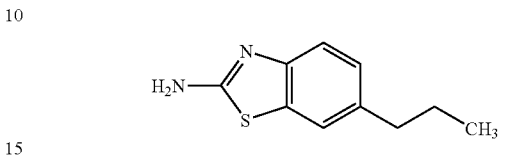

A solution of Br$_2$ (3.8 ml, 74 mmol, 2 equiv.) in glacial AcOH (18.5 ml) was added dropwise, at <25° C., to a stirred solution of 4-propylamine (5.0 g, 37 mmol, 1 equiv.) and ammonium thiocyanate (5.63 g, 74 mmol, 2 equiv.) in glacial AcOH (110 ml). The resulting mixture was stirred at r.t. for 2 h, diluted with H$_2$O (700 ml) and extracted with EtOAc (2×250 ml). The aqueous layer was alkalised with aqueous ammonia solution to pH 10 and extracted with EtOAc (3×300 ml). The combined alkaline extracts were washed with H$_2$O (2×200 ml), dried and evaporated to dryness under reduced pressure, to give the desired product as a white solid, 2.34 g (33% yield), mp 120-122° C. HPLC-MS (method 1): m/z 193 [M+H]$^+$, Rt=3.92 min.

Example 231

2,6-Difluoro-3-[(6-propyl-1,3-benzothiazol-2-yl)methoxy]benzenecarboxamide

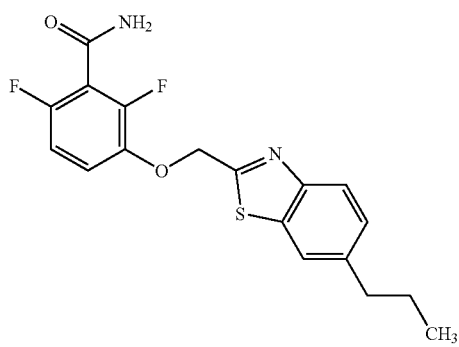

Synthesised from 6-propyl-1,3-benzothiazol-2-amine and 3-(cyanomethoxy)-2,6-difluorobenzenecarboxamide, according to Method K, scheme 26. Yield 18% (second step), mp 173-175° C. HPLC-MS (method 1): m/z 363 [M+H]$^+$, Rt=4.35 min.

Scheme 27:

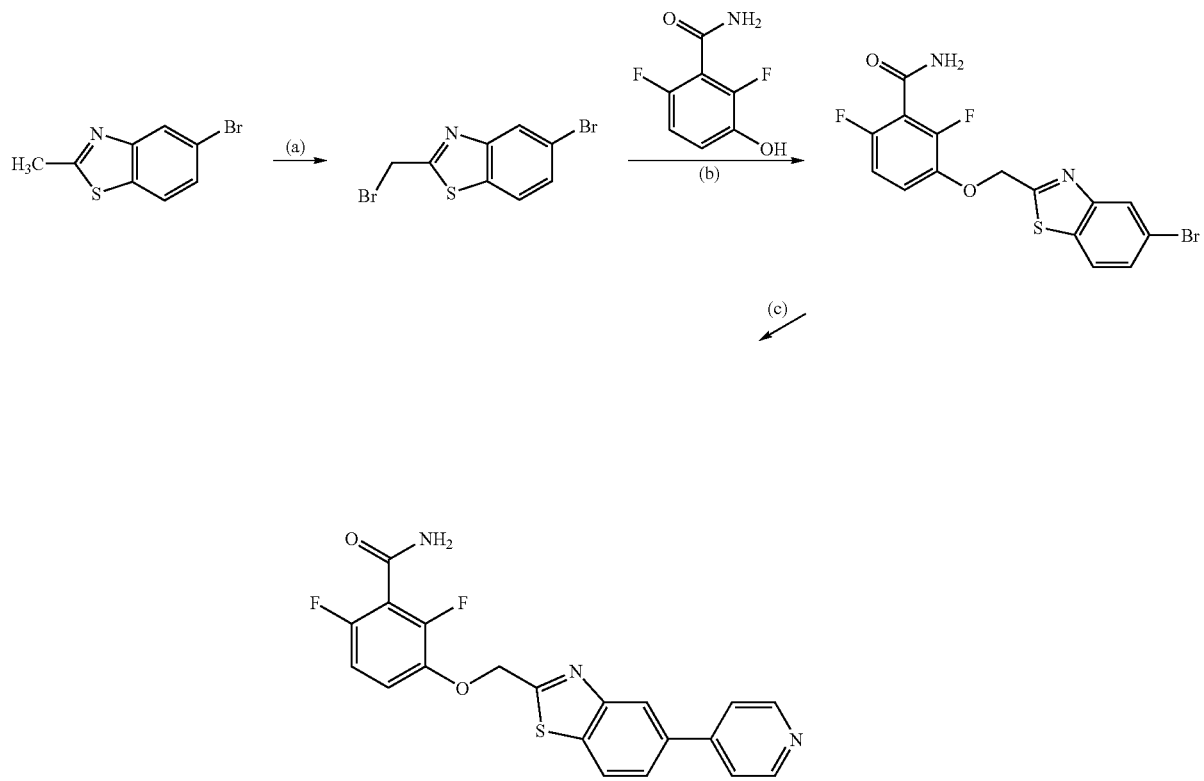

(a) NBS, α,α'-azoisobutyronitrile, CCl₄;
(b) K₂CO₃, DMF, 60° C.;
(c) 4-pyridine boronic acid, Na₂CO₃, Pd(PPh₃)₄, dioxane.

5-Bromo-2-(bromomethyl)-1,3-benzothiazole

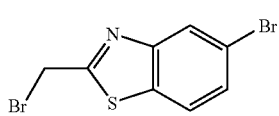

N-Bromosuccinimide (4.45 g, 25 mmol, 1.4 equiv.) and subsequently α,α'azoisobutyronitrile (110 mg, 0.7 mmol, 0.04 equiv.) were added to a solution of 5-bromo-2-methyl-benzothiazole (4.07 g, 17.85 mmol, 1 equiv.) in CCl₄ (110 ml). The reaction mixture was stirred at reflux for 24 hrs. After cooling, succinimide was removed by filtration and was rinsed with CCl₄ (100 ml). The filtrate was evaporated to dryness under reduced pressure and the orange solid residue was purified by column chromatography on silica, eluted with CH₂Cl₂/hexane (20%-70% gradient), to give the desired product as a white solid, 2.15 g (39% yield). Mp 116-117, HPLC-MS (method 1): m/z 308 [M+H]⁺, Rt=4.84 min. The reaction gave also 1.40 g (20% yield) of the by-product 5-bromo-2-dibromomethyl-benzothiazole, as well as 0.89 g (22%) of un-reacted starting material.

3-[(5-Bromo-1,3-benzothiazol-2-yl)methoxy]-2,6-difluorobenzenecarboxamide

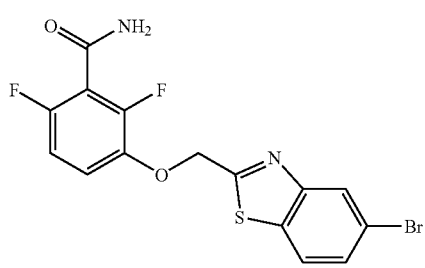

Synthesised from 2,6-difluoro-3-hydroxybenzenecarboxamide and 5-bromo-2-(bromomethyl)-1,3-benzothiazole, according to Method B, scheme 2. Yield 81%, mp 244-246° C., HPLC-MS (method 1): m/z 399, 401 [M+H]+, Rt=3.98 min.

Example 232

2,6-Difluoro-3-[5-(4-pyridinyl)-1,3-benzothiazol-2-yl]methoxybenzenecarboxamide

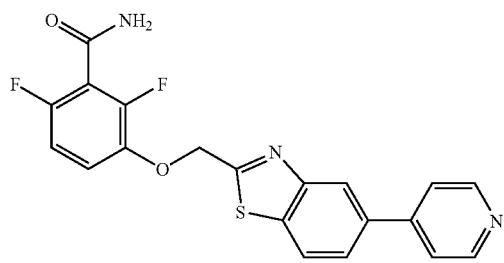

A mixture of 3-[(5-bromo-1,3-benzothiazol-2-yl)methoxy]-2,6-difluorobenzenecarboxamide (168 mg, 0.42 mmol, 1 equiv.), 4-pyridine boronic acid (98 mg, 0.63 mmol, 1.5 equiv.) and 2M aqueous $Na_2CO_3$ solution (0.42 ml, 0.82 mmol, 2 equiv.) were suspended in dioxane (3.5 ml) and the mixture was degassed and flushed with $N_2$. Tetrakis(triphenylphosphine)palladium(0) catalyst (37 mg, 0.031 mmol, 0.075 equiv.) was added and the reaction mixture was heated under reflux for 12 h. After cooling at r.t., the mixture was diluted with $H_2O$ and the precipitant solid was filtered and rinsed with $H_2O$, IMS, IMS/$Et_2O$ and $Et_2O$. Re-crystallised from $CH_3CN$, to give the desired product as an off-white solid, 47 mg (28% yield), mp 255-258° C. HPLC-MS: m/z 398 [M+H]+, Rt=3.28 min.

Examples 233-241 (Table K)

Examples 233-241 were synthesised from 2,6-difluoro-3-hydroxybenzenecarboxamide according to Method B, scheme 2.

| Example | 233 | 234 |
|---|---|---|
| Structure | ![structure 233] | ![structure 234] |
| Yield (%) | 58 | 25 |
| mp (° C.) | 207-209 | 198-199 |
| HPLC-MS: method no., m/z, ion | 1, 347, [M + H]+ | 1, 382, [M + H]+ |
| Rt (min) | 3.96 | 3.89 |

| Example | 235 | 236 |
|---|---|---|
| Structure | ![structure 235] | ![structure 236] |
| Yield (%) | 63 | 54 |
| mp (° C.) | 208-210 | 222-224 |
| HPLC-MS: method no., m/z, ion | 1, 347, [M + H]+ | 1, 361, [M + H]+ |
| Rt (min) | 3.84 | 4.13 |

-continued

| Example | 237 | 238 |
|---|---|---|
| Structure | (structure) | (structure) |
| Yield (%) | 6 (only ~75% pure) | 17 |
| mp (° C.) | — | 188-189 |
| HPLC-MS: method no., m/z, ion | 1, 362, [M + H]$^+$ | 1, 332, [M + H]$^+$ |
| Rt (min) | 3.75 | 3.17 |

| Example | 239 | 240 |
|---|---|---|
| Structure | (structure) | (structure) |
| Yield (%) | 60 | 44 |
| mp (° C.) | 177-178 | 164-165 |
| HPLC-MS: method no., m/z, ion | 1, 332, [M + H]$^+$ | 1, 332, [M + H]$^+$ |
| Rt (min) | 3.62 | 3.65 |

| Example | 241 |
|---|---|
| Structure | (structure) |
| Yield (%) | 77 |
| mp (° C.) | 172-173 |
| HPLC-MS: method no., m/z, ion | 1, 362, [M + H]$^+$ |
| Rt (min) | 3.76 |

Table of names of product compounds; Examples 233-241:

| Example | Compound name |
|---|---|
| 233 | 2,6-Difluoro-3-[(2-phenyl-1,3-thiazol-4-yl)methoxy]benzenecarboxamide |
| 234 | 3-[5-(4-Chlorophenyl)-1,3,4-thiadiazol-2-yl]methoxy-2,6-difluorobenzenecarboxamide |
| 235 | 2,6-Difluoro-3-[(4-phenyl-1,3-thiazol-2-yl)methoxy]benzenecarboxamide |
| 236 | 2,6-Difluoro-3-[2-(4-methylphenyl)-1,3-thiazol-4-yl]methoxybenzenecarboxamide |
| 237 | 3-[(2-Anilino-1,3-thiazol-4-yl)methoxy]-2,6-difluorobenzenecarboxamide |

-continued

| Example | Compound name |
|---|---|
| 238 | 2,6-Difluoro-3-[(5-phenyl-1,3,4-oxadiazol-2-yl)methoxy]benzenecarboxamide |
| 239 | 2,6-Difluoro-3-[(5-phenyl-1,2,4-oxadiazol-3-yl)methoxy]benzenecarboxamide |
| 240 | 2,6-Difluoro-3-[(3-phenyl-1,2,4-oxadiazol-5-yl)methoxy]benzenecarboxamide |
| 241 | 2,6-Difluoro-3-[3-(4-methoxyphenyl)-1,2,4-oxadiazol-5-yl]methoxybenzenecarboxamide |

Example 242

2,6-Difluoro-3-[3-(4-hydroxyphenyl)-1,2,4-oxadiazol-5-yl]methoxybenzenecarboxamide

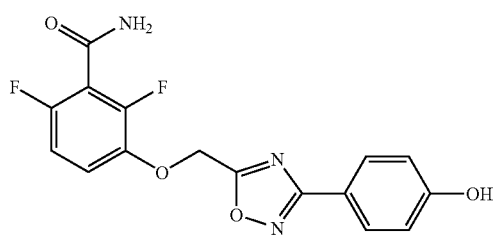

(Method L) Boron tribromide solution (1.0 M in CH$_2$Cl$_2$, 1.5 ml, 1.5 mmol, 2 equiv.) was added slowly, dropwise to stirred suspension of 2,6-difluoro-3-[3-(4-methoxyphenyl)-1,2,4-oxadiazol-5-yl]methoxybenzenecarboxamide (272 mg, 0.75 mmol, 1 equiv.) in CH$_2$Cl$_2$ (5 ml), at r.t., under N$_2$. The reaction mixture was stirred at r.t. for 4 h and poured into water (20 ml). CH$_2$Cl$_2$ (10 ml) was added and the biphasic mixture was stirred for 30 min. at r.t. The white un-dissolved solid was filtered, washed with water and Et$_2$O, to give 170 mg (65% yield), mp 209-210° C., HPLC-MS (method 1): m/z 348 [M+H]$^+$, Rt=3.00 min.

Examples 243-250 (Table L)

Examples 243-250 were Synthesised from 2,6-difluoro-3-hydroxybenzenecarboxamide according to Method B, scheme 2.

| Example | 243 | 244 | 245 |
|---|---|---|---|
| Structure | (structure shown) | No example | (structure shown) |
| Yield (%) | 38 | | 81 |
| mp (° C.) | 168-169 | | 173-174 |
| HPLC-MS: method no., m/z, ion | 1, 398, [M− H]$^-$ | | 1, 350, [M + H]$^+$ |
| Rt (min) | 4.27 | | 3.81 |

| Example | 246 | 247 |
|---|---|---|
| Structure | (structure shown) | (structure shown) |
| Yield (%) | 80 | 82 |
| mp (° C.) | 166-168 | 169-170 |
| HPLC-MS: method no., m/z, ion | 1, 407, [M + H + CH$_3$CN]$^+$ | 1, 346, [M + H]$^+$ |
| Rt (min) | 4.10 | 3.98 |

-continued

| Example | 248 | 249 |
|---|---|---|
| Structure | (structure) | (structure) |
| Yield (%) | 80 | 53 |
| mp (° C.) | 134-135 | 132-133 |
| HPLC-MS: method no., m/z, ion | 1, 374, [M + H]+ | 1, 388, [M + H]+ |
| Rt (min) | 4.47 | 4.62 |

| Example | 250 |
|---|---|
| Structure | (structure) |
| Yield (%) | 33 |
| mp (° C.) | 141-142 |
| HPLC-MS: method no., m/z, ion | 1, 360, [M + H]+ |
| Rt (min) | 4.24 |

Table of names of product compounds: Examples 243-250:

| Example | Compound name |
|---|---|
| 243 | 2,6-Difluoro-3-(3-[4-(trifluoromethyl)phenyl]-1,2,4-oxadiazol-5-ylmethoxy)benzenecarboxamide |
| 245 | 2,6-Difluoro-3-[3-(4-fluorophenyl)-1,2,4-oxadiazol-5-yl]methoxybenzenecarboxamide |
| 246 | 3-[3-(4-Chlorophenyl)-1,2,4-oxadiazol-5-yl]methoxy-2,6-difluorobenzenecarboxamide |
| 247 | 2,6-Difluoro-3-[3-(4-methylphenyl)-1,2,4-oxadiazol-5-yl]methoxybenzenecarboxamide |
| 248 | 2,6-Difluoro-3-[3-(4-isopropylphenyl)-1,2,4-oxadiazol-5-yl]methoxybenzenecarboxamide |
| 249 | 3-(3-[4-(tert-Butyl)phenyl]-1,2,4-oxadiazol-5-ylmethoxy)-2,6-difluorobenzenecarboxamide |
| 250 | 3-[3-(4-Ethylphenyl)-1,2,4-oxadiazol-5-yl]methoxy-2,6-difluorobenzenecarboxamide |

Scheme 28:

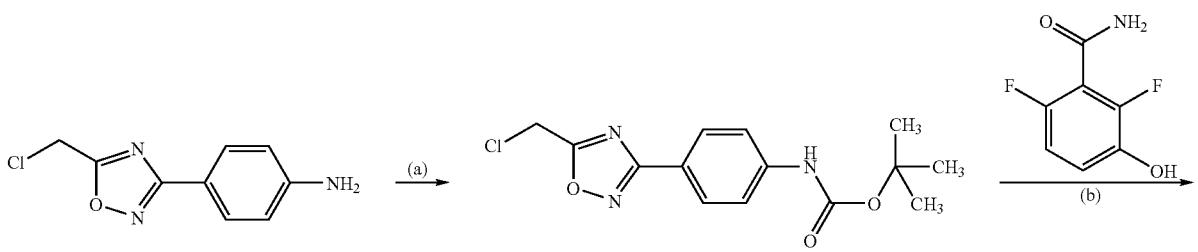

-continued

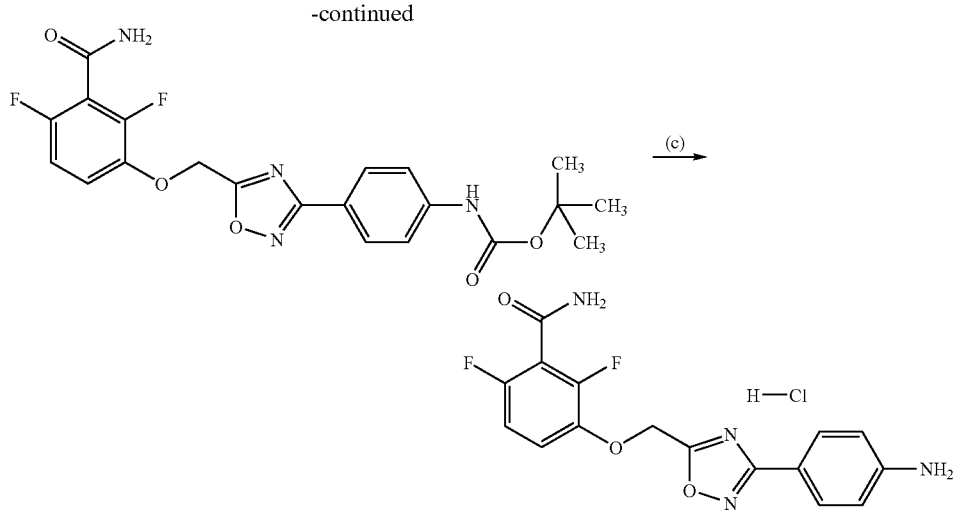

(a) (Boc)₂O, Et₃N, DMAP, THF;
(b) K₂CO₃, NaI, DMF, r.t;
(c) 4N HCl, dioxane.

tert-Butyl N-4-[5-(chloromethyl)-1,2,4-oxadiazol-3-yl]phenylcarbamate

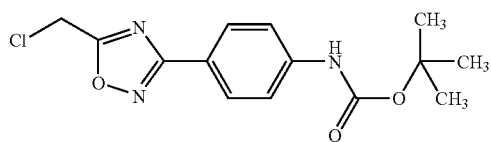

To a solution of 4-[5-(chloromethyl)-1,2,4-oxadiazol-3-yl]aniline (950 mg, 4.53 mmol, 1 equiv.), Et₃N (0.20 ml, 5.44 mmol, 1.2 equiv.) and dimethylaminopyridine (catalytic), Boc anhydride (1.04 g, 4.75 mmol, 1.05 equiv.) was added portionwise, and the reaction mixture was stirred at r.t. for 3 days. The solvent was evaporated under reduced pressure, the residue was triturated with Et₂O and the solid was removed by filtration. The filtrate was evaporated to dryness under reduced pressure and the residue was purified by column chromatography on silica, eluted with EtOAc/hexane (20%), to give a cream solid, 780 mg (55% yield). About 70% pure by HPLC-MS (method 1): m/z 308 [M−H]⁻, Rt=4.72 min. It was used without further purification on the next step.

tert-Butyl N-[4-(5-[3-(aminocarbonyl)-2,4-difluorophenoxy]methyl-1,2,4-oxadiazol-3-yl)phenyl]carbamate

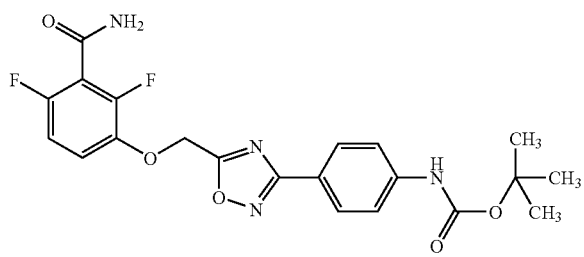

Synthesised from 2,6-difluoro-3-hydroxybenzenecarboxamide and tert-butyl N-4-[5-(chloromethyl)-1,2,4-oxadiazol-3-yl]phenylcarbamate, according to Method B, scheme 2, at r.t. Yield 42%, mp 165-166° C., HPLC-MS (method 1): m/z 447 [M+H]⁺, Rt=4.10 min.

Example 251

3-[3-(4-Aminophenyl)-1,2,4-oxadiazol-5-yl]methoxy-2,6-difluorobenzenecarboxamide hydrochloride salt

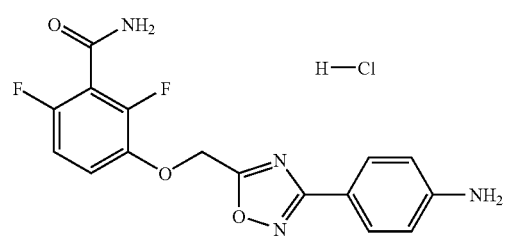

tert-Butyl N-[4-(5-[3-(aminocarbonyl)-2,4-difluorophenoxy]methyl-1,2,4-oxadiazol-3-yl)phenyl]carbamate (300 mg, 0.67 mmol, 1 equiv.) was dissolved in 4N HCl in dioxane (7 ml, 28 mmol, 42 equiv.) and the reaction mixture was stirred at r.t. overnight. Volatiles were removed under reduced pressure, the residue was triturated with dry Et₂O and the solid formed was filtered and rinsed with dry Et₂O. The crude product (200 mg) was taken-up in EtOH (2 ml) and was triturated with 2N HCl in Et₂O solution (0.3 ml) and dry Et₂O. The white solid was filtered and washed with dry Et₂O, to give 110 mg of the desired product (43% yield). HPLC-MS (method 1): m/z 347 [M+H−HCl]⁺, Rt=2.98 min.

Examples 252-266 (Table M)

Examples 252, 254-256 and 258-266 were synthesised from 2,6-difluoro-3-hydroxybenzenecarboxamide according to Method B, scheme 2. Examples 253 and 257 were synthesised from 2,6-difluoro-3-[3-(2-methoxyphenyl)-1,2,4-oxadiazol-5-yl]methoxybenzene carboxamide according to Method L.

| Example | 252 | 252a |
|---|---|---|
| Structure | (2-fluoro-6-fluoro-3-{[3-(2-methylphenyl)-1,2,4-oxadiazol-5-yl]methoxy}benzamide) | (2-fluoro-6-fluoro-3-{[3-(2-methoxyphenyl)-1,2,4-oxadiazol-5-yl]methoxy}benzamide) |
| Yield (%) | 60 | 73 |
| mp (° C.) | 148-149 | 263-264 |
| HPLC-MS: method no., m/z, ion | 1, 346, [M + H]⁺ | 1, 362, [M + H]⁺ |
| Rt (min) | 3.95 | 3.45 |
| Example | 253 | 254 |
| Structure | (2-fluoro-6-fluoro-3-{[3-(2-hydroxyphenyl)-1,2,4-oxadiazol-5-yl]methoxy}benzamide) | (2-fluoro-6-fluoro-3-{[3-(2-chlorophenyl)-1,2,4-oxadiazol-5-yl]methoxy}benzamide) |
| Yield (%) | 54 | 56 |
| mp (° C.) | 164-165 | 173-174 |
| HPLC-MS: method no., m/z, ion | 1, 348, [M + H]⁺ | 1, 366, [M + H]⁺ |
| Rt (min) | 3.52 | 3.82 |
| Example | 255 | 256 |
| Structure | (2-fluoro-6-fluoro-3-{[3-(3-chlorophenyl)-1,2,4-oxadiazol-5-yl]methoxy}benzamide) | (2-fluoro-6-fluoro-3-{[3-(3-methoxyphenyl)-1,2,4-oxadiazol-5-yl]methoxy}benzamide) |
| Yield (%) | 71 | 96 |
| mp (° C.) | 146-148 | 149-151 |
| HPLC-MS: method no., m/z, ion | 1, 367, [M + H]⁺ | 1, 362, [M + H]⁺ |
| Rt (min) | 4.10 | 3.75 |
| Example | 257 | 258 |
| Structure | (2-fluoro-6-fluoro-3-{[3-(3-hydroxyphenyl)-1,2,4-oxadiazol-5-yl]methoxy}benzamide) | (2-fluoro-6-fluoro-3-{[3-(3-trifluoromethylphenyl)-1,2,4-oxadiazol-5-yl]methoxy}benzamide) |
| Yield (%) | 37 | 76 |
| mp (° C.) | 197-199 | 155-157 |

| | 155 | 156 |
|---|---|---|
| | -continued | |
| HPLC-MS: method no., m/z, ion | 1, 348, [M + H]⁺ | 1, 400, [M + H]⁺ |
| Rt (min) | 3.11 | 4.23 |
| Example | 259 | 260 |
| Structure | 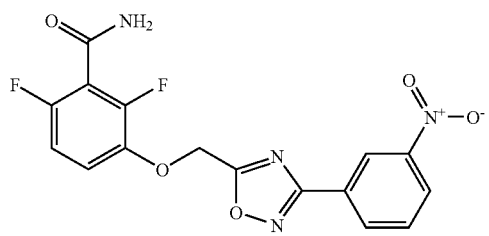 | 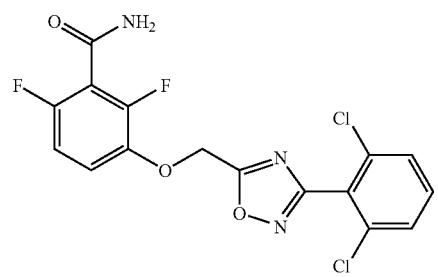 |
| Yield (%) | 62 | 64 |
| mp (° C.) | 179-180 | 155-157 |
| HPLC-MS: method no., m/z, ion | 1, 377, [M + H]⁺ | 1, 400, [M + H]⁺ |
| Rt (min) | 3.78 | 3.92 |
| Example | 261 | 262 |
| Structure | 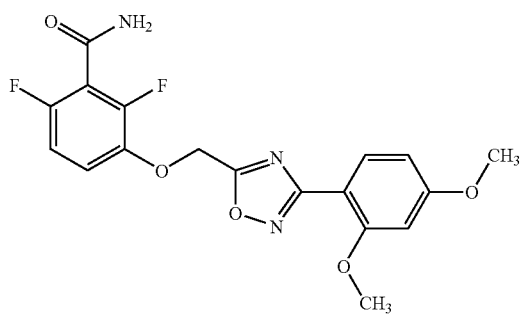 | 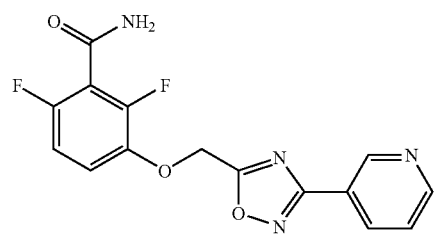 |
| Yield (%) | 24 | 36 |
| mp (° C.) | 192-194 | 195-197 |
| HPLC-MS: method no., m/z, ion | 1, 392, [M + H]⁺ | 1, 333, [M + H]⁺ |
| Rt (min) | 3.43 | 2.70 |
| Example | 263 | 264 |
| Structure | 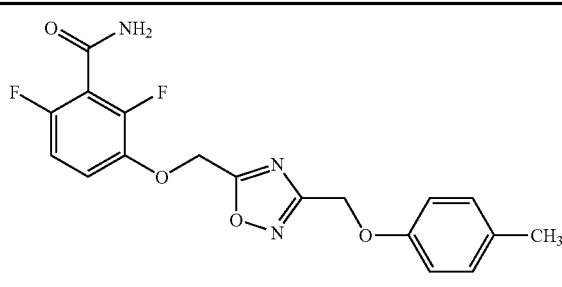 | 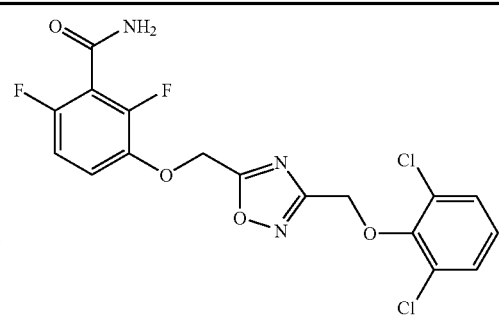 |
| Yield (%) | 79 | 30 |
| mp (° C.) | 137-139 | 128-130 |
| HPLC-MS: method no., m/z, ion | 1, 376, [M + H]⁺ | 1, 430, 432, [M + H]⁺ |
| Rt (min) | 3.88 | 4.0 |

-continued

| Example | 265 | 266 |
|---|---|---|
| Structure | (4-chlorobenzyl oxadiazole structure) | (benzyl oxadiazole structure) |
| Yield (%) | 83 | 47 |
| mp (° C.) | 123-125 | 88-89 |
| HPLC-MS: method no., m/z, ion | 1, 380, [M + H]$^+$ | 1, 346, [M + H]$^+$ |
| Rt (min) | 3.92 | 3.58 |

Table of names of product compounds; Examples 252-266:

| Example | Compound name |
|---|---|
| 252 | 2,6-Difluoro-3-[3-(2-methylphenyl)-1,2,4-oxadiazol-5-yl]methoxybenzenecarboxamide |
| 252a | 2,6-Difluoro-3-[3-(2-methoxyphenyl)-1,2,4-oxadiazol-5-yl]methoxybenzenecarboxamide |
| 253 | 2,6-Difluoro-3-[3-(2-hydroxyphenyl)-1,2,4-oxadiazol-5-yl]methoxybenzenecarboxamide |
| 254 | 3-[3-(2-Chlorophenyl)-1,2,4-oxadiazol-5-yl]methoxy-2,6-difluorobenzenecarboxamide |
| 255 | 3-[3-(3-Chlorophenyl)-1,2,4-oxadiazol-5-yl]methoxy-2,6-difluorobenzenecarboxamide |
| 256 | 2,6-Difluoro-3-[3-(3-methoxyphenyl)-1,2,4-oxadiazol-5-yl]methoxybenzenecarboxamide |
| 257 | 2,6-Difluoro-3-[3-(3-hydroxyphenyl)-1,2,4-oxadiazol-5-yl]methoxybenzenecarboxamide |
| 258 | 2,6-Difluoro-3-(3-[3-(trifluoromethyl)phenyl]-1,2,4-oxadiazol-5-ylmethoxy)benzenecarboxamide |
| 259 | 2,6-Difluoro-3-[3-(3-nitrophenyl)-1,2,4-oxadiazol-5-yl]methoxybenzenecarboxamide |
| 260 | 3-[3-(2,6-Dichlorophenyl)-1,2,4-oxadiazol-5-yl]methoxy-2,6-difluorobenzenecarboxamide |
| 261 | 3-[3-(2,4-Dimethoxyphenyl)-1,2,4-oxadiazol-5-yl]methoxy-2,6-difluorobenzenecarboxamide |
| 262 | 2,6-Difluoro-3-[3-(3-pyridinyl)-1,2,4-oxadiazol-5-yl]methoxybenzenecarboxamide |
| 263 | 2,6-Difluoro-3-(3-[(4-methylphenoxy)methyl]-1,2,4-oxadiazol-5-ylmethoxy)benzenecarboxamide |
| 264 | 3-(3-[(2,6-Dichlorophenoxy)methyl]-1,2,4-oxadiazol-5-ylmethoxy)-2,6-difluorobenzenecarboxamide |
| 265 | 3-[3-(4-Chlorobenzyl)-1,2,4-oxadiazol-5-yl]methoxy-2,6-difluorobenzenecarboxamide |
| 266 | 3-[(3-Benzyl-1,2,4-oxadiazol-5-yl)methoxy]-2,6-difluorobenzenecarboxamide |

Scheme 29:

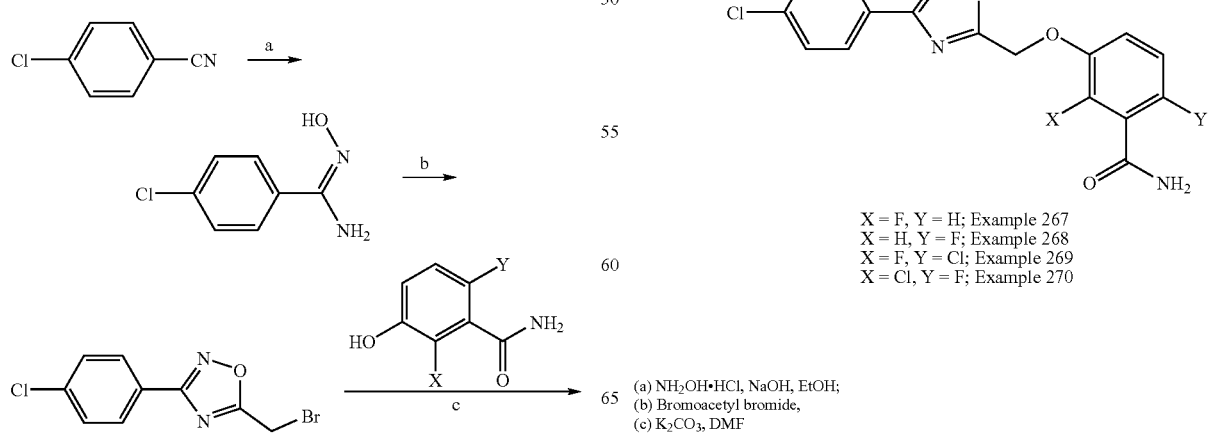

X = F, Y = H; Example 267
X = H, Y = F; Example 268
X = F, Y = Cl; Example 269
X = Cl, Y = F; Example 270

(a) NH$_2$OH•HCl, NaOH, EtOH;
(b) Bromoacetyl bromide;
(c) K$_2$CO$_3$, DMF

4-Chloro-N-hydroxy-benzamide

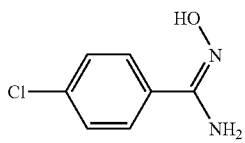

To a solution of 4-chlorobenzonitrile (10.0 g, 73.0 mmol) in EtOH (250 mL) was added hydroxylamine hydrochloride (5.03 g, 73.0 mmol) and NaOH (2.90 g, 73.0 mmol). The resulting reaction mixture was refluxed for 15 h. After the completion of the reaction (TLC monitoring), the mixture was concentrated, added EtOH and filtered. The filtrate was evaporated in vacuo and used as such for the next step (crude yield 12.0 g, 66%).

5-Bromomethyl-3-(4-chloro-phenyl)-[1,2,4]oxadiazole

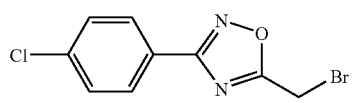

Bromoacetyl bromide (1.50 mL, 17.58 mmol) was added to 4-Chloro-N-hydroxy-benzamide (1.0 g, 5.86 mmol) and $K_2CO_3$ (3.18 g, 23.44 mmol). The reaction mixture was heated at 100° C. for 15 min. After the completion of the reaction mixture (TLC monitoring), water (100 mL) was added and extracted with ethyl acetate (3×50 mL). The combined organics was washed with water, brine, dried ($Na_2SO_4$), filtered and concentrated. The crude residue was purified over silica gel (60-120 M, 1% EtOAc-Hexane) to get the desired product (0.44 g, 28%) as a white solid.

Examples 267-270 (Table N)

The compounds of Examples 267-270 were synthesised according to the following general procedure: To a solution of 5-bromomethyl-3-(4-chloro-phenyl)[1,2,4]oxadiazole (A) in 2 ml of anhydrous DMF was added reactant (B) and potassium carbonate (C). The reaction mixture was stirred at 25° C. for 24 h under nitrogen atmosphere. The reaction mixture was evaporated to dryness under reduced pressure and the residue was purified by column chromatography on silica (230-400 M) using ethyl acetate/hexane (45:55) as the eluent to provide the product compound.

TABLE N

| Example | 267 |
|---|---|
| Product | 3-[3-(4-Chloro-phenyl)-[1,2,4]oxadiazol-5-ylmethoxy]-2-fluoro-benzamide |
| Reaction scheme | |
| Reactant (B) | 2-Fluoro-3-hydroxy-benzamide |
| Quantities of A; B; C | 0.03 g, 0.10 mmol; 0.017 g, 0.10 mmol; 0.053 g, 0.35 mmol |
| Yield | 0.019 g, 50%, off white solid |
| $^1$H-NMR (DMSO-$d_6$, 400 MHz) | δ 5.72 (s, 2H), 7.17-7.25 (m, 2H), 7.39-7.43 (m, 1H), 7.80 (m, 3 H), 7.80 (br s, 1H) and 8.03 (d, J = 8.80 Hz, 2H) |
| MS-ES+ | 348.07 |
| HPLC method no., Rt (min) | 8, 16.33 |

TABLE N-continued

| Example | 268 |
|---|---|
| Product | 5-[3-(4-Chloro-phenyl)-[1,2,4]oxadiazol-5-ylmethoxy]-2-fluoro-benzamide |
| Reaction scheme | 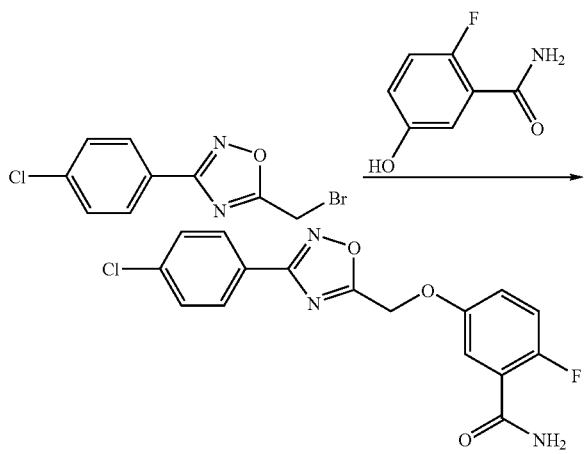 |
| Reactant (B) | 2-Fluoro-5-hydroxy-benzamide |
| Quantities of A; B; C | 0.07 g, 0.25 mmol; 0.04 g, 0.25 mmol; 0.124 g, 0.90 mmol |
| Yield | 0.025 g, 27%, white solid |
| $^1$H-NMR (DMSO-$d_6$, 400 MHz) | δ 5.63 (s, 2H), 7.23-7.33 (m, 3H), 7.65-7.73 (m, 4H) and 8.03 (d, J = 8.40 Hz, 2H) |
| MS-ES+ | 348.11 |
| HPLC method no., Rt (min) | 8, 16.56 |

| Example | 269 |
|---|---|
| Product | 6-Chloro-3-[3-(4-chloro-phenyl)-[1,2,4]oxadiazol-5-ylmethoxy]-2-fluoro-benzamide |
| Reaction scheme | 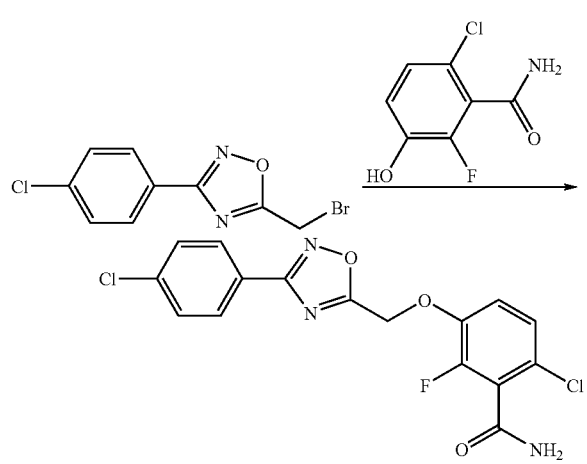 |
| Reactant (B) | 6-Chloro-2-fluoro-3-hydroxy-benzamide |
| Quantities of A; B; C | 0.07 g, 0.25 mmol; 0.048 g, 0.25 mmol; 0.124 g, 0.90 mmol |
| Yield | 0.070 g, 71%, white solid |
| $^1$H-NMR (DMSO-$d_6$, 400 MHz) | δ 5.74 (s, 2H), 7.30-7.39 (m, 2H), 7.67 (d, J = 8.40 Hz, 2H), 7.88 (br s, 1H), 8.03 (d, J = 8.40 Hz, 2H) and 8.16 (br s, 1H) |

TABLE N-continued

| | |
|---|---|
| MS-ES+ | 382.03 |
| HPLC method no., Rt (min) | 8, 16.53 |

| | |
|---|---|
| Example | 270 |
| Product | 2-Chloro-3-[3-(4-chloro-phenyl)-[1,2,4]oxadiazol-5-ylmethoxy]-6-fluoro-benzamide |
| Reaction scheme | 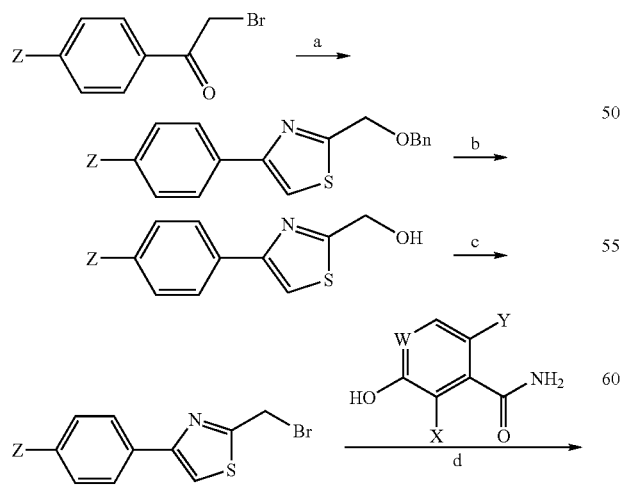 |
| Reactant (B) | 2-Chloro-6-fluoro-3-hydroxy-benzamide |
| Quantities of A; B; C | 0.070 g, 0.25 mmol; 0.048 g, 0.25 mmol; 0.124 g, 0.9 mmol |
| Yield | 0.013 g, 13%, white solid |
| ¹H-NMR (DMSO-d₆, 400 MHz) | δ 5.73 (s, 2H), 7.27-7.37 (m, 2H), 7.65 (d, J = 8.40 Hz, 2H), 7.87 (br s, 1H), 8.03 (d, J = 8.40 Hz, 2H) and 8.14 (br s, 1H) |
| MS-ES+ | 382.03 |
| HPLC method no., Rt (min) | 8, 16.48 |

Scheme 30:

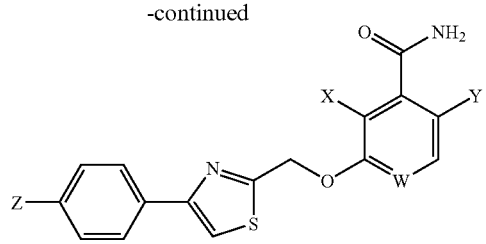

W = H, X = F, Y = H, Z = Cl; Example 271
W = H, X = H, Y = F, Z = Cl; Example 272
W = H, X = F, Y = Cl, Z = Cl; Example 273
W = H, X = Cl, Y = F, Z = Cl; Example 274
W = N, X = H, Y = H, Z = Cl; Example 275
W = H, X = F, Y = F, Z = CN; Example 276

(a) 2-Benzoloxy-thioacetamide, DMF;
(b) BBr₃, DCM,
(c) PBr₃, Toluene
(d) corresponding Phenols

2-Benzyloxymethyl-4-(4-chloro-phenyl)-thiazole

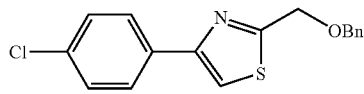

To the solution of 2-Benzyloxy-thioacetamide (3.0 g, 16.57 mmol) in 3 ml of DMF was added 2-Bromo-1-(4-chloro-phenyl)-ethanone (3.0 g, 12.87 mmol). The reaction mixture was heated at 130° C. for 24 h under nitrogen atmosphere. After the completion of the reaction mixture (TLC monitoring), water (25 mL) was added and extracted with ethyl acetate (3×50 mL). The combined organics was washed with water, brine, dried (Na$_2$SO$_4$), filtered and concentrated. The crude residue was purified over silica gel (230-400 M, 2% EtOAc-Hexane) to get the desired product (2.0 g, 49%). The corresponding cyano derivative was also prepared by the same general method.

[4-(4-Chloro-phenyl)-thiazol-2-yl]-methanol

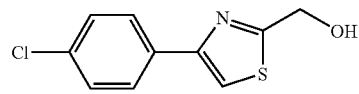

A solution of 2-Benzyloxymethyl-4-(4-chloro-phenyl)-thiazole (2.0 g, 6.34 mmol) in 25 ml of DCM was cooled to −78° C. followed by addition of BBr$_3$ (2.38 ml, 25.3 mmol). The reaction mixture was stirred at 25° C. for 2 h. After the completion of the reaction mixture (TLC monitoring), solution of NaHCO$_3$ (20 mL) was added at 0° C. and extracted with ethyl acetate (3×50 mL). The combined organics was washed with water, brine, dried (Na$_2$SO$_4$), filtered and concentrated. The crude residue was purified over silica gel (60-120 M, 40% EtOAc-Hexane) to get the desired product (0.8 g, 57%). The corresponding cyano derivative was also prepared by the same general method.

2-Bromomethyl-4-(4-chloro-phenyl)-thiazole

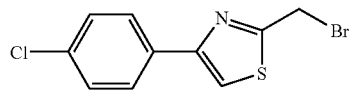

To the solution of [4-(4-Chloro-phenyl)-thiazol-2-yl]-methanol (0.80 g, 3.55 mmol) in 10 ml of toluene was added PBr$_3$ (0.51 ml, 5.33 mmol) and the reaction mixture was heated at 120° C. for 20 min under nitrogen atmosphere. After the completion of the reaction mixture (TLC monitoring), water (25 mL) was added and extracted with ethyl acetate (3×50 mL). The combined organics was washed with water, brine, dried (Na$_2$SO$_4$), filtered and concentrated to get the desired product (0.17 g, 17%). The corresponding cyano derivative was also prepared by the same general method.

Examples 271-276 (Table O)

The compounds of Examples 271-276 were synthesised according to the following general procedure: To a solution of reactant (A) in anhydrous DMF was added reactant (B) and potassium carbonate (C). The reaction mixture was stirred at 25° C. for 24 h under nitrogen atmosphere. The reaction mixture was evaporated to dryness under reduced pressure and the residue was purified by column chromatography on silica (60-120 M) using ethyl acetate/hexane as the eluent to provide the product compound.

TABLE O

| Example | 271 |
|---|---|
| Product | 3-[4-(4-Chloro-phenyl)-thiazol-2-ylmethoxy]-2-fluoro-benzamide |
| Reaction scheme | |
| Reactant (A) | 2-bromomethyl-4-(4-chloro-phenyl)-thiazole |
| Reactant (B) | 2-Fluoro-3-hydroxy-benzamide |
| Quantities A; B; C; volume DMF | 0.070 g, 0.24 mmol; 0.037 g, 0.24 mmol; 0.116 g, 0.8 mmol; 2 ml |
| Ratio ethyl acetate:hexane | 30:70 |

TABLE O-continued

| | |
|---|---|
| Yield | 0.035 g, 40%, white solid |
| $^1$H NMR (DMSO-$d_6$, 400 MHz) | δ 5.60 (s, 2H), 7.20 (m, 2H), 7.44 (m, 1H), 7.53 (d, J = 8.40 Hz, 2H), 7.66 (br s, 1H), 7.79 (br s, 1H), 8.0 (d, J = 8.40 Hz, 2H) and 8.25 (s, 1H) |
| MS-ES+ | 363.22 |
| HPLC method no., Rt (min) | 9, 16.91 |

| | |
|---|---|
| Example | 272 |
| Product | 5-[4-(4-Chloro-phenyl)-thiazol-2-ylmethoxy]-2-fluoro-benzamide |
| Reaction scheme | 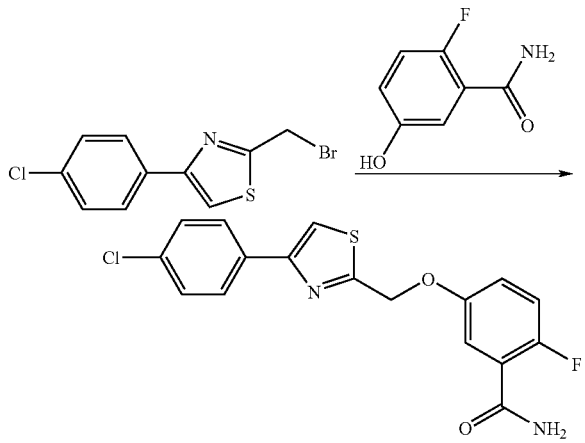 |
| Reactant (A) | 2-bromomethyl-4-(4-chloro-phenyl)-thiazole |
| Reactant (B) | 2-fluoro-5-hydroxy-benzamide |
| Quantities A; B; C; volume DMF | 0.07 g, 0.24 mmol; 0.037 g, 0.24 mmol; 0.116 g, 0.84 mmol; 2 ml |
| Ratio ethyl acetate:hexane | 30:70 |
| Yield | 0.020 g, 23%, white solid |
| $^1$H NMR (DMSO-$d_6$, 400 MHz) | δ 5.52 (s, 2H), 7.24 (m, 2H), 7.33 (m, 1H), 7.53 (d, J = 8.40 Hz, 2H), 7.72 (m, 2H), 8.01 (d, J = 8.40 Hz, 2H) and 8.25 (s, 1H) |
| MS-ES+ | 363.04 |
| HPLC method no., Rt (min) | 9, 17.06 |

| | |
|---|---|
| Example | 273 |
| Product | 6-Chloro-3-[4-(4-chloro-phenyl)-thiazol-2-ylmethoxy]-2-fluoro-benzamide |
| Reaction scheme | 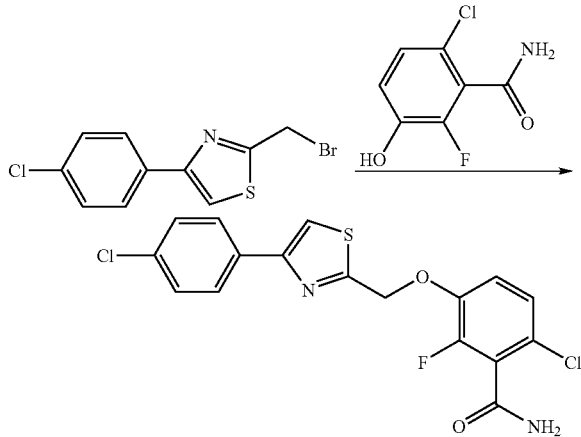 |

TABLE O-continued

| | |
|---|---|
| Reactant (A) | 2-bromomethyl-4-(4-chloro-phenyl)-thiazole |
| Reactant (B) | 6-chloro-2-fluoro-3-hydroxy-benzamide |
| Quantities A; B; C; volume DMF | 0.070 g, 0.24 mmol; 0.045 g, 0.24 mmol; 0.116 g, 0.8 mmol; 2 ml |
| Ratio ethyl acetate:hexane | 30:70 |
| Yield | 0.017 g, 17%, white solid |
| $^1$H NMR (DMSO-$d_6$, 400 MHz) | δ 5.62 (s, 2H), 7.29-7.32 (m, 1H), 7.37-7.41 (m, 1H), 7.53 d, J = 8.80 Hz, 2H), 7.86 (br s, 1H), 8.0 (d, J = 8.80 Hz, 2H), 8.14 (br s, 1H) and 8.26 (s, 1H) |
| MS-ES+ | 396.99 |
| HPLC method no., Rt (min) | 8, 17.00 |

| | |
|---|---|
| Example | 274 |
| Product | 2-Chloro-3-[4-(4-chloro-phenyl)-thiazol-2-ylmethoxy]-6-fluoro-benzamide |
| Reaction scheme | 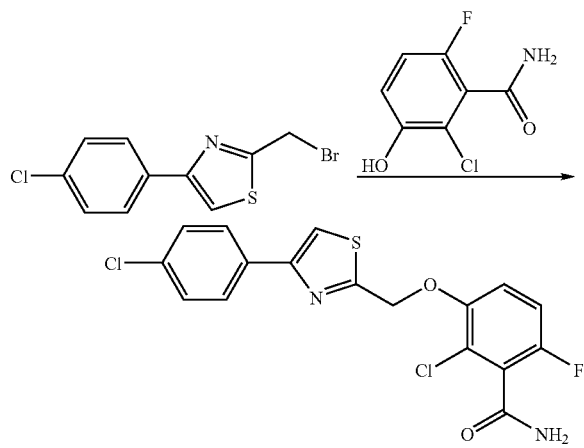 |
| Reactant (A) | 2-bromomethyl-4-(4-chloro-phenyl)-thiazole |
| Reactant (B) | 2-chloro-6-fluoro-3-hydroxy-benzamide |
| Quantities A; B; C; volume DMF | 0.07 g, 0.24 mmol; 0.045 g, 0.24 mmol; 0.116 g, 0.84 mmol; 2 ml |
| Ratio ethyl acetate:hexane | 30:70 |
| Yield | 0.042 g, 43%, white solid |
| $^1$H NMR (DMSO-$d_6$, 400 MHz) | δ 5.60 (s, 2H), 7.30 (m, 1H), 7.38 (m, 1H), 7.53 (d, J = 8.40 Hz, 2H), 7.86 (br s, 1H), 8.0 (d, J = 8.40 Hz, 2H), 8.13 (br s, 1H) and 8.24 (s, 1H) |
| MS-ES+ | 397.20 |
| HPLC method no., Rt (min) | 8, 16.98 |

| | |
|---|---|
| Example | 275 |
| Product | 2-[4-(4-Chloro-phenyl)-thiazol-2-ylmethoxy]-isonicotinamide |
| Reaction scheme | 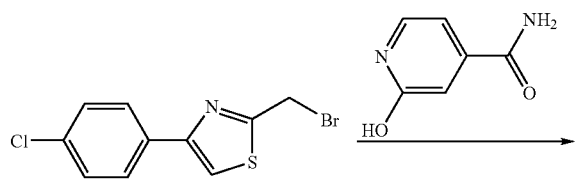 |

TABLE O-continued

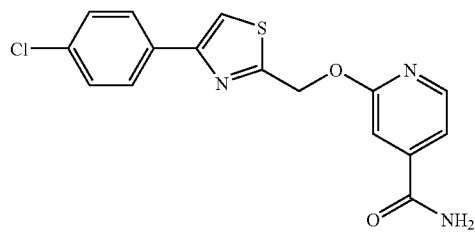

| | |
|---|---|
| Reactant (A) | 2-bromomethyl-4-(4-chloro-phenyl)-thiazole |
| Reactant (B) | 2-hydroxy-isonicotinamide |
| Quantities A; B; C; volume DMF | 0.10 g, 0.34 mmol; 0.048 g, 0.34 mmol; 0.167 g, 0.12 mmol; 2 ml |
| Ratio ethyl acetate:hexane | 30:70 |
| Yield | 0.027 g, 12%, white solid |
| $^1$H NMR (DMSO-$d_6$, 400 MHz) | δ 5.46 (s, 2H), 6.63 (m, 1H), 6.90 (s, 1H), 7.51 (d, J = 8.40 Hz, 2H), 7.70 (br s, 1H), 7.98 (m, 3H) and 8.15 (m, 2H) |
| MS-ES+ | 346.12 |
| HPLC method no., Rt (min) | 8, 14.96 |

| | |
|---|---|
| Example | 276 |
| Product | 3-[4-(4-Cyano-phenyl)-thiazol-2-ylmethoxy]-2,6-difluoro-benzamide |
| Reaction scheme | 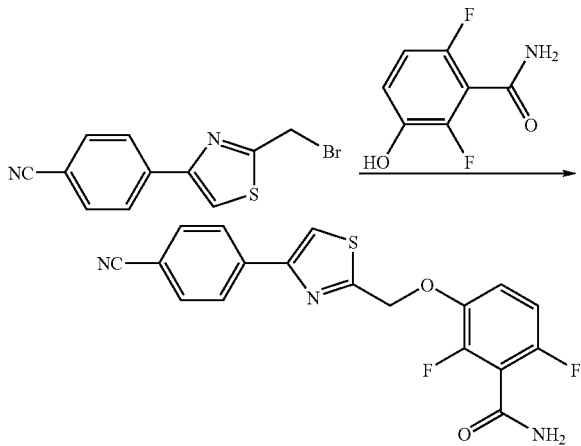 |
| Reactant (A) | 4-(2-Bromomethyl-thiazol-4-yl)-benzonitrile |
| Reactant (B) | 2,6-Difluoro-3-hydroxy-benzamide |
| Quantities A; B; C; volume DMF | 0.55 g, 1.9 mmol; 0.34 g, 1.90 mmol; 0.95 g, 6.92 mmol; 8 ml |
| Ratio ethyl acetate:hexane | 50:50 |
| Yield | 0.41 g, 56%, white solid |
| $^1$H NMR (DMSO-$d_6$, 400 MHz) | δ 5.60 (s, 2H), 7.12 (t, J = 8.80 Hz, 1H), 7.40 (m, 1H), 7.89 (br s, 1H), 7.94 (d, J = 8.40 Hz, 2H), 8.17 (m, 3H) and 8.48 (s, 1H) |
| MS-ES+ | 372.07 |
| HPLC method no., Rt (min) | 8, 15.52 |

Scheme 31:

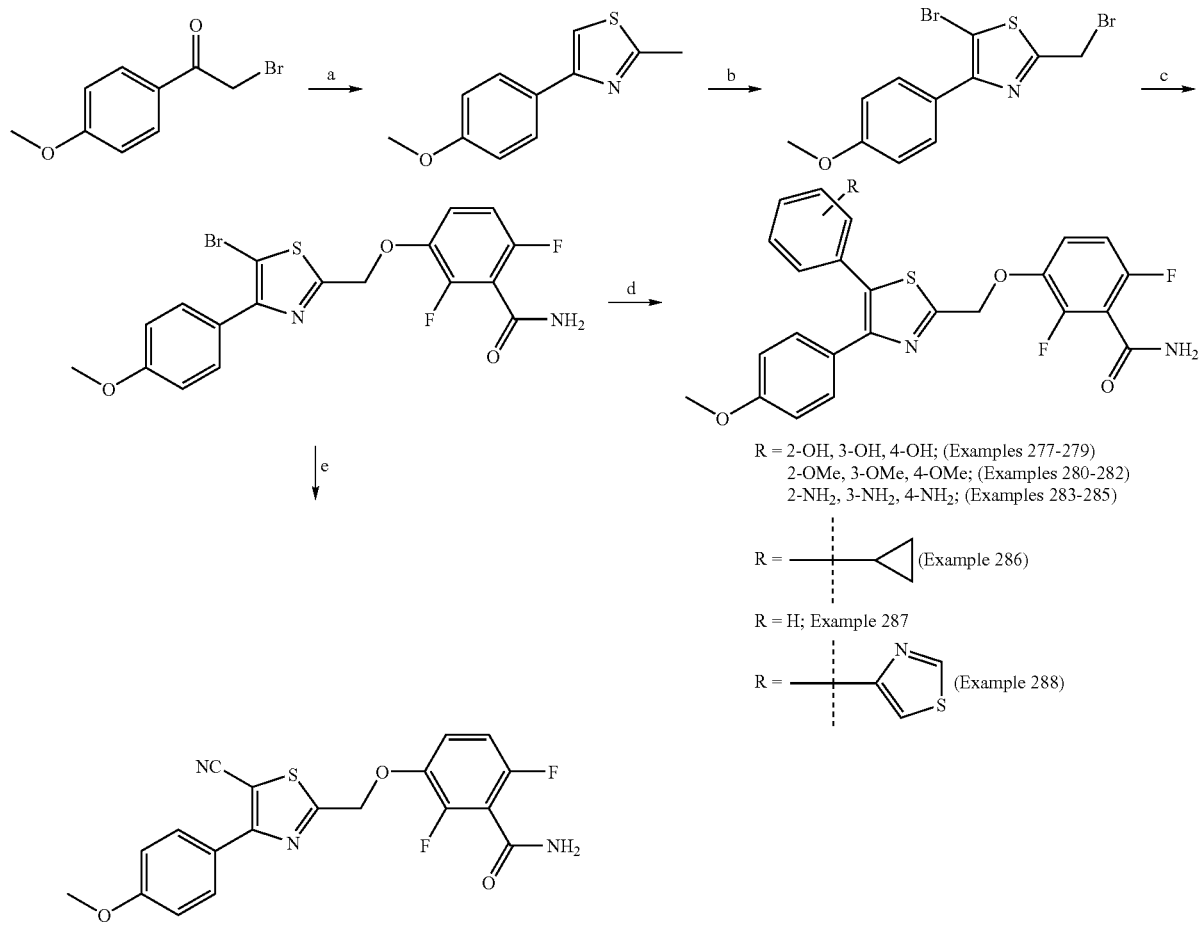

(a) Thioacetamide, DMF;
(b) NBS, CCl₄
(c) 2,6-difluoro-3-hydroxybenzamide, K₂CO₃, DMF
(d) corresponding boronic acids, Suzuki or Stille conditions
(e) CuCN, Pyridine.

4-(4-Methoxy-phenyl)-2-methyl-thiazole

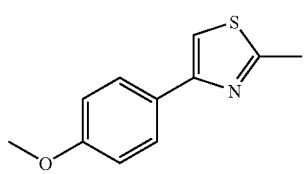

The mixture of thioacetamide (16.0 g, 213 mmol) and 2-bromo-1-(4-methoxy-phenyl)-ethanone (4.0 g, 17.5 mmol) was heated at 140° C. for 24 h under nitrogen atmosphere. After the completion of the reaction mixture (TLC monitoring), water (100 mL) was added and extracted with ethyl acetate (3×100 mL). The combined organics was washed with water, brine, dried (Na₂SO₄), filtered and concentrated. The crude residue was purified over silica gel (230-400 M, 1% EtOAc-Hexane) to get the desired product (2.5 g, 69%).

5-Bromo-2-bromomethyl-4-(4-methoxy-phenyl)-thiazole

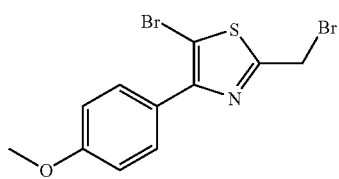

To the solution 4-(4-Methoxy-phenyl)-2-methyl-thiazole (5.0, 24.3 mmol) in CCl₄ (20 mL) was added NBS (7.43 g, 41.74 mmol) and the reaction mixture was heated at 100° C. for 2 h under nitrogen atmosphere. After the completion of the reaction mixture (TLC monitoring), the reaction mixture was evaporated to dryness under reduced pressure and the residue was purified by column chromatography on silica (230-400 M) using 1% ethyl acetate/hexane to give the desired product (3.0 g, 34%).

3-[5-Bromo-4-(4-methoxy-phenyl)-thiazol-2-yl-methoxy]-2,6-difluoro-benzamide

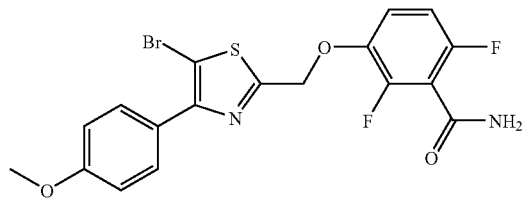

To a solution of 5-Bromo-2-bromomethyl-4-(4-methoxy-phenyl)-thiazole (0.50 g, 1.37 mmol) in 5 ml of anhydrous DMF was added 2,6-Difluoro-3-hydroxy-benzamide (0.23 g, 1.37 mmol) and potassium carbonate (0.75 g, 5.43 mmol). The reaction mixture was stirred at 25° C. for 24 h under nitrogen atmosphere. The reaction mixture was evaporated to dryness under reduced pressure and the residue was purified by column chromatography on silica (60-120 M) using ethyl acetate/hexane (30:70) as the eluent to provide the title compound (0.30 g, 48%).

Examples 277-287 (Table P)

The compounds of Examples 277-287 were synthesised according to the following general procedure: To a solution of 3-[5-bromo-4-(4-methoxy-phenyl)-thiazol-2-ylmethoxy]-2,6-difluoro-benzamide (A) in 5 ml of anhydrous DMF and water (2.5 ml) was added reactant (B) and potassium phosphate (C). The reaction mixture was degassed for 10 minutes followed by addition of dichlorobis(triphenyl phosphine) palladium (II) (D). The reaction mixture was heated at 120° C. for 12 h under the nitrogen atmosphere. After the completion of the reaction mixture (TLC monitoring), water (25 mL) was added and extracted with ethyl acetate (3×50 mL). The combined organics was washed with water, brine, dried ($Na_2SO_4$), filtered and concentrated. The crude residue was purified over silica gel (45% EtOAc-Hexane) to get the desired product compound.

TABLE P

| Example | 277 |
|---|---|
| Product | 2,6-Difluoro-3-[5-(2-hydroxy-phenyl)-4-(4-methoxy-phenyl)-thiazol-2-ylmethoxy]-benzamide |
| Reaction scheme | |
| Reactant (B) | 2-hydroxyphenyl boronic acid |
| Quantities A; B; C; D | 0.20 g, 0.44 mmol; 0.12 g, 0.88 mmol; 0.11 g, 0.53 mmol; 0.046 g, 0.068 mmol |
| Silica gel | 60-120M |
| Yield | 0.005 g, 3%, white solid |
| $^1$H NMR (DMSO-$d_6$, 400 MHz) | δ 3.72 (s, 3H), 5.54 (s, 2H), 6.80 (m, 3H), 6.85 (m, 1H), 7.08-7.23 (m, 3H), 7.39-7.46 (m, 3H), 7.88 (br s, 1H), 8.17 (br s, 1H) and 9.90 (br s, 1H) |
| MS-ES+ | 469.31 |
| HPLC method no., Rt (min) | 8, 16.04 |
| Example | 278 |
| Product | 2,6-Difluoro-3-[5-(3-hydroxy-phenyl)-4-(4-methoxy-phenyl)-thiazol-2-ylmethoxy]-benzamide |

TABLE P-continued

| | |
|---|---|
| Reaction scheme | 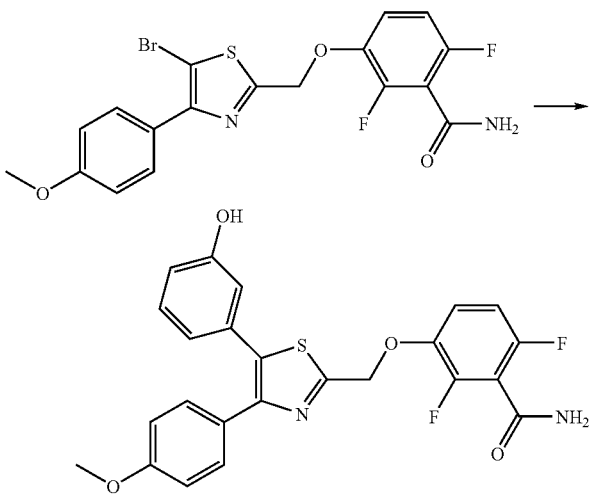 |
| Reactant (B) | 3-hydroxyphenyl boronic acid |
| Quantities A; B; C; D | 0.20 g, 0.44 mmol; 0.12 g, 0.88 mmol; 0.11 g, 0.53 mmol; 0.046 g, 0.068 mmol |
| Silica gel | 60-120M |
| Yield | 0.02 g, 10%, white solid |
| $^1$H NMR (DMSO-$d_6$, 400 MHz) | δ 3.75 (s, 3H), 5.54 (s, 2H), 6.77 (m, 3H), 6.91 (m, 2H), 7.16 (m, 2H), 7.45 (m, 3H), 7.89 (br s, 1H), 8.17 (br s, 1H) and 9.64 (br s, 1H) |
| MS-ES+ | 469.30 |
| HPLC method no., Rt (min) | 8, 15.70 |

| | |
|---|---|
| Example | 279 |
| Product | 2,6-Difluoro-3-[5-(4-hydroxy-phenyl)-4-(4-methoxy-phenyl)-thiazol-2-ylmethoxy]-benzamide |
| Reaction scheme | 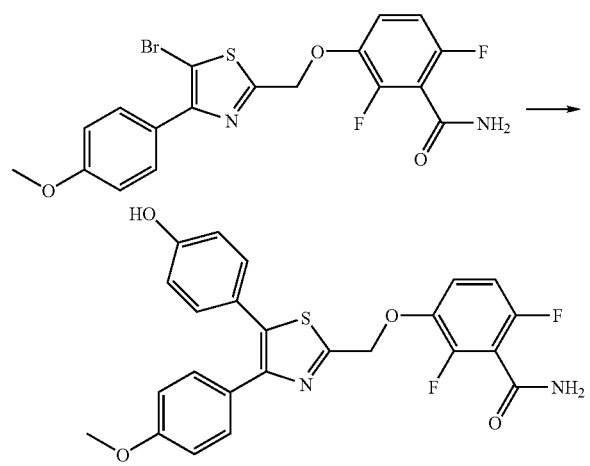 |
| Reactant (B) | 4-hydroxyphenyl boronic acid |
| Quantities A; B; C; D | 0.20 g, 0.44 mmol; 0.12 g, 0.88 mmol; 0.11 g, 0.53 mmol; 0.046 g, 0.068 mmol |
| Silica gel | 60-120M |
| Yield | 0.02 g, 10%, white solid |
| $^1$H NMR (DMSO-$d_6$, 400 MHz) | δ 3.74 (s, 3H), 5.52 (s, 2H), 6.78 (d, J = 8.40 Hz, 2H), 6.89 (d, J = 8.40 Hz, 2H), 7.13 (m, 3H), 7.37-7.45 (m, 3H), 7.89 (br s, 1H), 8.17 (br s, 1H) and 9.79 (br s, 1H) |
| MS-ES+ | 469.29 |
| HPLC method no., Rt (min) | 8, 15.60 |

TABLE P-continued

| Example | 280 |
|---|---|
| Product | 2,6-Difluoro-3-[5-(2-methoxy-phenyl)-4-(4-methoxy-phenyl)-thiazol-2-ylmethoxy]-benzamide |
| Reaction scheme | 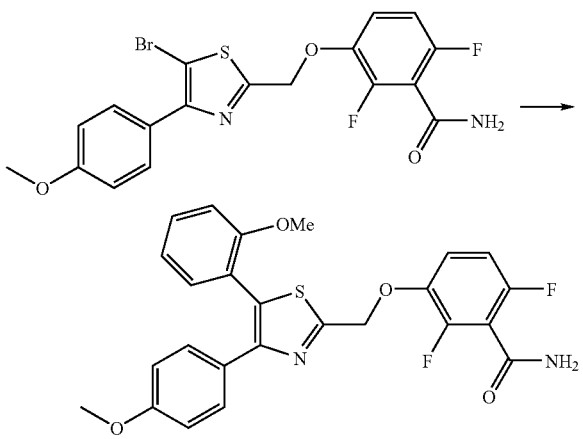 |
| Reactant (B) | 2-methoxyphenyl boronic acid |
| Quantities A; B; C; D | 0.10 g, 0.20 mmol; 0.06 g, 0.41 mmol; 0.05 g, 0.24 mmol; 0.021 g, 0.03 mmol |
| Silica gel | 60-120M |
| Yield | 0.019 g, 18%, white solid |
| ¹H NMR (DMSO-d₆, 400 MHz) | δ 3.70 (s, 3H), 3.72 (s, 3H), 5.54 (s, 2H), 6.85 (d, J = 8.80 Hz, 2H), 6.95 (m, 1H), 7.14-7.19 (m, 3H), 7.36 (d, J = 8.80 Hz, 2H), 7.44 (m, 2H), 7.87 (br s, 1H) and 8.16 (br s, 1H) |
| MS-ES+ | 483.40 |
| HPLC method no., Rt (min) | 9, 16.85 |

| Example | 281 |
|---|---|
| Product | 2,6-Difluoro-3-[5-(3-methoxy-phenyl)-4-(4-methoxy-phenyl)-thiazol-2-ylmethoxy]-benzamide |
| Reaction scheme | 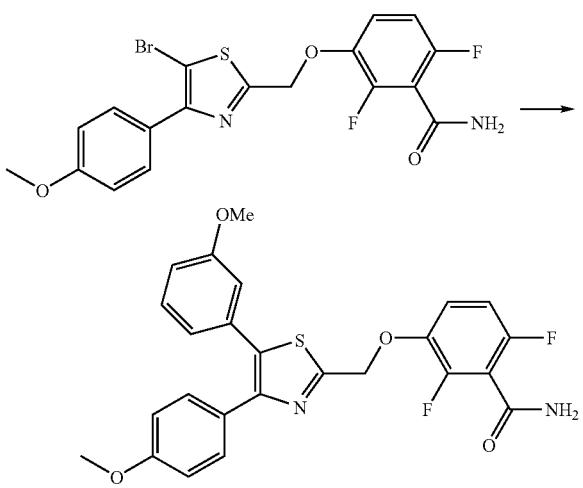 |
| Reactant (B) | 3-methoxyphenyl boronic acid |
| Quantities A; B; C; D | 0.10 g, 0.20 mmol; 0.06 g, 0.41 mmol; 0.05 g, 0.24 mmol; 0.021 g, 0.03 mmol |
| Silica gel | 60-120M |
| Yield | 0.025 g, 24%, white solid |
| ¹H NMR (DMSO-d₆, 400 MHz) | δ 3.69 (s, 3H), 3.75 (s, 3H), 5.55 (s, 2H), 6.89-6.96 (m, 5H), 7.14 (m, 1H), 7.31 (m, 1H), 7.38-7.46 (m, 3H), 7.89 (br s, 1H) and 8.17 (br s, 1H) |

TABLE P-continued

| | |
|---|---|
| MS-ES+ | 483.42 |
| HPLC method no., Rt (min) | 9, 16.97 |

| | |
|---|---|
| Example | 282 |
| Product | 2,6-Difluoro-3-[5-(4-methoxy-phenyl)-4-(4-methoxy-phenyl)-thiazol-2-ylmethoxy]-benzamide |
| Reaction scheme | 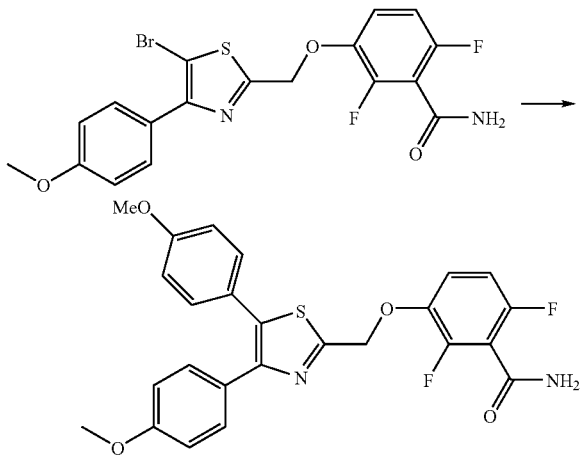 |
| Reactant (B) | 4-methoxyphenyl boronic acid |
| Quantities A; B; C; D | 0.10 g, 0.20 mmol; 0.06 g, 0.41 mmol; 0.05 g, 0.24 mmol; 0.021 g, 0.03 mmol |
| Silica gel | 60-120M |
| Yield | 0.018 g, 17%, yellow solid |
| $^1$H NMR (DMSO-$d_6$, 400 MHz) | δ 3.74 (s, 3H), 3.77 (s, 3H), 5.53 (s, 2H), 6.90 (d, J = 8.40 Hz, 2H), 6.97 (d, J = 8.40 Hz, 2H), 7.13 (m, 1H), 7.28 (d, J = 8.0 Hz, 2H), 7.39 (d, J = 8.0 Hz, 2H), 7.44 (m, 1H), 7.89 (br s, 1H) and 8.16 (br s, 1H) |
| MS-ES+ | 483.23 |
| HPLC method no., Rt (min) | 8, 17.03 |

| | |
|---|---|
| Example | 283 |
| Product | 2,6-Difluoro-3-[5-(2-amino-phenyl)-4-(4-methoxy-phenyl)-thiazol-2-ylmethoxy]-benzamide |
| Reaction scheme | 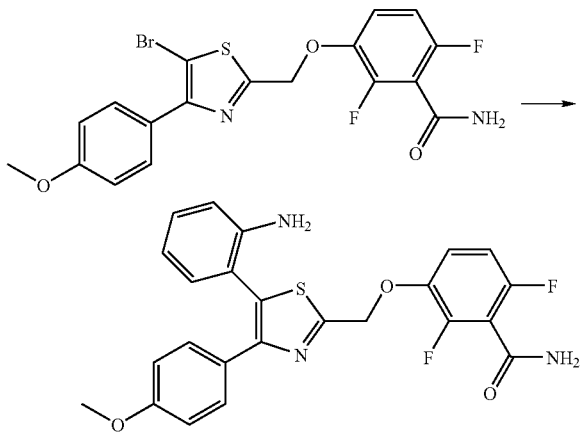 |
| Reactant (B) | 2-aminophenyl boronic acid |
| Quantities A; B; C; D | 0.10 g, 0.20 mmol; 0.09 g, 0.54 mmol; 0.10 g, 0.48 mmol; 0.021 g, 0.03 mmol |
| Silica gel | 60-120M |
| Yield | 0.042 g, 41%, light yellow solid |
| $^1$H NMR (DMSO-$d_6$, | δ 3.72 (s, 3H), 4.94 (br s, 2H), 5.54 (s, 2H), 6.57 (t, J = 7.20 Hz, 1H), 6.75 (d, J = 8.0 Hz, 1H), 6.84 |

| | |
|---|---|
| 400 MHz) | (m, 2H), 7.0 (m, 1H), 7.14 (m, 2H), 7.51 (m, 3H), 7.89 (br s, 1H) and 8.18 (br s, 1H) |
| MS-ES+ | 468.02 |
| HPLC method no., Rt (min) | 9, 16.70 |

| | |
|---|---|
| Example | 284 |
| Product | 2,6-Difluoro-3-[5-(3-amino-phenyl)-4-(4-methoxy-phenyl)-thiazol-2-ylmethoxy]-benzamide |
| Reaction scheme | 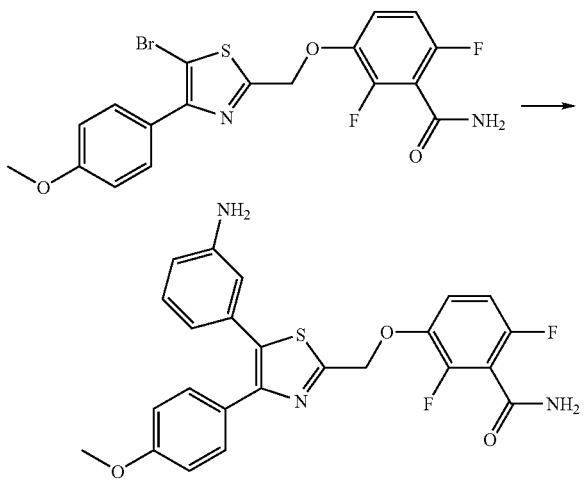 |
| Reactant (B) | 3-aminophenyl boronic acid |
| Quantities A; B; C; D | 0.10 g, 0.20 mmol; 0.07 g, 0.54 mmol; 0.102 g, 0.48 mmol; 0.021 g, 0.03 mmol |
| Silica gel | 60-120M |
| Yield | 0.015 g, 14%, light yellow solid |
| $^1$H NMR (DMSO-d$_6$, 400 MHz) | δ 3.74 (s, 3H), 5.25 (br s, 2H), 5.53 (s, 2H), 6.44 (m, 1H), 6.56 (m, 2H), 6.89 (m, 2H), 7.03 (m, 1H), 7.13 (m, 1H), 7.42 (m, 3H), 7.88 (br s, 1H) and 8.17 (br s, 1H) |
| MS-ES+ | 468.03 |
| HPLC method no., Rt (min) | 9, 16.04 |

| | |
|---|---|
| Example | 285 |
| Product | 2,6-Difluoro-3-[5-(4-amino-phenyl)-4-(4-methoxy-phenyl)-thiazol-2-ylmethoxy]-benzamide |
| Reaction scheme | 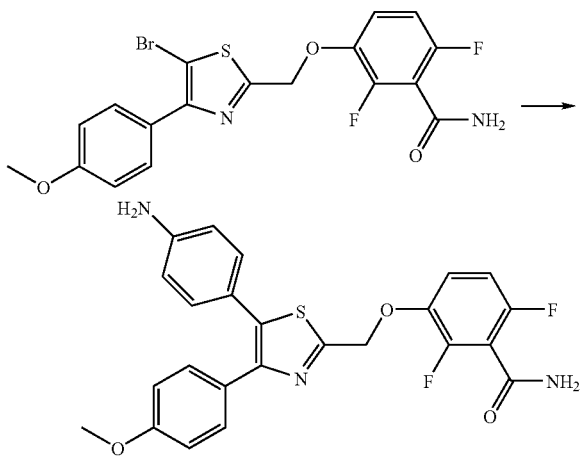 |
| Reactant (B) | 4-aminophenyl boronic acid |
| Quantities A; B; C; D | 0.10 g, 0.20 mmol; 0.07 g, 0.54 mmol; 0.102 g, 0.48 mmol; 0.021 g, 0.03 mmol |
| Silica gel | 60-120M |

TABLE P-continued

| | |
|---|---|
| Yield | 0.01 g, 9%, brown solid |
| ¹H NMR (DMSO-d₆, 400 MHz) | δ 3.74 (s, 3H), 5.42 (br s, 2H), 5.50 (s, 2H), 6.54 (m, 2H), 6.89 (d, J = 8.80 Hz, 2H), 6.99 (d, J = 8.40 Hz, 2H), 7.13 (m, 1H), 7.40 (m, 3H), 7.89 (br s, 1H) and 8.17 (br s, 1H) |
| MS-ES+ | 468.31 |
| HPLC method no., Rt (min) | 8, 16.06 |

| | |
|---|---|
| Example | 286 |
| Product | 3-[5-Cyclopropyl-4-(4-methoxy-phenyl)-thiazol-2-ylmethoxy]-2,6-difluoro-benzamide |
| Reaction scheme | |

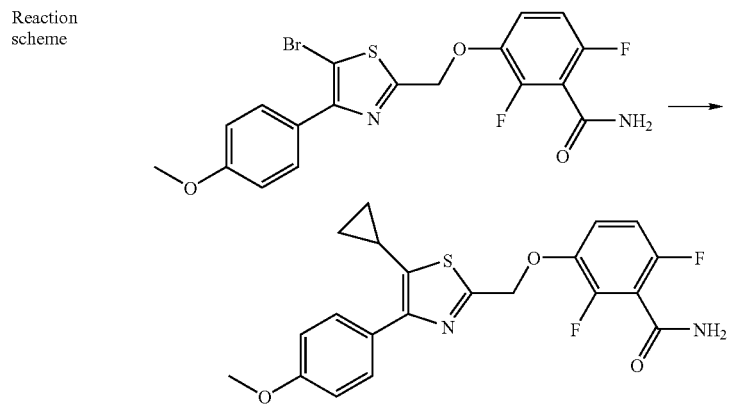

| | |
|---|---|
| Reactant (B) | cyclopropyl boronic acid |
| Quantities A; B; C; D | 0.10 g, 0.20 mmol; 0.37 g, 0.43 mmol; 0.05 g, 0.26 mmol; 0.021 g, 0.03 mmol |
| Silica gel | 230-400M |
| Yield | 0.01 g, 10%, white solid |
| ¹H NMR (DMSO-d₆, 400 MHz) | δ 0.66 (m, 2H), 1.11 (m, 2H), 2.20 (m, 1H), 3.80 (s, 3H), 5.44 (s, 2H), 7.02 (m, 2H), 7.11 (m, 1H), 7.39 (m, 1H), 7.80 (m, 2H), 7.88 (br s, 1H) and 8.16 (br s, 1H) |
| MS-ES+ | 417.11 |
| HPLC method no., Rt (min) | 9, 17.12 |

| | |
|---|---|
| Example | 287 |
| Product | 2,6-Difluoro-3-[4-(4-methoxy-phenyl)-5-phenyl-thiazol-2-ylmethoxy]-benzamide |
| Reaction scheme | |

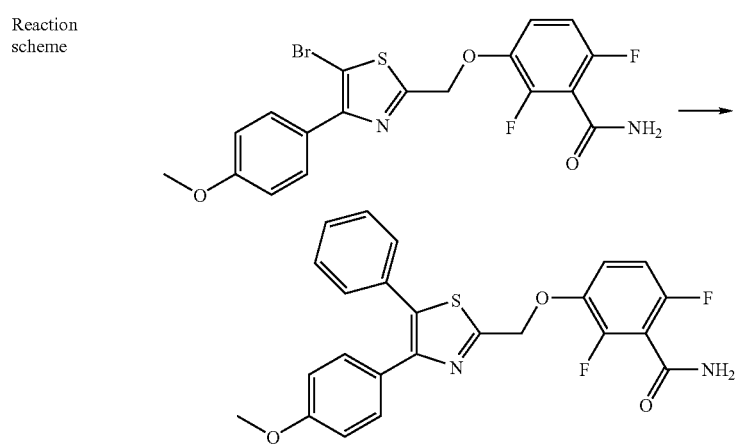

| | |
|---|---|
| Reactant (B) | phenyl boronic acid |
| Quantities A; B; C; D | 0.10 g, 0.20 mmol; 0.05 g, 0.43 mmol; 0.05 g, 0.26 mmol; 0.021 g, 0.03 mmol |
| Silica gel | 230-400M |
| Yield | 0.02 g, 22% |
| ¹H NMR | δ 3.75 (s, 3H), 5.56 (s, 2H), 6.90 (d, J = 8.80 Hz, 2H), 7.14 (t, J = 8.80 |

| | |
|---|---|
| (DMSO-d$_6$, 400 MHz) | Hz, 1H), 7.36-7.45 (m, 8H), 7.89 (br s, 1H) and 8.17 (br s, 1H) |
| MS-ES+ | 453.23 |
| HPLC method no., Rt (min) | 9, 13.35 |

Example 288

2,6-Difluoro-3-[4'-(4-methoxy-phenyl)-[4,5']bithiazolyl-2'-ylmethoxy]-benzamide

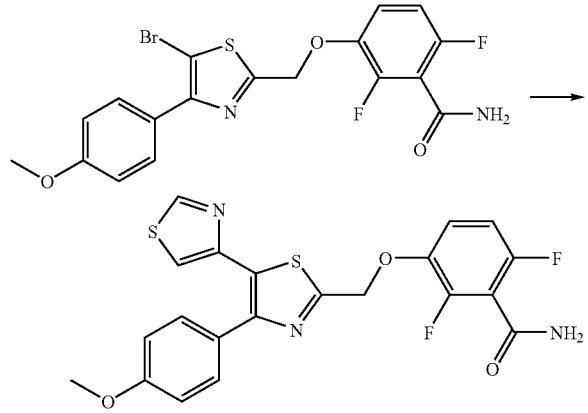

To a solution of 3-[5-bromo-4-(4-methoxy-phenyl)-thiazol-2-ylmethoxy]-2,6-difluoro-benzamide (0.20 g, 0.043 mmol) in 5 ml of anhydrous DMF was added 4-tributylstannyl thiazole (0.16 g, 0.43 mmol) and degassed the reaction mixture for 10 minutes. Tetrakis(triphenylphosphine) palladium (0) (0.05 g, 0.043 mmol) was then added and the reaction mixture was heated at 120° C. for 12 h under the nitrogen atmosphere. Then reaction mixture was cooled to room temperature added water (25 mL) and extracted the compound with ethyl acetate (3×50 mL). The combined organic layers were dried over anhydrous Na$_2$SO$_4$, and evaporated to dryness under reduced pressure. The compound was purified by column chromatography on silica (230-400 M) using ethyl acetate/Hexane (40:60) as the eluent to provide the title compound as white solid (0.072 g, 36%). $^1$H NMR (DMSO-d$_6$, 400 MHz): δ 3.80 (s, 3H), 5.56 (s, 2H), 7.01 (d, J=8.80 Hz, 2H), 7.13 (m, 1H), 7.41-7.50 (m, 4H), 7.90 (br s, 1H), 8.18 (br s, 1H) and 9.18 (s, 1H). MS ES+ (460.32), HPLC (method II) Rt=16.37 min.

Example 289

3-[5-Cyano-4-(4-methoxy-phenyl)-thiazol-2-ylmethoxy]-2,6-difluoro-benzamide

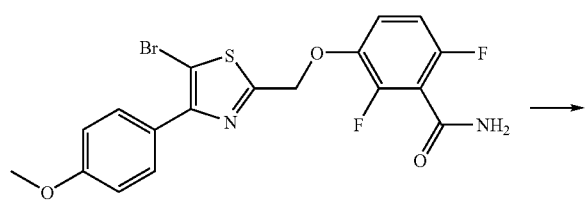

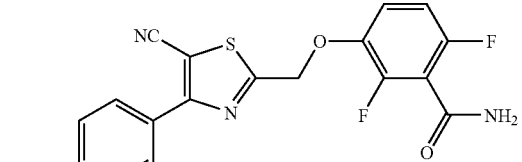

To a solution of 3-[5-bromo-4-(4-methoxy-phenyl)-thiazol-2-ylmethoxy]-2,6-difluoro-benzamide (0.20 g, 0.43 mmol) in pyridine (4.0 mL) was added CuCN (0.19 g, 2.19 mmol). The reaction mixture was heated to 150° C. in microwave for 2 h. After the completion of the reaction, pH was adjusted to 3-4 with 1N HCl solution and extracted with ethyl acetate (3×50 mL). The combined organics was washed with water, brine, dried (Na$_2$SO$_4$), filtered and concentrated. The crude residue was purified over silica gel (60-120 M, 45% EtOAc-Hexane) to get the desired product (0.02 g, 11%) as a brown solid. $^1$H NMR (DMSO-d$_6$, 400 MHz): δ 3.79 (s, 3H), 5.67 (s, 2H), 7.16 (m, 3H), 7.42 (m, 1H), 7.88 (br s, 1H), 8.03 (d, J=8.80 Hz, 2H) and 8.19 (br s, 1H). MS ES+ (402.07), HPLC (method I) Rt=16.60 min.

Scheme 32:

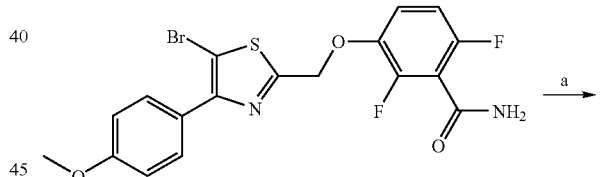

Ref: Scheme-3

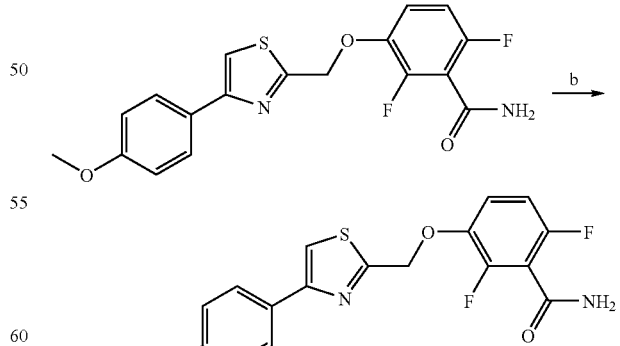

290

(a) Zn/Acetic acid;
(b) BBr$_3$/DCM

189

2,6-Difluoro-3-[4-(4-methoxy-phenyl)-thiazol-2-ylmethoxy]-benzamide

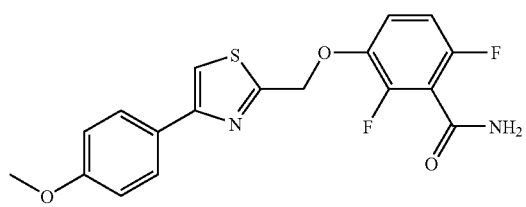

To a solution of 3-[5-bromo-4-(4-methoxy-phenyl)-thiazol-2-ylmethoxy]-2,6-difluoro-benzamide (2.0 g, 4.37 mmol) in the 50 ml of acetic acid was added Zn dust (2.0 g). The reaction mixture was heated at 120° C. for 1 h. After the completion of the reaction mixture (TLC monitoring), water (100 mL) was added and pH was adjusted to 8-9 with NaOH solution and extracted with ethyl acetate (3×150 mL). The combined organics was washed with water, brine, dried ($Na_2SO_4$), filtered and concentrated to get the desired product (0.8 g, 50%) as a white solid.

Example 290

2,6-Difluoro-3-[4-(4-hydroxy-phenyl)-thiazol-2-ylmethoxy]-benzamide

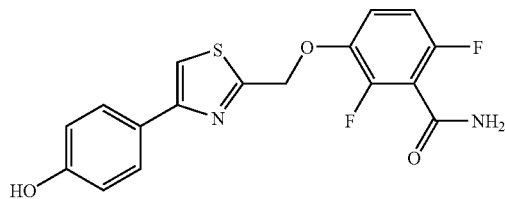

A solution of 2,6-Difluoro-3-[4-(4-methoxy-phenyl)-thiazol-2-ylmethoxy]-benzamide (0.20 g, 0.53 mmol) in 15 ml of DCM was cooled to −78° C. followed by addition of $BBr_3$ (0.2 ml, 2.14 mmol). The reaction mixture was stirred at 25° C. for 2 h. After the completion of the reaction mixture (TLC monitoring), solution of $NaHCO_3$ (20 mL) was added at 0° C. and extracted with ethyl acetate (3×50 mL). The combined organics was washed with water, brine, dried ($Na_2SO_4$), filtered and concentrated, the residue was purified by column chromatography on silica (60-120 M) using ethyl acetate/hexane (50:50) as the eluent to provide the title compound as light yellow solid (0.06 g, 31%). $^1$H NMR (DMSO-$d_6$, 400 MHz): δ 5.55 (s, 2H), 6.83 (d, J=8.40 Hz, 2H), 7.13 (m, 1H), 7.40 (m, 1H), 7.78 (d, J=8.80 Hz, 2H), 7.88 (br s, 1H), 7.91 (s, 1H), 8.17 (br s, 1H) and 9.64 (br s, 1H). MS ES+ (363.25), HPLC (method I) Rt=14.57 min.

Scheme 33:

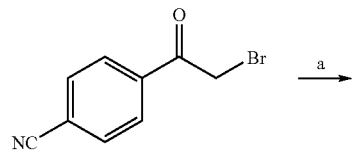

190

-continued

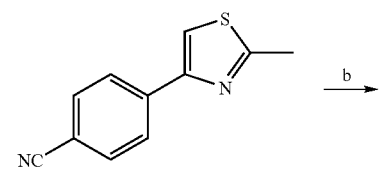

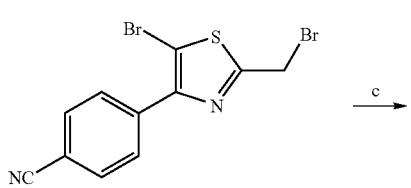

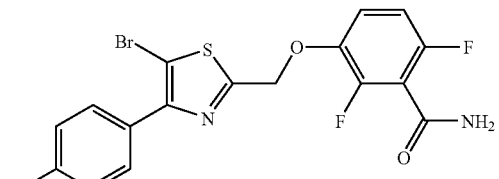

(a) Thioacetamide;
(b) NBS;
(c) 2,6-difluoro-3-hydroxy benzamide, $K_2CO_3$, DMF.

4-(2-Methyl-thiazol-4-yl)-benzonitrile

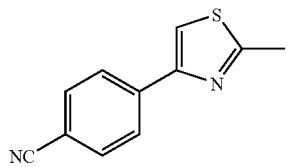

The compound was prepared following the general method as described in the preparation of 4-(4-Methoxy-phenyl)-2-methyl-thiazole (Scheme 31).

4-(5-Bromo-2-bromomethyl-thiazol-4-yl)-benzonitrile

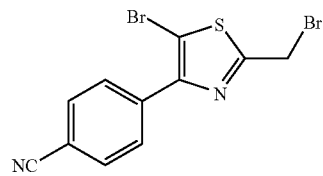

191

The compound was prepared following the general method as described in the preparation of 5-Bromo-2-bromomethyl-4-(4-methoxy-phenyl)-thiazole (Scheme 31).

Example 291

3-[5-Bromo-4-(4-cyano-phenyl)-thiazol-2-yl-methoxy]-2,6-difluoro-benzamide

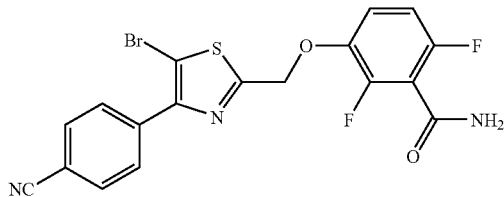

To a solution of 4-(5-Bromo-2-bromomethyl-thiazol-4-yl)-benzonitrile (0.43 g, 1.20 mmol) in 5 ml of anhydrous DMF was added 2,6-difluoro-3-hydroxy-benzamide (0.20 g, 1.20 mmol) and potassium carbonate (0.58 g, 4.20 mmol). The reaction mixture was stirred at 25° C. for 24 h under nitrogen atmosphere. The reaction mixture was evaporated to dryness under reduced pressure and the residue was purified by column chromatography on silica (60-120 M) using ethyl acetate/hexane (30:70) as the eluent to provide the title compound as a white solid (0.35 g, 66%). $^1$H NMR (DMSO-d$_6$, 400 MHz): δ 5.57 (s, 2H), 7.13 (m, 1H), 7.44 (m, 1H), 7.89 (br s, 1H), 8.0 (d, J=8.40 Hz, 2H), 8.10 (d, J=8.40 Hz, 2H) and 8.17 (br s, 1H). MS ES+ (450.09), HPLC (method I) Rt=16.127 min.

Scheme 34:

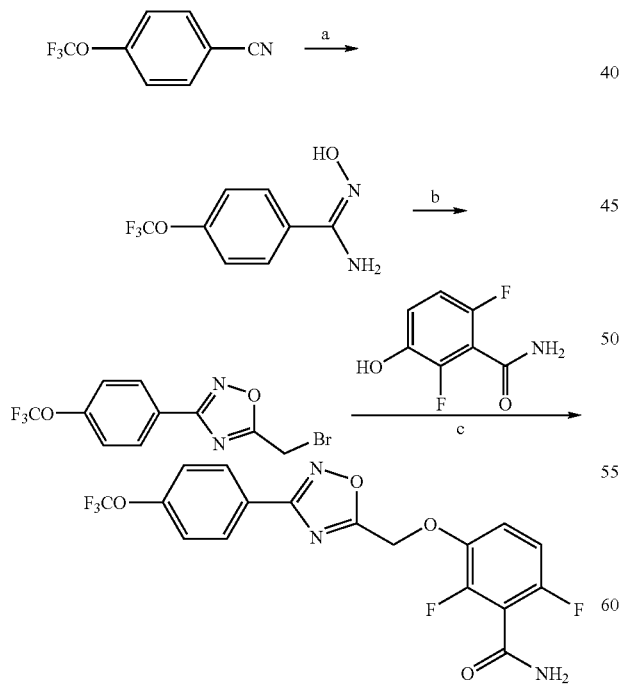

(a) NH$_2$OH·HCl, NaOH, EtOH;
(b) Bromoacetyl bromide;
(c) K$_2$CO$_3$, DMF.

192

Trifluoromethoxy phenyl-N-hydroxy-benzamide

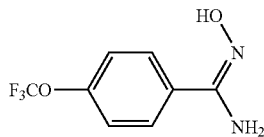

To a solution of 4-Trifluoromethoxybenzonitrile (1.0 g, 5.0 mmol) in EtOH (20 mL) was added hydroxylamine hydrochloride (0.365 g, 5.0 mmol) and NaOH (0.212 g, 5.0 mmol). The resulting reaction mixture was refluxed for 15 h. After the completion of the reaction (TLC monitoring), the mixture was concentrated, added EtOH and filtered. The filtrate was evaporated in vacuo and used as such for the next step (crude yield 12.0 g, 66%).

5-Bromomethyl-3-(Tri Fluoro Methoxy phenyl)-[1,2,4]oxadiazole

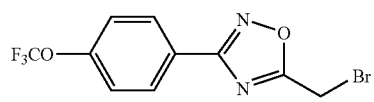

Bromoacetyl bromide (2.0 mL, 23.12 mmol) was added to trifluoromethoxy-N-hydroxy-benzamide (0.40 g, 5.86 mmol) and K$_2$CO$_3$ (0.87 g, 6.0 mmol). The reaction mixture was heated at 100° C. for 15 min. After the completion of the reaction mixture (TLC monitoring), water (100 mL) was added and extracted with ethyl acetate (3×50 mL). The combined organics was washed with water, brine, dried (Na$_2$SO$_4$), filtered and concentrated. The crude residue was purified over silica gel (60-120 M, 3% EtOAc-Hexane) to get the desired product (0.25 g, 43%) as a white solid.

Example 292

3-[3-(4-Trifluoromethoxy-phenyl)-[1,2,4]oxadiazol-5-ylmethoxy]-2-fluoro-benzamide

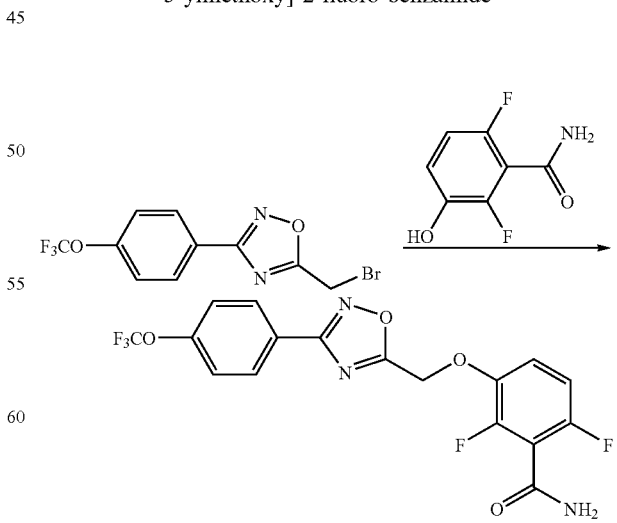

To a solution of 5-Bromomethyl-3-(Trifluoromethoxy phenyl)-[1,2,4]oxadiazole (0.24 g, 1.0 mmol) in 2.5 ml of anhydrous DMF was added 2,6-difluoro-3-hydroxy benzamide (0.18 g, 1.0 mmol) and potassium carbonate (0.516 g, 3.7 mmol). The reaction mixture was stirred at 25° C. for 24 h under nitrogen atmosphere. The reaction mixture was evaporated to dryness under reduced pressure and the residue was purified by column chromatography on silica (60-120 M) using ethyl acetate/hexane (50:50) as the eluent to provide the title compound as white solid (0.090 g, 20%). $^1$H NMR (DMSO-$d_6$, 400 MHz): δ 5.71 (s, 2H), 7.15 (t, J=7.60 Hz, 1H), 7.40 (m, 1H), 7.60 (d, J=8.0 Hz, 2H), 7.91 (br s, 1H), 8.15 (d, J=8.40 Hz, 2H) and 8.18 (br s, 1H). MS ES+ (416.28), HPLC (method I) Rt=16.79 min.

Scheme 35:

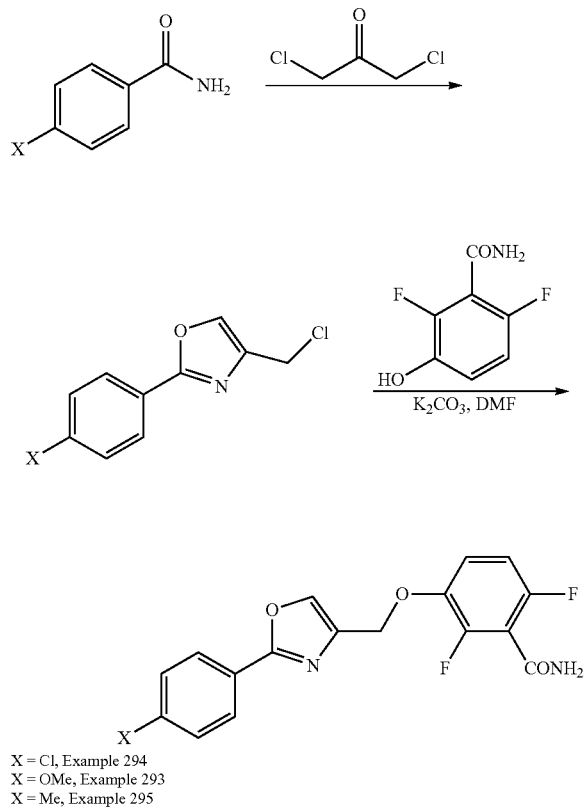

X = Cl, Example 294
X = OMe, Example 293
X = Me, Example 295

4-Chloromethyl-2-(4-methoxy-phenyl)-oxazole
(General method)

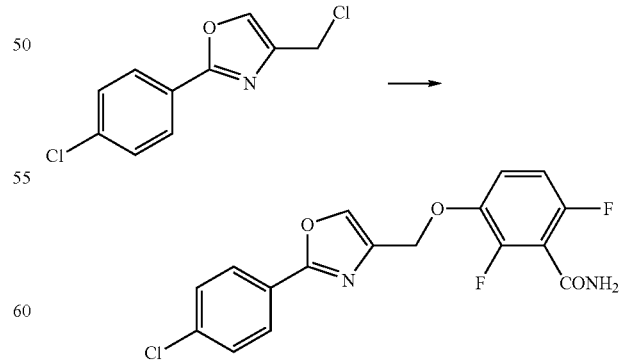

To a solution of 1,3 dichloroacetone (0.504 g, 3.90 mmol) in toluene (5 ml) was added 4-methoxy benzamide (0.30 g, 1.90 mmol). The reaction mixture was heated at 120° C. for 1 h. After the completion of the reaction mixture (TLC monitoring), the reaction mixture was evaporated to dryness under reduced pressure and the residue was purified over silica gel (230-400 M, 15% EtOAc-Hexane) to get the desired product (0.37 g, 83%).

Example 293

2,6-Difluoro-3-[2-(4-methoxy-phenyl)-oxazol-4-ylmethoxy]-benzamide

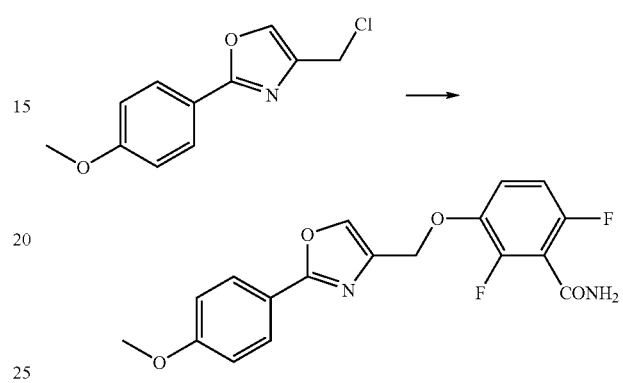

To a solution of 4-Chloromethyl-2-(4-methoxy-phenyl)-oxazole (0.100 g, 0.4 mmol) in 2 ml of anhydrous DMF was added 2,6-Difluoro-3-hydroxy-benzamide (0.077 g, 0.40 mmol) and potassium carbonate (0.216 g, 1.50 mmol). The reaction mixture was stirred at 25° C. for 24 h under nitrogen atmosphere. The reaction mixture was evaporated to dryness under reduced pressure and the residue was purified by column chromatography on silica (60-120 M) using ethyl acetate/hexane (50:50) as the eluent to provide the title compound as white solid (0.044 g, 27%). $^1$H NMR (DMSO-$d_6$, 400 MHz): δ 4.01 (s, 3H), 5.12 (s, 2H), 7.10 (m, 3H), 7.40 (m, 1H), 7.85 (br s, 1H), 7.93 (d, J=8.80 Hz, 2H), 8.13 (br s, 1H) and 8.25 (s, 1H). MS ES+ (361.16), HPLC (method I) Rt=15.47 min.

Example 294

3-[2-(4-Chloro-phenyl)-oxazol-4-ylmethoxy]-2,6-difluoro-benzamide

To a solution of 4-Chloromethyl-2-(4-chloro-phenyl)-oxazole (0.20 g, 0.87 mmol) in 2 ml of anhydrous DMF was added 2,6-Difluoro-3-hydroxy-benzamide (0.15 g, 0.78 mmol) and potassium carbonate (0.363 g, 2.60 mmol). The reaction mixture was stirred at 25° C. for 24 h under nitrogen atmosphere. The reaction mixture was evaporated to dryness under reduced pressure and the residue was purified by column chromatography on silica (60-120 M) using ethyl acetate/hexane (50:50) as the eluent to provide the title compound as white solid (0.10 g, 31%). $^1$H NMR (DMSO-d$_6$, 400 MHz): δ 5.14 9s, 2H), 7.12 (t, J=9.20 Hz, 1H), 7.40 (m, 1H), 7.63 (d, J=8.40, 2H), 7.85 (br s, 1H), 8.0 (d, J=8.40 Hz, 2H), 8.13 (br s, 1H) and 8.36 (s, 1H). MS ES+ (365.13), HPLC (method I) Rt=16.36 min.

Example 295

2,6-Difluoro-3-(2-p-tolyl-oxazol-4-ylmethoxy)-benzamide

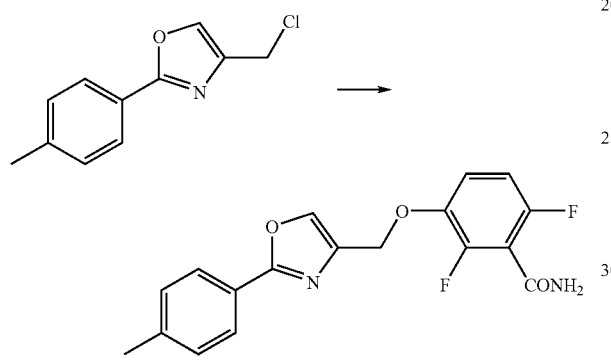

To a solution of 4-Chloromethyl-2-p-tolyl-oxazole (0.10 g, 0.50 mmol) in 2 ml of anhydrous DMF was added 2,6-Difluoro-3-hydroxy-benzamide (0.08 g, 0.50 mmol) and potassium carbonate (0.233 g, 1.50 mmol). The reaction mixture was stirred at 25° C. for 24 h under nitrogen atmosphere. The reaction mixture was evaporated to dryness under reduced pressure and the residue was purified by column chromatography on silica (60-120 M) using ethyl acetate/hexane (50:50) as the eluent to provide the title compound as white solid (0.03 g, 18%). $^1$H NMR (DMSO-d$_6$, 400 MHz): δ 2.37 (s, 3H), 5.13 (s, 2H), 7.11 (m, 1H), 7.36 (d, J=8.0 Hz, 2H), 7.41 (m, 1H), 7.88 (m, 3H), 8.12 (br s, 1H) and 8.29 (s, 1H). MS ES+ (345.24), HPLC (method I) Rt=16.07 min.

Scheme 36:

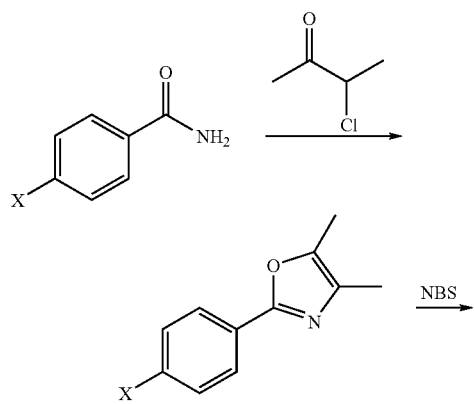

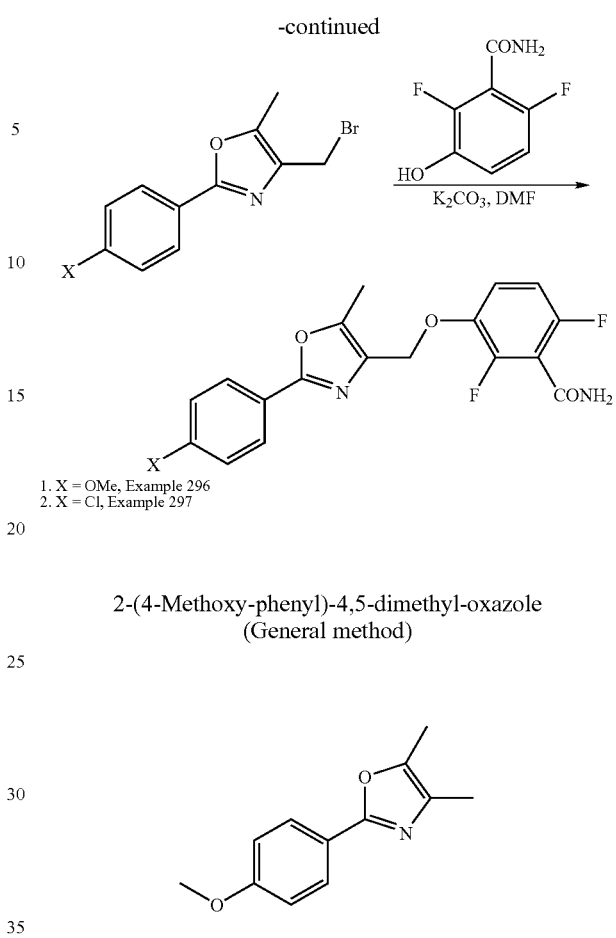

1. X = OMe, Example 296
2. X = Cl, Example 297

2-(4-Methoxy-phenyl)-4,5-dimethyl-oxazole
(General method)

A mixture of 3-Chloro-2-butanone (2.1 g, 10.0 mmol) and 4-methoxybenzamide (0.30 g, 1.0 mmol) was heated at 115° C. for 15 h under nitrogen atmosphere. After the completion of the reaction mixture (TLC monitoring), the reaction mixture was evaporated to dryness under reduced pressure and the residue was purified over silica gel (230-400 M, 20% EtOAc-Hexane) to get the desired product (0.17 g, 42%) as a white solid. The corresponding chloro derivative was also prepared by the same general method.

4-Bromomethyl-2-(4-methoxy-phenyl)-5-methyl-oxazole

To the solution of 4-Bromomethyl-2-(4-methoxy-phenyl)-5-methyl-oxazole (0.17 g, 0.80 mmol) in acetonitrile (4.0 mL) was added NBS (7.43 g, 41.74 mmol). The reaction mixture was stirred at 25° C. for 1 h under nitrogen atmosphere. After the completion of the reaction mixture (TLC monitoring), the reaction mixture was cooled to 0° C. and 2 ml of water was added. The resulting precipitate was filtered and dried to give the desired product (0.11 g, 46%). The corresponding chloro derivative was also prepared by the same general method.

Example 296

2,6-Difluoro-3-[2-(4-methoxy-phenyl)-5-methyl-oxazol-4-ylmethoxy]-benzamide

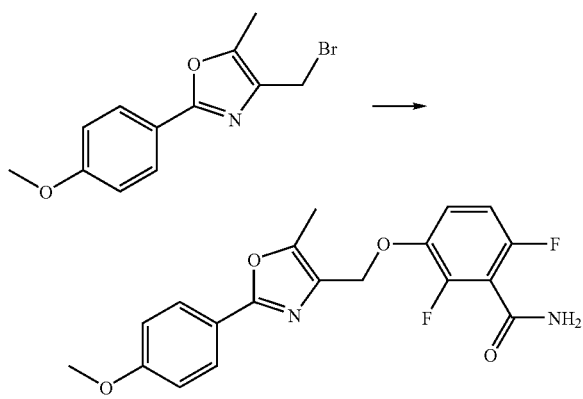

To a solution of 4-Bromomethyl-2-(4-methoxy-phenyl)-5-methyl-oxazole (0.10 g, 0.35 mmol) in 2 ml of anhydrous DMF was added 2,6-Difluoro-3-hydroxy-benzamide (0.061 g, 0.35 mmol) and potassium carbonate (0.171 g, 1.05 mmol). The reaction mixture was stirred at 25° C. for 24 h under nitrogen atmosphere. The reaction mixture was evaporated to dryness under reduced pressure and the residue was purified by column chromatography on silica (60-120 M) using ethyl acetate/hexane (50:50) as the eluent to provide the title compound as white solid (0.117 g, 87%). $^1$H NMR (DMSO-$d_6$, 400 MHz): δ 2.42 (s, 3H), 3.82 (s, 3H), 5.06 (s, 2H), 7.10 (m, 3H), 7.37 (m, 1H), 7.86 (m, 3H) and 8.13 (br s, 1H). MS ES+ (375.12), HPLC (method I) Rt=15.78 min.

Example 297

3-[2-(4-Chloro-phenyl)-5-methyl-oxazol-4-yl-methoxy]-2,6-difluoro-benzamide

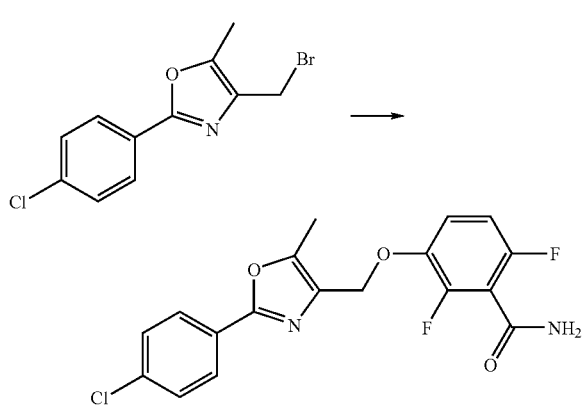

To a solution of 4-Bromomethyl-2-(4-chloro-phenyl)-5-methyl-oxazole (0.12 g, 0.42 mmol) in 2 ml of anhydrous DMF was added 2,6-Difluoro-3-hydroxy-benzamide (0.072 g, 0.42 mmol) and potassium carbonate (0.203 g, 1.20 mmol). The reaction mixture was stirred at 25° C. for 24 h under nitrogen atmosphere. The reaction mixture was evaporated to dryness under reduced pressure and the residue was purified by column chromatography on silica (60-120 M) using ethyl acetate/hexane (50:50) as the eluent to provide the title compound as white solid (0.01 g, 6%). $^1$H NMR (DMSO-$d_6$, 400 MHz): δ 2.49 (s, 3H), 5.09 (s, 2H), 7.11 (m, 1H), 7.38 (m, 1H), 7.60 (d, J=8.40 Hz, 2H), 7.85 (br s, 1H), 7.95 (d, J=8.40 Hz, 2H) and 8.13 (br s, 1H). MS ES+ (379.25), HPLC (method I) Rt=16.71 min Scheme 37:

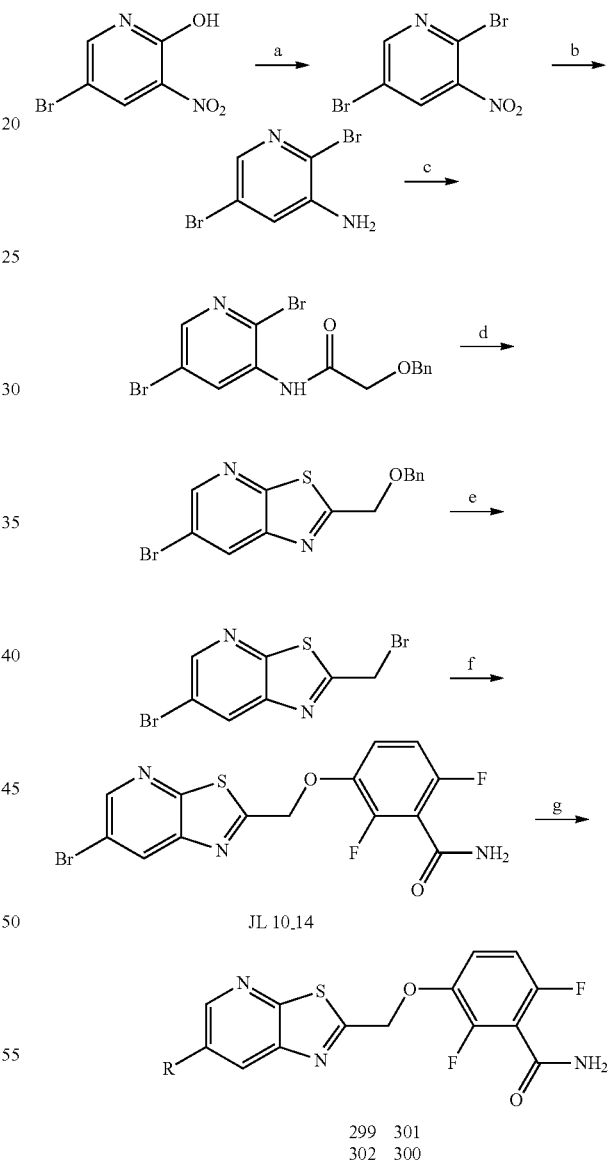

299 301
302 300

(a) PBr$_3$;
(b) SnCl$_2$•2H$_2$O;
(c) 2-Benzoyloxy acetyl chloride;
(d) Lawesson's reagent;
(e) BBr$_3$;
(f) 2,6-difluoro-3-hydroxy benzamide, K$_2$CO$_3$, DMF;
(g) Suzuki or Stannyl conditions.

2,5-Dibromo-3-nitro-pyridine

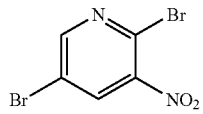

To a solution of 5-Bromo-3-nitro-pyridin-2-ol (10.0 g, 45.66 mmol) in 70 ml of toluene and 7 ml of DMF was added PBr$_3$ (6.60 ml, 68.49 mmol) and the reaction mixture was heated at 120° C. for 20 min under nitrogen atmosphere. After the completion of the reaction mixture (TLC monitoring), water (100 mL) was added and extracted with ethyl acetate (3×200 mL). The combined organics was washed with water, brine, dried (Na$_2$SO$_4$), filtered and concentrated to get the desired product (10.30 g, 80.03%).

2,5-Dibromo-pyridin-3-ylamine

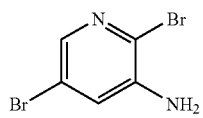

To the solution of 2,5-Dibromo-3-nitro-pyridine (10.30 g, 35.47 mmol) in the 100 ml of ethanol was added SnCl$_2$ (24.0 g, 106.42 mmol) slowly. The reaction mixture was heated at 80° C. for 2 h. After the completion of the reaction mixture (TLC monitoring), the reaction mixture was evaporated to dryness under reduced pressure. Water (250 mL) was added, white solid separated out, then, basified the reaction mixture with NaOH Solution. To this added the 250 ml of ethyl acetate. Filtered it and washed the residue with ethyl acetate, layers are separated, dried (Na$_2$SO$_4$), filtered, concentrated to give the desired product (6.20 g, 67.39%).

2-Benzyloxy-N-(2,5-dibromo-pyridin-3-yl)-acetamide

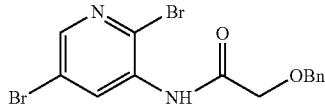

To the solution of 2,5-Dibromo-pyridin-3-ylamine (8.6 g, 34.12 mmol) in 50 ml of DCM was added triethylamine (5.3 ml, 37.53 mmol). Cooled the reaction mixture to 0° C. To this added the solution of 2-benzyloxy acetyl chloride (7.45 g, 40.95 mmol) in 35 ml of DCM. The reaction mixture was stirred at 25° C. for 12 hr. After the completion of the reaction mixture (TLC monitoring), the reaction mixture was evaporated to dryness under reduced pressure. The residue was purified by column chromatography on silica (60-120 M) using ethyl acetate/hexane (10:90) as the eluent to provide the title compound (3.2 g, 24.17%).

2-Benzyloxymethyl-5-bromo-thiazolo[5,4-b]pyridine

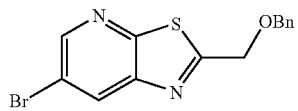

To the solution of 2-Benzyloxy-N-(2,5-dibromo-pyridin-3-yl)-acetamide (2.5 g, 6.248 mmol) in 30 ml of toluene was added Lawesson's reagent (1.51 g, 3.74 mmol). The reaction mixture was heated at 120° C. for 2 h. After the completion of the reaction mixture (TLC monitoring), the reaction mixture was evaporated to dryness under reduced pressure. The residue was purified by column chromatography on silica (60-120 M) using ethyl acetate/hexane (5:95) as the eluent to provide the title compound (1.60 g, 76.5%).

5-bromo-2-bromomethyl-thiazolo[5,4-b]pyridine

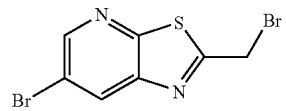

A solution of 2-Benzyloxymethyl-5-bromo-thiazolo[5,4-b]pyridine (1.60 g, 4.77 mmol) DCM (15 mL) was cooled to −78° C. followed by addition of BBr$_3$ (2.27 ml, 23.86 mmol). The reaction mixture was stirred at 25° C. for 2 h. After the completion of the reaction mixture (TLC monitoring), solution of NaHCO$_3$ (20 mL) was added at 0° C. and extracted with ethyl acetate (3×50 mL). The combined organics was washed with water, brine, dried (Na$_2$SO$_4$), filtered and concentrated to get the desired product (2.0 g, Crude yield).

Example 298

3-(5-bromo-thiazolo[5,4-b]pyridin-2-ylmethoxy)-2,6-difluoro-benzamide

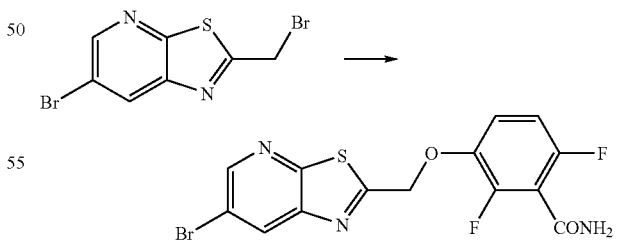

To a solution of 5-bromo-2-bromomethyl-thiazolo[5,4-b]pyridine (2.0 g, 6.493 mmol) in 10 ml of anhydrous DMF was added 2,6-Difluoro-3-hydroxy-benzamide (1.01 g, 5.84 mmol) and potassium carbonate (3.09 g, 22.72 mmol). The reaction mixture was stirred at 25° C. for 24 h under nitrogen atmosphere. The reaction mixture was evaporated to dryness under reduced pressure and the residue was purified by column chromatography on silica (60-120 M) using ethyl acetate/hexane (50:50) as the eluent to provide the title compound (1.80 g, 69%). $^1$H NMR (DMSO-d$_6$, 400 MHz): δ 5.72 (s, 2H), 7.12 (t, J=7.60 Hz, 1H), 7.39 (m, 1H), 7.90 (br s, 1H), 8.18 (br s, 1H) and 8.80 (m, 2H). MS ES+ (402.08), HPLC (method I) Rt=15.50 min.

3-(5-Allyl-thiazolo[5,4-b]pyridin-2-ylmethoxy)-2,6-difluoro-benzamide

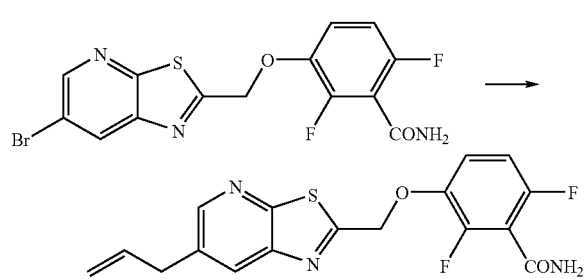

To a solution of 3-(5-bromo-thiazolo[5,4-b]pyridin-2-ylmethoxy)-2,6-difluoro-benzamide (0.15 g, 0.37 mmol) in 5 ml of anhydrous DMF was added allyl tributyltin (0.26 ml, 0.86 mmol) and degassed the reaction mixture for the 10 minutes. Tetrakis(triphenylphosphine) palladium (0) (0.007 g, 0.0056 mmol) was then added and the reaction mixture was heated at 120° C. for 1 h under the nitrogen atmosphere. Then reaction mixture was cooled to room temperature added water (25 mL) and extracted the compound with ethyl acetate. The combined organic layers were dried over anhydrous Na$_2$SO$_4$, and evaporated to dryness under reduced pressure. The compound was purified by column chromatography on silica (100-200 M) using ethyl acetate/Hexane (60:40) as the eluent to provide the title compound (0.10 g, 75%).

Example 299

2,6-Difluoro-3-(5-propyl-thiazolo[5,4-b]pyridin-2-ylmethoxy)-benzamide

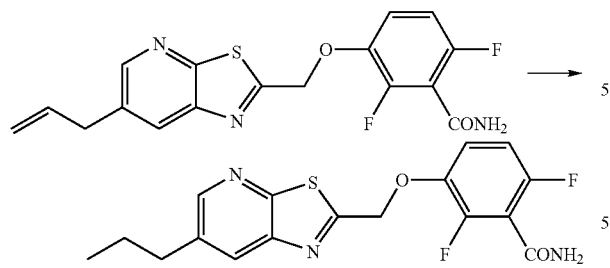

To a solution of 3-(5-Allyl-thiazolo[5,4-b]pyridin-2-ylmethoxy)-2,6-difluoro-benzamide (0.018 g, 0.049 mmol) in 5 ml of anhydrous methanol was added Pd—C (10%, 5 mg) and the reaction mixture was stirred at 25° C. for 12 h under hydrogen atmosphere. The reaction mixture was filtered over the bed of celite and the filtrate was evaporated to dryness under reduced pressure to give the title compound as white solid (0.0078 g, 43%). $^1$H NMR (DMSO-d$_6$, 400 MHz); δ 0.91 (m, 3H), 1.65 (m, 2H), 2.74 (m, 2H), 5.69 (s, 2H), 7.12 (m, 1H), 7.39 (m, 1H), 7.90 (br s, 1H), 8.18 (br s, 1H), 8.27 (br s, 1H) and 8.52 (br s, 1H). MS ES+ (364.11), HPLC (method I) Rt=15.85 min.

Example 300

2,6-Difluoro-3-[5-(1-methyl-1H-imidazol-2-yl)-thiazolo[5,4-b]pyridin-2-ylmethoxy]-benzamide

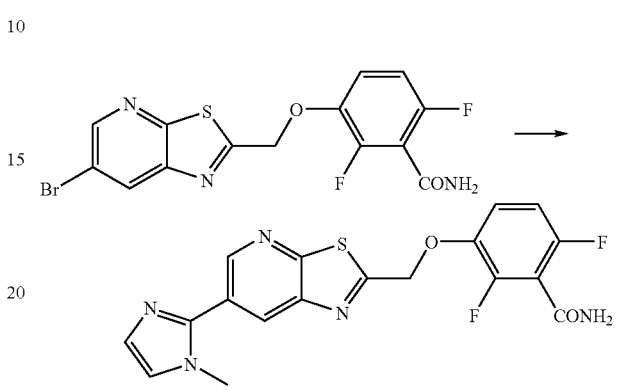

To a solution of 3-(5-bromo-thiazolo[5,4-b]pyridin-2-ylmethoxy)-2,6-difluoro-benzamide (0.10 g, 0.24 mmol) in 5 ml of anhydrous DMF was added 1-methyl-2-tributylstannanyl-1H-imidazole (0.120 g, 0.32 mmol) and degassed the reaction mixture for the 10 minutes. Tetrakis(triphenylphosphine) palladium (0) (0.004 g, 0.0037 mmol) was then added and the reaction mixture was heated at 120° C. for 12 h under the nitrogen atmosphere. The reaction mixture was then cooled to room temperature, added water (25 mL) and extracted the compound with ethyl acetate. The combined organic layers were dried over anhydrous Na$_2$SO$_4$, and evaporated to dryness under reduced pressure. The compound was purified by column chromatography on silica (230-400 M) using ethyl acetate/hexane (40:60) as the eluent to provide the title compound as brick red solid (0.020 g, 20%). $^1$H NMR (DMSO-d$_6$, 400 MHz): δ 3.14 (s, 3H), 5.67 (s, 2H), 7.07 (m, 1H), 7.28-7.37 (m, 2H), 7.87 (m, 2H), 8.28 (s, 1H), 8.53 (s, 1H) and 8.75 (br s, 1H). MS ES+ (402.22), HPLC (method I) Rt=12.05 min.

Example 301

2,6-Difluoro-3-[5-(1-methyl-1H-pyrrol-2-yl)-thiazolo[5,4-b]pyridin-2-ylmethoxy]-benzamide

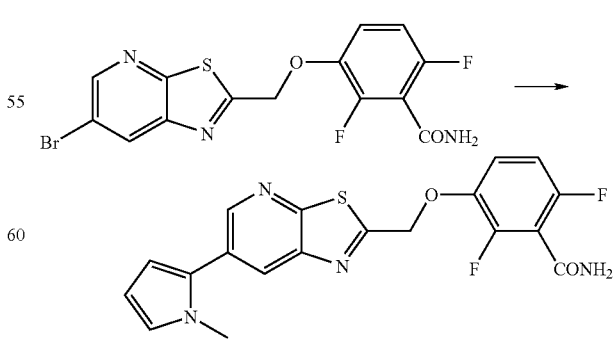

To a solution of 3-(5-bromo-thiazolo[5,4-b]pyridin-2-ylmethoxy)-2,6-difluoro-benzamide (0.10 g, 0.24 mmol) in 5 ml of anhydrous DMF was added 1-methyl-2-tributylstannanyl-1H-pyrrole (0.120 g, 0.32 mmol) and degassed the reaction mixture for the 10 minutes. Tetrakis(triphenylphosphine) palladium (0) (0.004 g, 0.0037 mmol) was then added and the reaction mixture was heated at 120° C. for 12 h under the nitrogen atmosphere. The reaction mixture was then cooled to room temperature, added water (25 mL) and extracted the compound with ethyl acetate. The combined organic layers were dried over anhydrous $Na_2SO_4$, and evaporated to dryness under reduced pressure. The compound was purified by column chromatography on silica (230-400 M) using ethyl acetate/Hexane (40:60) as the eluent to provide the title compound as yellow solid (0.032 g, 32%). $^1$H NMR (DMSO-$d_6$, 400 MHz): δ 3.73 (s, 3H), 5.72 (s, 2H), 6.13 (br s, 1H), 6.40 (br s, 1H), 6.97 (s, 1H), 7.12 (m, 1H), 7.42 (m, 1H), 7.90 (br s, 1H), 8.18 (br s, 1H), 8.48 (s, 1H) and 8.75 (s, 1H). MS ES+ (401.26), HPLC (method I) Rt=15.61 min.

Example 302

2,6-Difluoro-3-(5-phenyl-thiazolo[5,4-b]pyridin-2-ylmethoxy)-benzamide

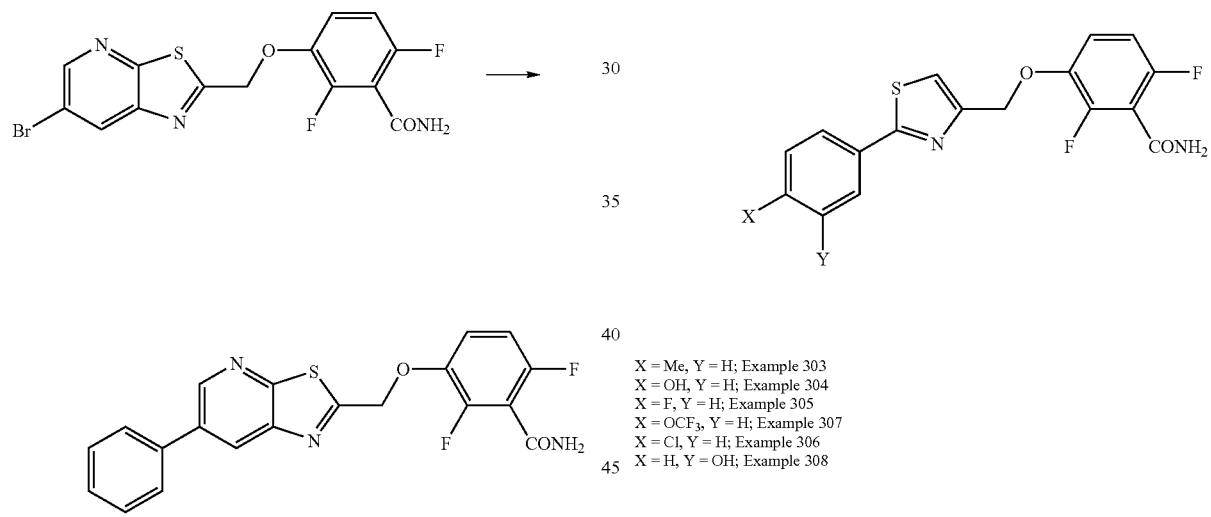

To a solution of 3-(5-bromo-thiazolo[5,4-b]pyridin-2-ylmethoxy)-2,6-difluoro-benzamide (0.20 g, 0.49 mmol) in 4 ml of DMF and water (2.0 ml) was added phenyl boronic acid (0.12 g, 0.99 mmol) and potassium phosphate (0.13 g, 0.59 mmol). The reaction mixture was degassed for 10 minutes followed by addition of dichlorobis(tri phenyl phosphine) palladium (II) (0.070 g, 0.099 mmol). The reaction mixture was heated at 120° C. for 2 h under the nitrogen atmosphere. After the completion of the reaction mixture (TLC monitoring), water (25 mL) was added and extracted with ethyl acetate (3×50 mL). The combined organics was washed with water, brine, dried ($Na_2SO_4$), filtered and concentrated. The crude residue was purified over silica gel (100-200 M, 60% EtOAc-Hexane) to get the desired product (0.080 g, 41%) as a beige solid. $^1$H NMR (DMSO-$d_6$, 400 MHz): δ 5.74 (s, 2H), 7.10 (m, 1H), 7.41-7.56 (m, 4H), 7.85 (m, 3H), 8.19 (m, 1H), 8.71 (br s, 1H) and 8.98 (br s, 1H). MS ES+ (398.09), HPLC (method I) Rt=16.07 min.

Scheme 38:

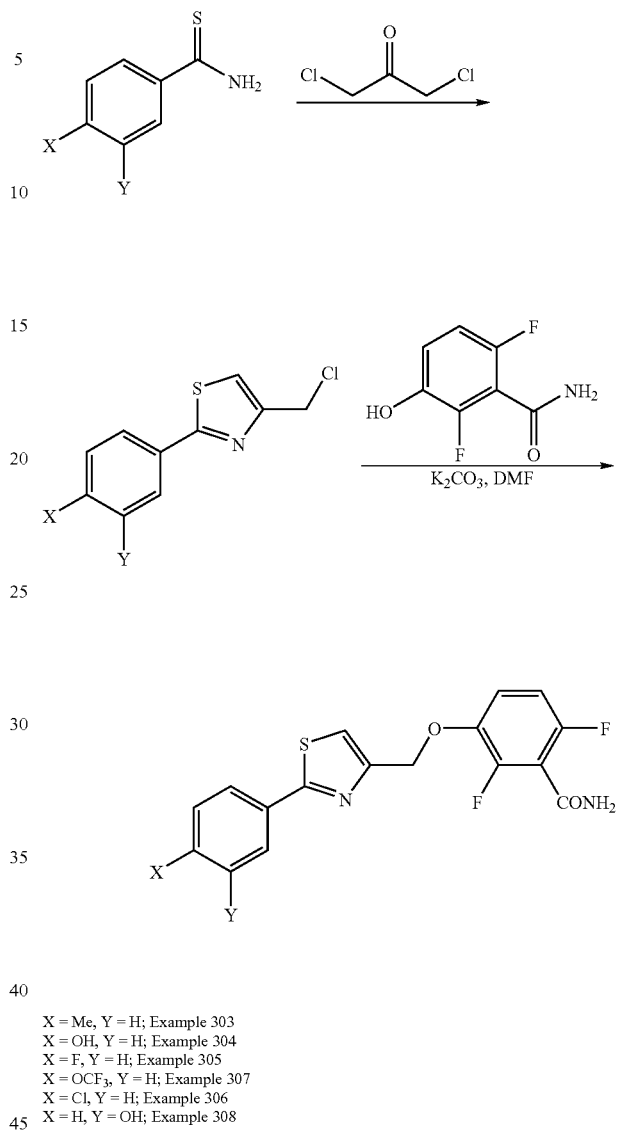

X = Me, Y = H; Example 303
X = OH, Y = H; Example 304
X = F, Y = H; Example 305
X = OCF$_3$, Y = H; Example 307
X = Cl, Y = H; Example 306
X = H, Y = OH; Example 308

4-Chloromethyl-2-n-tolyl-thiazole (Representative example)

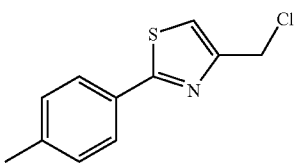

To a solution of 1,3 dichloroacetone (0.84 g, 6.62 mmol) in toluene (5 ml) was added 4-methylthiobenzamide (0.50 g, 3.31 mmol) and the reaction mixture was heated at 120° C. for 1 h. After the completion of the reaction mixture (TLC monitoring), the reaction mixture was evaporated to dryness under reduced pressure and the residue was purified over silica gel (230-400 M, 15% EtOAc-Hexane) to get the desired product (0.49 g, 67%). The other derivatives were also prepared by the same general method.

3-(4-Chloromethyl-thiazol-2-yl)-phenol

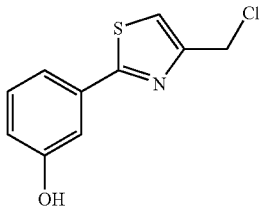

To a solution of 1,3 dichloroacetone (0.42 g, 3.26 mmol) in toluene (5 mL) was added 3-hydroxythiobenzamide (0.25 g, 1.63 mmol) and the reaction mixture was heated at 120° C. for 1 h. After completion of the reaction mixture (TLC monitoring), the reaction mixture was evaporated to dryness, added water and extracted with EtOAc (×3). The combined organics was washed with water, brine, dried ($Na_2SO_4$), filtered and concentrated. The crude residue was purified over silica gel (230-400 M, 10% EtOAc-Hexane) to get the desired product (0.14 g, 38%).

Scheme 39:

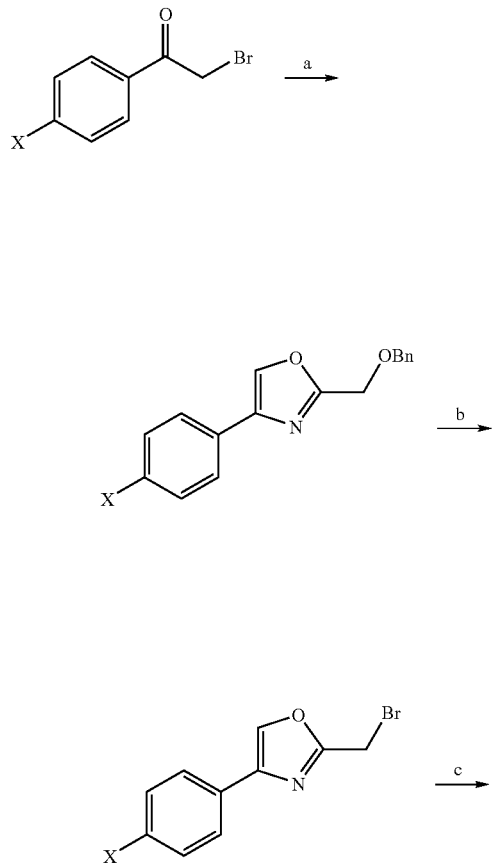

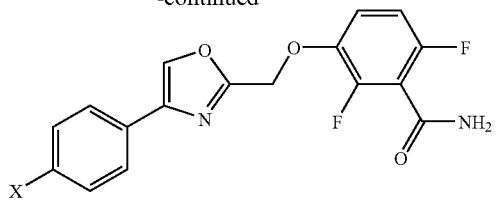

X = H, Example 310
X = Cl, Example 309

(a) 2-Benzyloxy acetamide, DMF;
(b) $BBr_3$, DCM;
(c) 2,6-Difluoro-3-hydroxybenzamide, $K_2CO_3$, DMF.

2-Benzyloxymethyl-4-(4-chloro-phenyl)-oxazole
(Representative Procedure)

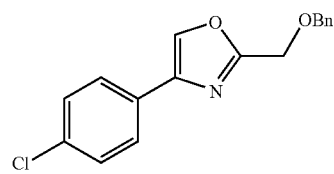

To a solution of 2-Benzyloxy-acetamide (1.40 g, 8.56 mmol) in 4 ml of DMF was added 2-Bromo-1-(4-chloro-phenyl)-ethanone (2.0 g, 8.56 mmol) and the reaction mixture was heated at 130° C. for 6 h under nitrogen atmosphere. After the completion of the reaction mixture (TLC monitoring), water (25 mL) was added and extracted with ethyl acetate (3×50 mL). The combined organics was washed with water, brine, dried ($Na_2SO_4$), filtered and concentrated. The crude residue was purified over silica gel (230-400 M, 10% EtOAc-Hexane) to get the desired product (1.1 g, 44%).

2-Bromomethyl-4-(4-chloro-phenyl)-oxazole
(Representative procedure)

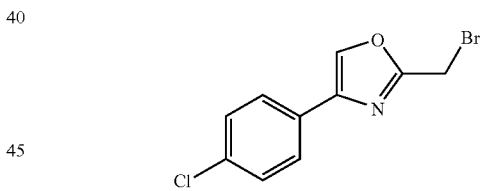

A solution of 2-Benzyloxymethyl-4-(4-chloro-phenyl)-oxazole (1.10 g, 3.6 mmol) in 10 ml of DCM was cooled to −78° C. followed by addition of $BBr_3$ (1.76 ml, 18.0 mmol). The reaction mixture was stirred at 25° C. for 2 h. After the completion of the reaction mixture (TLC monitoring), solution of $NaHCO_3$ (20 mL) was added at 0° C. and extracted with ethyl acetate (3×50 mL). The combined organics was washed with water, brine, dried ($Na_2SO_4$), filtered and concentrated to get the desired product (0.5 g, 49%, crude).

Examples 303-310 (Table Q)

The compounds of Examples 303-310 were synthesised according to the following general procedure: To a solution of reactant (A) in 2 ml of anhydrous DMF was added 2,6-Difluoro-3-hydroxy-benzamide (B) and potassium carbonate (C). The reaction mixture was stirred at 25° C. for 24 h under nitrogen atmosphere. The reaction mixture was evaporated to dryness under reduced pressure and the residue was purified by column chromatography on silica (60-120 M) using ethyl acetate/hexane (50:50) as the eluent to provide the product compound.

TABLE Q

| Example | 303 | 304 |
|---|---|---|
| Product | 2,6-Difluoro-3-(2-p-tolyl-thiazol-4-ylmethoxy)-benzamide | 2,6-Difluoro-3-[2-(4-hydroxy-phenyl)-thiazol-4-ylmethoxy]-benzamide |
| Reaction scheme | | |
| Reactant (A) | 4-Chloromethyl-2-p-tolyl-thiazole | 4-(4-Chloromethyl-thiazol-2-yl)-phenol |
| Quantities A; B; C | 0.100 g, 0.4 mmol; 0.069 g, 0.40 mmol; 0.18 g, 1.30 mmol | 0.25 g, 1.10 mmol; 0.17 g, 0.99 mmol; 0.535 g, 3.87 mmol |
| Yield | 0.022 g, 13%, white solid | 0.012 g, 3%, white solid |
| 1H NMR (DMSO-d6, 400 MHz) | δ 2.36 (s, 3H), 5.28 (s, 2H), 7.09 (t, J = 8.40 Hz, 1H), 7.33 (d, J = 8.0 Hz, 2H), 7.40 (m, 1H), 7.75 (s, 1H), 7.84 (m, 3H) and 8.13 (br s, 1H) | δ 5.25 (s, 2H), 6.85 (m, 2H), 7.09 (m, 1H), 7.40 (m, 1H), 7.66 (s, 1H), 7.78 (m, 2H), 7.85 (br s, 1H), 8.13 (br s, 1H) and 10.03 (br s, 1H) |
| MS-ES+ | 361.14 | 363.14 |
| HPLC method no., Rt (min) | 8, 16.63 | 8, 14.53 |

| Example | 305 | 306 |
|---|---|---|
| Product | 2,6-Difluoro-3-[2-(4-fluoro-phenyl)-thiazol-4-ylmethoxy]-benzamide | 3-[2-(4-Chloro-phenyl)-thiazol-4-ylmethoxy]-2,6-difluoro-benzamide |
| Reaction scheme | | |

TABLE Q-continued

| | | |
|---|---|---|
| Reactant (A) | 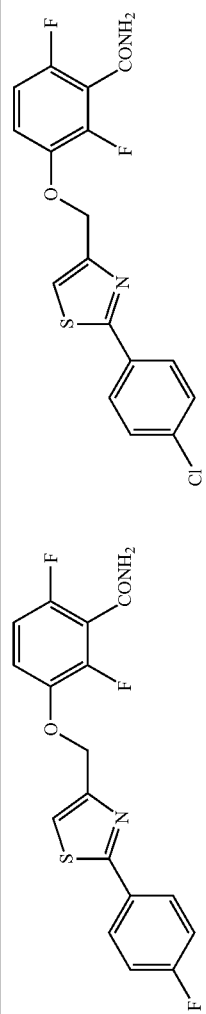 |  |
| Quantities A; B; C | 4-Chloromethyl-2-(4-fluoro-phenyl)-thiazole 0.15 g, 0.65 mmol; 0.10 g, 0.59 mmol; 0.27 g, 1.97 mmol | 4-Chloromethyl-2-(4-chloro-phenyl)-thiazole 0.06 g, 0.27 mmol; 0.04 g, 0.27 mmol; 0.12 g, 0.93 mmol |
| Yield | 0.06 g, 25%, white solid | 0.035 g, 34%, white solid |
| $^1$H NMR (DMSO-d$_6$, 400 MHz) | δ 5.29 (s, 2H), 7.11 (t, J = 8.80 Hz, 1H), 7.33–7.43 (m, 3H), 7.81 (s, 1H), 7.85 (br s, 1H), 8.0 (m, 2H) and 8.13 (br s, 1H) | δ 5.30 (s, 2H), 7.11 (m, 1H), 7.40 (m, 1H), 7.59 (d, J = 8.80 Hz, 2H), 7.86 (m, 2H), 7.97 (d, J = 8.80 Hz, 2H) and 8.14 (br s, 1H) |
| MS-ES+ | 365.03 | 381.16 |
| HPLC method no., Rt (min) | 8, 16.18 | 8, 16.88 |

| Example | 307 | 308 |
|---|---|---|
| Product | 2,6-Difluoro-3-[2-(4-trifluoromethoxy-phenyl)-thiazol-4-ylmethoxy]-benzamide | 2,6-Difluoro-3-[2-(3-hydroxy-phenyl)-thiazol-4-ylmethoxy]-benzamide |
| Reaction scheme | 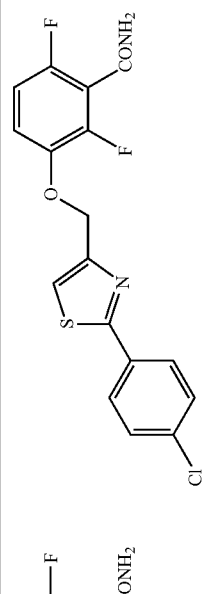 →  | 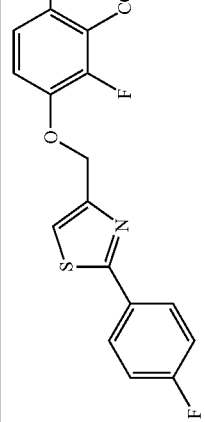 →  |
| Reactant (A) |  |  |
| Quantities A; B; C | 4-Chloromethyl-2-(4-trifluoromethoxy-phenyl)-thiazole 0.04 g, 0.11 mmol; 0.02 g, 0.11 mmol; 0.056 g, 0.38 mmol | 3-(4-Chloromethyl-thiazol-2-yl)-phenol 0.12 g, 0.53 mmol; 0.08 g, 0.49 mmol; 0.26 g, 1.93 mmol |
| Yield | 0.008 g, 16%, white solid | 0.014 g, 7%, white solid |

TABLE Q-continued

| Example | 309 | 310 |
|---|---|---|
| Product | 3-[4-(4-Chloro-phenyl)-oxazol-2-ylmethoxy]-2,6-difluoro-benzamide | 2,6-Difluoro-3-(4-phenyl-oxazol-2-ylmethoxy)-benzamide |
| Reaction scheme | | |
| Reactant (A) | 2-Bromomethyl-4-(4-chloro-phenyl)-oxazole | 2-Bromomethyl-4-phenyl-oxazole |
| Quantities A; B; C | 0.07 g, 0.24 mmol; 0.037 g, 0.24 mmol; 0.11 g, 0.84 mmol | 0.2 g, 0.84 mmol; 0.14 g, 0.84 mmol; 0.405 g, 2.94 mmol |
| Yield | 0.02 g, 22%, white solid | 0.04 g, 14%, light yellow solid |
| $^1$H NMR (DMSO-$d_6$, 400 MHz) | δ 5.38 (s, 2H), 7.12 (m, 1H), 7.40 (m, 1H), 7.52 (d, J = 8.40 Hz, 2H), 7.80 (d, J = 8.40 Hz, 2H), 7.88 (br s, 1H), 8.16 (br s, 1H) and 8.73 (s, 1H) | δ 5.39 (s, 2H), 7.13 (t, J = 8.80 Hz, 1H), 7.32-7.46 (m, 4H), 7.78 (d, J = 7.20 Hz, 2H), 7.88 (br s, 1H), 8.16 (br s, 1H) and 8.70 (s, 1H) |
| MS-ES+ | 365.03 | 331.15 |
| HPLC method no., Rt (min) | 9, 16.25 | 8, 15.46 |

Previous rows (from continued table):

| | | |
|---|---|---|
| $^1$H NMR (DMSO-$d_6$, 400 MHz) | δ 5.31 (s, 2H), 7.12 (t, J = 8.80 Hz, 1H), 7.40 (m, 1H), 7.52 (d, J = 8.40 Hz, 2H), 7.87 (br s, 2H), 8.09 (d, J = 8.40 Hz, 2H) and 8.15 (br s, 1H) | δ 5.29 (s, 2H), 6.89 (m, 1H), 7.09 (m, 1H), 7.28-7.41 (m, 4H), 7.78 (s, 1H), 7.86 (br s, 1H), 8.13 (br s, 1H) and 9.79 (s, 1H) |
| MS-ES+ | 431.21 | 363.12 |
| HPLC method no., Rt (min) | 8, 17.13 | 8, 14.66 |

Scheme 40:

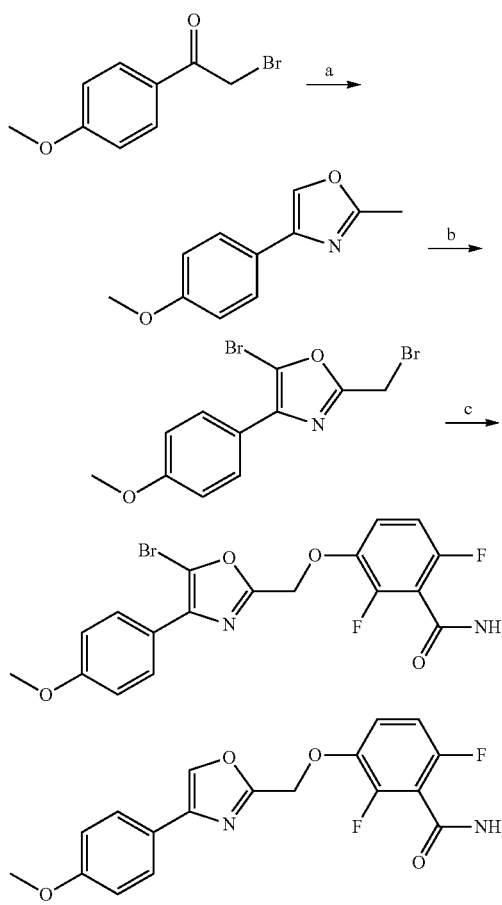

Example 311

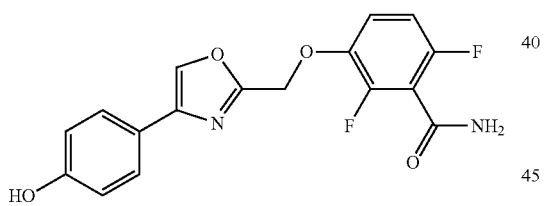

Example 312

(a) Acetamide;
(b) NBS, AIBN, CCl₄;
(c) 2,6-difluoro-3-hydroxy benzamide, K₂CO₃, DMF;
(d) Zn/Acetic aciid;
(e) BBr₃, DCM.

4-(4-Methoxy-phenyl)-2-methyl-oxazole

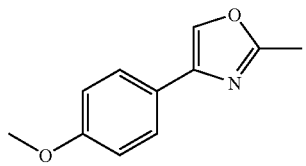

Prepared as per the method mentioned in Scheme 31.

5-Bromo-2-bromomethyl-4-(4-methoxy-phenyl)-oxazole

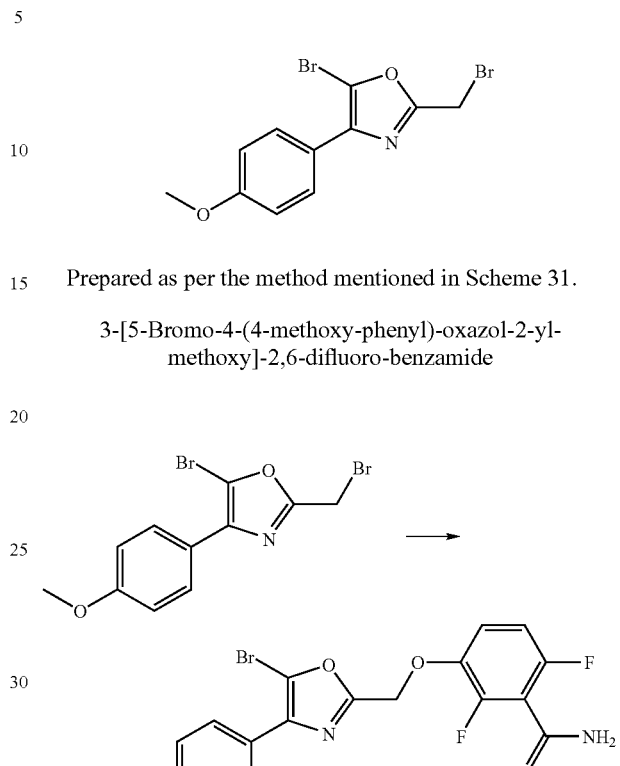

Prepared as per the method mentioned in Scheme 31.

3-[5-Bromo-4-(4-methoxy-phenyl)-oxazol-2-yl-methoxy]-2,6-difluoro-benzamide

Prepared as per the method mentioned in Scheme 31.

Example 311

2,6-Difluoro-3-[4-(4-methoxy-phenyl)-oxazol-2-ylmethoxy]-benzamide

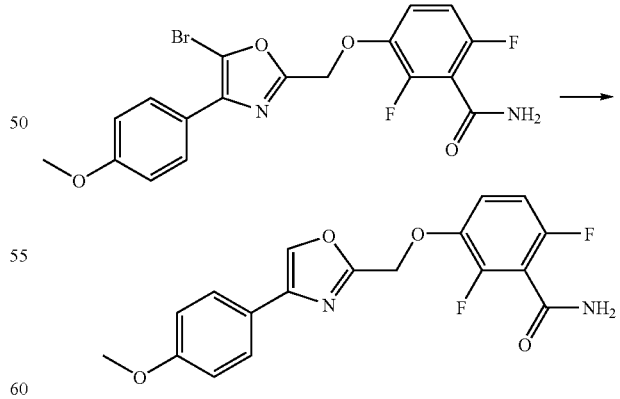

To a solution of 3-[5-Bromo-4-(4-methoxy-phenyl)-oxazol-2-ylmethoxy]-2,6-difluoro-benzamide (0.06 g, 0.13 mmol) in the 5 ml of acetic acid was added 50 mg of Zn dust. Reaction mixture was heated at 120° C. for 1 h. After the completion of the reaction mixture (TLC monitoring), water (25 mL) was added and pH was adjusted to 8-9 with NaOH solution and extracted with ethyl acetate (3×50 mL). The combined organics was washed with water, brine, dried (Na₂SO₄), filtered and concentrated to get the desired product (0.02 g, 40%) as a white solid. $^1$H NMR (DMSO-d₆, 400 MHz): δ 3.77 (s, 3H), 5.36 (s, 2H), 6.99 (d, J=8.40 Hz, 2H), 7.12 (m, 1H), 7.37 (m, 1H), 7.71 (d, J=8.40 Hz, 2H), 7.87 (br s, 1H), 8.15 (br s, 1H) and 8.56 (s, 1H). MS ES+ (361.24), HPLC (method I) Rt=15.41 min.

Example 312

2,6-Difluoro-3-[4-(4-hydroxy-phenyl)-oxazol-2-ylmethoxy]-benzamide

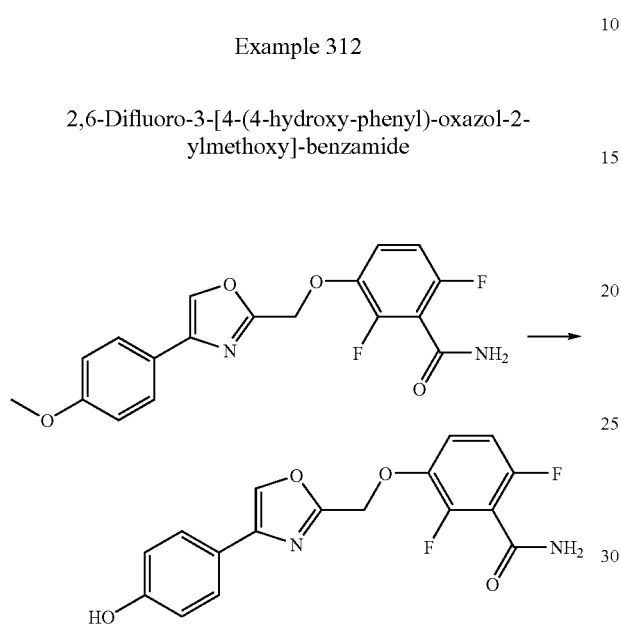

A solution of 2,6-Difluoro-3-[4-(4-methoxy-phenyl)-oxazol-2-ylmethoxy]-benzamide (0.20 g, 0.55 mmol) in 10 ml of DCM was cooled to −78° C. followed by addition of BBr₃ (0.10 ml, 2.20 mmol). The reaction mixture was stirred at 25° C. for 2 h. After the completion of the reaction mixture (TLC monitoring), solution of NaHCO₃ (20 mL) was added at 0° C. and extracted with ethyl acetate (3×50 mL). The combined organics was washed with water, brine, dried (Na₂SO₄), filtered and concentrated. The residue was purified by column chromatography on silica (60-120 M) using ethyl acetate/hexane (50:50) as the eluent to provide the title compound as white solid (0.012 g, 6%). $^1$H NMR (DMSO-d₆, 400 MHz): δ 5.35 (s, 2H), 6.82 (d, J=8.40 Hz, 2H), 7.14 (m, 1H), 7.38 (m, 1H), 7.58 (d, J=8.40 Hz, 2H), 7.87 (br s, 1H), 8.15 (br s, 1H), 8.47 (s, 1H) and 9.63 (s, 1H). MS ES+ (347.22), HPLC (method I) Rt=14.00 min.

Scheme 41:

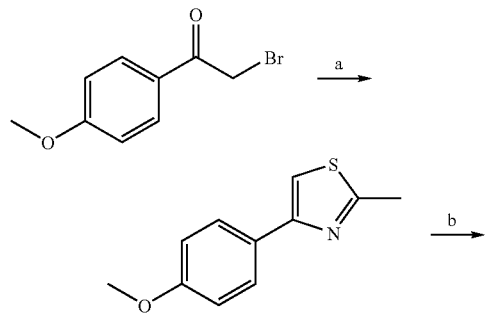

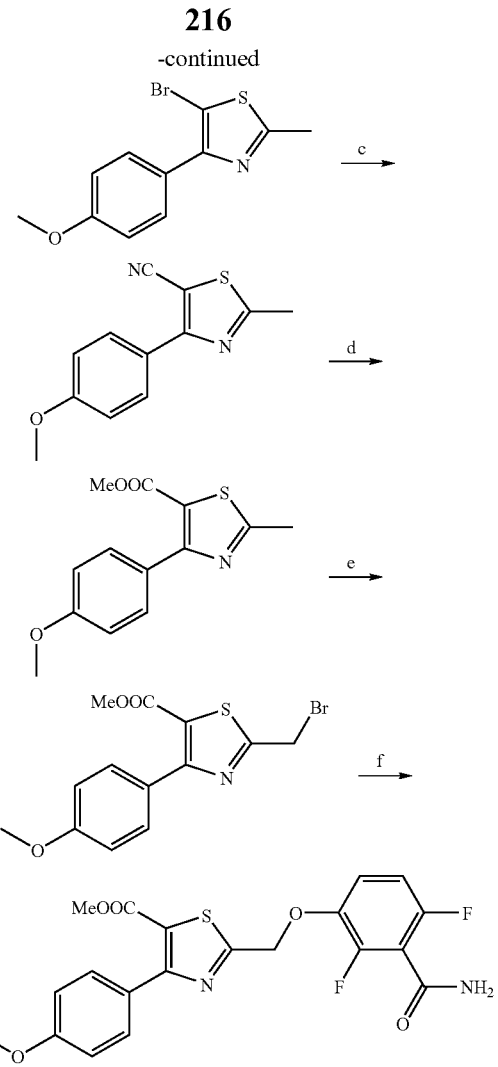

(a) Thioacetamide;
(b) NBS, AIBN, CCl₄;
(c) CuCN, Pyridine;
(d) MeOH, dry HCl;
(e) NBS, AIBN, CCl₄;
(f) 2,6-difluoro-3-hydroxy benzamide, K₂CO₃, DMF.

4-(4-Methoxy-phenyl)-2-methyl-thiazole

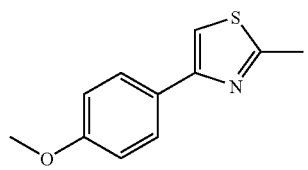

A mixture of thioacetamide (16.0 g, 213 mmol) and 2-Bromo-1-(4-methoxy-phenyl)-ethanone (4.0 g, 17.5 mmol) was heated at 140° C. for 24 h under nitrogen atmosphere. After the completion of the reaction mixture (TLC monitoring), water (25 mL) was added and extracted with ethyl acetate (3×50 mL). The combined organics was washed with water, brine, dried (Na₂SO₄), filtered and concentrated.

The crude residue was purified over silica gel (230-400 M, 1% EtOAc-Hexane) to get the desired product (2.5 g, 69%).

5-Bromo-4-(4-methoxy-phenyl)-2-methyl-thiazole

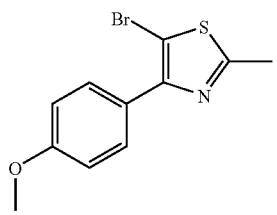

To the solution of 5-Bromo-2-bromomethyl-4-(4-methoxy-phenyl)-thiazole (5.0 g, 24.3 mmol) in the 20 ml of CCl₄ was added NBS (4.32 g, 24.3 mmol) and AIBN (0.4 g, 2.43 mmol). The reaction mixture was heated at 100° C. for 2 h under nitrogen atmosphere. After the completion of the reaction mixture (TLC monitoring), the reaction mixture was evaporated to dryness under reduced pressure and the residue was purified by column chromatography on silica (230-400 M) using 1% ethyl acetate/hexane eluent to give the desired product (4.0 g, 58%).

4-(4-Methoxy-phenyl)-2-methyl-thiazole-5-carbonitrile

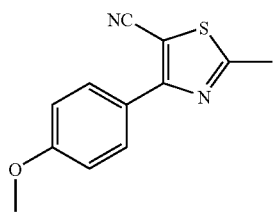

To a solution of 5-Bromo-4-(4-methoxy-phenyl)-2-methyl-thiazole (2.0 g, 7.0 mmol) in 15 ml of pyridine was added CuCN (3.10 g, 35.2 mmol) and the reaction mixture was heated to 150° C. in microwave for 2 h. After the completion of the reaction pH was adjusted to 3-4 with 1 N HCl solution and extracted with ethyl acetate (3×50 mL). The combined organics was washed with water, brine, dried (Na₂SO₄), filtered and concentrated. The crude residue was purified over silica gel (60-120 M, 12% EtOAc-Hexane) to get the desired product (1.5 g, 92%) as a white solid.

4-(4-Methoxy-phenyl)-2-methyl-thiazole-5-carboxylic acid methyl ester

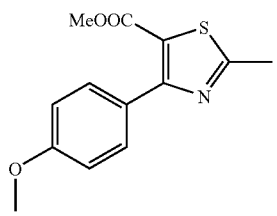

To a solution of 4-(4-Methoxy-phenyl)-2-methyl-thiazole-5-carbonitrile (0.50 g, 2.1 mmol) in 15 ml of methanol was passed dry HCl gas for 1 h at 0° C. The reaction mixture was stirred at 25° C. for 24 h. After the completion of the reaction mixture (TLC monitoring), The reaction mixture was evaporated to dryness under reduced pressure. Water (50 ml) was added and pH was adjusted to 7-8 with NaHCO₃ solution and extracted with ethyl acetate (3×50 mL). The combined organics was washed with water, brine, dried (Na₂SO₄), filtered and concentrated to get the desired product (0.25 g, 44%) as a white solid.

2-Bromomethyl-4-(4-methoxy-phenyl)-thiazole-5-carboxylic acid methyl ester

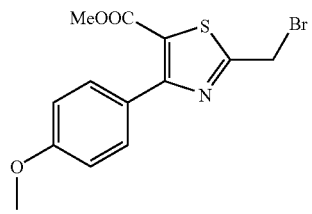

To the solution of 4-(4-Methoxy-phenyl)-2-methyl-thiazole-5-carboxylic acid methyl ester (0.25 g, 0.94 mmol) in the 20 ml of CCl₄ was added NBS (0.16 g, 0.94 mmol) and AIBN 0.015 g, 0.094 mmol). The reaction mixture was heated at 100° C. for 2 h under nitrogen atmosphere. After the completion of the reaction mixture (TLC monitoring), the reaction mixture was evaporated to dryness under reduced pressure and the residue was purified by column chromatography on silica (230-400 M) using 10% ethyl acetate/hexane as a eluent to give the desired product (0.078 g, 24%).

Example 313

2-(3-Carbamoyl-2,4-difluoro-phenoxymethyl)-4-(4-methoxy-phenyl)-thiazole-5-carboxylic acid methyl ester

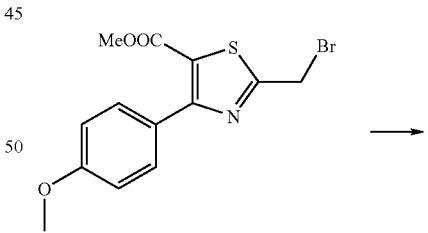

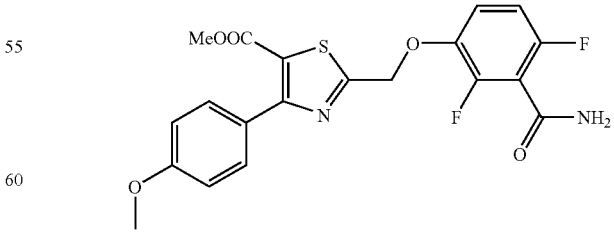

To a solution of 2-Bromomethyl-4-(4-methoxy-phenyl)-thiazole-5-carboxylic acid methyl ester (0.05 g, 0.14 mmol) in 2 ml of anhydrous DMF was added 2,6-Difluoro-3-hydroxy-benzamide (0.025 g, 0.14 mmol) and potassium carbonate (0.07 g, 0.50 mmol). The reaction mixture was stirred at 25° C. for 24 h under nitrogen atmosphere. The reaction mixture was evaporated to dryness under reduced pressure and the residue was purified by column chromatography on silica (60-120 M) using ethyl acetate/hexane (50:50) as the eluent to provide the title compound as white solid (0.025 g, 40%). $^1$H NMR (DMSO-d$_6$, 400 MHz): δ 3.76 (s, 3H), 3.81 (s, 3H), 5.60 (s, 2H), 7.01 (d, J=8.40 Hz, 2H), 7.12 (m, 1H), 7.41 (m, 1H), 7.74 (d, J=8.40 Hz, 2H), 7.90 (br s, 1H) and 8.18 (br s, 1H). MS ES+ (435.06), HPLC (method I) Rt=15.86 min.

Scheme 42:

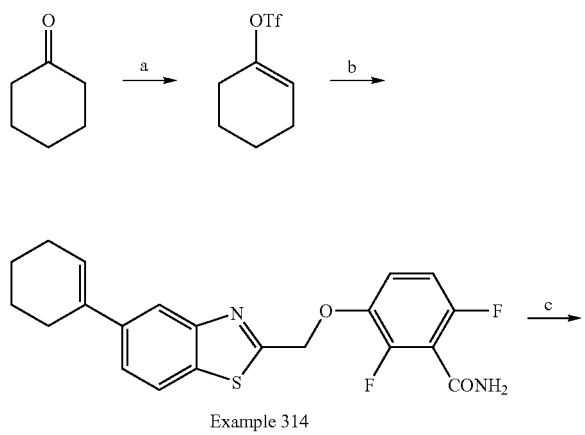

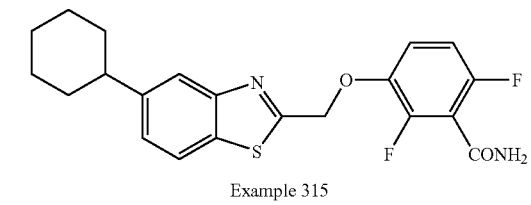

Example 315

(a) Triflic anhydride, pyidirine, DCM;
(b) 2,6-Difluoro-3-[5-(4,4,5,5-tetramethyl-[1,3,2]dioxaborolan-2-yl]-1H-inden-2-ylmethoxy]-benzamide, Pd catalyst, Potassium phosphate;
(c) H$_2$, Pd—C.

Trifluoromethanesulfonic acid cyclohex-1-enyl ester

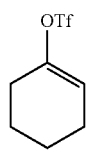

To a solution of cyclohexanone (5.0 g, 51 mmol) in the 80 ml of DCM was added pyridine (4.48 ml, 56.0 mmol) and the resulting reaction mixture was cooled to −78° C. To the reaction mixture the solution of triflic anhydride (7.40 ml, 56.0 mmol) in 30 ml of DCM was added over the period of 1 h. Reaction mixture was stirred at 25° C. for 24 h. After the completion of the reaction mixture (TLC monitoring), the reaction mixture was evaporated to dryness under reduced pressure. The residue was triturated with n-pentane and decanted the organic layer, dried (Na$_2$SO$_4$), filtered and concentrated to give the desired product (5.0 g, 42%).

Example 314

3-(5-Cyclohex-1-enyl-1H-inden-2-ylmethoxy)-2,6-difluoro-benzamide

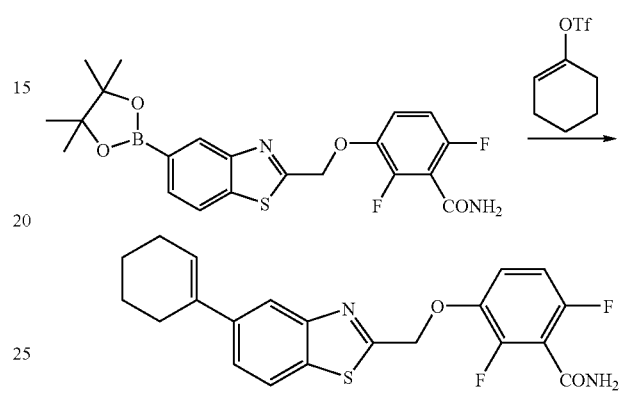

To a solution of 2,6-Difluoro-3-[5-(4,4,5,5-tetramethyl-[1,3,2]dioxaborolan-2-yl)-1H-inden-2-ylmethoxy]-benzamide (0.10 g, 0.20 mmol) in 3 ml of anhydrous DMF and water (1.5 ml) was added trifluoromethanesulfonic acid cyclohex-1-enyl ester (0.15 g, 0.60 mmol) and potassium phosphate (0.057 g, 0.20 mmol). The reaction mixture was degassed for 10 minutes followed by addition of dichlorobis(triphenyl phosphine) palladium (II) (0.02 g, 0.03 mmol). The reaction mixture was heated at 80° C. for 1 h under the nitrogen atmosphere. After the completion of the reaction mixture (TLC monitoring), water (25 mL) was added and extracted with ethyl acetate (3×50 mL). The combined organics was washed with water, brine, dried (Na$_2$SO$_4$), filtered and concentrated. The crude residue was purified over silica gel (230-400 M, 45% EtOAc-Hexane) to get the desired product (0.017 g, 19%) as a white solid. $^1$H NMR (DMSO-d$_6$, 400 MHz): δ 1.63 (m, 4H), 2.20 (m, 2H), 2.45 (m, 2H), 5.67 (s, 2H), 6.29 (m, 1H), 7.12 (m, 1H), 7.37 (m, 1H), 7.57 (m, 2H), 7.90 (br s, 1H), 8.03 (d, J=8.40 Hz, 1H) and 8.18 (br s, 1H). MS ES+ (401.16), HPLC (method II) Rt=14.13 min.

Example 315

3-(5-Cyclohexyl-1H-inden-2-ylmethoxy)-2,6-difluoro-benzamide

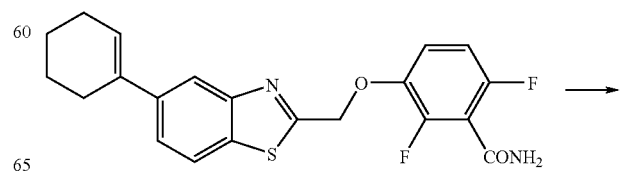

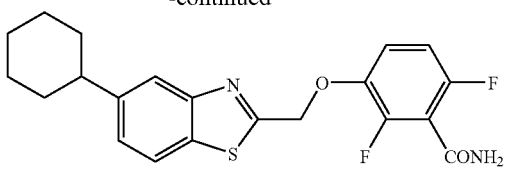

To a solution of 3-(5-Cyclohex-1-enyl-1H-inden-2-yl-methoxy)-2,6-difluoro-benzamide (0.01 g, 0.25 mmol) in 5 ml of anhydrous methanol was added Pd—C (10%, 100 mg). The reaction mixture was stirred at 25° C. for 48 h under hydrogen atmosphere. The reaction mixture was filtered over the bed of celite and evaporated to dryness under reduced pressure to give the title compound as white solid (0.01 g, 10%). $^1$H NMR (DMSO-$d_6$, 400 MHz); δ 1.40 (m, 6H), 1.72 (m, 4H), 2.63 (m, 1H), 5.66 (s, 2H), 7.09 (m, 1H), 7.35 (m, 2H), 7.83 (br s, 1H), 7.89 (d, J=8.40 Hz, 1H), 7.99 (d, J=8.40 Hz, 1H) and 8.18 (br s, 1H). MS ES+ (403.33), HPLC (method II) Rt=18.76 min.

Scheme 43:

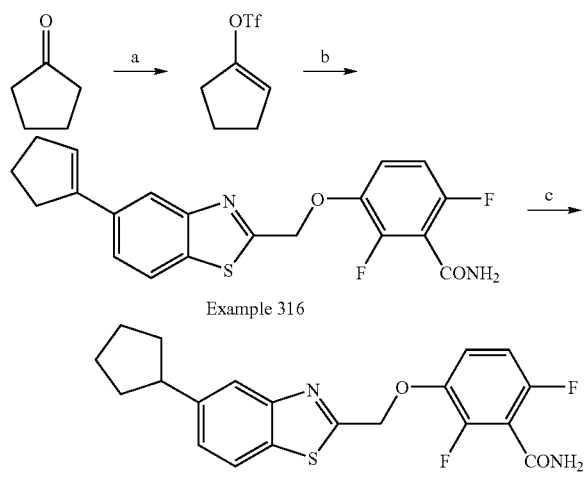

Example 316

Example 317

(a) Triflic anhydride, pyridine, DCM;
(b) 2,6-Difluoro-3-[5-(4,4,5,5-tetramethyl-[1,3,2]dioxaborolan-2-yl)-1H-inden-2-ylmethoxy]-benzamide, Pd catalyst, Potassium phosphate;
(c) H$_2$, Pd—C.

Trifluoro-methanesulfonic acid cyclopent-1-enyl ester

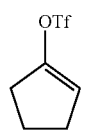

To a solution of cyclopentanone (5.0 g, 59 mmol) in the 80 ml of DCM was added pyridine (5.2 ml, 65.0 mmol) and the resulting reaction mixture was cooled to −78° C. To the reaction mixture the solution of triflic anhydride (9.2 ml, 65.0 mmol) in 30 ml of DCM was added over the period of 1 h. Reaction mixture was stirred at 25° C. for 24 h. After the completion of the reaction mixture (TLC monitoring), the reaction mixture was evaporated to dryness under reduced pressure. The residue was triturated with n-pentane and decanted the organic layer, dried (Na$_2$SO$_4$), filtered and concentrated to give the desired product (2.4 g, 22%).

Example 316

3-(5-Cyclopent-2-enyl-1H-inden-2-ylmethoxy)-2,6-difluoro-benzamide

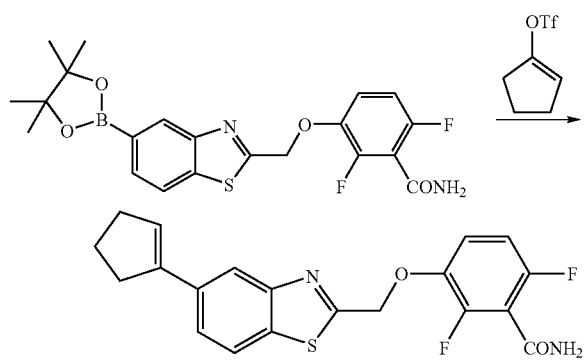

To a solution of 2,6-Difluoro-3-[5-(4,4,5,5-tetramethyl-[1,3,2]dioxaborolan-2-yl)-1H-inden-2-ylmethoxy]-benzamide (0.25 g, 0.56 mmol) in 7 ml of anhydrous DMF and water (3.5 ml) was added trifluoromethanesulfonic acid cyclopent-1-enyl ester (0.37 g, 1.70 mmol) and potassium phosphate (0.14 g, 0.60 mmol). The reaction mixture was degassed for 10 minutes followed by addition of dichlorobis(triphenyl phosphine) palladium (II) (0.05 g, 0.08 mmol). The reaction mixture was heated at 80° C. for 1 h under the nitrogen atmosphere. After the completion of the reaction mixture (TLC monitoring), water (25 mL) was added and extracted with ethyl acetate (3×50 mL). The combined organics was washed with water, brine, dried (Na$_2$SO$_4$), filtered and concentrated. The crude residue was purified over silica gel (230-400 M, 45% EtOAc-Hexane) to get the desired product (0.14 g, 65%) as a white solid. $^1$H NMR (DMSO-$d_6$, 400 MHz): δ 1.22 (m, 2H), 2.01 (m, 2H), 2.88 (m, 2H), 5.68 (s, 2H), 6.43 (s, 1H), 7.01 (t, J=9.20 Hz, 1H), 7.37 (m, 1H), 7.67 (d, J=8.40 Hz, 1H), 7.89 (br s, 1H), 7.94 (s, 1H), 8.07 (d, J=8.40 Hz, 1H) and 8.18 (br s, 1H). MS ES+ (387.15), HPLC (method II) Rt=13.74 min.

Example 317

3-(5-Cyclopentyl-1H-inden-2-ylmethoxy)-2,6-difluoro-benzamide

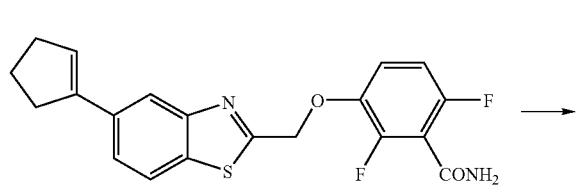

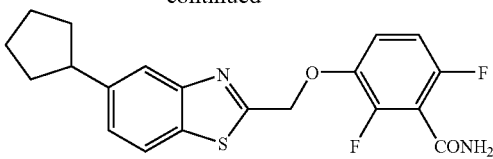

To a solution of 3-(5-Cyclopent-1-enyl-1H-inden-2-yl-methoxy)-2,6-difluoro-benzamide (0.05 g, 0.10 mmol) in 5 ml of anhydrous methanol was added Pd—C (10%, 100 mg). The reaction mixture was stirred at 25° C. for 48 h under hydrogen atmosphere. The reaction mixture was filtered over the bed of celite and evaporated to dryness under reduced pressure to give the title compound as white solid (0.005 g, 10%). $^1$H NMR (DMSO-$d_6$, 400 MHz); δ 1.22 (m, 2H), 1.67 (m, 4H), 1.80 (m, 2H), 2.07 (m, 2H), 3.20 (m, 1H), 5.67 (s, 2H), 7.09 (m, 1H), 7.37 (m, 2H), 7.87 (m, 2H), 8.0 (m, 1H) and 8.18 (br s, 1H). MS ES+ (389.12), HPLC (method II) Rt=18.19 min.

Examples 318 to 333

Scheme 44 (Examples 318-320):

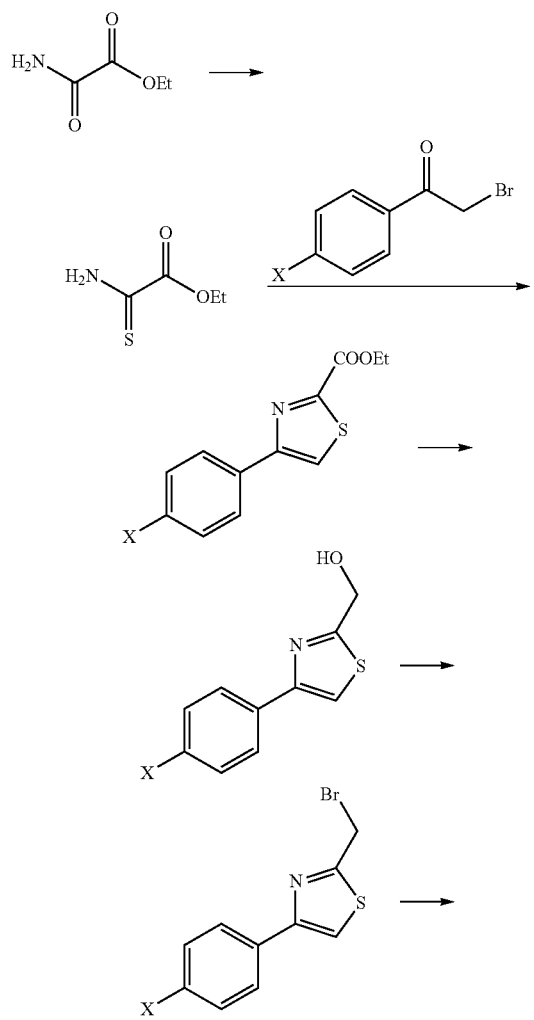

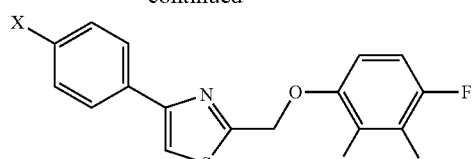

X = F, Example 318
X = CF$_3$, Example 319
X = OCF3, Example 320

(a) Lawesson's reagent;
(b) substituted bromoacetophenones;
(c) LAH, THF;
(d) PBr$_3$, Toluene;
(e) 2,6-dufluoro-3-hydroxy benzamide, K$_2$CO$_3$, DMF.

Ethylthio-oxamate

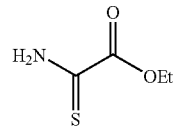

To the solution of ethyl oxamate (10.0 g, 85.30 mmol) in 120 ml of toluene was added Lawesson's reagent (24.15 g, 59.7 mmol) and the reaction mixture was heated at 120° C. for 12 h. After the completion of the reaction mixture (TLC monitoring), the reaction mixture was evaporated to dryness under reduced pressure. The residue was purified by column chromatography on silica (230-400 M) using ethyl acetate/hexane (5:95) as the eluent to provide the title compound (1.8 g, 16%).

4-(4-Trifluoromethyl-phenyl)-thiazole-2-carboxylic acid ethyl ester (Representative example)

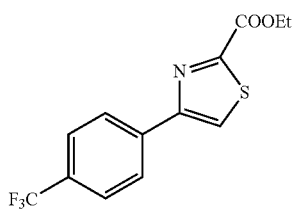

To the solution of 2-Bromo-1-(4-trifluoromethyl-phenyl)-ethanone (0.50 g, 0.80 mmol) in 7 ml of ethanol was added ethyl thio-oxamate (0.15 g, 1.14 mmol). The reaction mixture was heated at 80° C. for 2 h under nitrogen atmosphere. After the completion of the reaction mixture (TLC monitoring), the reaction mixture was concentrated under reduced pressure, water (25 mL) was added and extracted with ethyl acetate (3×50 mL). The combined organics was washed with water, brine, dried (Na$_2$SO$_4$), filtered and concentrated. The crude residue was purified over silica gel (230-400 M, 2% EtOAc- Hexane) to get the desired product (0.21 g, 76%). The other derivatives were also prepared by the same general method.

[4-(4-Trifluoromethyl-phenyl)-thiazol-2-yl]-methanol

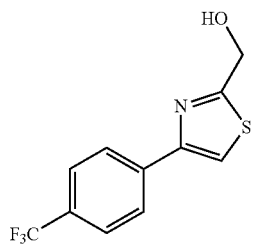

To an ice-cold suspension of LAH (0.056 g, 1.40 mmol) the 8 ml of anhydrous THF was added dropwise a solution of 4-(4-Trifluoromethyl-phenyl)-thiazole-2-carboxylic acid ethyl ester (0.21 g, 0.71 mmol) in the 5 ml of THF. The reaction mixture was stirred at 25° C. for 1 h. After the completion of the reaction mixture (TLC monitoring), cooled the reaction mixture to 0° C. and quenched with 2.5 ml of water followed by the addition of 15% NaOH solution (2 mL) and finally 4 ml of water. The resulting solution was filtered through celite bed and the filtrate was concentrated under reduced pressure. Water (50 mL) was added and extracted with ethyl acetate (3×50 mL). The combined organics was washed with water, brine, dried (Na$_2$SO$_4$), filtered and concentrated to give the desired product (0.13 g, 70%). The other derivatives were also prepared by the same general method.

2-Bromomethyl-4-(4-trifluoromethyl-phenyl)-thiazole

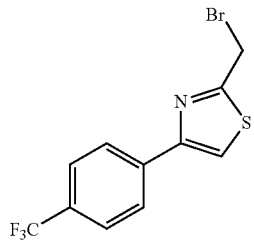

To the solution of [4-(4-Trifluoromethyl-phenyl)-thiazol-2-yl]-methanol (0.13 g, 0.50 mmol) in 2 ml of toluene was added PBr$_3$ (0.072 ml, 0.752 mmol) and the reaction mixture was heated at 120° C. for 20 min under nitrogen atmosphere. After the completion of the reaction mixture (TLC monitoring), water (25 mL) was added and extracted with ethyl acetate (3×50 mL). The combined organics was washed with water, brine, dried (Na$_2$SO$_4$), filtered and concentrated. The crude residue was purified over silica gel (230-400 M, 1% EtOAc-Hexane) to get the desired product (0.04 g, 25%). The other derivatives were also prepared by the same general method.

Scheme 45 (Example 321):

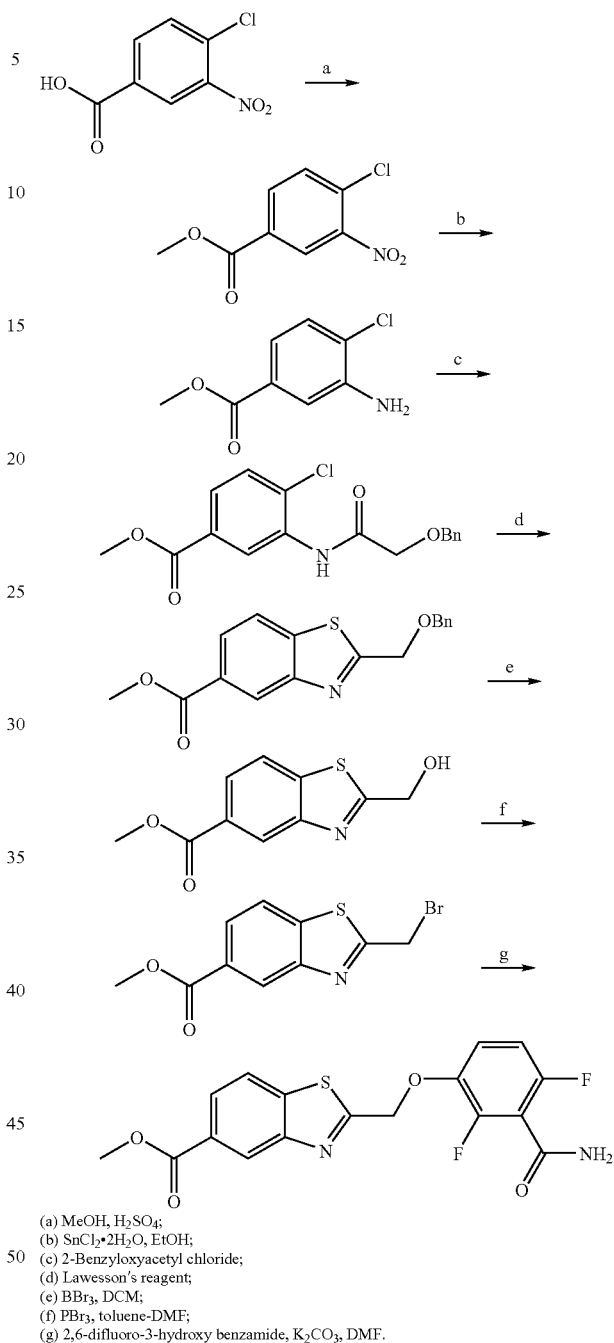

(a) MeOH, H$_2$SO$_4$;
(b) SnCl$_2$·2H$_2$O, EtOH;
(c) 2-Benzyloxyacetyl chloride;
(d) Lawesson's reagent;
(e) BBr$_3$, DCM;
(f) PBr$_3$, toluene-DMF;
(g) 2,6-difluoro-3-hydroxy benzamide, K$_2$CO$_3$, DMF.

4-Chloro-3-nitro-benzoic acid methyl ester

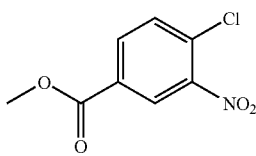

To a Solution of 4-chloro-3-nitrobenzoic acid (5.0 g, 24.81 mmol) in 50 ml of methanol was added H₂SO₄ (2 ml, 37.02 mmol) and the reaction mixture was heated at 70° C. for 5 h. After completion of the reaction mixture (TLC monitoring), the reaction mixture was evaporated to dryness under reduced pressure. Water (50 mL) was added and extracted with ethyl acetate (3×50 mL). The combined organics was, dried (Na₂SO₄), filtered and concentrated to give the desired product (5.04 g, 94%).

3-Amino-4-chloro-benzoic acid methyl ester

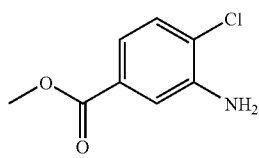

To a solution of 4-Chloro-3-nitro-benzoic acid methyl ester (5.0 g, 23.19 mmol) in 100 ml of ethanol was added SnCl₂.2H₂O (26.0 g, 115.96 mmol) and the reaction mixture was heated at 80° C. for 2 h. After the completion of the reaction mixture (TLC monitoring), the reaction mixture was evaporated to dryness under reduced pressure. Water (100 mL) was added, basified the reaction mixture with NaOH solution and extracted with hot EtOAc (3×250 mL).

The combined organics was dried over Na₂SO₄, filtered and concentrated to give the desired product (3.0 g, 69%).

3-(2-Benzyloxy-acetylamino)-4-chloro-benzoic acid methyl ester

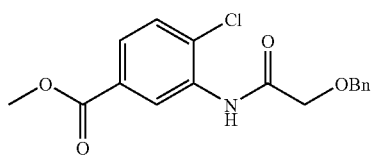

A solution of carbonic acid monobenzyl ester (3.50 g, 21.0 mmol) in the 50 ml of DCM and 0.50 ml of DMF was cooled to −78° C. followed by addition of oxalyl chloride (11.79 ml, 105 mmol). The resulting reaction mixture was stirred at room temperature for 1 h. After the completion of the reaction mixture (TLC monitoring), concentrated it to give 2-benzyloxyacetyl chloride (3.0 g, 96%). To an ice cold solution of 3-amino-4-chloro-benzoic acid methyl ester in 10 ml of DCM was added triethylamine (2.47 ml, 17.78 mmol) followed by addition of 2-benzyloxyacetyl chloride (3.0 g, 17.78 mmol) in 10 ml of DCM. The reaction mixture was stirred at 25° C. for 12 hr. After the completion of the reaction mixture (TLC monitoring), the reaction mixture was evaporated to dryness under reduced pressure. The residue was purified by column chromatography on silica (60-120 M) using ethyl acetate/hexane (5:95) as the eluent to provide the title compound (1.70 g, 31%).

3-(2-Benzyloxy-thioacetylamino)-4-chloro-benzoic acid methyl ester

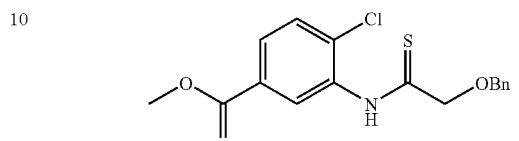

To the solution of 3-(2-Benzyloxy-acetylamino)-4-chloro-benzoic acid methyl ester (1.70 g, 5.10 mmol) in 20 ml of toluene was added Lawesson's reagent (1.03 g, 2.50 mmol) and the reaction mixture was heated at 120° C. for 2 h. After the completion of the reaction mixture (TLC monitoring), the reaction mixture was evaporated to dryness under reduced pressure. The residue was purified by column chromatography on silica (60-120 M) using ethyl acetate/hexane (5:95) as the eluent to provide the title compound (1.20 g, 67%).

2-Benzyloxymethyl-benzothiazole-6-carboxylic acid methyl ester

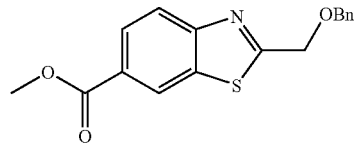

To a solution of 3-(2-Benzyloxy-thioacetylamino)-4-chloro-benzoic acid methyl ester (1.20 g, 3.40 mmol) in the 8 ml of NMP was added NaH (0.12 g, 5.10 mmol) portion wise. The reaction mixture was heated at 160° C. for 3 h. After the completion of the reaction mixture (TLC monitoring), the reaction mixture was poured into 150 ml of ice-cold water and extracted with ethyl acetate (3×150 mL). The combined organics was dried (Na₂SO₄), filtered and concentrated to give the desired product. (1.07 g, 56%).

2-Hydroxymethyl-benzothiazole-6-carboxylic acid methyl ester

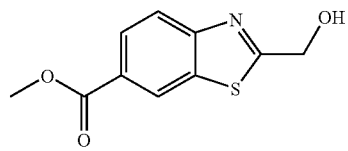

A solution of 2-Benzyloxymethyl-benzothiazole-6-carboxylic acid methyl ester (0.10 g, 0.32 mmol) in 2 ml of DCM was cooled to −78° C. followed by addition of BBr₃ (0.06 ml, 0.64 mmol). The reaction mixture was stirred at 25° C. for 2 h. After the completion of the reaction mixture (TLC monitoring), solution of NaHCO₃ (20 mL) was added at 0° C. and extracted with ethyl acetate (3×50 mL). The combined organics was washed with water, brine, dried (Na₂SO₄), filtered and concentrated to get the desired product (0.08 g, Crude yield).

2-Bromomethyl-benzothiazole-6-carboxylic acid methyl ester

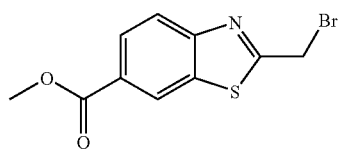

To a solution of 2-Hydroxymethyl-benzothiazole-6-carboxylic acid methyl ester (0.08 g, 0.40 mmol) in 5 ml of toluene and 1 ml of DMF was added PBr₃ (0.06 ml, 0.60 mmol). The reaction mixture was heated at 120° C. for 20 min under nitrogen atmosphere. After the completion of the reaction mixture (TLC monitoring), water (25 mL) was added and extracted with ethyl acetate (3×50 mL). The combined organics was washed with water, brine, dried (Na₂SO₄), filtered and concentrated to get the desired product (0.044 g, 36%).

Scheme 46 (Example 322):

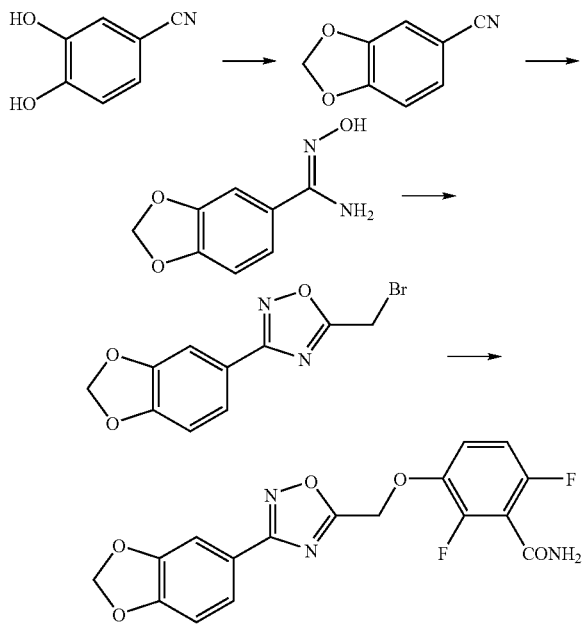

Benzo[1,3]dioxole-5-carbonitrile

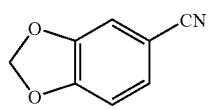

To a solution of 3,4 Dihydroxy benzonitrile (5.0 g, 37.0 mmol) in 20 ml of DMF was added dibromomethane (19.25 g, 110.0 mmol) and potassium carbonate (25.50 g, 184.90 mmol). The reaction mixture was heated at 120° C. for 2 h under the nitrogen atmosphere. After the completion of the reaction mixture (TLC monitoring), reaction mixture was cooled to room temperature. Water (50 ml) was added to the reaction mixture and extracted the compound with ethyl acetate (3×100 mL). The combined organic layers were dried over anhydrous Na₂SO₄, and evaporated to dryness under reduced pressure to give the title compound as yellow solid (5.16 g, 94.8%).

N-Hydroxy-benzo[1,3]dioxole-5-carboxamidine

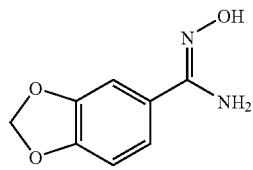

To a solution of Benzo[1,3]dioxole-5-carbonitrile (5.0 g, 33.9 mmol) in EtOH (100 mL) was added hydroxylamine hydrochloride (4.68 g, 67.90 mmol) and NaOH (2.71 g, 67.9 mmol). The resulting reaction mixture was refluxed for 12 h. After the completion of the reaction (TLC monitoring), the mixture was concentrated, added EtOH and filtered. The filtrate was evaporated under reduced pressure and used as such for the next step (crude yield 4.8 g, 78.68%).

3-Benzo[1,3]dioxol-5-yl-5-bromomethyl-[1,2,4]oxadiazole

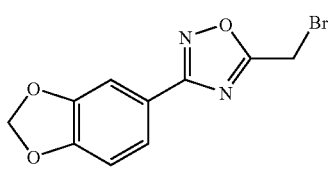

Bromoacetyl bromide (0.22 g, 1.10 mmol) was added to N-Hydroxy-benzo[1,3]dioxole-5-carboxamidine (0.40 g, 0.55 mmol) and K₂CO₃ (0.38 g, 0.78 mmol). The reaction mixture was heated at 100° C. for 15 min. After the completion of the reaction mixture (TLC monitoring), water (25 mL) was added and extracted with ethyl acetate (3×50 mL). The combined organics was washed with water, brine, dried (Na₂SO₄), filtered and concentrated. The crude residue was purified over silica gel (60-120 M, 5% EtOAc-Hexane) to get the desired product (0.05 g, 31%).

Scheme 47 (Examples 323):

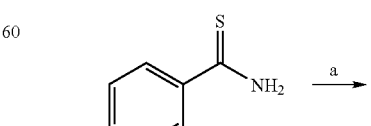

2-(4-Methoxy-phenyl)-thiazole-4-carboxylic acid ethyl ester

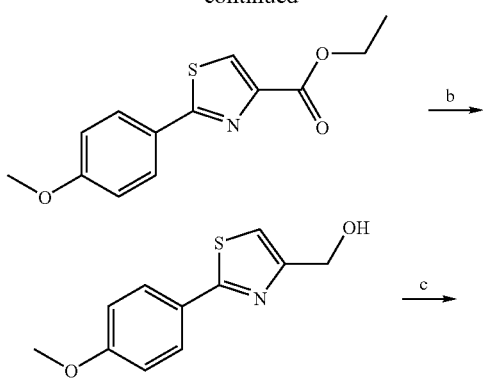

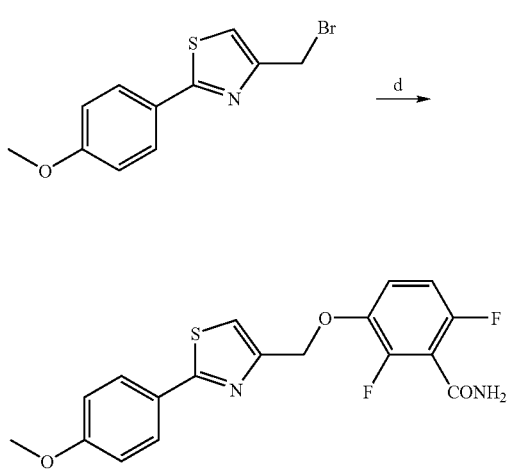

(a) Ethyl bromopyruvate, EtOH;
(b) LAH, THF;
(c) PBr₃, toluene;
(d) 2,6-difluoro-3-hydroxy benzamide, K₂CO₃, DMF.

2-(4-Methoxy-phenyl)-thiazole-4-carboxylic acid ethyl ester

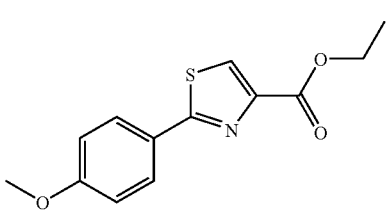

To an ice-cold solution of 4-methoxy-thiobenzamide (0.50 g, 2.98 mmol) in ethanol (25 ml) was added triethylamine (0.41 ml, 2.98 mmol) followed by dropwise addition of ethyl bromopyruvate (0.56 ml, 4.40 mmol). The reaction mixture was heated at 65° C. for 12 h. After the completion of the reaction mixture (TLC monitoring), the reaction mixture was evaporated to dryness under reduced pressure, water (25 mL) was added and extracted with ethyl acetate (3×50 mL). The combined organics was washed with water, brine, dried (Na₂SO₄), filtered and concentrated. The crude residue was purified over silica gel (60-120 M, 10% EtOAc-Hexane) to get the desired product (0.38 g, 48%).

[2-(4-Methoxy-phenyl)-thiazol-4-yl]-methanol

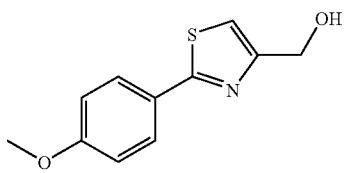

To an ice-cold suspension of LAH (0.08 g, 2.07 mmol) in 10 ml of anhydrous THF was added a solution of 2-(4-Methoxy-phenyl)-thiazole-4-carboxylic acid ethyl ester (0.26 g, 0.98 mmol) in 5 ml of THF. The reaction mixture was heated up to 60° C. for 1 h. After the completion of the reaction mixture (TLC monitoring), the reaction mixture was cooled to 0° C., water (2.0 ml) was added followed by the addition of 15% NaOH solution (2 mL) and finally 4 ml of water. The resulting solution was filtered through celite bed and concentrated under reduced pressure; water (25 mL) was added and extracted with ethyl acetate (3×50 mL). The combined organics was washed with water, brine, dried (Na₂SO₄), filtered and concentrated to give the desired product (0.14 g, 64%).

4-Bromomethyl-2-(4-methoxy-phenyl)-thiazole

To a solution of [2-(4-Methoxy-phenyl)-thiazol-4-yl]-methanol (0.12 g, 0.50 mmol) in 3 ml of toluene was added PBr₃ (0.078 ml, 0.813 mmol) and the reaction mixture was heated at 120° C. for 20 min under nitrogen atmosphere. After the completion of the reaction mixture (TLC monitoring), water (25 mL) was added and extracted with ethyl acetate (3×50 mL). The combined organics was washed with water, brine, dried (Na₂SO₄), filtered and concentrated to get the desired product (0.13 g, 84%).

Scheme 48 (Example 324):

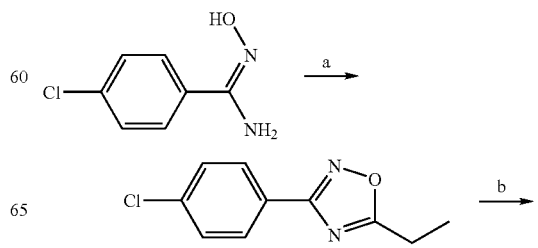

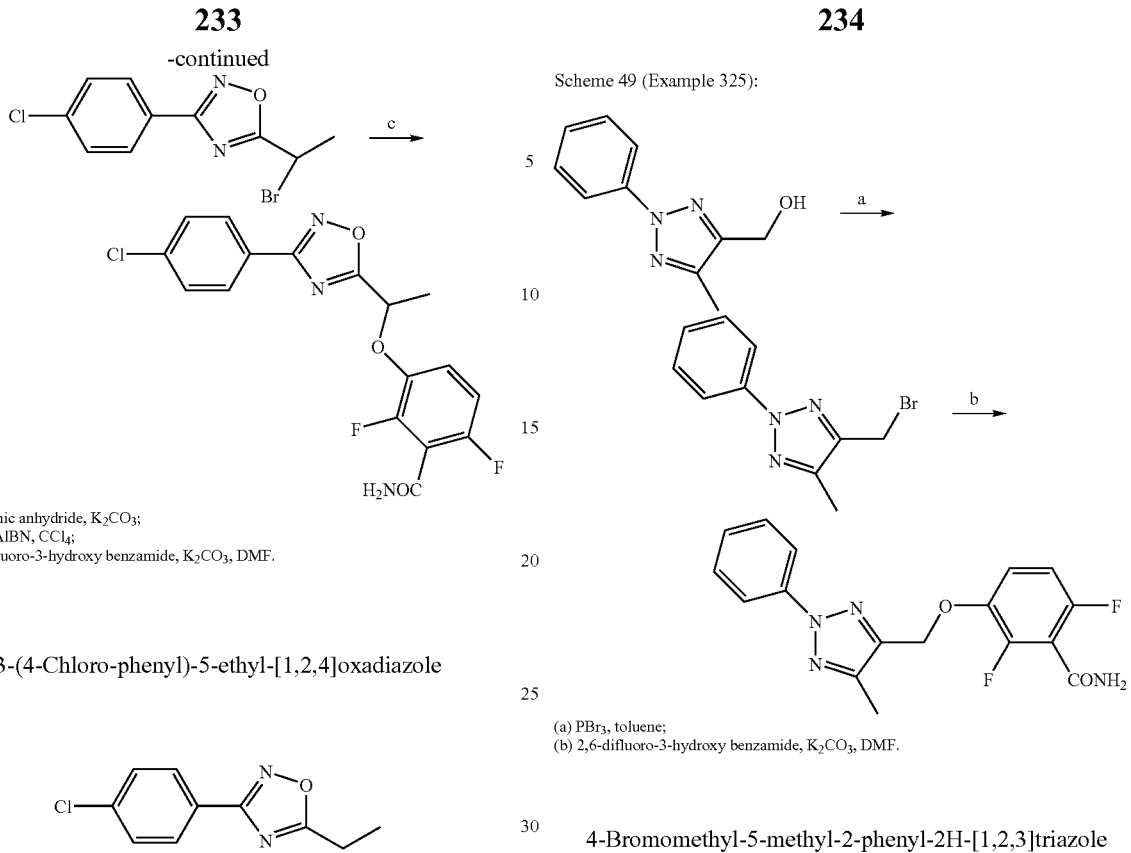

(a) Propionic anhydride, K₂CO₃;
(b) NBS, AIBN, CCl₄;
(c) 2,6-difluoro-3-hydroxy benzamide, K₂CO₃, DMF.

3-(4-Chloro-phenyl)-5-ethyl-[1,2,4]oxadiazole

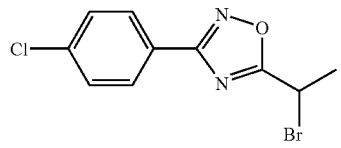

Propionic anhydride (0.75 mL, 5.79 mmol) was added to 4-Chloro-N-hydroxy-benzamide (0.50 g, 2.89 mmol) and K₂CO₃ (2.0 g, 14.48 mmol). The reaction mixture was heated at 100° C. for 30 min. After the completion of the reaction mixture (TLC monitoring), the reaction mixture was cooled to 0° C., added water (25 mL) and extracted with ethyl acetate (3×50 mL). The combined organics was washed with water, brine, dried (Na₂SO₄), filtered and concentrated. The crude residue was purified over silica gel (60-120 M, 5% EtOAc-Hexane) to get the desired product (0.29 g, 48%).

5-(1-Bromo-ethyl)-3-(4-chloro-phenyl)-[1,2,4]oxa-diazole

To a solution of 3-(4-Chloro-phenyl)-5-ethyl-[1,2,4]oxa-diazole (0.29 g, 1.38 mmol) in CCl₄ (10 mL) was added NBS (0.24 g, 1.38 mmol) and AIBN (0.02 g, 0.0001 mmol). The reaction mixture was heated at 100° C. for 2 h under nitrogen atmosphere. After the completion of the reaction mixture (TLC monitoring), the reaction mixture was evaporated to dryness under reduced pressure and the residue was purified by column chromatography on silica (230-400 M) using 1% ethyl acetate/hexane as eluent to give the desired product (0.12 g, 30%).

Scheme 49 (Example 325):

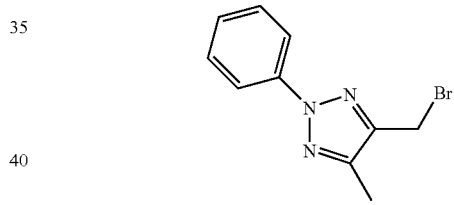

(a) PBr₃, toluene;
(b) 2,6-difluoro-3-hydroxy benzamide, K₂CO₃, DMF.

4-Bromomethyl-5-methyl-2-phenyl-2H-[1,2,3]triazole

To a solution of (5-Methyl-2-phenyl-2H-[1,2,3]triazol-4-yl)-methanol (0.25 g, 1.30 mmol) in 10 ml of toluene was added PBr₃ (0.53 g, 1.90 mmol) and the reaction mixture was heated at 120° C. for 20 min under nitrogen atmosphere. After the completion of the reaction mixture (TLC monitoring), water (25 mL) was added and extracted with ethyl acetate (3×50 mL). The combined organics was washed with water, brine, dried (Na₂SO₄), filtered and concentrated to get the desired product (0.30 g, 90%) as a yellow solid.

Scheme 50 (Examples 326):

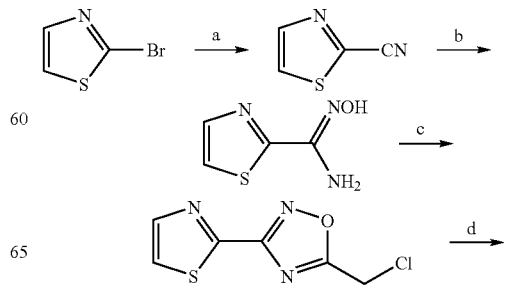

-continued

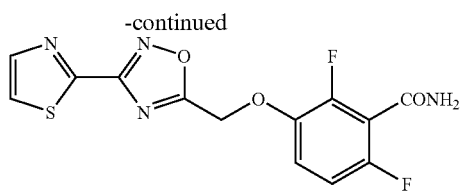

(a) CuCN, Pyridine;
(b) Hydroxylamine hydrochloride, ethanol;
(c) chloroacetyl chloride;
(d) 2,6-difluoro-3-hydroxy benzamide, K$_2$CO$_3$, DMF.

Thiazole-2-carbonitrile

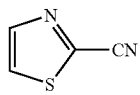

To a solution of 2-bromothiazole (1.0 g, 6.09 mmol) in 4 ml of pyridine was added CuCN (1.09 g, 12.19 mmol). The reaction mixture was heated to 150° C. for 3 h. After the completion of the reaction, pH was adjusted to 3-4 with 1N HCl solution and extracted with ethyl acetate (3×50 mL). The combined organics was washed with water, brine, dried (Na$_2$SO$_4$), filtered and concentrated to get the desired product (0.42 g, 63%).

N-Hydroxy-thiazole-2-carboxamidine

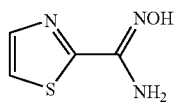

To a solution of thiazole-2-carbonitrile (0.42 g, 3.80 mmol) in EtOH (20 mL) was added hydroxylamine hydrochloride (0.53 g, 7.60 mmol) and pyridine (0.27 g, 3.40 mmol). The resulting reaction mixture was refluxed for 15 h. After the completion of the reaction (TLC monitoring), the mixture was concentrated, added EtOH and filtered. The filtrate was evaporated under reduced pressure and used as such for the next step (crude yield 0.50 g, 91% crude yield).

5-Chloromethyl-3-thiazol-2-yl-[1,2,4]oxadiazole

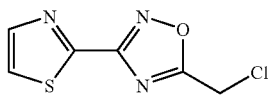

Chloroacetyl Chloride (5.0 mL, 44.5 mmol) was added to N-Hydroxy-thiazole-2-carboxamidine (0.50 g, 3.49 mmol) and K$_2$CO$_3$ (1.0 g, 7.20 mmol). The reaction mixture was heated at 100° C. for 15 min. After the completion of the reaction mixture (TLC monitoring), water (25 mL) was added and extracted with ethyl acetate (3×50 mL). The combined organics was washed with water, brine, dried (Na$_2$SO$_4$), filtered and concentrated. The crude residue was purified over silica gel (230-400 M, 10% EtOAc-Hexane) to get the desired product (0.18 g, 25%) as a white solid.

Scheme 51 (Example 327):

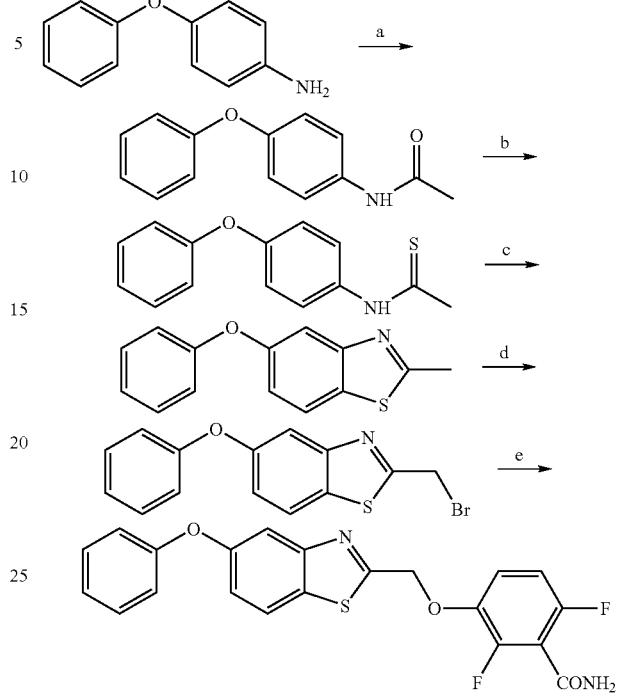

(a) acetyl chloride, Et$_3$N;
(b) Lawesson's reagent;
(c) Br$_2$, DCM;
(d) NBS, AIBN CCl$_4$;
(e) 2,6-difluoro-3-hydroxy benzamide, K$_2$CO$_3$, DMF.

N-(4-Phenoxy-phenyl)-acetamide

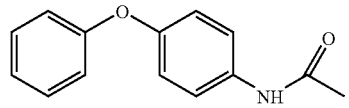

To an ice-cold solution of 4-phenoxy-phenylamine (1.0 g, 5.39 mmol) in 10 ml of DCM was added triethylamine (0.90 ml, 5.93 mmol) followed by acetyl chloride (0.50 g, 6.47 mmol). The reaction mixture was stirred at 25° C. for 2 h. After the completion of the reaction mixture (TLC monitoring), water was added extracted with DCM (3×50 mL). The combined organics was dried (Na$_2$SO$_4$), filtered and concentrated to get the desired product (1.20 g, crude yield).

N-(4-Phenoxy-phenyl)-thioacetamide

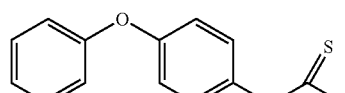

To a solution of N-(4-phenoxy-phenyl)-acetamide (1.20 g, 5.28 mmol) in 10 ml of toluene was added Lawesson's reagent (1.50 g, 3.70 mmol). The reaction mixture was heated at 120° C. for 2 h. After the completion of the reaction (TLC monitoring), the reaction mixture was evaporated to dryness under reduced pressure. The residue was purified by column chromatography on silica (60-120 M) using ethyl acetate/hexane (5:95) as the eluent to provide the title compound (0.78 g, 60.7%).

2-Methyl-6-phenoxy-benzothiazole

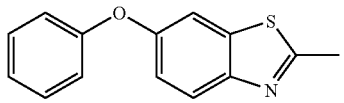

To an ice-cold solution of N-(4-phenoxy-phenyl)-thioacetamide (0.78 g, 3.20 mmol) in 10 ml of DCM was added Br$_2$ (0.32 ml, 6.40 mmol) dropwise. The reaction mixture was heated at 45° C. for 2 h. After the completion of the reaction (TLC monitoring), the reaction mixture was evaporated under reduced pressure. The residue was basified with NH$_4$OH solution and extracted with ethyl acetate. The combined organics were, dried, (Na$_2$SO$_4$), filtered and concentrated. The residue was purified by column chromatography on silica (230-400 M) using ethyl acetate/hexane (3:97) as the eluent to provide the title compound (0.08 g, 10.3%).

2-Bromomethyl-6-phenoxy-benzothiazole

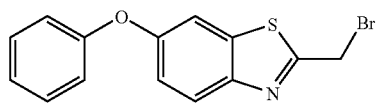

To a solution of 2-methyl-6-phenoxy-benzothiazole (0.06 g, 0.24 mmol) in 5 ml of CCl$_4$ was added NBS (0.039 g, 0.22 mmol) and AIBN (0.004 g, 0.024 mmol). The reaction mixture was heated at 100° C. for 2 h under nitrogen atmosphere. After the completion of the reaction mixture (TLC monitoring), the reaction mixture was evaporated to dryness under reduced pressure and the residue was purified by column chromatography on silica (230-400M) using 1% ethyl acetate/hexane eluent to give the desired product (0.005 g, 6.3%).

Scheme 52 (Example 330):

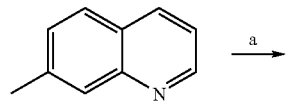

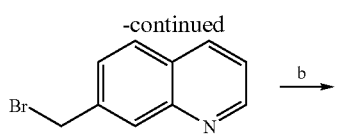

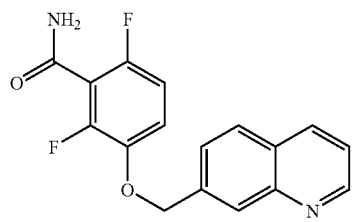

(a) NBS, AIBN, CCl$_4$;
(b) 2,6-difluoro-3-hydroxy benzamide, K$_2$CO$_3$, DMF.

7-Bromomethyl-quinoline

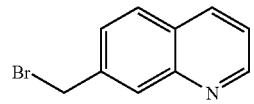

To a solution of 7-methylquinoline (0.10 g, 0.70 mmol) in 5 ml of CCl$_4$ was added NBS (0.14 g, 0.77 mmol) and AIBN (0.025 g, 0.15 mmol). The reaction mixture was heated at 100° C. for 2 h under nitrogen atmosphere. After the completion of the reaction mixture (TLC monitoring), the reaction mixture was evaporated to dryness under reduced pressure and the residue was purified by column chromatography on silica (230-400M) using 1% ethyl acetate/hexane eluent to give the desired product (0.090 g, 58%).

Examples 318-333 (Table R)

The compounds of Examples 318-333 were synthesised according to the following general procedure: To a solution of reactant (A) in anhydrous DMF was added 2,6-Difluoro-3-hydroxy-benzamide (B) and potassium carbonate (C). The reaction mixture was stirred at 25° C. for 24 h under nitrogen atmosphere. The reaction mixture was evaporated to dryness under reduced pressure and the residue was purified by column chromatography on silica using ethyl acetate/hexane as the eluent to provide the product compound.

TABLE R

| Example | 318 | 319 |
|---|---|---|
| Product | 2,6-Difluoro-3-[4-(4-fluoro-phenyl)-thiazol-2-ylmethoxy]-benzamide | 2,6-Difluoro-3-[4-(4-trifluoromethyl-phenyl)-thiazol-2-ylmethoxy]-benzamide |
| Reaction scheme | | |
| Reactant (A) | 2-Bromomethyl-4-(4-fluoro-phenyl)-thiazole | 2-Bromomethyl-4-(4-trifluoromethyl-phenyl)-thiazole |
| Quantities A; B; C; volume DMF | 0.30 g, 1.10 mmol; 0.17 g, 0.99 mmol; 0.52 g, 3.5 mmol; 2 ml | 0.04 g, 0.01 mmol; 0.02 g, 0.01 mmol; 0.05 g, 0.30 mmol; 2 ml |
| Ethyl acetate: hexane ratio Silica | 50:50 | 50:50 |
| | 230-400M | 60-120M |
| Yield | 0.035 g, 8%, white solid | 0.017 g, 33%, white solid |
| $^1$H NMR (DMSO-d$_6$, 400 MHz) | δ 5.58 (s, 2H), 7.15 (d, J = 8.80 Hz, 1H), 7.32 (m, 2H), 7.44 (m, 1H), 7.89 (br s, 1H), 8.03 (m, 2H) and 8.18 (s, 2H) | δ 5.61 (s, 2H), 7.15 (t, J = 8.80 Hz, 1H), 7.45 (m, 1H), 7.84 (d, J = 8.40 Hz, 2H), 7.89 (br s, 1H), 8.20 (m, 3H) and 8.43 (s, 1H) |
| MS-ES+ | 364.97 | 415.23 |
| HPLC method no., Rt (min) | 9, 16.50 | 8, 16.96 |

| Example | 320 | 321 |
|---|---|---|
| Product | 2,6-Difluoro-3-[4-(4-trifluoromethoxy)-thiazol-2-ylmethoxy]-benzamide | 2-(3-Carbamoyl-2,4-difluoro-phenoxymethyl)-benzothiazole-6-carboxylic acid methyl ester |

TABLE R-continued

| Reaction scheme | 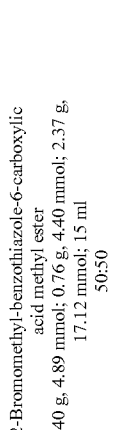 | |
|---|---|---|
| Reactant (A) | 2-Bromomethyl-4-(4-trifluoromethoxy-phenyl)-thiazole | 2-Bromomethyl-benzothiazole-6-carboxylic acid methyl ester |
| Quantities A; B; C; volume DMF | 0.14 g, 0.40 mmol; 0.07 g, 0.04 mmol; 0.16 g, 1.2 mmol; 2 ml | 1.40 g, 4.89 mmol; 0.76 g, 4.40 mmol; 2.37 g, 17.12 mmol; 15 ml |
| Ethyl acetate: hexane ratio Silica | 50:50 | 50:50 |
| Yield | 230-400M 0.005 g, 2%, white solid | 60-120M 1.20 g, 64.8%, white solid |
| 1H NMR (DMSO-d6, 400 MHz) | δ 5.59 (s, 2H), 7.12 (m, 1H), 7.46 (d, J = 8.40 Hz, 2H), 7.87 (br s, 1H), 8.09 (d, J = 8.80 Hz, 2H), 8.16 (br s, 1H) and 8.27 (s, 1H) | δ 3.91 (s, 3H), 5.74 (s, 2H), 7.12 (m, 1H), 7.40 (m, 1H), 7.90 (br s, 1H), 8.0 (d, J = 8.40 Hz, 1H), 8.18 (br s, 1H), 8.32 (d, J = 8.40 Hz, 1H) and 8.52 (s, 1H) |
| MS-ES+ | 431.28 | 379.11 |
| HPLC method no., Rt (min) | 8, 17.10 | 9, 15.22 |
| Example | 322 | 323 |
| Product | 3-(3-Benzo[1,3]dioxol-5-yl-[1,2,4]oxadiazol-5-ylmethoxy)-2,6-difluoro-benzamide | 2,6-Difluoro-3-[2-(4-methoxy-phenyl)-thiazol-4-ylmethoxy]-benzamide |
| Reaction scheme | 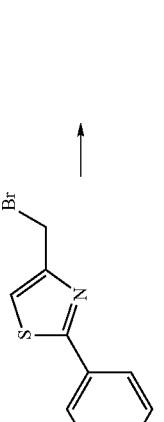 | |

TABLE R-continued

| Reactant (A) | 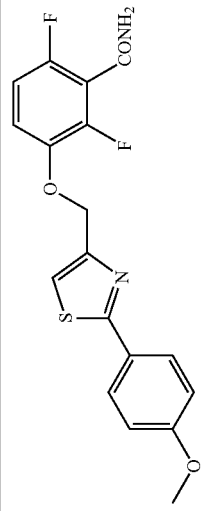 | 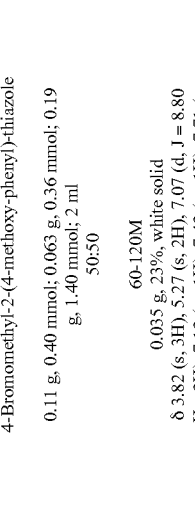 |
|---|---|---|
| | 3-Benzo [1,3]dioxol-5-yl-5-bromomethyl-[1,2,4]oxadiazole | 4-Bromomethyl-2-(4-methoxy-phenyl)-thiazole |
| Quantities A; B; C; volume DMF Ethyl acetate: hexane ratio | 0.30 g, 1.06 mmol; 0.18 g, 1.06 mmol; 0.312 g, 3.70 mmol; 2 ml 50:50 | 0.11 g, 0.40 mmol; 0.063 g, 0.36 mmol; 0.19 g, 1.40 mmol; 2 ml 50:50 |
| Silica Yield $^1$H NMR (DMSO-d$_6$, 400 MHz) | 60-120M 0.13 g, 32.67%, white solid δ 5.66 (s, 2H), 6.14 (s, 2H), 7.10 (m, 2H), 7.38 (m, 1H), 7.45 (s, 1H), 7.56 (m, 1H), 7.90 (br s, 1H) and 8.18 (br s, 1H) | 60-120M 0.035 g, 23%, white solid δ 3.82 (s, 3H), 5.27 (s, 2H), 7.07 (d, J = 8.80 Hz, 2H), 7.12 (m, 1H), 7.42 (m, 1H), 7.71 (s, 1H), 7.89 (m, 3H) and 8.14 (br s, 1H) |
| MS-ES+ | 376.16 | 377.21 |
| HPLC method no., Rt (min) | 8, 15.43 | 8, 15.93 |
| Example | 324 | 325 |
| Product | 3-{1-[3-(4-Chloro-phenyl)-[1,2,4]oxadiazol-5-yl]-ethoxy}-2,6-difluoro-benzamide | 2,6-Difluoro-3-(5-methyl-2-phenyl-2H-[1,2,3]triazol-4-ylmethoxy)-benzamide |
| Reaction scheme | 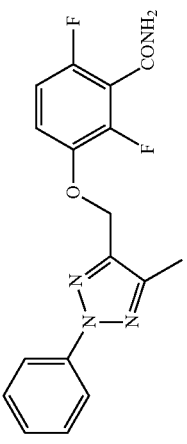 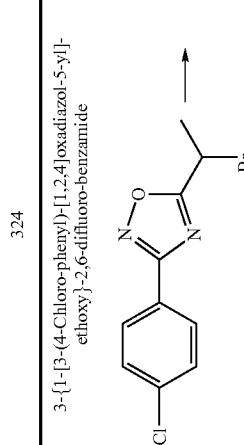 | 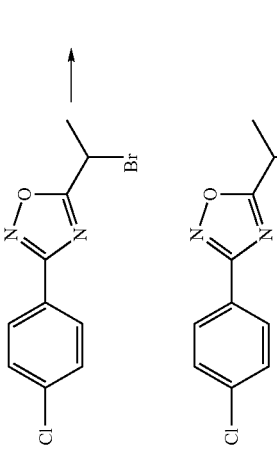 |

TABLE R-continued

| | | | |
|---|---|---|---|
| Reactant (A) | 5-(1-Bromo-ethyl)-3-(4-chloro-phenyl)-[1,2,4]oxadiazole | | 4-Bromomethyl-5-methyl-2-phenyl-2H-[1,2,3]triazole |
| Quantities A; B; C; volume DMF | 0.11 g, 0.38 mmol; 0.05 g, 0.34 mmol; 0.18 g, 1.33 mmol; 2 ml | | 0.23 g, 0.90 mmol; 0.15 g, 0.90 mmol; 0.44 g, 3.1 mmol; 5 ml |
| Ethyl acetate: hexane ratio Silica | 50:50 | | 50:50 |
| Yield | 60-120M 0.06 g, 41%, white solid | | 60-120M 0.03 g, 9.5%, white solid |
| $^1$H NMR (DMSO-$d_6$, 400 MHz) | δ 1.81 (d, J = 6.80 Hz, 3H), 5.98 (q, J = 6.80 Hz, 1H), 7.08 (m, 1H), 7.40 (m, 1H), 7.66 (d, J = 8.40 Hz, 2H), 7.88 (br s, 1H), 8.02 (d, J = 8.40 Hz, 2H) and 8.16 (br s, 1H) | | δ 2.39 (s, 3H), 5.34 (s, 2H), 7.12 (m, 1H), 7.40 (m, 2H), 7.55 (m, 2H), 7.86 (br s, 1H), 7.96 (d, J = 8.0 Hz, 2H) and 8.14 (br s, 1H) |
| MS-ES+ | 380.09 | | 345.20 |
| HPLC method no., Rt (min) | 8, 16.81 | | 8, 16.18 |
| Example | 326 | 327 | |
| Product | 2,6-Difluoro-3-(3-thiazol-2-yl-[1,2,4]oxadiazol-5-ylmethoxy)-benzamide | 2,6-Difluoro-3-(5-phenoxy-benzothiazol-2-ylmethoxy)-benzamide | |
| Reaction scheme | | | |
| Reactant (A) | 5-Chloromethyl-3-thiazol-2-yl-[1,2,4]oxadiazole | 2-bromomethyl-5-phenoxy-benzothiazole | |
| Quantities A; B; C; volume DMF | 0.18 g, 0.89 mmol; 0.014 g, 0.89 mmol; 0.36 g, 2.68 mmol; 2 ml | 0.005 g, 0.015 mmol; 0.003 g, 0.015 mmol; 0.008 g, 0.054 mmol; 1 ml | |
| Ethyl acetate: hexane ratio Silica | 45:55 | 50:50 | |
| Yield | 230-400M 0.10 g, 33%, lemon yellow solid | 60-120M 0.001 g, 16%, white solid | |
| $^1$H NMR (DMSO-$d_6$, 400 MHz) | δ 5.73 (s, 2H), 7.11-7.16 (m, 1H), 7.37-7.43 (m, 1H), 7.90 (br s, 1H) and 8.16-8.19 (m, 3H) | δ 5.76 (s, 2H), 7.03-7.23 (m, 5H), 7.35-7.43 (m, 3H), 7.56 (m, 1H), 7.90 (br s, 1H) and 8.14-8.18 (m, 2H) | |
| MS-ES+ | 339.20 | 413.24 | |
| HPLC method no., Rt (min) | 8, 13.99 | n/a | |

TABLE R-continued

| Example | 328 | 329 |
|---|---|---|
| Product | 3-[3-(4-Difluoromethoxy-3-methoxy-phenyl)-[1,2,4]oxadiazol-5-ylmethoxy]-2,6-difluoro-benzamide | 3-[3-(4-Chloro-3-nitro-phenyl)-[1,2,4]oxadiazol-5-ylmethoxy]-2,6-difluoro-benzamide |
| Reaction scheme | | |
| Reactant (A) | (a) 2,6-difluoro-3-hydroxy benzamide, K₂CO₃, DMF | (a) 2,6-difluoro-3-hydroxy benzamide, K₂CO₃, DMF |
| | 5-chloromethyl-3-(4-difluoromethoxy-3-methoxy-phenyl)-[1,2,4]oxadiazole | 5-chloromethyl-3-(4-chloro-3-nitro-phenyl)-[1,2,4]oxadiazole |
| Quantities A; B; C; volume DMF | 0.10 g, 0.34 mmol; 0.059 g, 0.34 mmol; 0.16 g, 1.20 mmol; 2 ml | 0.15 g, 0.54 mmol; 0.085 g, 0.49 mmol; 0.26 g, 1.90 mmol; 2 ml |
| Silica Ethyl acetate: hexane ratio | 60-120M 50:50 | 60-120M 50:50 |
| Yield | 0.035 g, 23%, white solid | 0.06 g, 26%, white solid |
| ¹H NMR (DMSO-d₆, 400 MHz) | δ 3.92 (s, 3H), 5.70 (s, 2H), 7.14 (m, 1H), 7.22 (s, 1H), 7.40 (m, 2H), 7.65 (m, 2H), 7.91 (br s, 1H) and 8.19 (br s, 1H) | δ 5.76 (s, 2H), 7.13 (m, 1H), 7.40 (m, 1H), 7.90 (br s, 1H), 8.01 (d, J = 8.40 Hz, 1H), 8.18 (br s, 1H), 8.29 (m, 1H) and 8.61 (s, 1H) |
| MS-ES+ | 428.27 | 411.15 |
| HPLC method no, Rt (min) | 8, 15.96 | 8, 16.20 |

| Example | 330 | 331 |
|---|---|---|
| Product | 2,6-Difluoro-3-(quinolin-7-ylmethoxy)-benzamide | 3-(3-Chloro-benzyloxy)-2,6-difluoro-benzamide |

TABLE R-continued

| Reaction scheme | | |
|---|---|---|
| Reactant (A) | 7-bromomethylquinoline | 1-bromomethy-3-chlorobenzene |
| Quantities A; B; C; volume DMF | 0.90 g, 0.40 mmol; 0.071 g, 0.40 mmol; 0.19 g, 1.40 mmol; 2 ml | 0.20 g, 0.98 mmol; 0.17 g, 0.98 mmol; 0.47 g, 3.45 mmol; 2 ml |
| Ethyl acetate: hexane ratio | 50:50 | 40:60 |
| Silica | 60-120M | 60-120M |
| Yield | 0.012 g, 10%, white solid | 0.14 g, 48%, white solid |
| $^1$H NMR (DMSO-d$_6$, 400 MHz) | δ 5.44 (s, 2H), 7.07 (m, 1H), 7.33 (m, 1H), 7.54 (m, 1H), 7.66 (m, 1H), 7.86 (br s, 1H), 8.04 (d, J = 8.40 Hz, 1H), 8.08 (s, 1H), 8.15 (br s, 1H), 8.37 (d, J = 8.40 Hz, 1H) and 8.91 (m, 1H) | δ 5.19 (s, 2H), 7.07 (t, J = 9.20 Hz, 1H), 7.27 (m, 1H), 7.42 (m, 3H), 7.51 (s, 1H), 7.86 (br s, 1H) and 8.14 (br s, 1H) |
| MS-ES+ | 315.02 | 298.05 |
| HPLC method no., Rt (min) | 9, 12.46 | 9, 16.37 |

| Example | 332 | 333 |
|---|---|---|
| Product | 2,6-Difluoro-3-(3-nitro-benzyloxy)-benzamide | 2,6-Difluoro-3-[2-(5-methyl-2-p-tolyl-oxazol-4-yl)-ethoxy]-benzamide |
| Reaction scheme | | |

TABLE R-continued

| | | |
|---|---|---|
| | 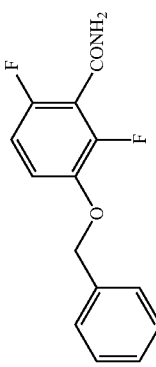 |  |
| Reactant (A) | (a) 2,6-difluoro-3-hydroxy benzamide, K₂CO₃, DMF | (a) 2,6-difluoro-3-hydroxy benzamide, K₂CO₃, DMF |
| | 1-Bromomethyl-3-nitro-benzene | 4-(2-Bromo-ethyl)-5-methyl-2-p-tolyl-oxazole |
| Quantities A; B; C; volume DMF | 0.216 g, 1.0 mmol; 0.17 g, 1.0 mmol; 0.48 g, 3.5 mmol; 2 ml | 0.10 g, 0.35 mmol; 0.061 g, 0.35 mmol; 0.17 g, 1.24 mmol; 2 ml |
| Ethyl acetate: hexane ratio | 50:50 | 50:50 |
| Silica | 60-120M | 60-120M |
| Yield | 0.11 g, 35%, white solid | 0.022 g, 16%, white solid |
| ¹H NMR (DMSO-d₆, 400 MHz) | δ 5.34 (s, 2H), 7.07 (m, 1H), 7.30 (m, 1H), 7.72 (t, J = 8.0 Hz, 1H), 7.90 (m, 2H), 8.15 (br s, 1H), 8.23 (d, J = 8.40 Hz, 1H) and 8.33 (br s, 1H) | δ 2.34 (br s, 6H), 2.93 (t, J = 6.40 Hz, 2H), 4.26 (t, J 6.40 Hz, 2H), 7.04 (t, J = 8.80 Hz, 1H), 7.21-7.31 (m, 3H), 7.80 (d, J = 8.0 Hz, 2H), 7.84 (br s, 1H) and 8.11 (br s, 1H) |
| MS-ES+ | 309.23 | 373.21 |
| HPLC method no., Rt (min) | 9, 15.32 | 8, 16.61 |

Scheme 53:

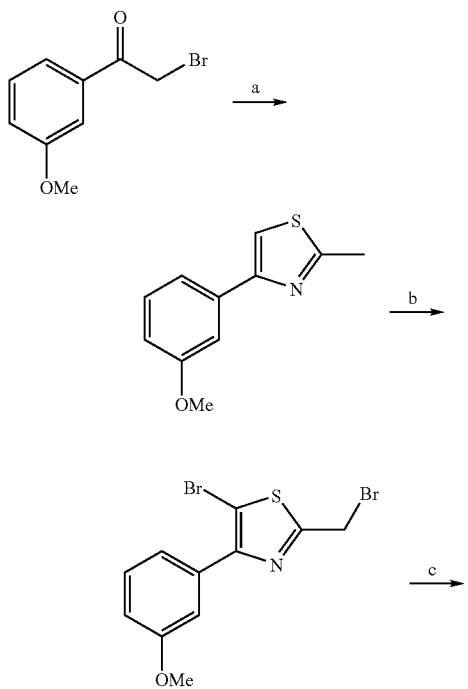

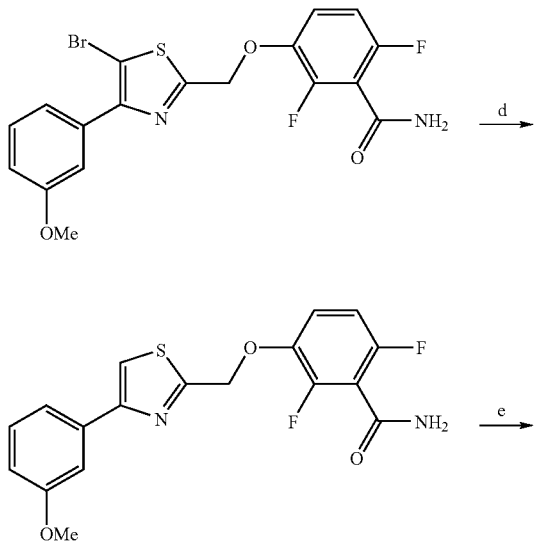

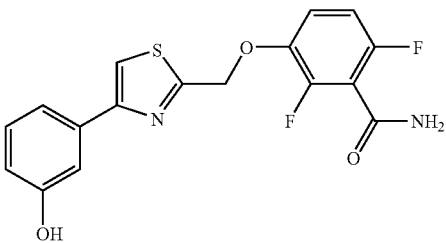

(a) Thioacetamide, DMF;
(b) NBS, AIBN, CCl₄,
(c) 2,6-difluoro-3-hydroxybenzamide, K₂CO₃, DMF
(d) Zn, AcOH
(e) BBr₃, DCM.

4-(3-Methoxy-phenyl)-2-methyl-thiazole

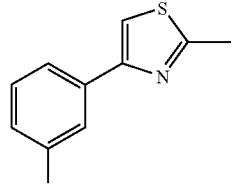

A mixture of thioacetamide (8.0 g, 106.0 mmol) and 2-bromo-1-(3-methoxy-phenyl)-ethanone (2.0 g, 8.81 mmol) was heated at 140° C. for 6 h under nitrogen atmosphere. After completion of the reaction mixture (TLC monitoring), water (50 mL) was added and extracted with ethyl acetate (3×50 mL). The combined organics was washed with water, brine, dried (Na₂SO₄), filtered and concentrated. The crude residue was purified over silica gel (230-400 M, 2% EtOAc-Hexane) to get the desired product (1.5 g, 83%).

5-Bromo-2-bromomethyl-4-(3-methoxy-phenyl)-thiazole

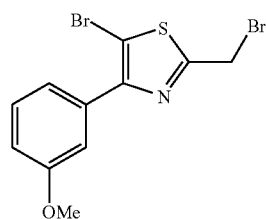

To a solution 4-(3-methoxy-phenyl)-2-methyl-thiazole (1.50, 7.30 mmol) in the 20 ml of CCl₄ was added NBS (2.60 g, 14.60 mmol) and AIBN (0.12 g, 0.73 mmol). The reaction mixture was heated at 100° C. for 2 h under nitrogen atmosphere. After completion of the reaction mixture (TLC monitoring), the reaction mixture was evaporated to dryness under reduced pressure and the residue was purified by column chromatography on silica (230-400 M) using 2% ethyl acetate/hexane as a eluent to give the desired product (1.20 g, 45%).

3-[5-Bromo-4-(3-methoxy-phenyl)-thiazol-2-yl-methoxy]-2,6-difluoro-benzamide

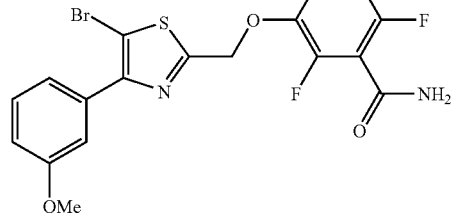

To a solution of 5-Bromo-2-bromomethyl-4-(3-methoxy-phenyl)-thiazole (0.80 g, 2.20 mmol) in 5 ml of anhydrous DMF was added 2,6-Difluoro-3-hydroxy-benzamide (0.38 g, 2.20 mmol) and potassium carbonate (1.06 g, 7.70 mmol). The reaction mixture was stirred at 25° C. for 24 h under nitrogen atmosphere. The reaction mixture was evaporated to dryness under reduced pressure and the residue was purified by column chromatography on silica (60-120 M) using ethyl acetate/hexane (50:50) as the eluent to provide the title compound as white solid (0.50 g, 49%).

2,6-Difluoro-3-[4-(3-methoxy-phenyl)-thiazol-2-ylmethoxy]-benzamide

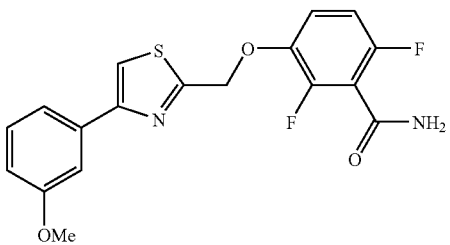

To the solution of 3-[5-bromo-4-(3-methoxy-phenyl)-thiazol-2-ylmethoxy]-2,6-difluoro-benzamide (0.50 g, 1.10 mmol) in the 10 ml of acetic acid was added Zn dust (0.50 g, w/w). The reaction mixture was heated at 120° C. for 1 h. After the completion of the reaction mixture (TLC monitoring), water (50 mL) was added and pH was adjusted to 8-9 with NaOH solution and extracted with ethyl acetate (3×100 mL). The combined organics was washed with water, brine, dried (Na$_2$SO$_4$), filtered and concentrated to get the desired product (0.22 g, 53%).

Example 334

2,6-Difluoro-3-[4-(3-hydroxy-phenyl)-thiazol-2-ylmethoxy]-benzamide

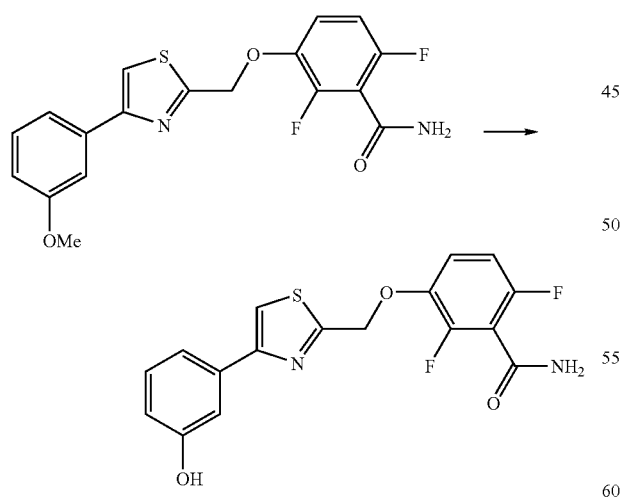

A solution of 2,6-Difluoro-3-[4-(3-methoxy-phenyl)-thiazol-2-ylmethoxy]-benzamide (0.20 g, 0.53 mmol) in 15 ml of DCM was cooled to −78° C. followed by addition of BBr$_3$ (0.20 ml, 2.14 mmol). The reaction mixture was stirred at 25° C. for 2 h. After the completion of the reaction mixture (TLC monitoring), solution of NaHCO$_3$ (20 mL) was added at 0° C. and extracted with ethyl acetate (3×50 mL). The combined organics was washed with water, brine, dried (Na$_2$SO$_4$), filtered and concentrated. The residue was purified by column chromatography on silica (60-120 M) using ethyl acetate/hexane (50:50) as the eluent to provide the title compound as white solid (0.065 g, 33%). $^1$H NMR (DMSO-d$_6$, 400 MHz): δ 5.60 (s, 2H), 6.74 (m, 1H), 7.10 (m, 1H), 7.24 (m, 1H), 7.37-7.45 (m, 3H), 7.90 (br s, 1H), 8.10 (s, 1H), 8.17 (br s, 1H) and 9.55 (s, 1H). MS ES+ (362.99), HPLC (method II) Rt=14.95 min.

Minimum Inhibitory Concentration (MIC) Testing

Compounds of this invention were tested for antimicrobial activity by susceptibility testing in liquid media. MICs for compounds against each strain were determined by a broth microdilution method according to the National Committee for Clinical Laboratory Standards (NCCLS) guidelines. (NCCLS. 2000. Methods for dilution antimicrobial susceptibility tests for bacteria that grow aerobically—fifth edition. Approved standard M7-A5. NCCLS, Wayne, Pa.)

Briefly, test compounds are prepared in 100 μl of 1.6% DMSO solution in multiwell plates. Several bacterial colonies from a freshly streaked plate are transferred to an appropriate rich broth, such as Mueller Hinton. The cell suspension is adjusted to an optical density of 0.09 and further diluted 1:100 with warm 2× broth. This cell suspension is dispensed into the wells containing compound solution so that the final volume is 200 μl. The plates are incubated overnight (16-20 hours) at 37° C. and turbidity is scored by eye and quantified spectrophotometrically. The MIC is defined as the lowest concentration inhibiting visible growth.

Compounds of the current invention were found to have antimicrobial activity in the MIC assay described above.

Results

Table 1 shows the Minimal Inhibitory Concentration (MIC) of the Examples against *Bacillus subtilis* 168$_{CA}$. Activities were scored as 'A' if the MIC was ≦8 micrograms/ml, 'B' if the MIC was 16 to 64 micrograms/ml and 'C' if the MIC was greater than 64 micrograms/ml.

TABLE 1

*Bacillus subtilis* MICs

| Example | Activity |
|---------|----------|
| 1 | A |
| 2 | C |
| 3 | C |
| 4 | C |
| 5 | B |
| 6 | C |
| 7 | C |
| 8 | B |
| 9 | C |
| 10 | A |
| 11 | C |
| 12 | B |
| 13 | B |
| 14 | B |
| 15 | B |
| 16 | C |
| 17 | B |
| 18 | C |
| 19 | A |
| 20 | A |
| 21 | B |
| 22 | B |
| 23 | B |
| 24 | A |
| 25 | C |
| 26 | C |
| 27 | C |

TABLE 1-continued

Bacillus subtilis MICs

| Example | Activity |
|---------|----------|
| 28 | A |
| 29 | B |
| 30 | C |
| 31 | B |
| 32 | A |
| 33 | C |
| 34 | B |
| 35 | B |
| 36 | A |
| 37 | C |
| 38 | A |
| 39 | B |
| 40 | A |
| 41 | B |
| 42 | B |
| 43 | B |
| 44 | A |
| 45 | A |
| 46 | A |
| 47 | A |
| 48 | A |
| 49 | A |
| 50 | A |
| 51 | A |
| 52 | A |
| 53 | C |
| 54 | B |
| 55 | A |
| 56 | A |
| 57 | A |
| 58 | A |
| 59 | A |
| 60 | B |
| 61 | A |
| 62 | A |
| 63 | A |
| 64 | A |
| 65 | A |
| 66 | A |
| 67 | A |
| 68 | A |
| 69 | A |
| 70 | A |
| 71 | A |
| 72 | B |
| 73 | A |
| 74 | A |
| 75 | A |
| 76 | A |
| 77 | B |
| 78 | A |
| 79 | B |
| 80 | B |
| 81 | A |
| 82 | A |
| 83 | A |
| 84 | A |
| 85 | A |
| 86 | A |
| 87 | A |
| 88 | A |
| 89 | A |
| 90 | A |
| 91 | A |
| 92 | A |
| 93 | A |
| 94 | A |
| 95 | B |
| 96 | B |
| 97 | A |
| 98 | A |
| 99 | A |
| 100 | A |
| 101 | B |
| 102 | A |
| 103 | A |

TABLE 1-continued

Bacillus subtilis MICs

| Example | Activity |
|---------|----------|
| 104 | A |
| 105 | A |
| 106 | A |
| 107 | A |
| 108 | B |
| 109 | A |
| 110 | A |
| 111 | A |
| 112 | A |
| 113 | A |
| 114 | A |
| 115 | B |
| 116 | B |
| 117 | A |
| 118 | A |
| 119 | A |
| 120 | A |
| 121 | A |
| 122 | A |
| 123 | A |
| 124 | A |
| 125 | A |
| 126 | A |
| 127 | A |
| 128 | A |
| 129 | C |
| 130 | A |
| 131 | B |
| 132 | A |
| 133 | A |
| 134 | B |
| 135 | A |
| 136 | A |
| 137 | B |
| 138 | C |
| 139 | A |
| 140 | C |
| 141 | A |
| 142 | A |
| 143 | C |
| 144 | C |
| 145 | B |
| 146 | A |
| 147 | B |
| 148 | A |
| 149 | A |
| 150 | A |
| 151 | A |
| 152 | B |
| 153 | A |
| 154 | A |
| 155 | A |
| 156 | A |
| 157 | A |
| 158 | A |
| 159 | A |
| 160 | A |
| 161 | A |
| 162 | A |
| 163 | A |
| 164 | A |
| 165 | A |
| 166 | C |
| 167 | B |
| 168 | C |
| 169 | C |
| 170 | C |
| 171 | B |
| 172 | C |
| 173 | C |
| 174 | B |
| 175 | A |
| 176 | A |
| 177 | A |
| 178 | B |
| 179 | C |

TABLE 1-continued

Bacillus subtilis MICs

| Example | Activity |
|---|---|
| 180 | A |
| 181 | A |
| 182 | C |
| 183 | B |
| 184 | B |
| 185 | C |
| 186 | A |
| 187 | B |
| 188 | B |
| 189 | C |
| 190 | B |
| 191 | B |
| 192 | C |
| 193 | B |
| 194 | C |
| 195 | A |
| 196 | A |
| 197 | B |
| 198 | B |
| 199 | C |
| 200 | A |
| 201 | A |
| 202 | A |
| 203 | C |
| 204 | B |
| 205 | A |
| 206 | A |
| 207 | A |
| 208 | A |
| 209 | B |
| 210 | A |
| 211 | A |
| 212 | A |
| 213 | A |
| 214 | B |
| 215 | A |
| 216 | A |
| 217 | A |
| 218 | A |
| 219 | A |
| 220 | A |
| 221 | A |
| 222 | A |
| 223 | A |
| 224 | B |
| 225 | C |
| 226 | B |
| 227 | A |
| 228 | A |
| 229 | A |
| 230 | A |
| 231 | A |
| 232 | B |
| 233 | A |
| 234 | A |
| 235 | A |
| 236 | A |
| 237 | B |
| 238 | B |
| 239 | B |
| 240 | A |
| 241 | A |
| 242 | A |
| 243 | A |
| 244 | |
| 245 | A |
| 246 | A |
| 247 | A |
| 248 | A |
| 249 | A |
| 250 | A |
| 251 | B |
| 252 | A |
| 253 | B |
| 254 | A |
| 255 | A |

TABLE 1-continued

Bacillus subtilis MICs

| Example | Activity |
|---|---|
| 256 | A |
| 257 | A |
| 258 | A |
| 259 | A |
| 260 | A |
| 261 | B |
| 262 | B |
| 263 | A |
| 264 | B |
| 265 | A |
| 266 | B |
| 267 | A |
| 268 | A |
| 269 | A |
| 270 | A |
| 271 | A |
| 272 | A |
| 273 | A |
| 274 | A |
| 275 | B |
| 276 | A |
| 277 | A |
| 278 | A |
| 279 | A |
| 280 | A |
| 281 | A |
| 282 | A |
| 283 | A |
| 284 | A |
| 285 | A |
| 286 | A |
| 287 | A |
| 288 | A |
| 289 | A |
| 290 | A |
| 291 | A |
| 292 | A |
| 293 | A |
| 294 | A |
| 295 | A |
| 296 | A |
| 297 | A |
| 298 | A |
| 299 | A |
| 301 | A |
| 302 | A |
| 303 | A |
| 304 | A |
| 305 | A |
| 306 | A |
| 307 | A |
| 308 | A |
| 309 | A |
| 310 | A |
| 311 | A |
| 312 | B |
| 313 | A |
| 314 | A |
| 315 | A |
| 316 | A |
| 317 | A |
| 318 | A |
| 319 | A |
| 320 | A |
| 321 | A |
| 322 | A |
| 323 | A |
| 324 | A |
| 325 | A |
| 326 | B |
| 327 | A |
| 328 | A |
| 329 | A |
| 330 | B |
| 331 | A |
| 332 | B |

TABLE 1-continued

Bacillus subtilis MICs

| Example | Activity |
|---|---|
| 333 | A |
| 334 | B |

Some of the compounds of the Examples were also tested for activity against the pathogenic organism *Staphylococcus aureus* ATCC29213. Table 2 shows the MICs of the Examples against *Staphylococcus aureus*. Activities were again scored as 'A' if the MIC was $\leq 8$ micrograms/ml, 'B' if the MIC was 16 to 64 micrograms/ml and 'C' if the MIC was greater than 64 micrograms/ml.

TABLE 2

Staphylococcus aureus MICs

| Example | Activity |
|---|---|
| 1 | A |
| 5 | B |
| 8 | B |
| 12 | A |
| 15 | B |
| 17 | B |
| 18 | C |
| 19 | A |
| 24 | A |
| 26 | C |
| 27 | C |
| 28 | C |
| 29 | B |
| 30 | C |
| 31 | B |
| 32 | B |
| 36 | C |
| 39 | B |
| 40 | A |
| 41 | B |
| 42 | B |
| 43 | B |
| 45 | A |
| 46 | A |
| 47 | B |
| 49 | A |
| 51 | B |
| 52 | A |
| 53 | C |
| 54 | B |
| 55 | A |
| 56 | A |
| 57 | B |
| 58 | A |
| 59 | B |
| 60 | B |
| 61 | A |
| 62 | A |
| 64 | A |
| 65 | A |
| 66 | A |
| 67 | A |
| 68 | A |
| 69 | A |
| 70 | A |
| 71 | A |
| 72 | B |
| 73 | A |
| 74 | A |
| 75 | A |
| 76 | A |
| 77 | B |
| 78 | A |
| 79 | B |
| 80 | B |
| 81 | A |

TABLE 2-continued

Staphylococcus aureus MICs

| Example | Activity |
|---|---|
| 82 | A |
| 83 | B |
| 84 | A |
| 85 | A |
| 86 | A |
| 87 | A |
| 88 | A |
| 89 | A |
| 90 | A |
| 91 | A |
| 93 | B |
| 94 | A |
| 95 | C |
| 98 | A |
| 99 | A |
| 100 | A |
| 101 | B |
| 102 | A |
| 103 | A |
| 104 | A |
| 105 | A |
| 106 | A |
| 107 | A |
| 108 | B |
| 109 | B |
| 111 | A |
| 114 | A |
| 115 | A |
| 116 | B |
| 117 | A |
| 118 | A |
| 119 | A |
| 120 | A |
| 121 | A |
| 122 | A |
| 123 | A |
| 124 | A |
| 125 | A |
| 126 | A |
| 127 | A |
| 128 | B |
| 129 | B |
| 130 | A |
| 132 | A |
| 133 | A |
| 134 | B |
| 135 | A |
| 136 | A |
| 137 | B |
| 138 | C |
| 139 | A |
| 140 | A |
| 141 | A |
| 143 | A |
| 144 | C |
| 145 | C |
| 146 | B |
| 147 | B |
| 148 | A |
| 149 | B |
| 150 | B |
| 151 | B |
| 152 | B |
| 153 | A |
| 155 | A |
| 156 | A |
| 157 | A |
| 158 | A |
| 159 | A |
| 161 | A |
| 162 | A |
| 163 | A |
| 164 | A |
| 165 | A |
| 166 | C |
| 167 | B |

TABLE 2-continued

Staphylococcus aureus MICs

| Example | Activity |
|---|---|
| 168 | C |
| 169 | C |
| 170 | C |
| 171 | B |
| 172 | C |
| 173 | C |
| 174 | B |
| 175 | A |
| 176 | B |
| 177 | A |
| 178 | B |
| 179 | C |
| 180 | B |
| 181 | B |
| 182 | C |
| 183 | B |
| 184 | B |
| 185 | C |
| 186 | B |
| 187 | B |
| 188 | B |
| 189 | C |
| 190 | B |
| 191 | B |
| 192 | C |
| 193 | B |
| 194 | C |
| 195 | B |
| 196 | B |
| 197 | B |
| 200 | B |
| 201 | B |
| 202 | B |
| 204 | B |
| 205 | A |
| 206 | C |
| 207 | B |
| 208 | A |
| 209 | C |
| 210 | A |
| 211 | B |
| 212 | B |
| 213 | B |
| 214 | B |
| 215 | A |
| 216 | A |
| 217 | A |
| 218 | A |
| 219 | A |
| 220 | A |
| 221 | A |
| 222 | A |
| 223 | A |
| 224 | C |
| 225 | C |
| 226 | B |
| 227 | A |
| 228 | B |
| 229 | A |
| 230 | A |
| 231 | A |
| 232 | A |
| 233 | A |
| 235 | A |
| 236 | A |
| 237 | B |
| 239 | B |
| 240 | A |
| 241 | A |
| 242 | A |
| 243 | A |
| 245 | A |
| 246 | A |
| 247 | A |
| 248 | A |
| 249 | A |

TABLE 2-continued

Staphylococcus aureus MICs

| Example | Activity |
|---|---|
| 250 | A |
| 251 | B |
| 252 | A |
| 256 | B |
| 257 | A |
| 260 | A |
| 262 | B |
| 263 | B |
| 265 | B |
| 266 | B |
| 267 | A |
| 268 | B |
| 269 | A |
| 270 | A |
| 271 | A |
| 272 | A |
| 273 | A |
| 274 | A |
| 275 | B |
| 276 | A |
| 277 | A |
| 278 | A |
| 279 | A |
| 280 | A |
| 281 | A |
| 282 | A |
| 283 | A |
| 284 | A |
| 285 | A |
| 286 | A |
| 287 | A |
| 288 | A |
| 289 | A |
| 290 | A |
| 291 | A |
| 292 | A |
| 293 | A |
| 294 | A |
| 295 | A |
| 296 | A |
| 297 | A |
| 298 | A |
| 299 | A |
| 300 | B |
| 301 | B |
| 302 | A |
| 303 | A |
| 304 | A |
| 305 | A |
| 306 | A |
| 307 | A |
| 308 | B |
| 309 | A |
| 310 | B |
| 311 | A |
| 312 | A |
| 313 | A |
| 314 | B |
| 315 | A |
| 316 | A |
| 317 | A |
| 318 | A |
| 319 | A |
| 320 | A |
| 321 | A |
| 322 | A |
| 323 | A |
| 324 | A |
| 325 | B |
| 326 | B |
| 327 | A |
| 331 | B |
| 333 | A |
| 334 | A |

Some of the Examples were also tested for activity against other bacterial species. Table 3 shows the MICs of the Examples against various bacterial species. Activities were again scored as 'A' if the MIC was ≦8 micrograms/ml, 'B' if the MIC was 16 to 64 micrograms/ml and 'C' if the MIC was greater than 64 micrograms/ml.

TABLE 3

MICs against various bacteria

| | Activity | | | |
|---|---|---|---|---|
| Example | Bacillus cereus ATCC 14579 | Staphylococcus epidermidis ATCC 12228 | Staphylococcus haemolyticus ATCC 29970 | Staphylococcus saprophyticus ATCC 15305 |
| 46 | | A | | |
| 84 | | A | | |
| 87 | | A | | |
| 88 | | A | | |
| 175 | | A | | |
| 215 | | A | | |
| 177 | | A | | |
| 217 | A | A | | A |
| 218 | A | A | A | A |
| 236 | A | | | A |
| 111 | | | | A |
| 208 | A | | | A |
| 114 | A | | | A |
| 106 | A | A | A | A |
| 246 | A | A | A | A |
| 242 | | A | A | |
| 135 | | | A | |
| 139 | | A | A | |
| 287 | | | A | |
| 271 | | A | | |
| 282 | | A | | |
| 311 | | A | | |

Some of the Examples were also tested for activity against staphylococcal clinical isolates. Table 4 shows the MICs of the examples against various clinical isolates. Activities were again scored as 'A' if the MIC was ≦8 micrograms/ml, 'B' if the MIC was 16 to 64 micrograms/ml and 'C' if the MIC was greater than 64 micrograms/ml.

TABLE 4

MICs against clinical isolates

| Organism | No. | Oxacillin (S/R[1]) | Antibiotic Susceptibility[2] | Other Information | Example - Activity 217 | 236 | 218 |
|---|---|---|---|---|---|---|---|
| S. aureus | 0100 | S | | ATCC 29213 | A | A | A |
| | 1134 | S | | Hospital | A | A | A |
| | 753 | S | | Hospital | A | A | A |
| | 1662 | S | | Hospital | A | A | A |
| | 1015 | R | Van-S, LZD-S | Hospital | A | A | A |
| | 1135 | R | Van-S, LZD-S | Hospital | A | A | A |
| | 2012 | R | Van-I, LZD-S | Hospital | A | A | A |
| | 2018 | R | Van-I, LZD-S | Hospital | A | A | A |
| | 1651 | R | Van-S, LZD-R | Hospital (G2576T, G) | A | A | A |
| | 1652 | R | Van-S, LZD-R | Hospital (T2500T, A) | A | A | A |
| | 1725 | R | Van-S, LZD-R | Hospital (G2576T) | A | A | A |
| | 2011 | R | Tet-R, MI-S | Hospital (tetK) | A | A | A |
| | 757 | R | Tet-R, MI-R | Hospital (tetM) | A | A | A |
| | 1729 | R | Tet-R, MI-R | Hospital | A | A | A |
| | 2147 | R | CC-S, SXT-S | Community | A | A | A |
| | 2142 | R | CC-S, SXT-S | Community | A | A | A |
| | 2158 | R | CC-R, Doxy-I | Community | A | A | A |
| | 2150 | R | CC-R, SXT-S | Community | A | A | A |
| | 2149 | R | CC-R (iMLS), SXT-S | Community | A | A | A |
| | 2175 | R | TMP-R | Community | A | A | A |
| | 2143 | R | Rif-R | Community | A | A | A |
| S. epidermidis | 835 | S | | | A | A | A |
| | 1139 | S | | | A | A | A |
| | 831 | R | | | A | A | A |
| | 1142 | R | | | A | A | A |
| | 1144 | R | | | A | A | A |

[1]S, susceptible; I, intermediate; R, resistant
[2]Van, vancomycin; LZD, linezolid; Tet, tetracycline; MI, minocycline; CC, clindamycin; SXT, trimethoprim/sulfamethoxazole; Doxy, doxycycline; iMLS, inducible macrolide-lincosamide-streptogramin B resistance; TMP, trimethoprim; Rif, rifampin Some of the Examples were also tested for activity in a mouse *Staphylococcus aureus* septicaemia model of infection. Table 5 shows the survival at day 7 of infected mice treated with a single intraperitoneal dose of 100 mg/kg of each Example at 1 hour after intraperitoneal inoculation with a lethal dose of *Staphylococcus aureus*.

TABLE 5

| Murine Survival | |
|---|---|
| Example | Percent survival |
| Vehicle control | 0 |
| 218 | 100 |
| 106 | 100 |
| 241 | 100 |
| 247 | 100 |
| 246 | 100 |

The invention claimed is:
1. A compound of the formula I or a salt, thereof

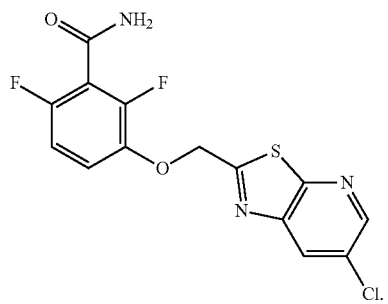

UNITED STATES PATENT AND TRADEMARK OFFICE
CERTIFICATE OF CORRECTION

PATENT NO. : 8,088,791 B2  
APPLICATION NO. : 12/293608  
DATED : January 3, 2012  
INVENTOR(S) : David Ryall Brown et al.

Page 1 of 1

It is certified that error appears in the above-identified patent and that said Letters Patent is hereby corrected as shown below:

ON THE TITLE PAGE:
    Item (73): Assignee:
        Please replace "Biots" with --Biota--

Signed and Sealed this
Twenty-second Day of May, 2012

David J. Kappos
*Director of the United States Patent and Trademark Office*